(12) United States Patent
Marlin

(10) Patent No.: US 10,390,908 B2
(45) Date of Patent: Aug. 27, 2019

(54) UNIVERSAL ALIGNING ADAPTOR SYSTEM AND METHODS

(71) Applicant: Gerald M. Marlin, Potomac, MD (US)

(72) Inventor: Gerald M. Marlin, Potomac, MD (US)

( * ) Notice: Subject to any disclaimer, the term of this patent is extended or adjusted under 35 U.S.C. 154(b) by 223 days.

(21) Appl. No.: 15/162,305

(22) Filed: May 23, 2016

(65) Prior Publication Data

US 2016/0262852 A1    Sep. 15, 2016

Related U.S. Application Data

(63) Continuation of application No. 14/085,286, filed on Nov. 20, 2013, now Pat. No. 9,364,299.

(Continued)

(51) Int. Cl.
*A61C 8/00* (2006.01)
*A61C 9/00* (2006.01)
(Continued)

(52) U.S. Cl.
CPC .............. *A61C 8/006* (2013.01); *A61B 6/032* (2013.01); *A61B 6/14* (2013.01); *A61B 6/145* (2013.01); *A61B 6/4085* (2013.01); *A61C 8/0001* (2013.01); *A61C 8/008* (2013.01); *A61C 8/009* (2013.01); *A61C 8/0012* (2013.01); *A61C 8/0053* (2013.01); *A61C 8/0068* (2013.01); *A61C 8/0089* (2013.01); *A61C 9/004* (2013.01); *A61C 9/0006* (2013.01); *A61C 13/0004* (2013.01); *A61C 2008/0084* (2013.01)

(58) Field of Classification Search
CPC ..... A61C 8/0001; A61C 9/004; A61C 9/0046; A61C 9/0053; A61C 13/0004
See application file for complete search history.

(56) References Cited

U.S. PATENT DOCUMENTS 5,135,395 A   8/1992 Marlin
5,180,303 A   1/1993 Hornberg et al.
(Continued)

OTHER PUBLICATIONS

International Search Report for International Application No. PCT/US12/71029, dated May 2, 2014, pp. 1-6.

*Primary Examiner* — Ralph A Lewis
(74) *Attorney, Agent, or Firm* — Sterne, Kessler, Goldstein & Fox P.L.L.C.

(57) ABSTRACT

A system for dental implant restoration is provided. It includes universal aligning adaptors and prosthetic components having co-operable indices, which together form a translational, integrating system which aligns, synchronizes, and references the prosthetic components about an implant's central axis of rotation. Rotation of an adaptor about a prosthetic component, with its reference point becoming aligned to a predetermined reference point on the prosthetic component, followed by the rotation of the adaptor/prosthetic component assembly about the implant, situates the prosthetic component in a predetermined position such that all other prosthetic components become synchronized to the adaptor's reference point. The prosthetic component is mechanical for clinical or lab bench use, or is virtual for restoration design in a software program, prior to milling prosthetic abutments or devices. Abutments, healing caps and screw access holes are realigned to preferred positions and synchronized with minimal deviation from the ideal direction.

11 Claims, 53 Drawing Sheets

Related U.S. Application Data

(60) Provisional application No. 61/796,837, filed on Nov. 20, 2012.

(51) Int. Cl.
 *A61C 13/00* (2006.01)
 *A61B 6/03* (2006.01)
 *A61B 6/00* (2006.01)
 *A61B 6/14* (2006.01)

(56) References Cited

U.S. PATENT DOCUMENTS

| | | |
|---|---|---|
| 5,238,405 A | 8/1993 | Marlin |
| 5,350,301 A | 9/1994 | De Buck |
| 5,350,302 A | 9/1994 | Marlin |
| 5,439,380 A | 8/1995 | Marlin |
| 5,564,921 A | 10/1996 | Marlin |
| 5,658,147 A | 8/1997 | Phimmasone |
| 5,662,475 A | 9/1997 | Mena |
| 5,863,200 A | 1/1999 | Hamada |
| 5,873,722 A | 2/1999 | Lazzara et al. |
| 5,888,066 A | 3/1999 | Morgan |
| 5,904,483 A | 5/1999 | Wade |
| 5,947,733 A | 9/1999 | Sutter et al. |
| 6,012,923 A | 1/2000 | Bassett |
| 6,068,479 A | 5/2000 | Kwan |
| 6,168,436 B1 | 1/2001 | O'Brien |
| 6,244,867 B1 | 6/2001 | Aravena et al. |
| 6,254,387 B1 | 7/2001 | Bergstrom |
| 6,299,447 B1 | 10/2001 | Zuest |
| 6,358,052 B1 | 3/2002 | Lustig |
| 6,386,876 B1 | 5/2002 | Lee |
| 6,565,357 B1 | 5/2003 | Lazzara |
| 6,592,370 B2 | 7/2003 | Morgan |
| 6,663,388 B1 | 12/2003 | Shar et al. |
| 6,726,480 B1 | 4/2004 | Sutter et al. |
| 7,322,824 B2 | 1/2008 | Schmidt |
| 7,491,058 B2 | 2/2009 | Jomeus |
| 7,988,449 B2 * | 8/2011 | Amber ................ A61C 8/0001 433/213 |
| 8,007,279 B2 | 8/2011 | Bassett |
| 8,118,596 B2 | 2/2012 | Niznick |
| 8,142,193 B2 | 3/2012 | Bar Shalom |
| 8,185,224 B2 | 5/2012 | Powell |
| 2005/0202368 A1 | 9/2005 | Ganley |
| 2007/0259315 A1 | 11/2007 | Last-Pollak |
| 2008/0057476 A1 | 3/2008 | Zettler et al. |
| 2010/0112521 A1 | 5/2010 | Chapel et al. |
| 2012/0072178 A1 | 3/2012 | Beaudry et al. |
| 2012/0141951 A1 * | 6/2012 | Bellanca ............. A61C 8/0001 433/72 |
| 2012/0231418 A1 | 9/2012 | Layton |
| 2013/0108985 A1 | 5/2013 | Amber et al. |
| 2013/0196290 A1 | 8/2013 | Hellington et al. |
| 2013/0273492 A1 | 10/2013 | Suttin, Sr. et al. |
| 2014/0080095 A1 | 3/2014 | Suttin et al. |

* cited by examiner

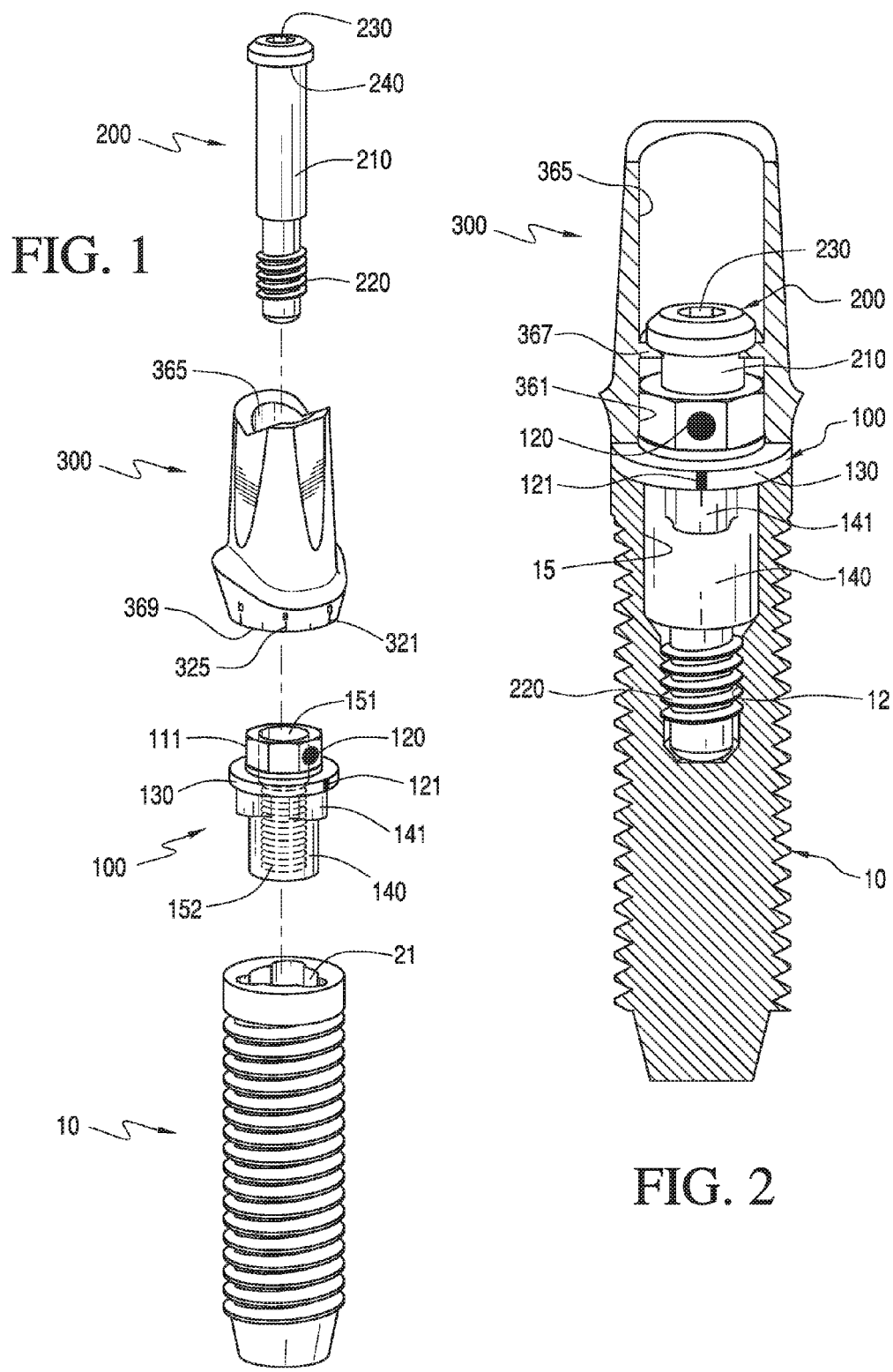

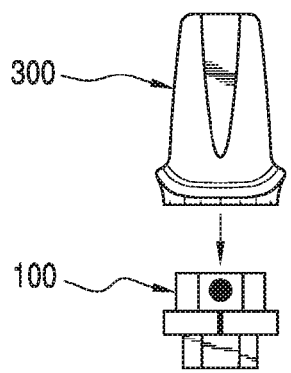
FIG. 12A
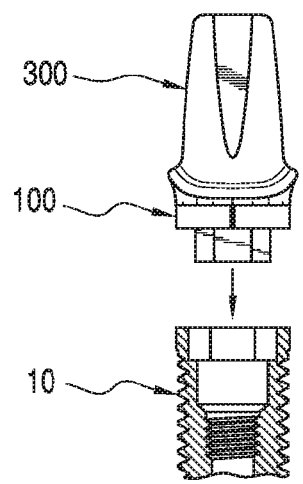
FIG. 12B
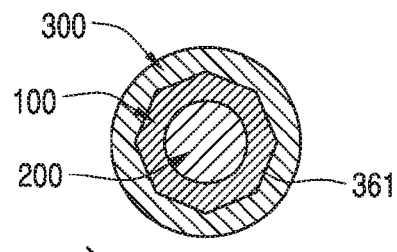 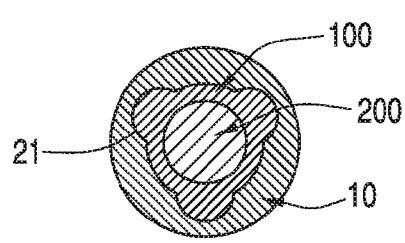
FIG. 13
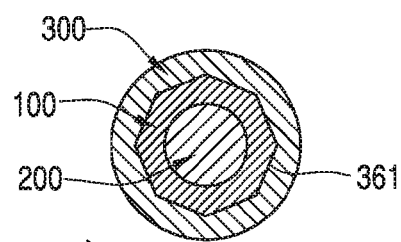 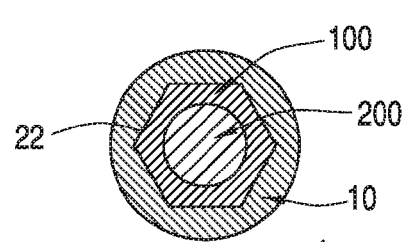
FIG. 14
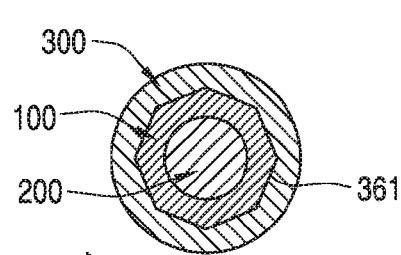 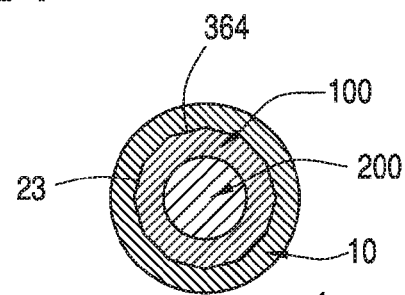
FIG. 15

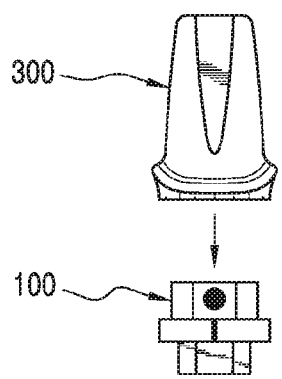
FIG. 20A
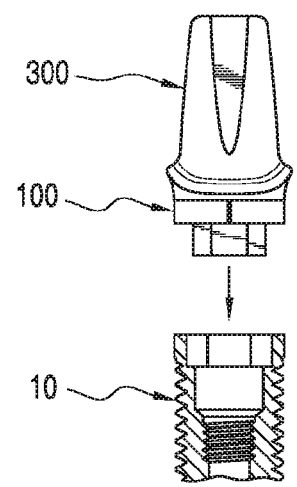
FIG. 20B
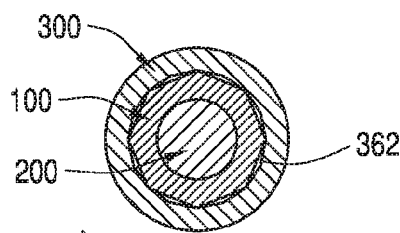 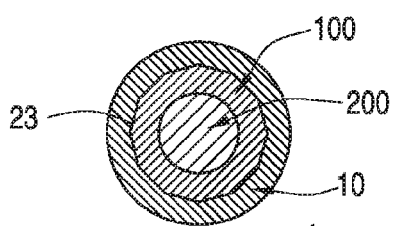
FIG. 21
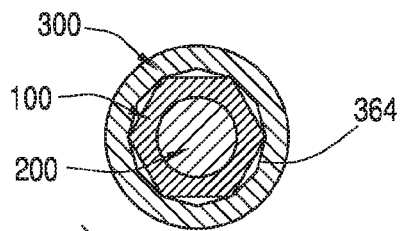 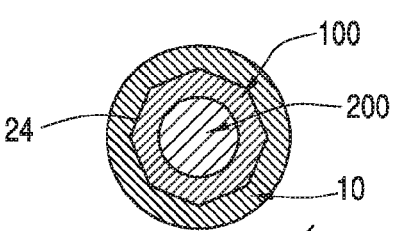
FIG. 22
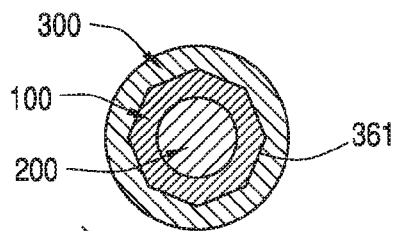 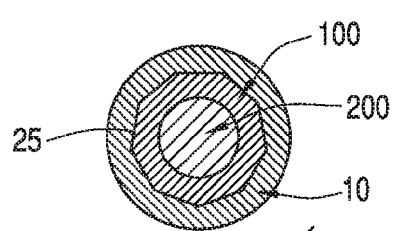
FIG. 23

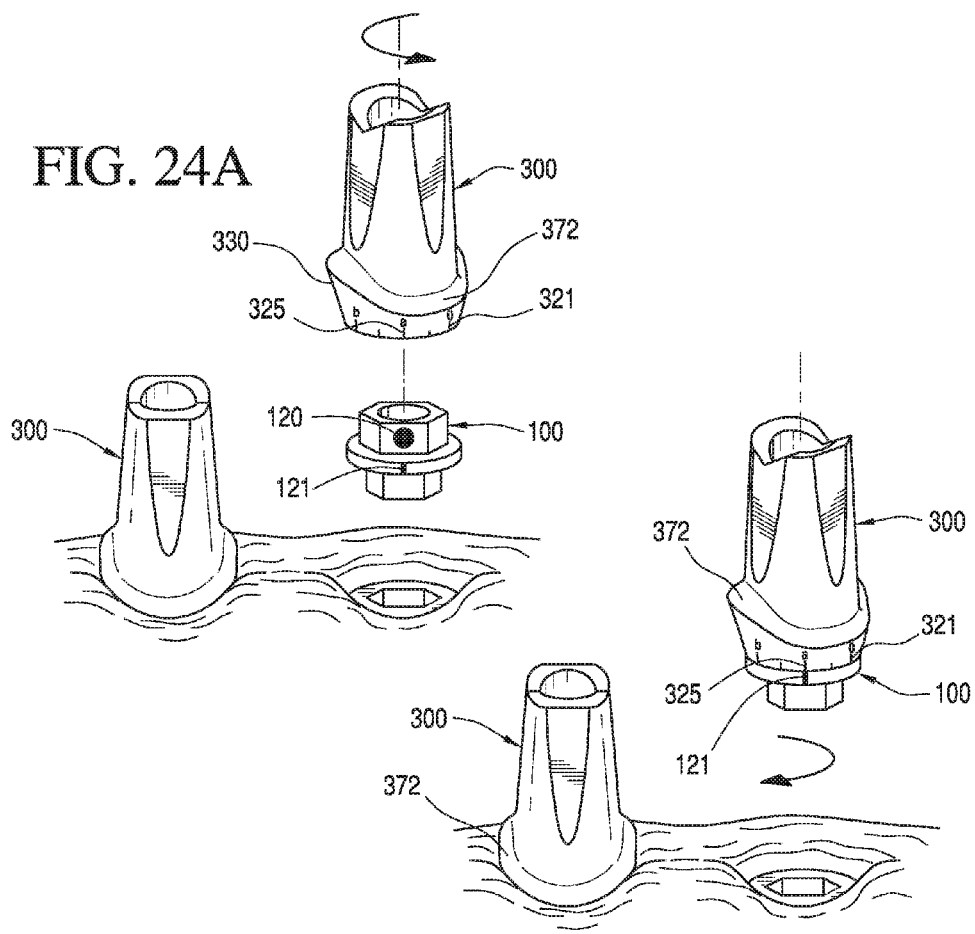
FIG. 24A
FIG. 24B
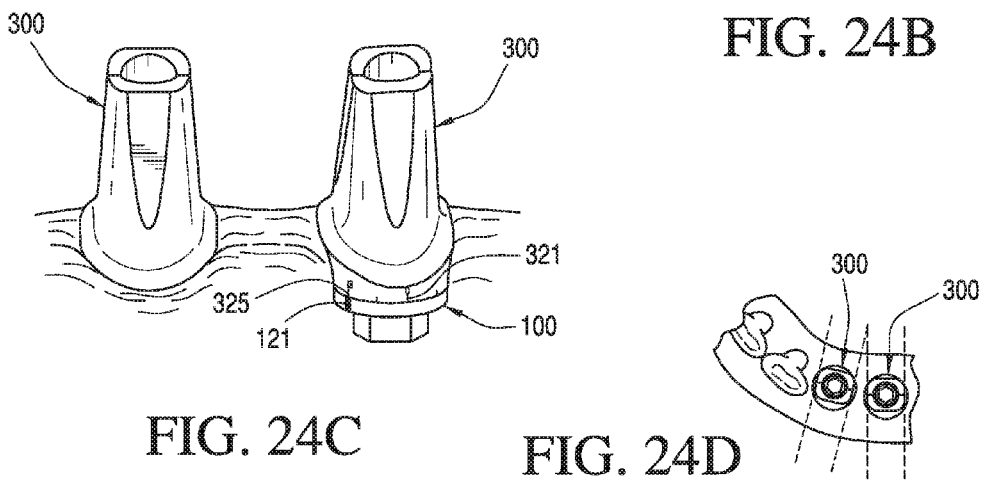
FIG. 24C
FIG. 24D

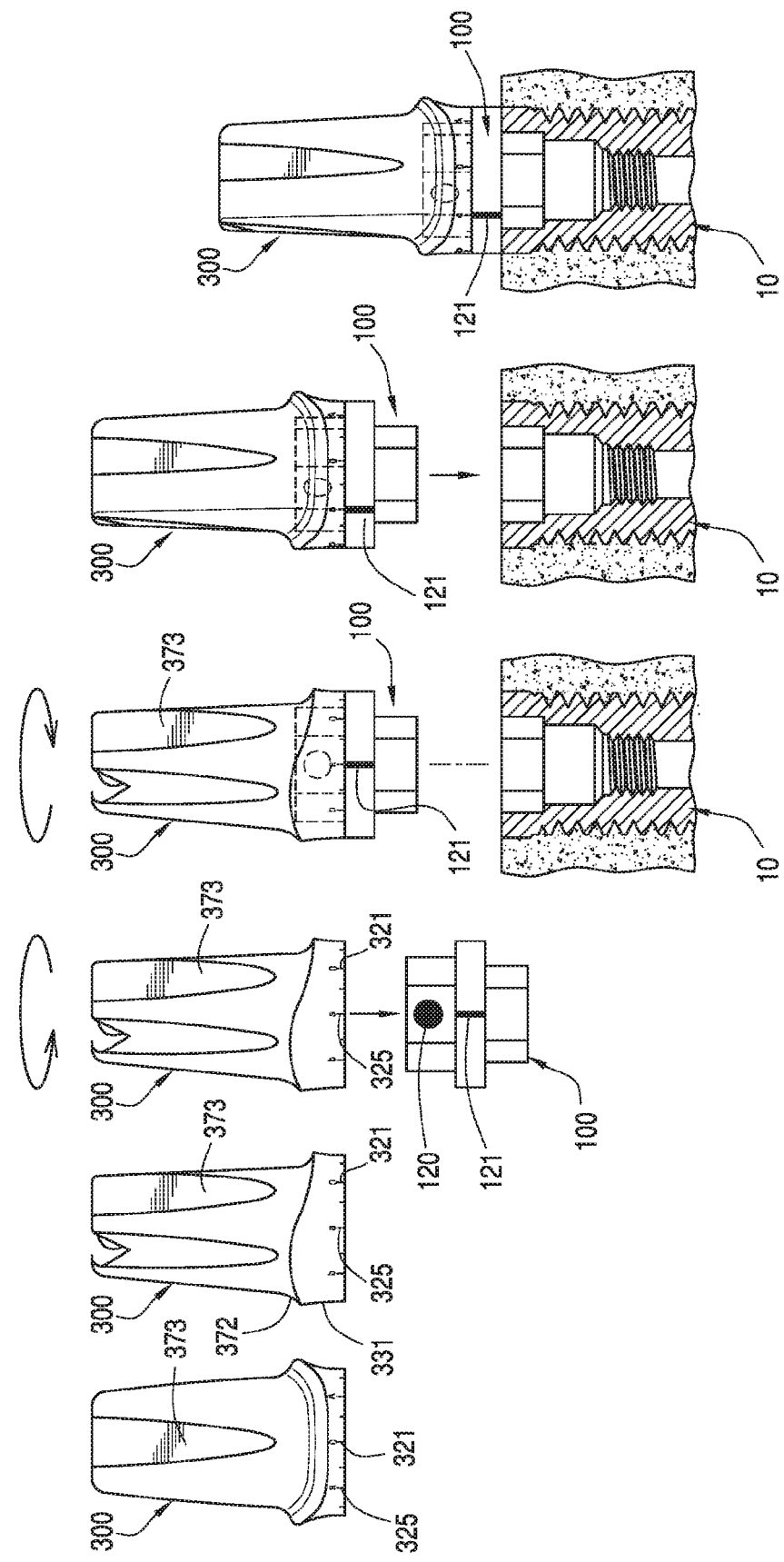

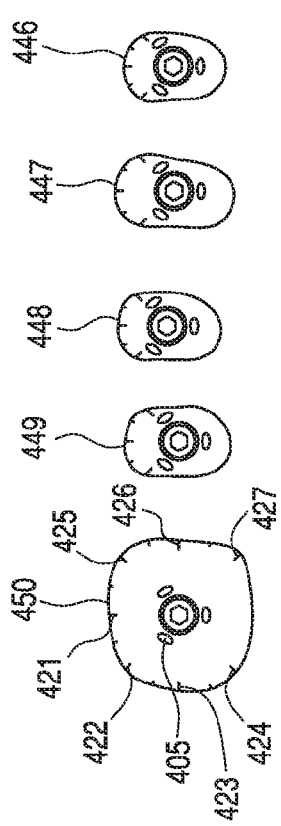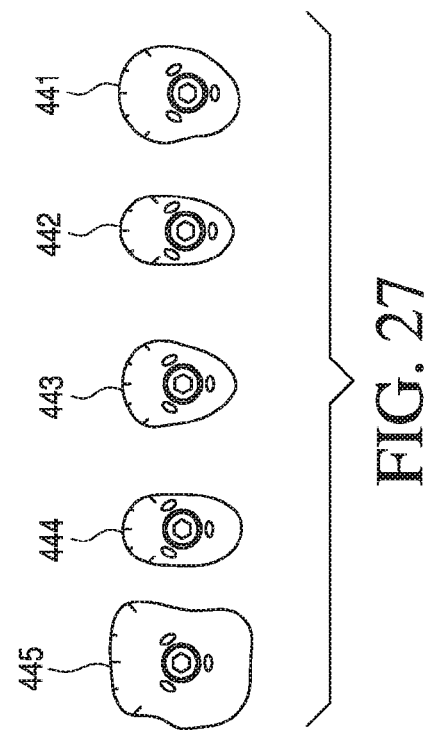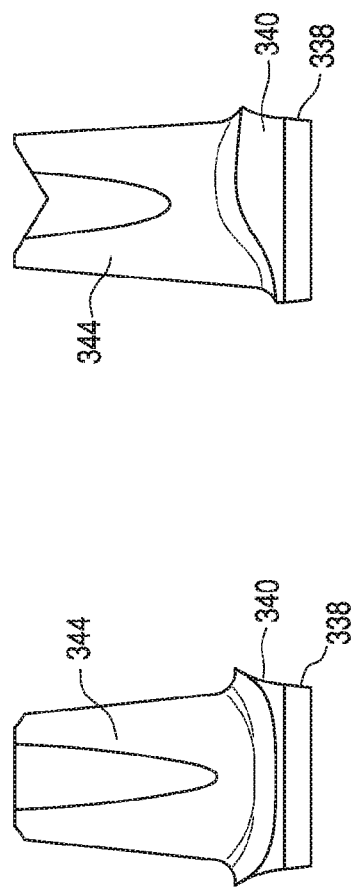

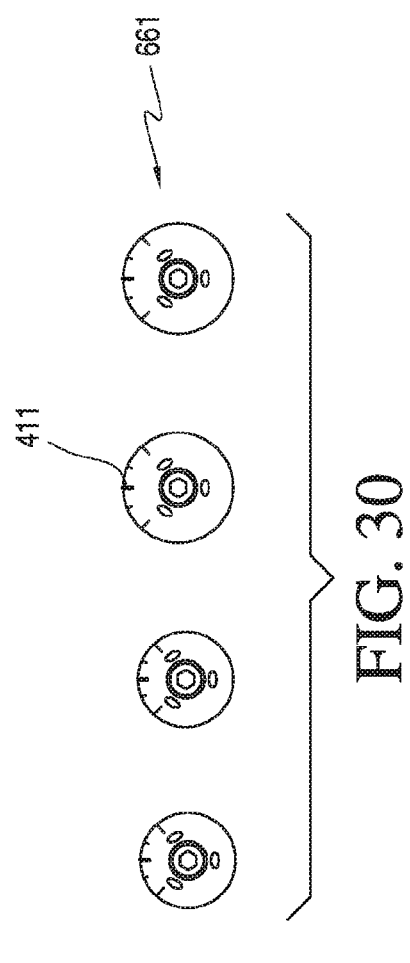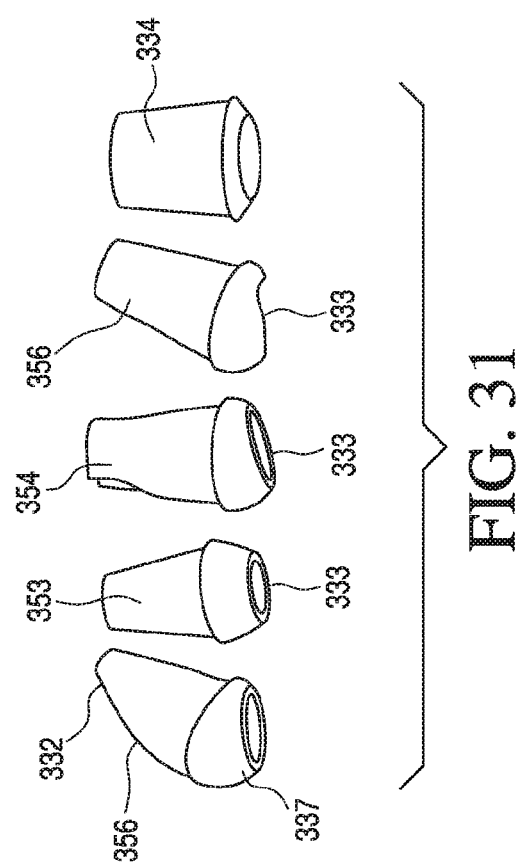

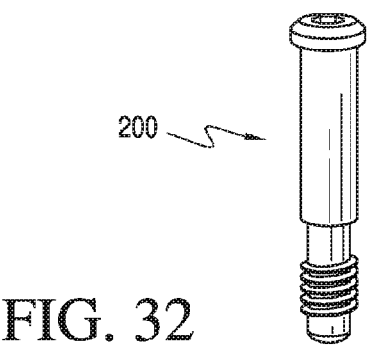
FIG. 32
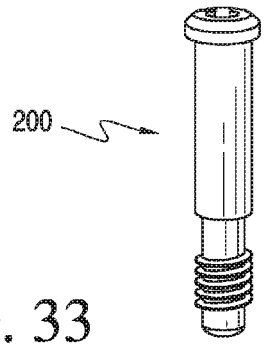
FIG. 33
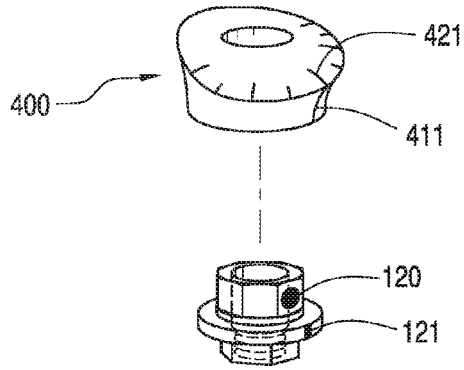
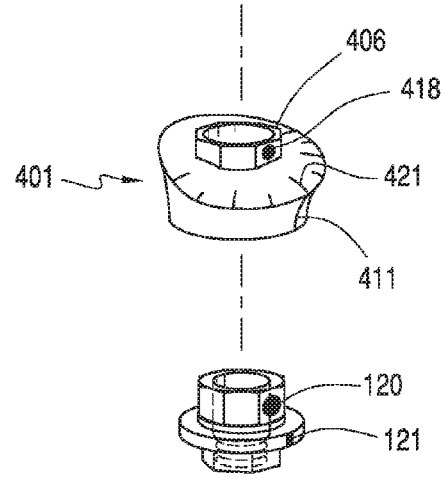
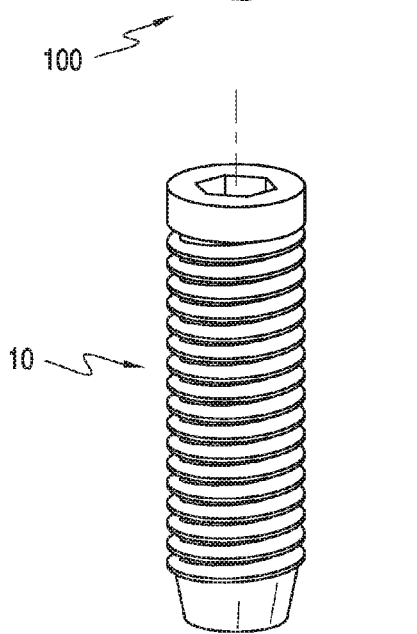
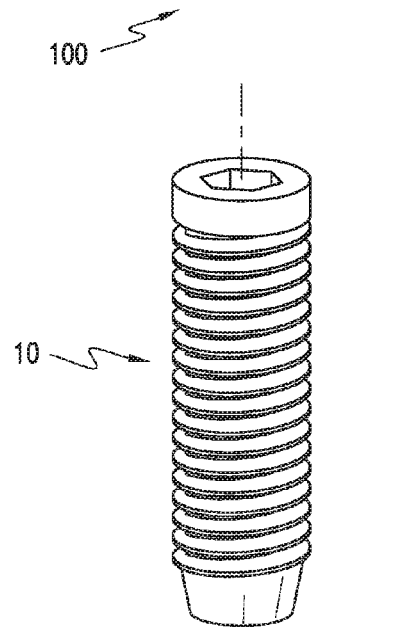

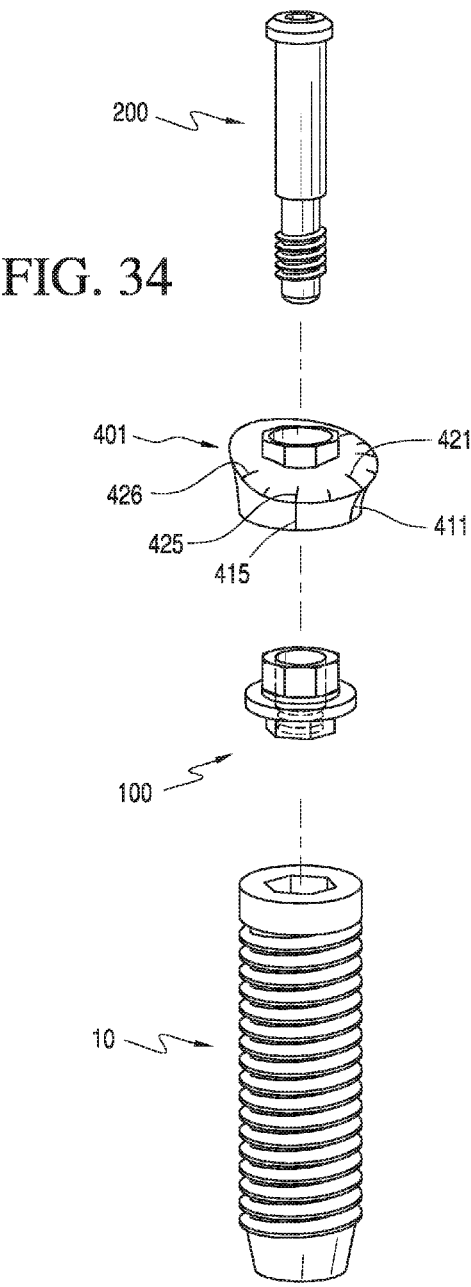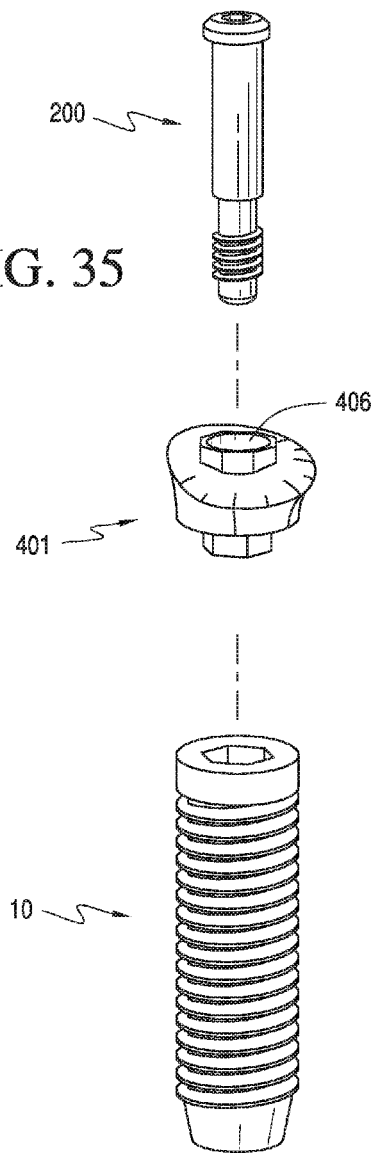

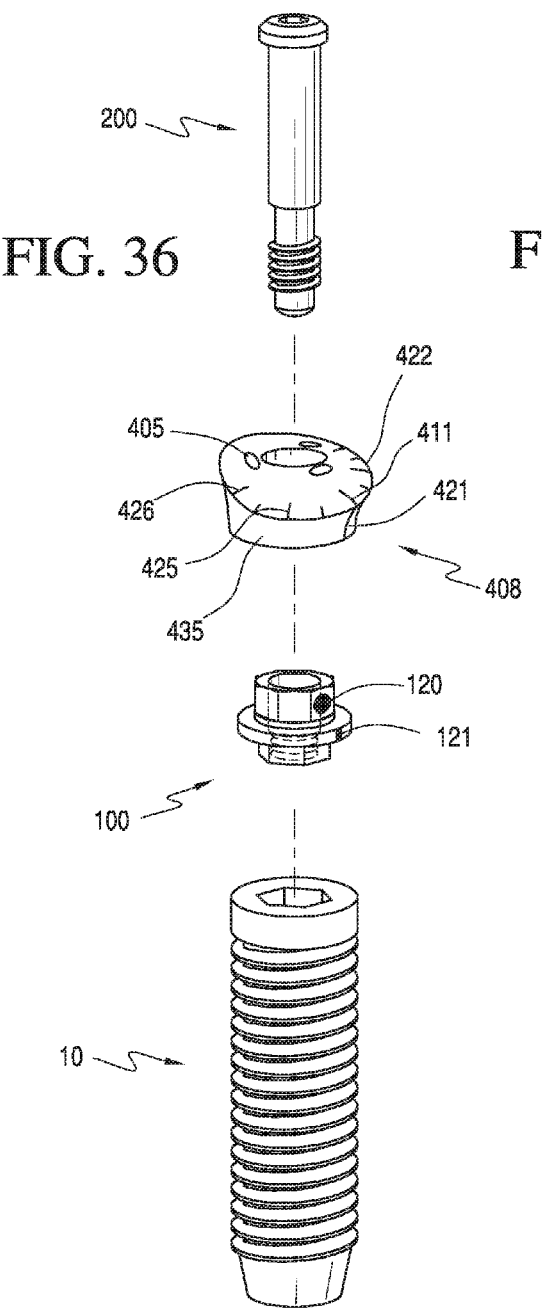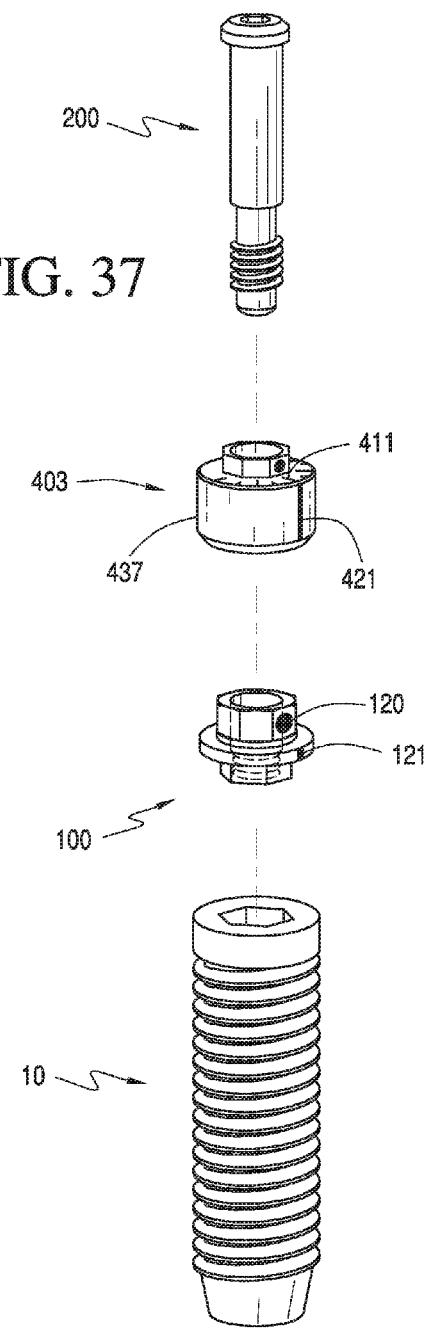

FIG. 38
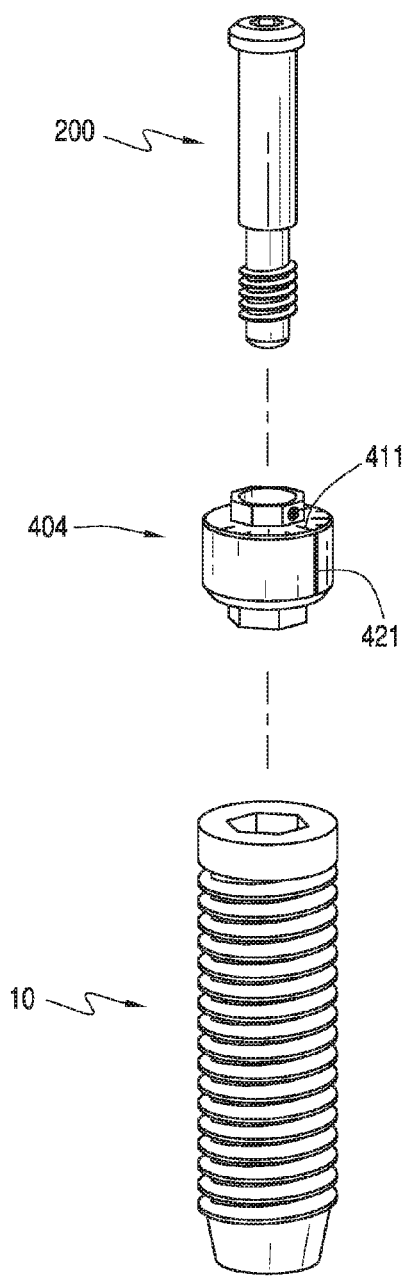
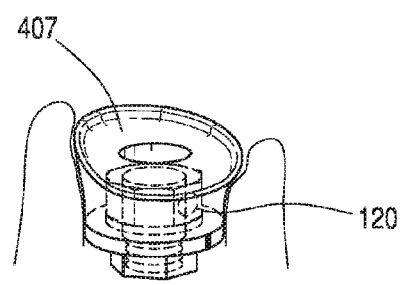
FIG. 39A
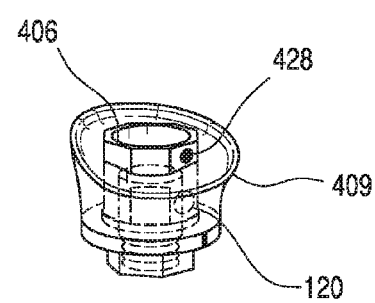
FIG. 39B

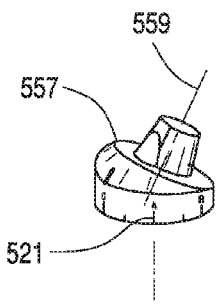
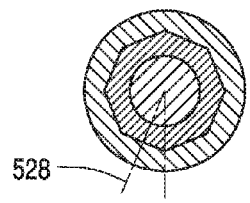
FIG. 58B
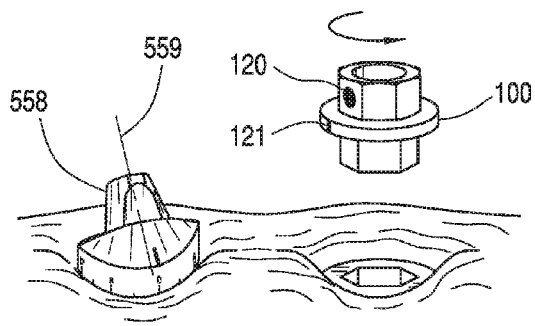
FIG. 58A
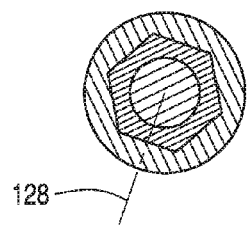
FIG. 58C
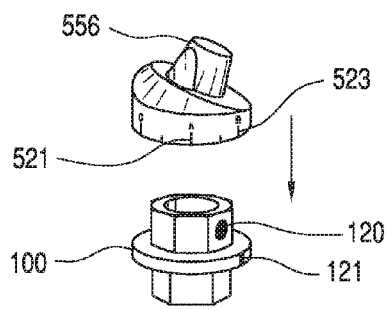
FIG. 59

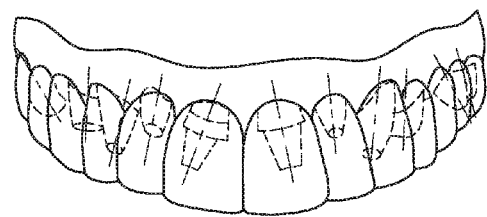
FIG. 62
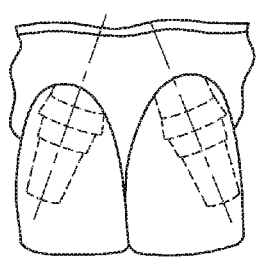 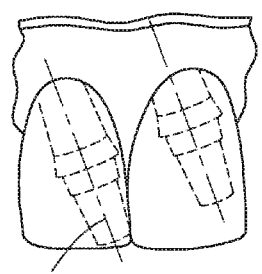 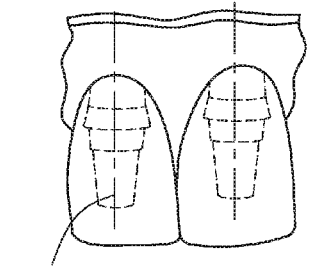
FIG. 63　　　FIG. 64　　　FIG. 65
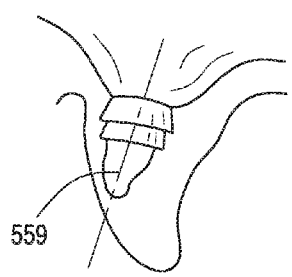 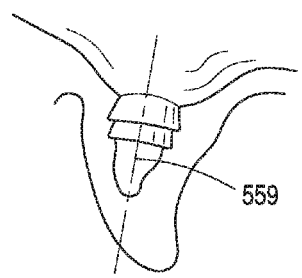
FIG. 66　　　FIG. 67

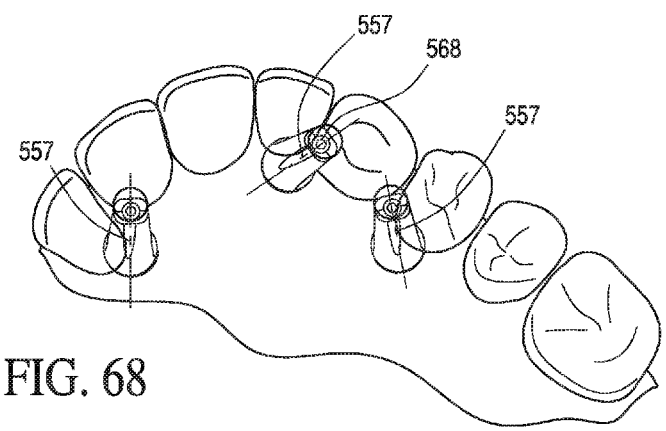
FIG. 68
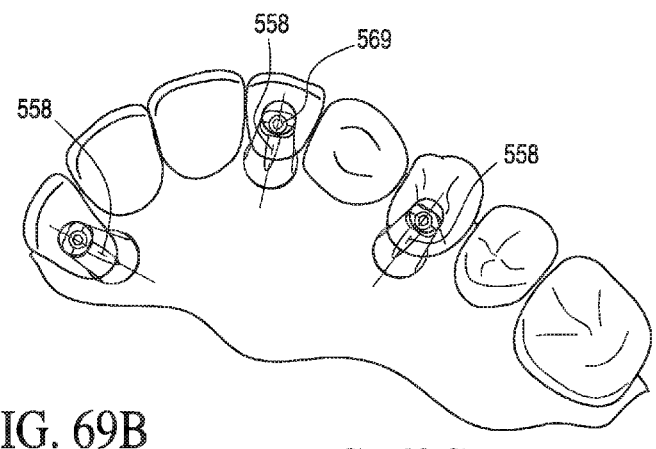
FIG. 69C
FIG. 69A
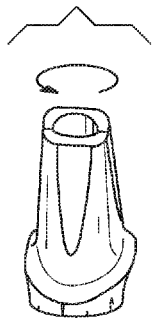
FIG. 69B
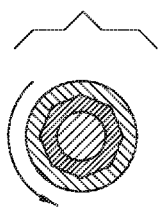
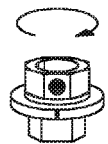
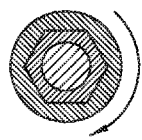

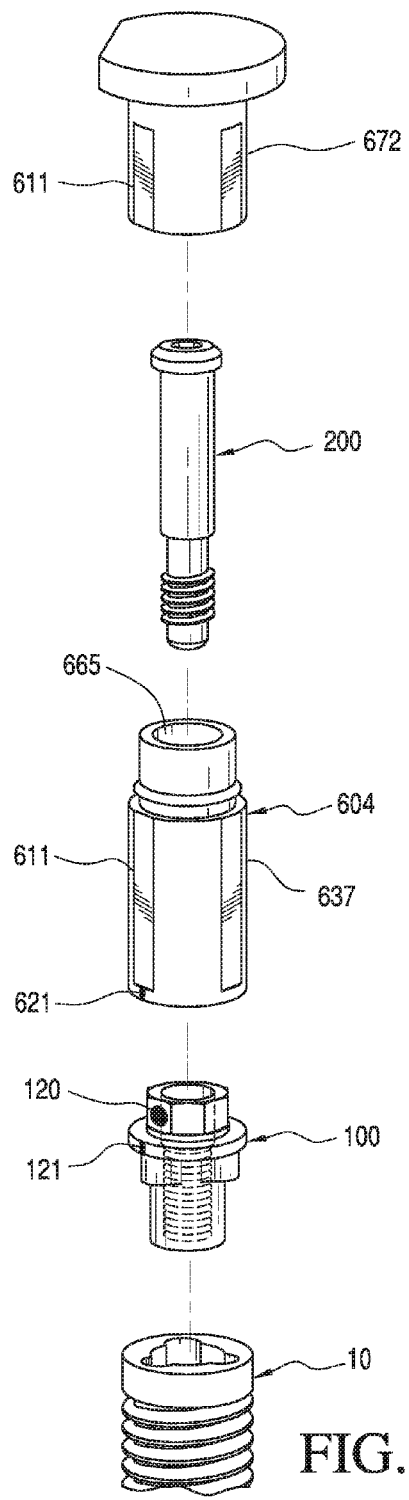
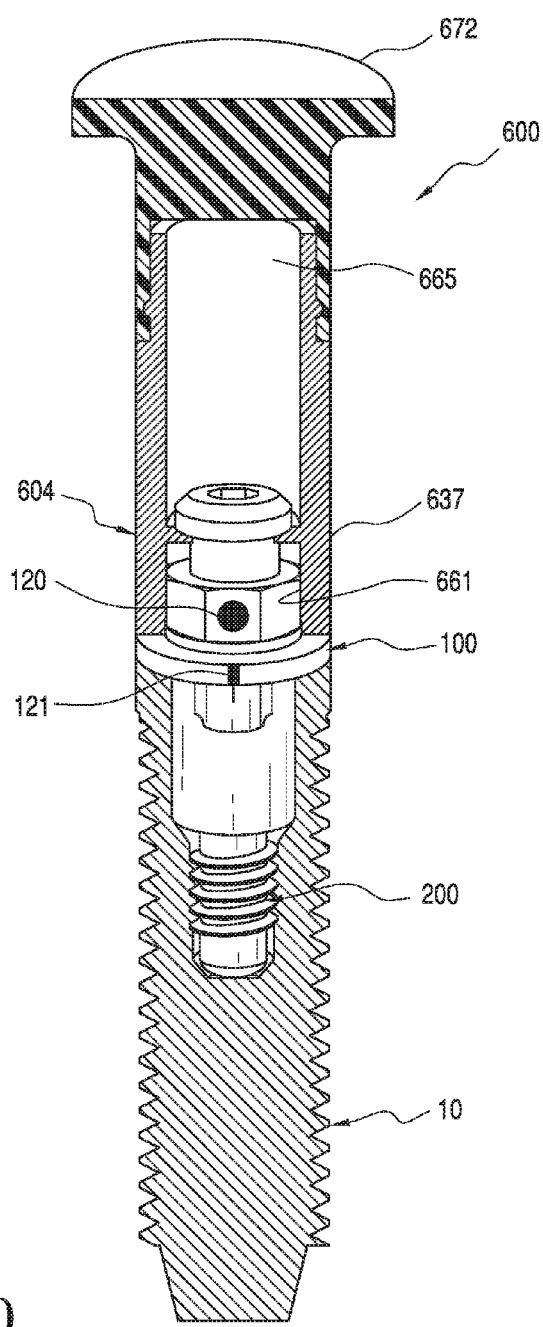
FIG. 70
FIG. 71

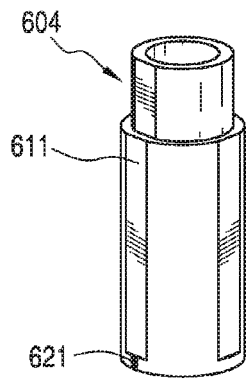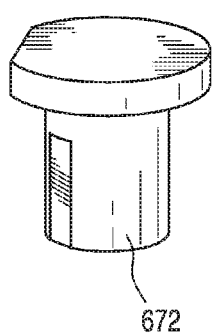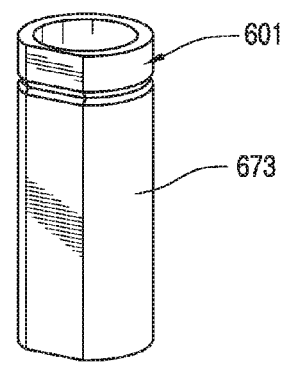
FIG. 72　　　FIG. 73　　　FIG. 74
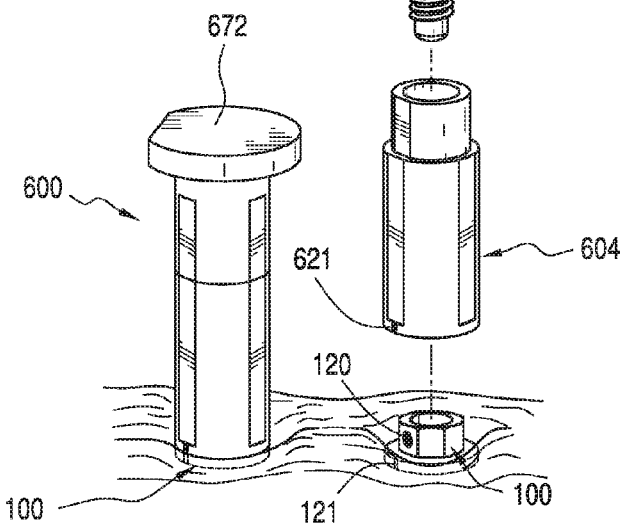
FIG. 75

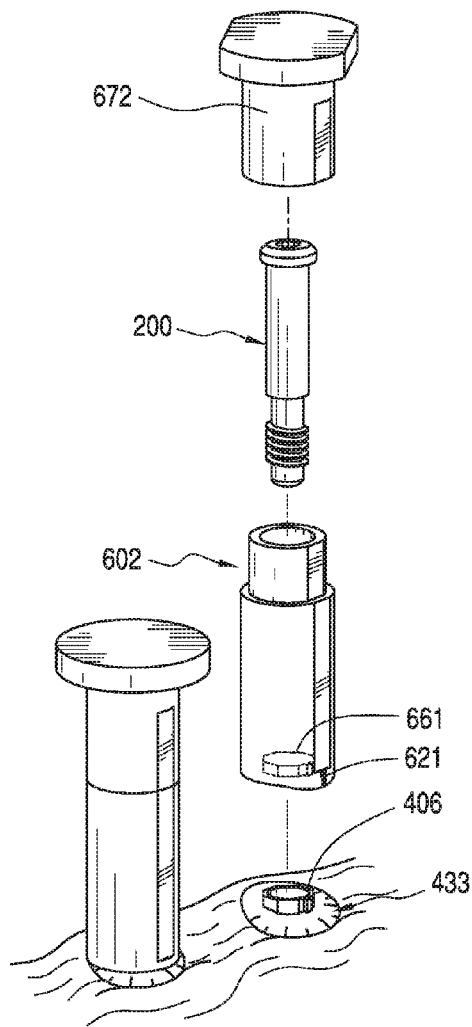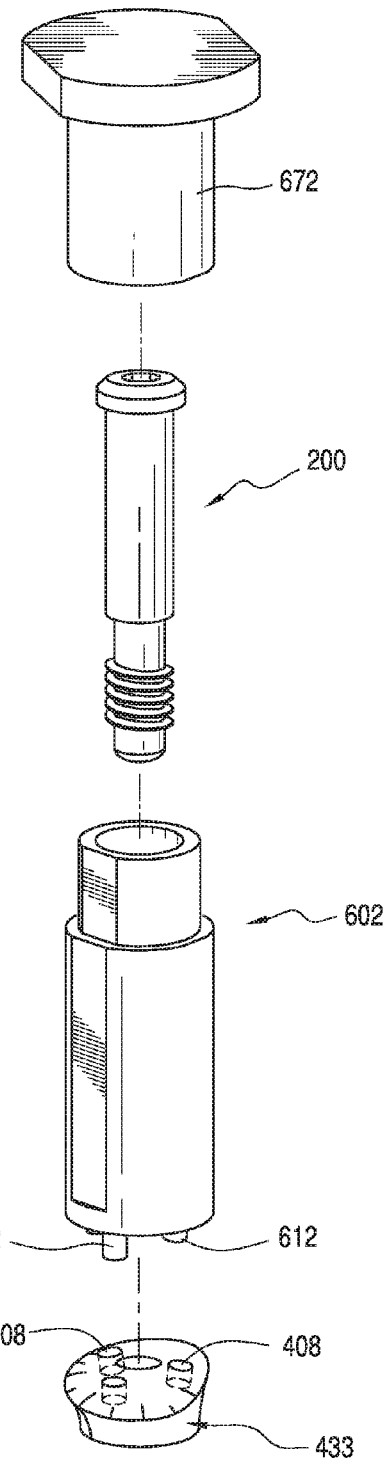
FIG. 76
FIG. 77

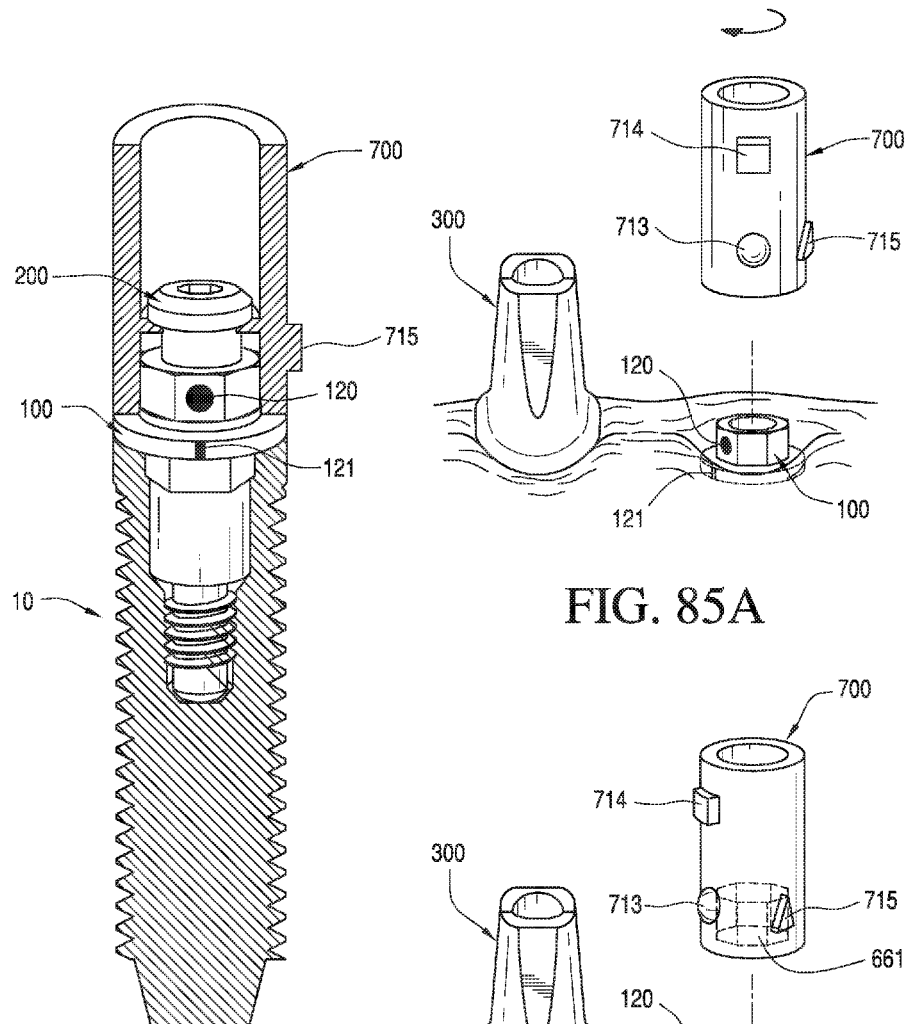

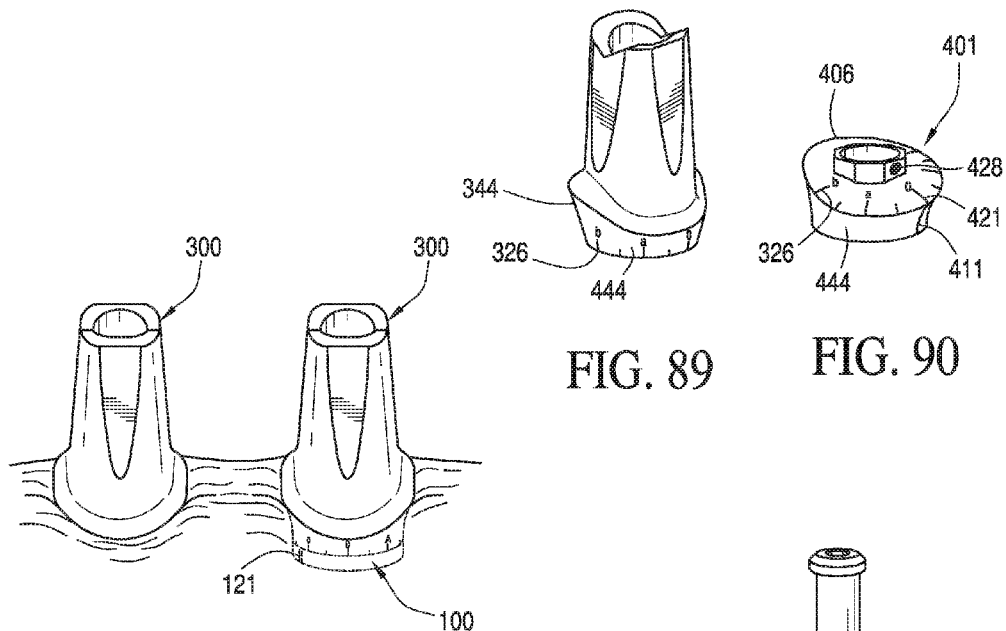
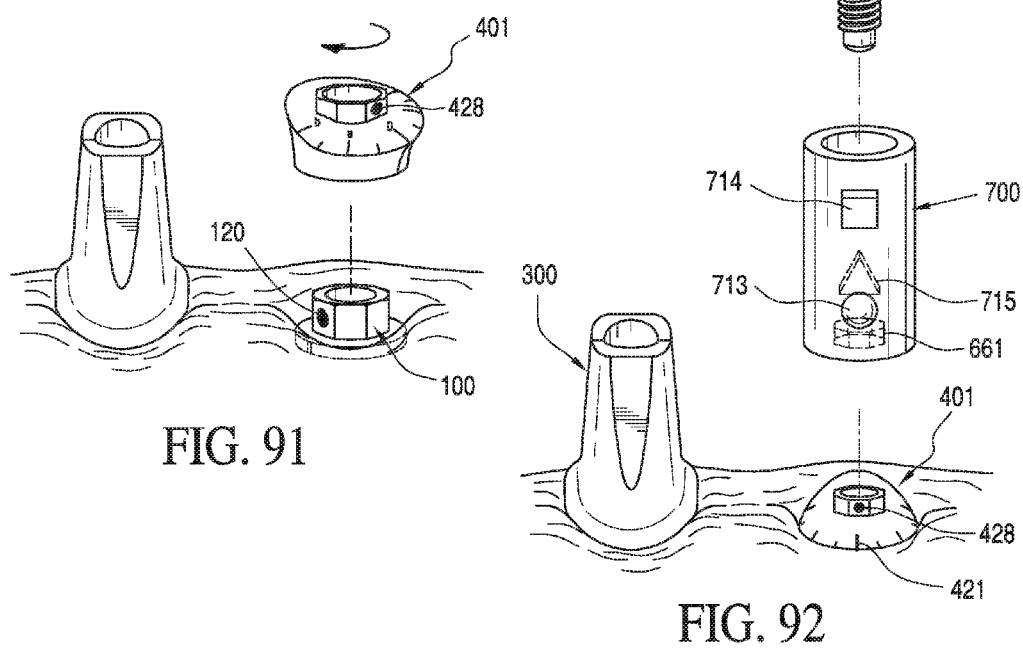
FIG. 88 FIG. 89 FIG. 90 FIG. 91 FIG. 92

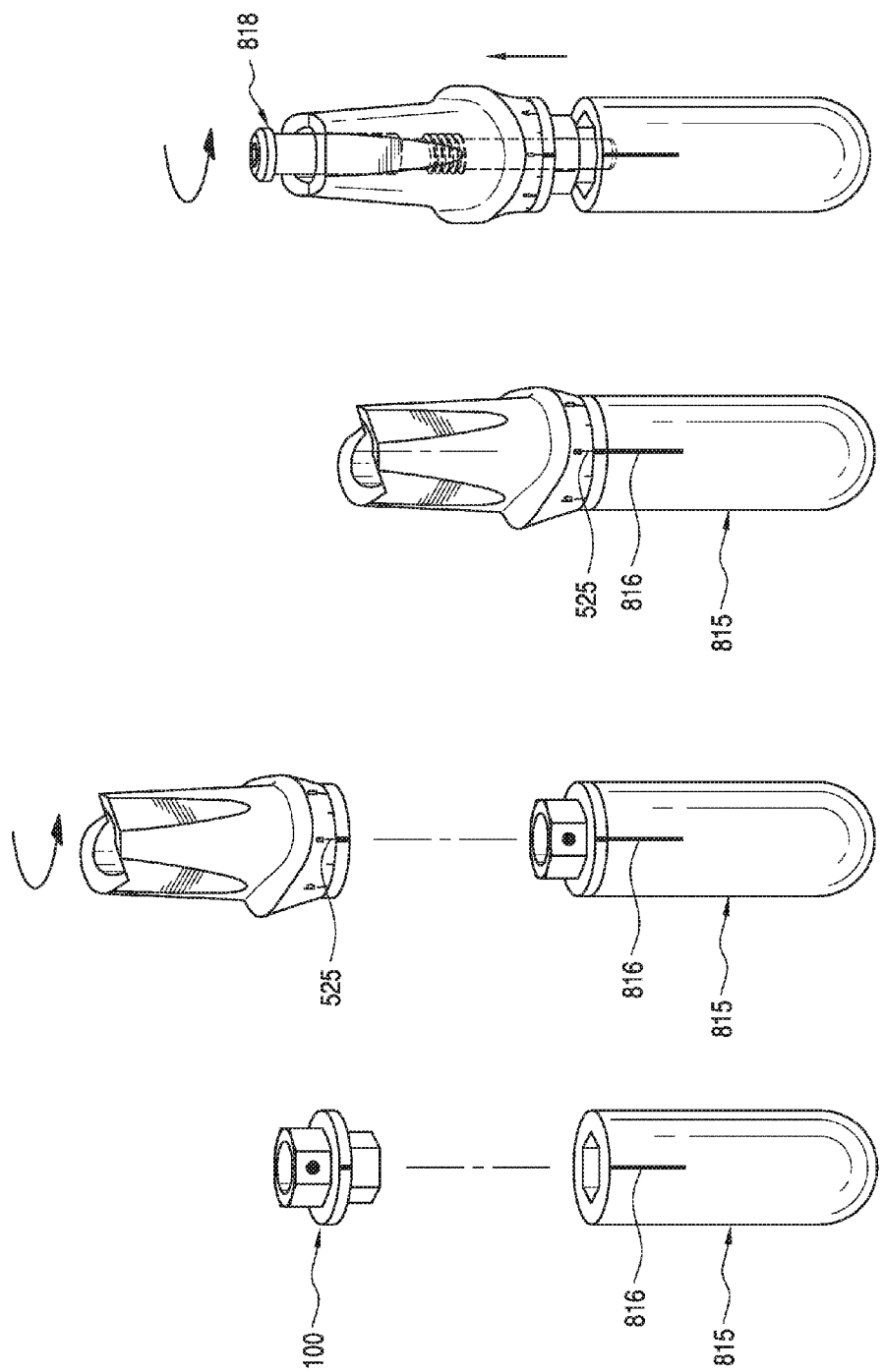

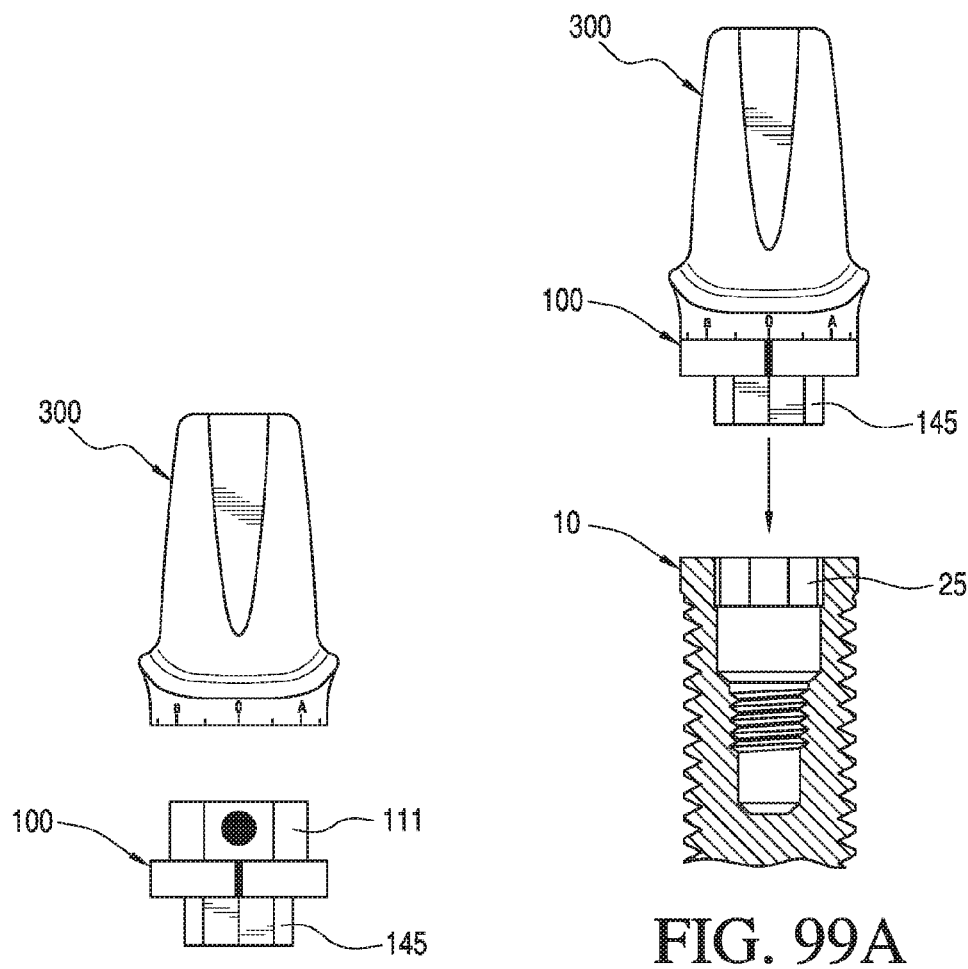
FIG. 98
FIG. 99A
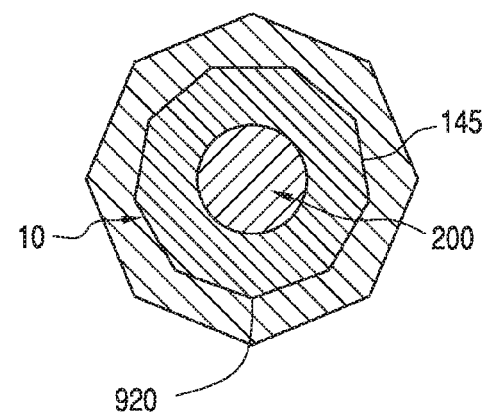
FIG. 99B

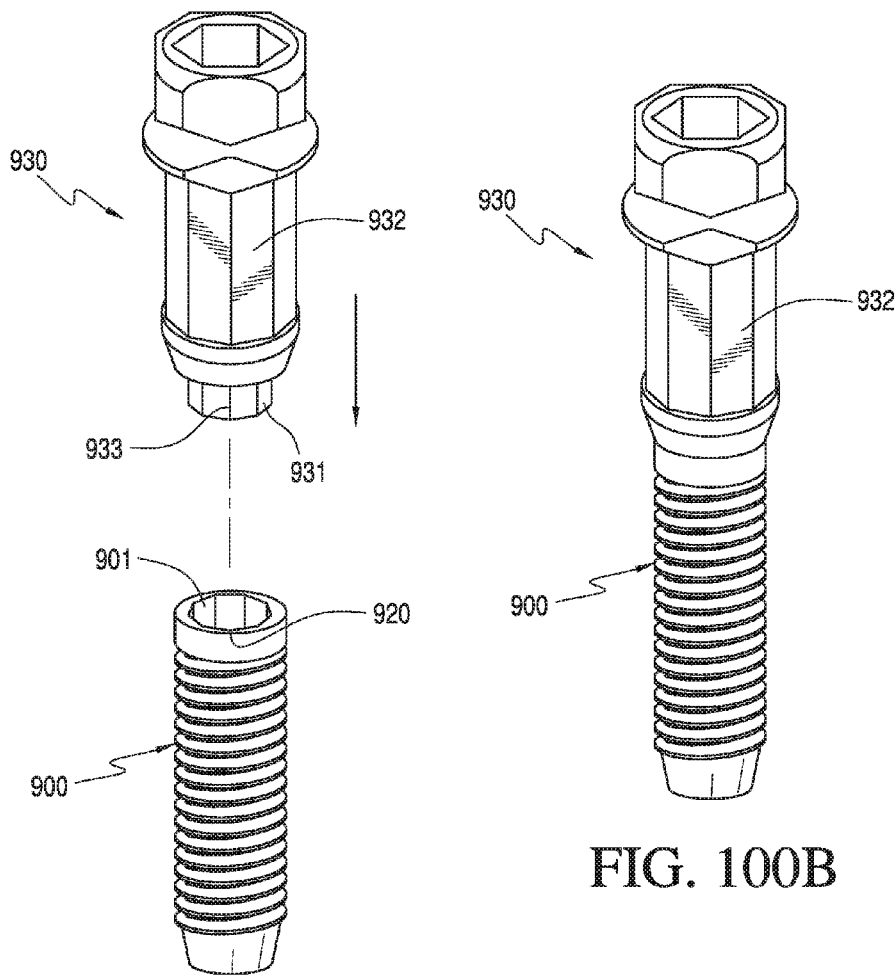
FIG. 100A
FIG. 100B
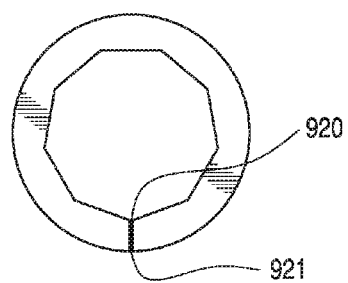
FIG. 100C

UNIVERSAL ALIGNING ADAPTOR SYSTEM AND METHODS

CROSS-REFERENCE TO RELATED APPLICATIONS/INCORPORATION BY REFERENCE

This application is a continuation of U.S. patent application Ser. No. 14/085,286, filed Nov. 20, 2013, which claims the benefit of U.S. Provisional Patent Application No. 61/796,837, filed Nov. 20, 2012. The contents of each of these applications are expressly incorporated herein by reference in their entireties.

FIELD OF THE INVENTION

This application relates to restoration of implant fixtures including systems, components and methods for their restoration.

THE TECHNOLOGY

The present application discloses, through a plurality of device and method innovations, a Universal Aligning Adaptor System and novel developments in implant restorative dentistry. The present application further establishes unique methods for coordinated physical and/or virtual alignment, referencing and synchronization of prosthetic dental devices across all stages of the restorative process, from surgical planning to dental prosthesis fabrication. Through a revolutionary structure of relational geometry, the present application affords a quantifiable associative linkage of prosthetic dental devices to an underlying implant and to each other, such that the prosthetic dental devices can be positioned and situated to a high degree of aesthetic and clinical satisfaction using an automated and/or interactive clinical and/or digital protocol.

Implant misalignment can result from inherent perturbations in the process of drilling osteotomy sites and the subsequent surgical insertion of the implant fixtures into the bone. This misalignment can now be overcome via the present application's innovations, including, but not limited to, the use of a plurality of predetermined horizontal rotational reference points. These reference points include an index for the demarcation of the specific angular relationships between an implant and its restorative elements. These reference points can be used alone or in combination with Universal Aligning Adaptors to couple the indices of co-operable, referencing, interim and/or final prosthetic dental components for interconnection with each other in relation to the underlying implant index to obtain a registration of the realigned mutual geometry of the componentry referenced to the implant. Accordingly, the application allows for a precise aesthetic and clinically ideal alignment and positioning of the final dental prosthesis via synchronization of the indices.

The present application provides significant improvements over conventional approaches, including those established in, and covered under, this inventor's previous devices and methods, "Implant Collar and Post System" U.S. Pat. Nos. 5,195,395; 5,238,405; and 5,350,302; and "Method of Forming an Abutment Post" U.S. Pat. Nos. 5,439,380 and 5,564,921. In particular, the linkage and use of the indices provides a coordinating structure to facilitate the alignment and situation of prosthetic dental devices over the jaw in a precise, repeatable and clinically ideal manner. The present application obviates the need for a collar-type device requiring "fit-and-test" horizontal rotations for dental prosthesis alignment, that process being subject to the limitations of practitioner accuracy and expertise. As such, the present application is designed to eliminate practitioner error when, for example, either impressions or intraoral, bench, CT, or other imaging/sensing scans are taken and models are made and/or digital data is collated, as the restorative componentry can only be connected and inserted in a set manner as dictated by the alignment, referencing and synchronization mechanism afforded by the indices.

This application relates to the prosthodontic restoration of previously placed dental implant fixtures that have been surgically implanted in the edentulous area(s) of the alveolar bone, and are ready for restoration with a crown, set of crowns, or a bridge or any type of screw borne prosthesis using one or more universal aligning adaptors, prosthetic components with co-operable indices, and a predetermined clinical and/or digital protocol. The universal aligning adaptor system aligns and synchronizes all prosthodontic restoration componentry. Thus, using referencing devices that include an array of impression posts, intraoral or bench scanning posts, or CT scan posts one can register the newly established, preferred position and/or gingival architecture of an abutment and/or the preferred screw access hole locations for the fabrication of one of the prostheses listed above.

BACKGROUND OF THE INVENTION

"Surgical error" is inherent to the drilling of the osteotomy sites and the subsequent insertion of the implant fixtures, and, more often than not, results in implants being placed at a less than an ideal vertical angle or horizontal position. Some of the causes of the vertical angulation/position issue include tilting a hand piece by even just a few degrees, which can result in the head of the implant being misdirected several or more millimeters away from its intended position; drilling osteotomy sites without using a surgical guide, which can result in random implant fixture placement; and compensating for existing natural bony undercuts by angling the drill during site preparation. Any one of these errors can dramatically alter the implant's position away from its intended ideal location.

However, while vertical angulation can be an impediment to easy fabrication of implant abutments and/or prostheses with natural anatomic form, the most insidious and compounding problem is the misalignment of the implants' indexes. This misalignment results from arbitrary insertion of the implants by a surgeon, as the surgeon's first priority is properly securing the implants to the bone. In securing an implant to the bone, the surgeon is solely concerned with either sufficiently tightening the implant without over-tightening and thereby potentially stripping the bone during the tightening procedure, or with placing the implant at the crest of bone or below it as a first priority. An implant that has been over-tightened or under-tightened is at risk of failure. Because proper securement of the implant is the primary, if not only, consideration of the surgeon, the surgeon cannot guarantee that the implants' indexes are situated so that their axes bisect the ridge in the sagittal plane at their center points. In fact, this frequent misalignment of the indexes magnifies vertical angle and positional issues, especially as the number of sides of the implant index decrease, which severely limits the rotational options to increasingly coarse increments. For example, a dodecagon with twelve sides has a 30° rotation, an octagon with eight sides exhibits a 45° rotation, a hexagon with six sides turns with a 60° rotation, and a tripod with three sides has a 120° rotation which, at a minimum, requires altered six sided abutments just to achieve a 60° rotation (see FIGS. 13-23).

To varying degrees, even experienced practitioners can find it challenging to fabricate restorations that are not too bulky or that have access holes in locations that are not too difficult to manipulate (see FIGS. 62-69C). As a result of these issues, implant companies have gone to great lengths to compensate for these "off-angle" implants with abutment and prosthesis products that by-pass these misaligned indexes, have anatomic forms that have to be cast or milled from the bottom up to compensate for the misalignment; or have connecting cylinders that lack anti-rotation features to avoid parallelism issues, to name just a few.

The universal system of the present application resolves these angulation/misalignment problems for all implants by rotating the abutments and/or prosthetic components in 15° increments or less, regardless of whether the implant's index is a dodecagon (23), octagon (24), hexagon (22), nonagon (25), quadragon (not shown) or even a trichannel (21) (see FIGS. 13-23). As shown in FIGS. 2 and 3, the implant's index (15) comprises an internal mating surface which is intended to pair with an external mating surface of the corresponding index of the adaptor.

In certain embodiments, the abutment/adaptor assembly achieves an optimal positioning within a maximal 7.5° deviation from the ideal direction when rotating in 15° increments. Along with this repositioning capability, the universal system can realign the implant indexes such that the abutments, healing caps, impression posts, scanning posts, and screw access holes are situated and aligned by the newly reestablished relationship of the primary and secondary indicia of the universal aligning adaptor and its prosthetic components having co-operable indices.

The innovative devices and methods to be used in conjunction with the universal aligning adaptor to realign, situate, and standardize abutment placement; to synchronize all prosthetic components, and to reference them is described below.

SUMMARY OF THE PRESENT INVENTIONS

Overview

The Universal System dramatically redefines the way dental implants are restored. It provides a unique combination of universal aligning adaptors and prosthetic componentry having co-operable indices with a universal preconfigured clinical and/or digital protocol to align, synchronize, and reference these components around the implant's central axis of rotation, which eliminates the outsized negative influence that implant index misalignment has had on implant restoration up until now. Prosthetic components, devices and prostheses no longer have less than ideal emergence profiles and positions, and those that are screw retained are no longer encumbered with screw access holes exiting in awkward locations. When the prosthetic components' co-operable indices include primary and secondary indicia, they are rotatable about their individual adaptors to position them in preferred vertical and horizontal predetermined positions, and they are then synchronized to the primary indicia of the adaptors in their new positions. Once aligned and synchronized, they are easily registered by impression, intraoral or bench scan or cone beam CT scan (CBCT) posts and techniques, which are situated in relation to the primary indicia of the adaptors, and, thereby, allows for the systematic fabrication of prosthetic devices and prostheses, regardless of any particular implant's index configuration or misalignment. The Universal System has been developed to serve every skill level of practitioner, every member of the implant team, every circumstance, and every type of implant restoration that is seated on any implant, regardless of the index configuration or misalignment. The Universal Aligning Adaptor system can be used with either a two stage insertion/restoration process or with a single stage, immediate load procedure.

The innovations described in this application and summarized below (the Universal Aligning Adaptor System, the Universal Contour Abutment System, the Universal Multifunction Abutment System, the Universal Impression, 3D Imaging and Milling System, Method of Aligning, Synchronizing, Referencing and Forming a Set of Universal Abutments, and Method of Aligning, Synchronizing, 3D Imaging, and Milling Prosthetic Components and Devices) comprise a complete system for restoring any previously placed dental implant fixtures, which is referred to as the Universal System. The Universal Aligning Implant System provides an ideal implant index for inserting implants in a predictable, consistent manner or for making precise horizontal angle corrections, in 5° increments when necessary.

The Central Axis of Rotation and the Primary Indicium

Irrespective of the available multitude of applied dental devices and techniques, the discipline of implant restorative dentistry has a common goal: produce an aesthetically pleasing restoration by situating prosthetic dental componentry within the mouth in a clinically ideal manner. Ironically, a major challenge to achieving a successful outcome arises from one of the very first steps in the restorative process, specifically, anchoring the underlying implant device to the jaw. When surgically inserted, the positioning of the implant screw is subject to a number of complicating factors, including, but not limited to: physiology of the anchoring bone structures, precision of the surgical guides and templates, and accuracy and skill of the practitioner. The result is that the central axis of the implant, the line of reference extending along the body of the implant device, from the screw point outwards through the implant head at the jaw surface, is almost never coincident with the desired central axis of rotation, the target line of reference established by the coaxial configuration of the planned topmost prosthetic component as it is situated over the implant's ideal device location. As such, a clinically ideal restoration can only be achieved by employing a coordinated system to correct such inherent misalignment, in effect transforming the otherwise immutable central axis of the implant into a workable central axis of rotation. To wit, when an underlying implant is misaligned such that an abutment engaging the implant is not coincident with the desired central axis of rotation, there now exists a unique two- or three-space rotational transformation enabling mechanical or virtual repositioning of the abutment to allow it to become so aligned. This transformation is established by a universal referencing device, comprised of a universal aligning adaptor having a primary indicium reference point and an overlaying prosthetic insert having co-operable primary and secondary indicia. The predetermined rotation of the adaptor about the prosthetic insert via the re-established central axis of rotation situates the insert in a generally desired horizontal and vertical position, thus identifying the alignment and synchronization points for all other co-operable componentry. The location of the adaptor's primary indicium in relation to the implant's index is the reference point for registering the necessary transformation, which, in turn, determines the seating of the interim preferred abutment or healing cap, prior to fabricating final prosthetic components and/or devices with the same alignment by an automated and/or interactive clinical and/or digital protocol.

The registration of the location of the primary indicium of the adaptor by an impression, a scan, or both identifies the desired central axis of rotation for the fabrication of a custom cast or pressable abutment or a milled abutment, or any other abutment fabricated by any means.

When an abutment is created from a digital file after the repositioning of the clinical abutment, the data for this desired central axis of rotation is translated to a software program's device methods and controls to perform an automated virtual realignment of the corresponding virtual abutment in the program prior to milling the actual abutment. As such, when the implant's index alignment is captured by an intraoral or bench scan or CBCT scan taken directly on the implant, the rotation of the adaptor and the referencing device can be performed in the software program according to the automated and/or interactive digital protocol, which establishes the preferred position.

Since the scan post is seated in relation to the primary indicium of the adaptor, wherein the co-operable indices include primary and secondary indicia such that the primary indicium of the adaptor is rotatable in relation to the primary and secondary indicia of any prosthetic insert, it thus provides a predictable, reproducible intraoral, bench, CBCT (or other tomographic) scan. When taking a CBCT scan of the scan post in relation to the hard structures of the jaw (including bone, teeth, and implants), its location is defined in absolute, three dimensional terms, as directed by the unique design of the scan post, in combination with the universal automated and/or interactive clinical and digital protocol.

Both the intraoral or bench scan and the CBCT scan posts can have identical primary and secondary indicia, which have been set in relation to the primary indicium reference point of the adaptor. Final prosthetic devices can be fabricated from an intraoral, bench, or CBCT scan, but their images can also be merged by overlaying their respective primary indicia. The data for the implant position, the contour and angulation of the bone, and the gingival contours are now incorporated into a single image, along with the position, geometry, and angulation of the ideal abutment at that particular implant site. From this point, a final abutment or set of abutments can be fabricated, along with their overlying prosthetic devices in appropriate cases using an automated protocol.

The Universal System provides the automated clinical and/or digital protocol for the fabrication of final abutments, including prostheses with or without impressions having been taken. In one method, this protocol begins with the sculpting of the gingival tissue by the surgeon or restorative dentist, using the universal interim healing cap or interim abutment as a surgical stent as the interim component is inserted so that the tissue conforms to its architecture. Taking this method one step further, when an impression or scan post is seated on an indexed healing cap having the identical gingival architecture as the interim healing cap or abutment, and when the final abutment is developed using that same matching gingival configuration, the process becomes fully automated. Merging the subgingival device configurations data with the surface topography data allows the cast, pressed or milled abutment to be fabricated such that they replicate the ideal emergence profile. From the beginning, the gingiva has been effectively molded to the architecture of the abutment, rather than the abutment being molded to accommodate the gingiva after it has been fabricated, which can be quite time consuming and less accurate.

Furthermore, if the restorative process is accomplished via the combination of an intraoral scan and a CBCT scan without any impression having been taken, the abutments and their overlaying copings and/or frameworks can be simultaneously fabricated, since the positions of co-operable components are absolute as determined by the CBCT scan, thus the universal clinical and digital protocol is fully automated.

The restorative process begins with the surgeon or restorative dentist first rotating the interim healing cap or interim abutment having a base with any preferred subgingival architecture to an ideal position and sculpting the tissue over the implant until the interim device is fully seated. Once the tissue has molded to the interim device, in a preferred embodiment, it is removed and a matching indexed healing cap is inserted in the same position with the scan post seated on the indexed healing cap in relation to the primary indicium of the adaptor. The scan post can also be seated directly on the adaptor such that their primary indicia are coincident (without an interfacing indexed healing cap). In either example, the intraoral or bench scan and/or the CBCT scan are taken and, if their images are to be taken together, their images can be merged via their primary and secondary indicia, such that these reference points overlay one other. The merged data now incorporates the following: the absolute position of the preferred abutment relative to the hard structures of the jaw (bone, teeth and implants); either the configuration of the healing cap or interim abutment, since it is an identified part from a library of healing caps or interim abutments, or the scan of the healing cap developed sulcus; and the surface topography around that implant. This data can then be input via the Universal Scan Code into the milling devices codes of the milling software program and the virtual abutment can then be auto-rotated in the program into the previously established, preferred clinical position of the healing cap or interim abutment, which, in turn, has been set according to the location of the primary indicium of the adaptor (position a, b, c, etc.). The configuration of the preformed gingival base used in the interim healing cap or interim abutment can then be incorporated into the data for the abutment (for example a particular maxillary central incisor). Since all of the components are linked via the primary indicium of the adaptor, the final abutments and copings and overlaying prosthesis can be fabricated. The same principals apply when fabricating a castable or pressable abutment in the laboratory. The technician merely uses the castable or pressable gingival base having the same configuration as the interim one, and, therefore, he does not have to make any adjustments to the gingival contours.

The Practical Application of the Technology

When the implants are ready for restoration, Universal Aligning Adaptors with mating indexes for their respective implants can be connected to a Universal Contour or Universal Multifunction Abutment. The Universal Aligning Adaptors can be rotated to ideal positions according to a set of primary and/or secondary indicia that define the rotation and its aligning mechanism. The combined adaptor/abutment assemblies can then be rotated as needed and connected to the implants. In another technique, the Universal Aligning Adaptor can be first rotated to a predetermined, ideal position on the implant, with the abutment then being seated to its ideal position. Once the newly established position is registered, one of the overlying restorations is created, which, in turn, is seated on the adaptor/abutment assemblies. The process can be completed either clinically with physical components or virtually within a software program. The components and methods for registering and creating the aligned and synchronized prosthetic components, devices and prostheses are covered, in detail in the Universal Impression, 3D Imaging, and Milling System, Method of Aligning, Synchronizing, Referencing and Forming a Set of Universal Abutments, and Method of Aligning, Synchronizing, 3D Imaging, and Milling Prosthetic Components and Devices sections of this application. The specific prostheses that are directly connected to the adaptor are covered in the Universal Contour Abutment System and the Universal Multifunction Abutment System sections of this application. Cast, pressable, and milled abutments of the universal system can also be fabricated such that they are directly connected to the implant without any adaptor, after the preferred positions of the abutments have been established, synchronized, and referenced as described below.

The Universal Aligning Adaptor is a translational, integrating device that aligns and synchronizes all componentry seated on its shoulder according to a preconfigured clinical and/or digital protocol wherein the primary indicium on its top end (abutment engaging index on its top surface) is positioned in relation to a primary or secondary indicium of its overlying abutment, regardless of the index or configuration of the underlying implant upon which it is being seated (see FIGS. 25A-F). The aligning or realigning of the primary indicia of the adaptor with the primary and secondary indicia of the abutment, as it is rotated into an ideal position, creates a set of reference planes that synchronize the seating of the abutment and all subsequent componentry in relation to the adaptor's primary indicium, and, thereby, to each other and to the implant's index. As such, no matter what the misalignment of the implant's index, healing caps and abutments can be realigned and situated in their sagittal and coronal planes, drawn along their respective primary indicium lines, and substantially perpendicular to the ridge of the jaw. These reference planes can then be utilized to seat the adaptor/abutment assembly at the indicated point, or at another preferred, predetermined position in relation to it (see FIGS. 24A-I).

The primary indicium of the adaptor and the primary and secondary indicia of its prosthetic components that have co-operable indices can be any type of mark or identifying polyhedron. In certain embodiments, the mark or identifying polyhedron is a protrusion. In other embodiments, the mark or identifying polyhedron is painted or etched onto the surface of the adaptor. In one embodiment, the primary indicium of the adaptor is a sphere or other protruding polyhedron, which, in certain embodiments, may be spring loaded with the primary and secondary indicia of the prosthetic devices having a matching recess at each of its secondary indicia such that the adaptor engages the secondary indium with a "positive feel" to ensure its proper seating during the rotation (see FIGS. 1-2, 9A-10C).

In some embodiments, the predetermined rotation of the adaptor's primary indicium around the prosthetic component's primary and secondary indicia and the adaptor/prosthetic component assembly around the implant defines the alignment of the adaptor and its overlying componentry, wherein these definitive increments of rotation ensure a more exact alignment and establish a reference point in relation to the implant's rotational position for synchronization of all other prosthetic componentry. In certain embodiments, the universal aligning adaptor has a top end stud on its top surface configured to receive a prosthetic component and is comprised of any polygon having "n" equal sides that is dissimilar to the polygon at its bottom surface that engages the implant index, and has a randomly chosen primary indicium on one of the "n" sides. When the adaptor is rotated according to the universal automated and/or interactive clinical and/or digital protocol, the primary indicium on its top end will rotate in finite increments that are 15° or less, when the top end polygon is an octagon and the bottom end polygon engages an implant with either a trichannel, hexagon, dodecagon, or any other index whose "n" sides is a multiple of 3, and will rotate in 10° increments when the polygon at the top end is a nonagon and the one at the bottom end is a quadragon. When the top end polygon of the adaptor is a hexagon and the bottom end polygon is an octagon, its primary indicium will also rotate in the same 15° increments. In either case, this translates to a rotation of an abutment or healing cap or other prosthetic component, device, or prosthesis around the implant with a maximal 7.5° deviation from the ideal direction, being at most ½ turn between rotational increments, such that any further turn is nothing more than a mirror image rotation of the previous one. With this dramatic reduction in rotation to 15° increments for a trichannel (vs. 120° rotation), hexagon (vs. 60° rotation), dodecagon (vs. 30° rotation), or octagon (vs. 45° rotation), or with the reduction in rotation to 10° increments for a quadragon (when the abutment engaging index is a nonagon) vs. (90° rotation), any of these implants having their indexes misaligned during placement by the surgeon can be more effectively restored by precisely positioning the appropriate vertical angle correcting abutment such that the abutment's, prosthetic device's, or prosthesis's proper emergence profile and anatomic form are ideally situated, and/or have a screw access channel that is relocated closer to the central axis of the replacement tooth used to restore that implant than is presently available. In addition, it opens the door for including anterior screw down crowns because of the precisely positioned lingual crown fixation screw. Furthermore, with the primary indicium of the adaptor being rotated in relation to a primary or secondary indicium of the overlying abutment as described above, the rotation can be predetermined and automated.

The universal automated, interactive clinical and/or digital protocol that is applied to the universal aligning adaptor having prosthetic componentry with co-operable indices can allow for the rotation of the prosthetic components to ideal positions using predetermined reference points to effect the rotation. With this protocol, predetermined primary and secondary referencing rotation points can be provided for an automated rotation of the universal aligning adaptor with varying degrees of rotation. These referencing rotation points are different for each implant having a different index. For example, a predetermined counter clockwise rotation of the adaptor to a predetermined position "a" around the abutment for the hexagon indexed implant, will result in a needed 15° horizontal rotation of the abutment to a preferred position after the adaptor/abutment assembly is subsequently rotated such that the abutment's primary indicium is substantially perpendicular to the ridge of the jaw at that preferred position (see Tables 1-5, infra). However, in order to achieve the rotation of the adaptor around the abutment and the adaptor/abutment assembly around the implant for a trichannel indexed implant, the predetermined rotation position of the adaptor around the abutment is a clockwise rotation to position "B," a second rotation stop, which will result in the abutment being situated in the preferred position after the rotation of the abutment/adaptor assembly. The universal automated clinical and digital protocol has sets of rotation points for creating predetermined horizontal rotations that are specific for each different implant index. These rotations are achieved either clinically, digitally within a software program, or on a working model.

Incorporating the scan code and the milling device codes of the universal automated and/or interactive clinical and digital protocol into any software program for milling abutments and/or prostheses ideally situates virtual abutments prior to milling them, which improves their anatomic form. When "dialing in" the primary indicium reference point in relation to the primary or secondary indicium of the abutment, the virtual abutment can be automatically rotated into position. In certain embodiments, the virtual abutment can be directly rotated to negotiate the preferred position or can be used to adjust the auto rotated virtual abutment's position. Of course, the rotation of the virtual or the preformed abutment is contingent on translating the interim abutment's or healing caps' position as it is referenced by using the above protocol, or, via the interactive aspect of the protocol, the technician can modify the rotation into a more preferred location (see FIGS. 10A-11C, 24A-25F).

Once alignment is completed, synchronization of the referencing devices (universal impression posts, intraoral or bench scanning posts and CT scan imaging posts) occurs as they are seated such that their primary or secondary indicia are situated in relation to the same primary indicium of the adaptor. The devices and methods of registering the location of the primary indicium and the chosen primary or secondary indicia of the abutment or healing cap are covered in detail in the Universal Impression, 3D Imaging, and Milling System, Method of Aligning, Synchronizing, Referencing and Forming a Set of Universal Abutments, and Method of Aligning, Synchronizing, 3D Imaging, and Milling Prosthetic Components and Devices sections of this application.

The universal aligning analog (see FIG. 94) is a translational, synchronizing analog that can be a one piece, double index component that, at its top end, replicates the adaptor's abutment engaging index, configuration, and position, and on its shank has the same polygonal configuration as the bottom end of the adaptor that engages the index of the implant being restored. The shank of the analog can be tapered enough to be removable, but not so much as to affect its immobility when being used in the model. In one embodiment, a cross linking (horizontal) fixation screw can also be used to further secure the analog. The universal aligning analog provides rotation for realignment of an abutment to another preferred position, after a model has been fabricated in order to make an additional horizontal and/or vertical angle correction. In short, it is removable and rotatable, and corrects for implant misalignment. In one embodiment, it provides the exact same 15° increments of rotation as provided by certain embodiments of the adaptor around the abutment and the assembly around the implant. And, therefore, it can mimic the aligning process of the adaptor as outlined in the automated and/or interactive clinical protocol described above. If a milled abutment is to be fabricated to fit on an adaptor or directly to the implant's index, then a scanning post can be inserted on the analog such that its primary indicium overlays that of the analog and a bench scan can be performed. Once the abutment of any type is ready for restoration and the crown has been fabricated, the technician inserts the abutment on an adaptor such that the appropriate secondary indicium is seated over the adaptor's primary indicium that is in the same position established by the analog (for example, position "a" vs. "b").

The universal aligning analog is particularly useful for prepositioning abutments in a CT scan generated model prior to the conversion of a full denture to a screw retained transitional prosthesis after the insertion and immediate load of four or more implants. Abutments can be repositioned by rotating the analog such that its primary indicium is located under one of the primary or secondary indicia of a chosen abutment, which is then relocated to a more ideal situation on the model. The screw access holes are then precisely drilled in the denture in a more centered location. The denture is then seated over the abutments and their adaptors such that they are positioned as they were on the model, which will align them within the previously drilled access holes.

By providing alignment and synchronization of all components, and referencing devices along with the protocol for registering the adaptor position all of which correct for abutment misalignment, the Universal Aligning Adaptor System breaks open the door for extensive innovation in all areas of implant restoration including new advances in intraoral and bench scanning and CBCT scanning. The system can even facilitate the merging of the images obtained from both the intraoral or bench scan and the cone beam CT scan.

As a result of the alignment, synchronization, and referencing possible when using either a physical or a virtual aligning adaptor, the prosthetic component, device, or prosthesis can be ideally positioned. As stated, the universal aligning adaptor is a translational, integrating device that aligns, synchronizes, and references all of the other componentry. All of the examples described below are only just that, examples. They are not introduced as evidence that this is the only embodiment being claimed in each case. In short, in most cases, only one embodiment out of many is being presented to provide an overview of the technology.

The Universal Contour Abutment System

The Universal Contour Abutment System (see FIGS. 27-48) discloses a set of physical or virtual preformed universal contour abutments having asymmetric configurations for restoring implants with a crown, set of crowns, or bridge, which can be rotated around their adaptors followed by their adaptor/assemblies around the implants until their custom gingival contours and/or tooth preparations are ideally situated. It simplifies fabrication of castable and pressable abutments by providing him with a preformed shape to customize, in preference to free hand waxing them. The contour abutment system provides comprehensive tissue engineering that extends from implant exposure until final abutment insertion that begins with the insertion of healing caps and/or interim abutments having the desired gingival contours which initiates tissue training; is followed by registration with impression, scanning, or imaging posts with or without matching gingival contours which are used to register these contours as described above; and final preformed, cast, pressed, or milled abutments with matching gingival contours to replace the interim devices. As stated, when creating milled abutments, virtual abutments can be clinically mechanically rotated or auto rotated in a software program by integrating the universal aligning scan code with the milling device codes and controls of the program as shown in this patent application. The Universal Contour Abutment System also demonstrates a unique set of guided tissue punches that foster precise gingival incision lines over any implant, regardless of its angle or index misalignment. The Universal Contour Abutment System can also have a plurality of abutments with screw threads that are ideally positioned in relation to the abutments' primary indicia for the best esthetics and function when affixing anterior and posterior screw retained crowns of any type to them. For the first time, screw retained crowns with predictably located screw thread channels in ideal positions are available for any implant at any vertical angle with any index alignment.

The Universal Multifunction Abutment System

The Universal Multifunction Abutment System (see FIGS. 49-69C) discloses a set of physical or virtual universal multifunction abutments used for restoring implants with a screw retained hybrid prosthesis, an overdenture prosthesis, a crown, set of crowns, or bridge with or without denture flanges. The Multifunction Abutments can be rotated around adaptors followed by their adaptor/assemblies around the implants until their screw access holes are more in line with the central axis of the replacement teeth seated on the prosthesis, which provides them with improved anatomic form and function. Due to the finite, 15° increments of horizontal rotation and the ability for its vertical angle correcting abutments to, therefore, be close to parallel, this system provides a set of accessory components that interface with a polyhedron on the top end of the multifunction abutment having a flat or other appropriate configuration at its primary indicium site. Therefore, when the primary indicium of the multi-function abutment, which has been ideally positioned so that the screw access hole approximates the center of the occlusal table, receives a cylinder or other polyhedron, it has a positive "seat" while being anti-rotational. Since the receiving polyhedron on the multifunction abutment is also tapered, the anti-rotational polygon of multiple units does not interfere with the seating of several connecting cylinders because of a parallelism issue. With the existing screw retaining devices, the seating of cylinders is a very cumbersome process, since they are designed without any positive seat to avoid parallelism issues and, therefore, pivot when being seated. This system also has a bonding sleeve that can be seated over either the multifunction abutment's cylinder or any cylinder used with any other implant abutment and provides a stronger union between the screw-retained prosthesis and the cylinder as they are connected by an adhesive. The bonding sleeve can also be used during bite registration procedures as a vertical stop and can also prevent wax from entering the screw access hole and contaminating the threads. In addition, it can be a very effective vertical stop when converting a denture to transitional screw retained prosthesis during the immediate load full arch procedure. After the necessary steps are completed, the vertical stop can then be cut flush with the denture. The finite increments of rotation and the bonding sleeve provide a dramatic improvement in technique for the immediate insertion of 4 or more implants and the conversion of the patient's denture to a screw retained transitional prosthesis in a single day procedure. It dramatically cuts down on wasted "chair time", while increasing predictability of achieving the desired results. The multifunction abutments can come as preformed, millable, pressable, and castable versions, the latter three of which can be fabricated with a significant reduction of bulky contours.

The Universal Impression, 3D Imaging, and Milling System

The Universal Impression, 3D Imaging, and Milling System (see FIGS. 70-92) discloses a set of devices for identifying and registering the primary indicium of a universal aligning adaptor, after it has been rotated into a predetermined, preferred position to compensate for index misalignment. All of the registration devices can be used interchangeably over the same adaptor at its primary indicium reference point, since they all share the same internal configuration and indicia which engages the index of the adaptor or an indexed healing cap with the same indexing. The subset of registration devices includes an impression post, an intraoral or bench scanning post, and a CT scan imaging post, all of which have primary and secondary indicia.

The external configuration of the impression post is structured to be easily impressed and seated inside of the resulting impression. In certain embodiments, it can have an external flat overlying the internal flat which, in turn, is over the primary indicium such that it facilitates the seating of the impression post on the adaptor or the universal aligning post inside of it when it is in the impression. As an alternative, the operator may choose to use a registration coping, which has an internal and external primary indicium which guides it into place and provides an absolute seat for the analog as its primary indicium is aligned with that of the registration coping, which prevents operator error. Multiple registration copings can be connected with bonding rods for additional stability.

The external configurations of the intraoral and bench scan post and the CT scan imaging post are designed to facilitate the 3D imaging performed in each case. When possible, the external configurations of the scanning and the CT scan imaging posts are the same so that the images can be merged. In one embodiment, the external configurations have one or more polyhedrons that can be easily identified in the scans/imaging process. The scanning post is composed of a material that can easily be picked up by the scanner, while the scan imaging post is composed of any type of material that will avoid X-ray scatter. The identifying polyhedrons can be enhanced in each version.

Because the scan post for the intraoral or bench scan and the scan post for the CBCT scan are both registering the primary indicium of the universal aligning adaptor, and because their own primary indicia are in identical relative positions, their scan images can be merged. This allows the images of the implant adaptor to soft tissue and the implant adaptor to hard tissue (bone, implant, and teeth) to be combined. As a result, the final abutment and prosthetic devices can be fabricated from these scans. The Universal System can facilitate the milling of abutments and overlying prosthetic devices by including its scan code of the automated and/or interactive clinical and digital protocol scan code into the milling device codes and controls of the milling software program. Specifically, the protocol by either manual rotation or by autorotation realigns a virtual abutment into an ideal position. The prepositioned milled abutment can then be fabricated off of the data from such rotation, thereby reducing the need for additional milling of non-parallel side, which preserves the emergence profile.

The Method of Aligning, Synchronizing, Referencing, and Forming a Set of Universal Abutments The Method of Aligning, Synchronizing, Referencing, and Forming a Set of Universal Abutments discloses multiple methods for restoring implants using the universal aligning adaptor in combination with an automated and/or interactive clinical and/or digital protocol to realign and synchronize abutments into preferred positions utilizing their primary and secondary indicia. The following descriptions summarize the methods that are described. The first technique encompasses a unique indexed healing cap that registers the adaptor/implant indexing, its preformed gingival architecture, and the gingival contours overlying the implant. It has an external or internal index on its top end, which is a replica of the underlying index of the adaptor such that its primary indicium is situated at the center point of the healing cap, when it has been situated in a preferred, predetermined position. In another embodiment, the indexed healing cap is connected to the implant and has an external or internal index, which, in this case, replicates the implant's index. An impression can also be taken directly on a multifunction abutment after it has been rotated into a preferred position such that the primary indicium of the abutment and, therefore, the impression post is in its preferred position. Secondly, a preformed abutment that has a primary indicium at its center point is rotated such that it is aligned when it is ideally situated, synchronized, and referenced to identify and register its preferred position. Third, the methods of using the universal aligning adaptor in combination with preformed healing caps having specific gingival contours at the exposure of the implant for tissue training, which is followed by an impression that registers that geometry, and then a final abutment whose base is a replica of the original healing cap. Fourth, a method of facilitating the immediate load of four or more implants after their insertion, wherein the universal aligning adaptor, in combination with the multifunction abutment, simplifies the process due to the finite increments of rotation that are 15° or less for all implants and the use of the universal aligning analog to compensate for any further horizontal angle correction. Fifth, the method of converting any preexisting abutment to a universal aligning abutment, by adding primary and secondary indicia increments to the abutment, along with an automated and/or interactive clinical and/or digital protocol. Finally, the use of the ideal implant having a primary indicium that is referenced for its restoration and the use of the nonagon implant index within that context that has a specific vertex as its primary indicium.

Method of Aligning, Synchronizing, 3D Imaging, and Milling Prosthetic Components and Devices Method of Aligning, Synchronizing, 3D Imaging, and Milling Prosthetic Components and Devices describes various methods of translating the automated and/or interactive clinical protocol to a digital protocol such that a virtual adaptor can be rotated in a software program by using the scan code of the automated and/or interactive clinical and digital protocol, which is incorporated into the milling device codes and controls of the milling software program. The second method describes the creation of milled abutments for a screw borne prosthesis as the preferred abutments instead of preformed ones. The next method describes the creation of milled abutments as crown and bridge abutments such that they have an ideal anatomic form regardless of the implant's index misalignment, as they are being rotated before being milled. The fourth method shows how the virtual universal aligning adaptor, in combination with the automated and/or interactive clinical and/or digital protocol, can be used in a CT scan software program to create a milled abutment or set of abutments with ideal anatomic form and function, along with a milled coping or framework. The next method discloses how the universal system merges intraoral or bench scan images with those of a CT scan. Finally, the last method demonstrates how to translate the data from a previously rotated, preformed abutment to a virtual milled abutment prior to milling the physical one.

The Universal Aligning, Synchronizing Implant

The Universal Aligning, Synchronizing Implant discloses an implant having an internal or external index with "n" regular sides and a primary indicium reference point from which all of its prosthetic componentry having co-operable indices are synchronized. Its co-operable componentry can also be rotated in combination with an adaptor using an automated and/or interactive clinical and digital protocol to ideally position them in finite increments, when the implant has not been inserted such that its primary indicium is bisecting the ridge of the jaw at a 90° angle where the center point of the projected abutment will be located.

At least one embodiment provides a nonagon implant having an internal or external index that is a regular 9 sided polygon having 9 equal sides and 9 vertexes with 9 lines of symmetry each of which extend from a particular vertex 180° to an opposing side, with only one of the 9 vertexes having a symmetry line that bisects its opposing side, and, therefore, serves as the index's primary indicium reference point for the ideal insertion of the implant and for aligning and synchronizing all prosthetic componentry having co-operable indices.

While each inventions disclosed enhances the universal system, many of them are to be considered on their own merits as stand-alone products, as well, since they can be used on any implant without a universal aligning adaptor. They are not limited to the preferred embodiments presented in these patent applications. While most of the innovations are based upon the universal aligning adaptor described in this patent application, several of them are applicable to any type of adaptor seated on a dental implant or to an implant without an interfacing adaptor, such as the indexed healing cap described above.

BRIEF DESCRIPTION OF THE DRAWINGS

The accompanying drawings, which are incorporated herein and form part of the specification, illustrate the present invention and, together with the description, further serve to explain the principles of the invention and to enable a person skilled in the relevant art(s) to make and use the invention.

FIGS. 1-8 show various aspects of the universal adaptor/abutment assembly.

FIGS. 12A-23 illustrate some of the possible combinations of adaptor and implant indexes to create ideal horizontal rotations.

FIGS. 24A-J show the adaptor/abutment predetermined rotation combinations using their primary and secondary indicia to optimally situate the abutment such that it is within a maximal 7.5° deviation from the ideal position.

FIGS. 25A-F illustrate different embodiments of the universal abutment.

FIGS. 27-31 provide several examples of asymmetric and symmetric contour healing caps and abutments that can be used in combination with universal aligning adaptors so that they are ideally positioned.

FIGS. 32-39B illustrate several configurations of universal healing caps that are rotated into ideal positions to establish tissue training some of which serve as platforms to receive impression and scanning posts.

FIGS. 40-46B disclose paralleling posts in combination with adaptors used for implant site preparation and guided tissue punches that make a precise cut of the implant's overlying gingiva.

FIGS. 58A-61 illustrate the method of realigning a misaligned universal multifunction abutment via the primary indicium of the adaptor and its primary and secondary indicia to center it over the implant.

FIGS. 62-67 show the limits of rotating anterior and posterior vertical angle correcting abutments around misaligned hexagon indexes without realigning and situating abutment center lines using aligning adaptors vs. the results achieved when aligning adaptors are used with the abutments.

FIGS. 68-69C show the compounding effects of restoring misaligned, angled implants around the curve of the arch.

FIGS. 70-83 reveal six methods of taking impressions with the universal impression system.

FIGS. 84-92 reveal universal scanning posts for taking an intraoral or bench scan or CBCT scan of any implant.

FIGS. 97A-D discloses a carrier/aligning tool.

FIGS. 98-102 reveal the nonagon implant which has a nine sided index with a vertex or situating primary indicium, and, which, in combination with a universal aligning adaptor, provides an absolute 5° horizontal rotation of all prosthetic components until they approach the center line.

Figure 3:
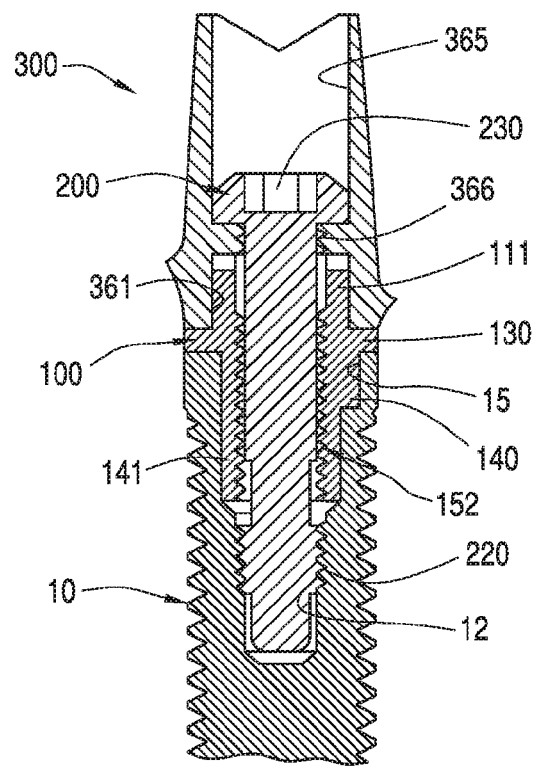

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements.

For convenience, the description numbers have been grouped according to the part to which they are affixed, but have also been organized according to their function. For example, 121 is a primary indicium on the adaptor, whereas the primary indicia on other components also end in 21 (321, abutment; 421, healing cap; 521, multifunction abutment; 621, impression post; 721, scanning post; 921, nonagon implant). The categories are as follows: 10 implant; 100 adaptor; 200 fixation screw; 300 crown and bridge abutment; 400 healing cap; 500 multifunction abutment; 600 impression post; 700 scanning post; 800 auxiliary componentry; and 900 the nonagon implant. The reader can determine from the first digit, which type of component he or she is observing. At the end of this section, the reader will find a complete catalogue of the labels used in these drawings, along with a brief description.

DETAILED DESCRIPTION OF THE DRAWINGS

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

The embodiments described in the following "detailed description of the drawings" covers all aspects of clinical and digital implant restoration, since the prosthetic components are available as mechanical and "virtual" components with the latter utilized in a software program for fabricating final abutments and/or devices. For example a universal aligning adaptor can be used according to an automated and/or interactive clinical and/or digital protocol to be rotated around an implant to a predetermined, preferred position, and the virtual version of the adaptor (a digital adaptor facsimile) can be used in a software program to effect that very same rotation.

It is understood that the section headings used in the present application are merely intended to orient the reader to various aspects of the disclosed Adaptor System. The section headings are not intended to limit the disclosed and claimed inventions. Similarly, the section headings are not intended to suggest that materials, features, aspects, methods, or procedures described in one section do not apply in another section. Therefore, descriptions of materials, features, aspects, methods or procedures described in one section are intended to apply to other sections as it would be understood to those skilled in the art.

I. Rotation, Alignment, and Synchronization

FIGS. 1-3 illustrate one embodiment of a universal aligning adaptor/abutment assembly for use with restoring dental implants with crowns, such as with the Universal Contour Abutment System and Method of Aligning, Synchronizing, Referencing, and Forming a Set of Universal Abutments and Method of Aligning, Synchronizing, 3D Imaging, and Milling Prosthetic Components and Devices described herein.

FIG. 1 is a frontal view showing the universal aligning adaptor (100) prior to its being connected to a co-operable abutment post (300) having primary and secondary indicia. The universal aligning adaptor (100) is configured to be seated on an implant (10). There is a vast array of possible embodiments in addition to the examples shown in FIGS. 1-25F. In another preferred embodiment the universal aligning adaptor/abutment assembly is used with the Universal Multifunction Abutment System components for restoring implants with screw borne crowns, hybrid prostheses, over dentures or other screw borne prostheses, which will be discussed later (See FIGS. 49-69C).

In FIGS. 1 (frontal view) and 2 (side elevation view), the implant (10), itself, is represented as it exists after placement in the bone. In this example, it has a threaded portion (12) to receive a fixation screw (200). The universal aligning adaptor (100) is seated on the implant (10) and has at one end an external stem or post (140). In certain embodiments, the universal aligning adaptor (100) is configured to fit inside the index of the implant. As depicted in FIG. 1, the universal aligning adaptor (100) has a tripod stem (141) configured to fit inside trichannel index (15) of the implant. In a number of other embodiments, the trichannel receptor of the implant may be replaced by a hexagon (6 sided), dodecagon (12 sided), octagon (8 sided), a nonagon (9 sided) index or any other polyhedron that serves as the implant's index, depending upon the internal configuration of the implant chosen by the manufacturer, which interfaces with a universal aligning adaptor with a matching protruding index (140).

With an implant having an octagon index (24, not shown here), the adaptor could have a hexagon protrusion (112, not shown here). These are not the only implant configurations that may be restored via the universal aligning adaptor, which may have many other means of varying dimensions and of such a nature as to fit into several different types of manufactured implants having various indexes, internal configurations, dimensions and internal thread diameters.

FIG. 1 shows the primary indicium of the adaptor (120) and the primary (321) and secondary (325) indicia of the abutment, which provide directed rotation of the adaptor about the abutment, which aligns and synchronizes all co-operable componentry. The abutment (300) can be connected to the adaptor (100) such that the primary indicium of the adaptor (120, 121) is positioned under one of the primary (321) or secondary (325) indicia of the abutment. The alignment of the primary indicium of the adaptor (120, 121) relative to the primary (321) or secondary (325) indicia of the abutment provides the surgeon, restorative dentist, or technician (herein referred to as the "operator") with an automated, interactive clinical and/or digital protocol to realign the abutment to an ideal position after the rotation of the combined assembly. The primary indicium of the aligning adaptor (120, 121) therein serves as a reference point for the identification and registration of the mutual geometry of all assembly elements for the fabrication of final prosthetic components and/or devices by an automated and/or interactive clinical and/or digital protocol.

The abutment can have gingival contours, such as standard gingival contour (330), scalloped collar gingival contour (331), anterior shaped gingival collar, medium posterior gingival shaped collar, large posterior shaped gingival collar, maxillary contour shaped gingival collar, mandibular contour shaped gingival collar, or cylindrical collar (337). It is understood that the shape of the gingival contour depends on the intended position of the adaptor/prosthesis. The gingival collar also can have a depth extension (338) depending again on the intended position of the adaptor/prosthesis. Indeed, it is understood that gingival depth can vary from one patient to the next and also from one tooth position to the next within a given patient. Therefore, it is contemplated that one can design custom gingival collar depths and shapes to respond to these differences in gingival depths and shapes.

In the clinical version of the system, the alignment of the primary indicia of the adaptor relative to the primary or secondary indicia of the abutment is considered to be "automated" in that these relative positions instantly direct the operator towards rotating the abutment to its ultimate orientation for ideal position within the dental prosthesis. The indicia are also "interactive" in that the operator may elect to override the predetermined orientation by further rotating the adaptor about the abutment. In addition, the automated and interactivity features of the present system can be used with a milling software program such that the program utilizes the indicia information to autorotate the abutments to predetermined positions or to modify those positions. In the clinical version of the system, the surgeon or restorative dentist would have access to a kit or library of existing components which would allow him or her to complete the "loading" of the implant using the components and procedures of the present application. In the digital version of the system, it is contemplated that, the indicia information of the universal scan post/adaptor/abutment would be incorporated into a milling software program such that the orientation information provided by the indicia could be used to better enhance the functionality of abutment and prosthesis fabrication by a computer-driven milling program, in contrast to the present state of the art. The technician would have access to that library of components.

Throughout the present application, reference is made to the making of prosthetic components, such as abutments and the like, and final restorative components by "milling". It is understood herein that the milling refers to any computer-driven process for making prosthetic components or devices. Such methods include 3D printing techniques, milling, etc.

In at least certain embodiments, the primary indicium of the universal aligning adaptor is a sphere of appropriate shape and size to intimately contact one of the primary or secondary indicia of the abutment post, which are recessed spheres for a "snap" fit. In at least certain embodiments, the snap fit between the sphere of the adaptor and the recess of the abutment post can be released for disengagement. Although the snap fit is exemplified through a sphere and a corresponding recess, it is understood that the snap fit can be formed through any shaped protrusion and corresponding recess. Additionally, although the snap fit is exemplified as the male component residing on the adaptor and the female component residing on the abutment, the snap fit embodiments can also be configured such that the male component is on the abutment and the female component is on the adaptor.

Once realignment is completed, the assembly can be affixed to the implant (10) by a fixation screw (200), which, in this example, extends through the octagon stud (111) at the top at the screw access channel (151) and the tripod external post (141) at the bottom, which interfaces with the trichannel (21) passage of the implant.

The rotation shown in FIGS. 1, 11A-C, 24A-K, 32-39B, 54A-C, 55, 54A-58C, 59, 60A-C, 61, 69A-C, and 88-96 can be preformed either clinically with physical components or virtually in a software program, as described above, by conveying its scan code to a designing program for preplanning or to the milling device codes of a milling program as described below.

The adaptor has many embodiments below its flange or collar (130), which, at its top end, can be the same size as the head of the implant or can be one of a different size such as when the surgeon or restorative dentist creates platform switching by choosing an adaptor having a base diameter that is smaller or larger than the interfacing implant head. It is composed of any suitable restorative material such as but not limited to titanium, titanium alloy, either one of those materials coated with nitrile or any other material for esthetics or function, zirconia, a ceramic, or other suitable material.

With the embodiment shown in FIGS. 1-3, the base of the abutment (300) is configured to seat upon the universal aligning adaptor's (100) stud or projection (111), which is at the incisal or top end of the adaptor, wherein the stud or projection has a conforming diameter with the female receiving polygon (internal interfacing index) of the abutment. The stud or projection (111) upon which the abutment is seated is not limited to an octagon (as shown in FIG. 1) or hexagon, but can have the shape of any suitable polyhedron. The base of the abutment can come in a variety of standardized sizes, shapes and contours. In at least certain embodiments, the abutment base is customizable.

Figure 4:
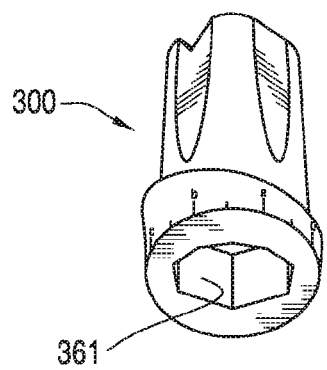
Figure 5:
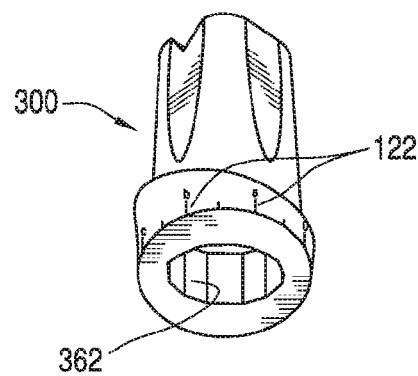

In at least certain embodiments, the stud (111) of the adaptor allows a precise interdigitation with the abutment along with the ability for them to be rotated about each other when not connected to the implant (10). In certain embodiments, the stud and abutment can be rotated about each other until the primary indicium of the adaptor (120) is aligned via a predetermined rotation under one of the primary (321) and secondary (325) indicia of the abutment, after which, they are combined with the implant. In certain embodiments, the adaptor/abutment assembly can be rotated in 15° or 7.5° increments, which results in a maximal 7.5° or 3.75° deviation from the ideal position, depending upon whether the internal interfacing index of the abutment is an octagon (361) as shown in FIG. 4 or a hexadecagon (362) as shown in FIG. 5. Explained in a slightly different way, the adaptor/abutment assembly in certain of the described embodiments can be rotated in 15° increments, which means to the surgeon or restorative dentist that the assembly could be in a maximal 7.5° deviation in the clockwise or counterclockwise direction. In other embodiments, the adaptor/abutment assembly can be rotated 7.5° increments, which means to the surgeon or restorative dentist that the assembly could be in a maximal 3.75° deviation in the clockwise or counterclockwise direction. Other embodiments allow for even smaller degrees of rotation than 15° or 7.5° and therefore in the clockwise and counterclockwise direction, these embodiments provide even less degrees of deviation to the surgeon or restorative dentist.

It is understood that the selected primary or secondary indicia can vary by rotational direction (clockwise vs. counter clockwise) and by stop number (e.g., a, b, c or A, B, C) and can be different for each implant index (hexagon vs. trichannel vs. octagon, etc.) to establish the finite increments of rotation. These indicia increments (122) are ideally correlated to the underlying implant index and/or adaptor index. Therefore, to the extent that an adaptor/implant combination is designed to achieve 15° increments of rotation, each indicia increment on the adaptor visually represents that increment of rotation to the surgeon, restorative dentist, or technician. Other embodiments described herein are capable of achieving 7.5° increments or rotation and even smaller increments of rotation. It is understood that the indicia increments (122) for such embodiment would reflect such degrees of rotation.

Tables 1-4, below, show one method of using a set of predetermined rotation points as a part of the Universal automated and/or interactive clinical and/or digital protocol, wherein an adaptor is rotated about an abutment prior to the two being combined into an assembly, and said assembly is then rotated about, and seated onto, an underlying implant. The table could also be used to first rotate the adaptor to a set position over the implant, followed by the post being rotated and inserted over the adaptor. The table columns describe the prosthesis orientations achievable by rotating an adaptor about an abutment to the indicia settings stated in the topmost row (e.g. 0, A, B, C, 180, c, b, a in Table 1), while the table rows describe the prosthesis orientations achievable by rotating the adaptor/abutment assembly about the underlying implant and seating said assembly at the implant stop angles stated in the leftmost column (e.g. 0°, 120°, 240° in Table 1). Thus, the tables describe, for the particular mutual geometry of an adaptor and overlying implant device, the set of all possible prosthesis orientations achievable for given combinations of adaptor/abutment indicia settings and assembly rotations. For example, Table 1, below, illustrates how the Universal automated and/or interactive clinical and/or digital protocol can be used to correct for misalignment of an underlying Tri-channel-index (three-sided) implant. By itself, the trichannel index implant yields just three possible final prosthesis orientations: 0°, 120°, and 240°, corresponding to the three physical implant stop angles provided by the device. The introduction of the Universal Aligning Adaptor with an upper index having a different polygonal configuration than the implant's index, however, gives rise to twenty-four possible final prosthesis orientations when the upper index is an octagon, each obtained by a different combination of adaptor/abutment indicia setting and assembly rotation. For instance, when the adaptor is rotated about the abutment to indicia setting "C", and the combined assembly is then rotated 240° and seated onto the underlying implant, the net result is a 15° correction of the final prosthesis orientation towards the buccal. Likewise, the selections of indicia setting "c" and a 120° combined assembly rotation also produces a net 15° correction of the final prosthesis orientation, but towards the lingual.

The various combinations are not arbitrary—they are well defined given the mutual geometry of the adaptor and underlying implant—and cover a full 360° in 15° increments, however, as seen in the tables, they are not monotonic. Nonetheless, there is little or no work to be done to determine the optimal pairing: by employing the Universal automated and/or interactive clinical and/or digital protocol, the practitioner need only look up the desired final prosthesis orientation in the appropriate table, configure the adaptor/abutment assembly at the designated indicia setting, and then rotate the combined assembly to the designated implant stop angle. The result is an automatic correction for the misalignment of the underlying implant, and positioning of the final prosthesis at an optimal orientation. Of course, after fitting, the practitioner is free to choose a different pairing for overriding aesthetic and/or clinical concerns, wherein the combined assembly is simply removed, the adaptor/abutment assembly is reconfigured (for example, to indicia setting "b" instead of "C"), and finally recombined and re-rotated to the indicated implant stop angle (here, achieving a net 30° rotation to the buccal). In essence, the Universal automated and/or interactive clinical and/or digital protocol enables optimal positioning of a final prosthesis, irrespective of the alignment of the underlying implant's index, in a simple, three-step process: analyze how far off the implant is from the surgical planning (preferred location); look up the preferred, predetermined rotation point; and rotate the physical or virtual components. Moreover, it achieves 15° or smaller increments of correction, such that the final prosthesis orientation will be no more than 7.5° away from any target reference angle. In the case of the Tri-channel-index implant, the benefit is quite clear: using just the implant index for rotation, a prosthesis with an intended orientation of, for example, 85°, can only be positioned at 120°, producing an unacceptable 35° angular misalignment. With a Universal adaptor configured at indicia setting "B" and implant stop angle 0°, however, the prosthesis becomes oriented at 90°, yielding a mere 5° angular misalignment. This 85% reduction in angular misalignment is clearly superior with regard to clinical stability and aesthetic acceptance.

TABLE 1

Indicia Setting for Tri-channel Implant

|  | 0 | A | B | C | 180 | c | b | a |
|---|---|---|---|---|---|---|---|---|
| Assembly Rotation | 0° | 0° | 45° | 90° | 135° | 180° | 225° | 270° | 315° |
|  | 120° | 120° | 165° | 210° | 255° | 300° | 345° | 30° | 75° |
|  | 240° | 240° | 285° | 330° | 15° | 60° | 105° | 150° | 195° |

Tables 2-5, below, show the achievable orientations for different adaptor/abutment/implant geometric configurations. As previously mentioned, the adaptor has independent upper and lower indexes with different geometrical shapes, the lower index matching that of the implant so that the adaptor can be seated upon it. Here, the mutual geometries afford multiple settings which all achieve the same desired prosthesis orientation. Table 2, below, shows four 15° rotation points (two buccal, two lingual) for the Hexagon implant, Table 3 indicates eight 15° rotation points (four buccal, four lingual) for the Dodecagon implant, Table 4 depicts four 15° rotation points (two buccal, two lingual) for the Octagon implant with a Hexagon upper-index adaptor. Table 5, below, shows the superiority of the nonagon implant that rotates in 5° increments, as opposed to the 15° increments of rotation for the other implants of Tables 1-4. Therefore, although the other embodiments of Tables 1-4 are far superior to existing implant technologies in that the surgeon or restorative dentist can have several positions to correct to 15° or less, the nonagon can routinely allow the surgeon or restorative dentist to be within 5° of the preferred, aesthetic position and increases the number of possible positions that allow for even 0° of misalignment. The practitioner is free to use any of the available settings to achieve an aesthetically correct alignment of the abutment or other prosthetic component over the underlying implant.

Not to belabor the point, but to make clear the power of the present invention, the conventional implants presently available only allow for the coarse increments of rotation dictated by their indices and their indices alone. Therefore, the trichannel only allows for 120° of rotation. Likewise, the hexagon implant only allows for 60° of rotation.

The present invention establishes very fine increments of rotation in 15° rotation or less and even 5° of rotation or less for the nonagon implant.

TABLE 2

Indicia Setting for the Hexagon Implant

|  | 0 | A | B | C | 180 | c | b | a |
|---|---|---|---|---|---|---|---|---|
| Assembly Rotation | 0° | 0° | 45° | 90° | 135° | 180° | 225° | 270° | 315° |
|  | 60° | 60° | 105° | 150° | 195° | 240° | 285° | 330° | 15° |
|  | 120° | 120° | 165° | 210° | 255° | 300° | 345° | 30° | 75° |
|  | 180° | 180° | 225° | 270° | 315° | 0° | 45° | 90° | 135° |
|  | 240° | 240° | 285° | 330° | 15° | 60° | 105° | 150° | 195° |
|  | 300° | 300° | 345° | 30° | 75° | 120° | 165° | 210° | 255° |

TABLE 3

Indicia Setting for the Dodecagon Implant

|  | 0 | A | B | C | 180 | c | b | a |
|---|---|---|---|---|---|---|---|---|
| Assembly Rotation | 0° | 0° | 45° | 90° | 135° | 180° | 225° | 270° | 315° |
|  | 30° | 30° | 75° | 120° | 165° | 210° | 255° | 300° | 345° |
|  | 60° | 60° | 105° | 150° | 195° | 240° | 285° | 330° | 15° |
|  | 90° | 90° | 135° | 180° | 225° | 270° | 315° | 0° | 45° |
|  | 120° | 120° | 165° | 210° | 255° | 300° | 345° | 30° | 75° |
|  | 150° | 150° | 195° | 240° | 285° | 330° | 15° | 60° | 105° |
|  | 180° | 180° | 225° | 270° | 315° | 0° | 45° | 90° | 135° |
|  | 210° | 210° | 255° | 300° | 345° | 30° | 75° | 120° | 165° |
|  | 240° | 240° | 285° | 330° | 15° | 60° | 105° | 150° | 195° |
|  | 270° | 270° | 315° | 0° | 45° | 90° | 135° | 180° | 225° |
|  | 300° | 300° | 345° | 30° | 75° | 120° | 165° | 210° | 255° |
|  | 330° | 330° | 15° | 60° | 105° | 150° | 195° | 240° | 285° |

TABLE 4

Indicia Setting for the Octagon Implant

|  | 0 | A | B | 180 | b | A |
|---|---|---|---|---|---|---|
| Assembly Rotation | 0° | 0° | 60° | 120° | 180° | 240° | 300° |
|  | 45° | 45° | 105° | 165° | 225° | 285° | 345° |
|  | 90° | 90° | 150° | 210° | 270° | 330° | 30° |
|  | 135° | 135° | 195° | 255° | 315° | 15° | 75° |
|  | 180° | 180° | 240° | 300° | 0° | 60° | 120° |
|  | 225° | 225° | 285° | 345° | 45° | 105° | 165° |
|  | 270° | 270° | 330° | 30° | 90° | 150° | 210° |
|  | 315° | 315° | 15° | 75° | 135° | 195° | 255° |

TABLE 5

Indicia Setting

|  | 0 | A | B | C | 180 | c | b | a |
|---|---|---|---|---|---|---|---|---|
| Assembly Rotation | 0° | 0° | 45° | 90° | 135° | 180° | 225° | 270° | 315° |
|  | 40° | 40° | 85° | 130° | 175° | 220° | 265° | 310° | 355° |
|  | 80° | 80° | 125° | 170° | 215° | 260° | 305° | 350° | 35° |
|  | 120° | 120° | 165° | 210° | 255° | 300° | 345° | 30° | 75° |
|  | 160° | 160° | 205° | 250° | 295° | 340° | 25° | 70° | 115° |
|  | 200° | 200° | 245° | 290° | 335° | 20° | 65° | 110° | 155° |
|  | 240° | 240° | 285° | 330° | 15° | 60° | 105° | 150° | 195° |
|  | 280° | 280° | 325° | 10° | 55° | 100° | 145° | 190° | 235° |
|  | 320° | 320° | 5° | 50° | 95° | 140° | 185° | 230° | 275° |

In summary, these tables illustrate the use of a set of predetermined reference points as a part of the Universal automated and/or interactive clinical and/or digital protocol, employing a Universal Aligning Adaptor for implants of any index to achieve reproducible increments of rotation of 15° or less. While the rotation point for the primary indicium of the adaptor is different for each, the protocols are the same, and yield optimally oriented final prosthesis positioning in any clinical situation.

The fixation screw (200) is configured to thread into the internal screw threads of the implant (12). The shoulder of the screw head (240) is configured to engage an internal shoulder of the abutment (367) and thereby tighten the abutment to the adaptor by tightening the universal aligning adaptor (100)/abutment (300) assembly to the implant via the fixation screw. The fixation of the adaptor and abutment to the implant are not limited to any one screw or internal abutment configuration. After the adaptor and abutment are either first connected to each other or after the adaptor is inserted into the implant in a predetermined position, and the abutment is then inserted on the adaptor with its primary indicium situated in an ideal position, the fixation screw can be used to secure the abutment/adaptor complex to the implant.

The collar of the abutment tapers from the bottom end (369) at the flange to a larger, standardized size in order to more naturally represent the size and shape of a natural tooth abutment at the top end. As shown in FIGS. 4 and 5, the embodiment in this example has a female receiving polygon (internal interfacing index) of either an internal octagon (361) with eight sides or a hexadecagon (362) with sixteen sides which is configured to engage the stud of the adaptor (111). With an abutment having an octagon receptacle (shown in FIG. 4), the octagon configuration of the stud, in combination with any implant with a hexagon (6 sides), tripod (3 sides), or dodecagon (12 sides) indexing, allows for the rotation of the post head in the horizontal plane in predetermined 15° increments (a maximal 7.5° deviation from the ideal direction) shown in FIGS. 3A, 3B, and 3C for each of these implants. This ability to rotate in 15° increments is achieved independently of the implant's index while not being dependent upon the location of the octagon in relationship to the implant's index, since there is no offset. This horizontal rotation allows for a precise repositioning of the post prior to affixing it to the implant. The abutment can also be configured with a hexadecagon (16 sided) receptacle (shown in FIG. 5), which allows for the same rotation of the post head in 7.5° increments (a maximal 3.75° deviation from the ideal direction). If the implant has an octagon index instead of a hexagon configuration, then an adaptor with a hexagon stud is connected to an abutment with a matching hexagon or dodecagon receptacle which, therein, achieves the same horizontal rotation as noted above.

The rotation of the adaptor/abutment assembly with a nonagon (9 sided) indexed implant can occur in 5° increments, when the adaptor stud is an octagon, which is shown and described, in detail, in FIGS. 23 and 98-102.

The head of the abutment (300) has an internal cylindrical passage (365) to receive a fixation screw (200). The fixation screw, itself, has a shank (210) and it can have an internal hex hole (230) to receive a driver. The threads (220) engage the internal threads (12) of the implant, while the head of the screw engages the internal shoulder (367) of the post. Although exemplified as having threads (220) to secure the screw to the implant, it is understood that other mechanisms, such as a snap fit mechanism, can be used to secure the screw (200) to the implant (12).

In at least certain embodiments, the adaptor, itself, has internal threads (152) beginning above its collar that engage the fixation screw threads (220) prior to seating the assembly on the implant. This can make it easier to carry the assembly to the implant and prevents screw droppage during the surgical procedure. The adaptor is not limited to having this internal thread. Additionally, the universal adaptor can come in different shapes, sizes, configurations and contours than the ones exemplified in the present figures. Because of the large variety of different adaptors, only a few of them are presented in the figures here.

Figure 6:
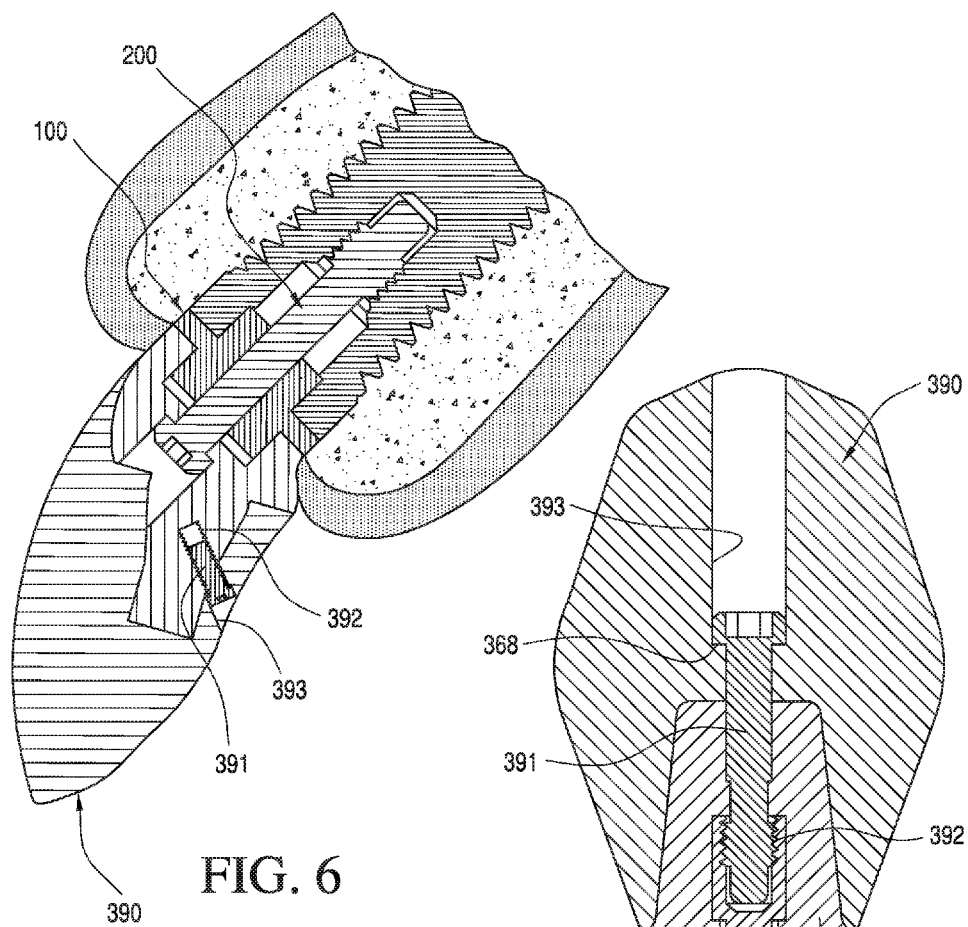

FIG. 6 depicts a 30° angle correcting anterior abutment (356) that is secured to the implant with a fixation screw (200) and receives a screw down crown (390) that is affixed to the abutment with its own crown fixation screw (391), which is received in a channel (393) within the crown. This channel (393) further extends into the abutment and the channel of the crown and the channel of the abutment are configured to be aligned with each other. At least the channel portion of the abutment contains a threaded section configured to mate with the threads of the crown fixation screw. In other embodiments, at least a portion of the crown channel is also threaded. This screw down crown is particularly useful with an anterior angled tooth where retrievability is important. In the context of dental prosthetic components, esthetics can be marred when the exit point of the fixation screw is frontally visible. Because this crown fixation screw is ideally positioned in a set, predictable manner, located approximately 180° from the abutment's primary indicium, which itself has been situated in an ideal position, the fixation screw is not frontally visible.

This system provides the missing capability to routinely screwing down crowns rather than cementing them. It provides two or more methods of engaging that fixation screw. One such method is machined threads in the milled post. Another such method involves tubes with threads in the patterns that become the cast pressable or other abutments made from a pattern.

Figure 7:
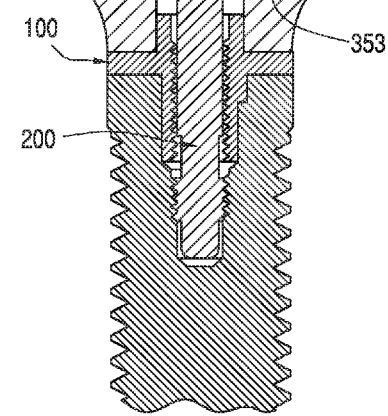

FIG. 7 depicts a screw down crown (390) seated on a 0°, non-angled abutment (353) such that its primary indicium and that of the adaptor are aligned (not shown), and is secured to the abutment fixation screw (200) with its own crown fixation screw (391). In this embodiment, the head of the abutment fixation screw contains threads (392) to receive the crown fixation screw (391).

At least one embodiment provides an assembly for use in the process of dental restoration relevant to dental implant prosthetics a contour abutment intended for receiving a screw retained crown (FIGS. 6 and 7) and an adaptor having co-operable indicia wherein the abutment has the geometry of a natural tooth preparation and has internal screw threads that are positioned in the esthetic zone approximately 180° from the primary indicium of the abutment after it has first been ideally situated such that a crown, set of crowns, or bridge are receivable on the abutment and are retained by the fixation screws that engage the abutment fixation screw threads comprising the steps of rotating an abutment to a preferred horizontal and vertical position, creating the screw threads by milling them, setting internally threaded tubes, die tapping, or by another appropriate way at that location such that the threads are ideally positioned in the esthetic zone and at the most ideal pitch for receiving a driver that is carrying the screw, and creating the overlying prosthetic component with a stop for securing the prosthetic component on the abutment and affixing it with a fixation screw that engages the internal threads.

Figure 8:
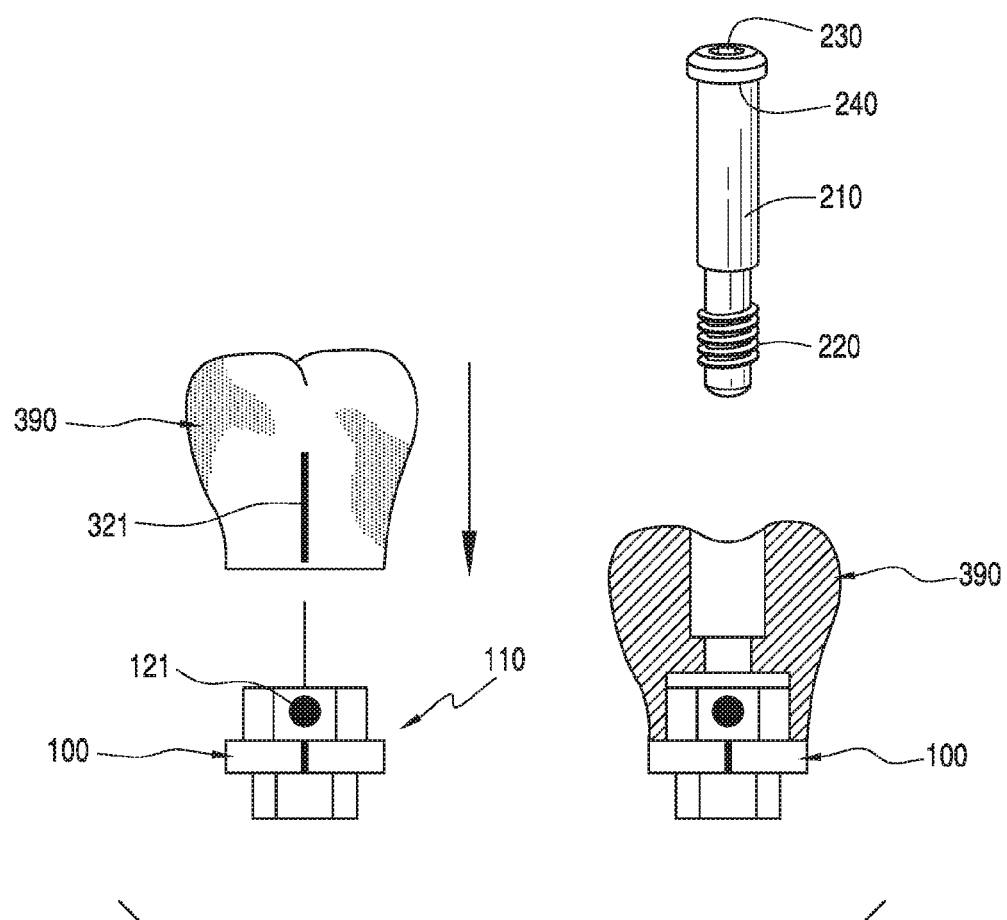

For areas where the interocclusal distance is shorter than desired, FIG. 8 provides a universal contour abutment/coping one piece combination (300) having a primary indicium (321) that is seated on the adaptor (100) such that their primary indicia (121 and 321) overly each other and are secured together to the implant without an abutment post. The adaptor (100) has a projection on the base away from the implant (110), i.e., a stud. The stud as described elsewhere herein can be any polygon shape, including a hexagon, an octagon, a nonagon, a dodecagon, etc. The coping/abutment component can come in a number of configurations and can be composed of several different materials. For example it can be a preformed one to receive a porcelain bake, a castable one that is also modifiable, a pressable one, or a milled abutment and/or crown and be composed of any suitable restorative material such as but not limited to a precious metal, semiprecious metal, zirconia, or titanium alloy. In an alternate aspect of the invention, the coping/abutment component can be manufactured from an additive manufacturing process, such as stereolithography. It can also receive a porcelain bake or be an abutment/coping/veneer that is milled from a block of porcelain, zirconia, composite or other suitable restorative material. Even though FIG. 8 represents a posterior coping without the veneering material shown, it can be of any posterior or anterior tooth shape.

As shown throughout these patent application drawings, the adaptor and its prosthetic components have co-operable primary and secondary indices that indicate predetermined positions, which can then dictate the placement of follow-on components in relation to the location of the primary indicium of the adaptor. This can begin with the interim abutment or healing cap insertion, after it is rotated on the adaptor off of the implant using the primary indicium of the adaptor (121) in combination with the primary (321) or secondary (322 and others) indicia of the abutment and the assembly is, in turn, rotated on the implant FIGS. 9A-C, or is rotated on the adaptor after it has been first rotated and seated on the implant as shown in FIGS. 3A-C. 324 is the third indicium counterclockwise rotation stop.

Additionally, the adaptor can be used on multiple implant indexes as shown in FIGS. 13-23. Once the adaptor (100)/abutment (300) or the adaptor (100)/healing cap (400) assembly is affixed to the implant with the fixation screw (200), the insertion of all other components such as impression or scanning posts is dictated by the primary indicium of the adaptor (120, 121) in relation to the primary or secondary indicium of the abutment or healing cap after the appropriate rotations. For example, in FIGS. 70-92, when the impression post (600) or the scanning post (700) is inserted on the adaptor at its primary indicia reference points (120 or 121) or on the healing caps at their primary indicia reference points (411, 421), they are capturing the previously established position of the rotated abutment or healing cap (see FIGS. 58A-58C, 59, 60A-60C, and 61) in relation to the implant's index. It is understood that the positioning of the impression or scan post on the adaptor is not limited by situating the primary indicia over each other, even though this may be a preferred embodiment. This is covered, in detail, in the Universal Impression, 3D Imaging, and Milling System, and the Method of Aligning, Synchronizing, Referencing, and Forming a Set of Universal Abutments and Method of Aligning, Synchronizing, 3D Imaging, and Milling Prosthetic Components and Devices sections of this application. In these embodiments shown throughout the "detailed descriptions," the primary indicium on the adaptor is a circle or any other indicating reference mark or polyhedron on any one of the flats of the projection of the adaptor (120) that is chosen to be the reference point for positioning all other co-operable follow-on components. As stated, in at least certain embodiments, this circle is a protrusion and the overlying components have matching recesses. The primary and secondary indicia are not limited to these configurations, but can be any type of referencing indicator that delineates the primary and/or secondary indicia, and in any combination such as where one can be on the collar of the adaptor without also having one on the post or vice versa. In certain embodiments, directly below this indicium is one on the collar of the adaptor (121) to assist the surgeon or restorative dentist with visualizing the primary reference plane on the adaptor flat, after it is covered by the seated component. The indicium on the abutment post (321) is positioned directly at its 0° reference point of the adaptor which is its primary indicium (121). With vertical angle correcting abutments, the primary indicium of the abutment is approximately 180° from the midpoint of the vertical angle correcting portion of the abutment. The use of the primary indicium relationship to the vertical angle correcting portion of the abutment is not limited to this embodiment but can be any one of a plurality of positional relationships between the primary indicium and the angle correction component. For example FIG. 1 shows a secondary indicium (325), which is a rotation point on the abutment, and is an example of the use of the secondary indicia during rotation, which is described, in great detail, throughout these detailed descriptions. 326 is the second indicium counterclockwise rotation stop.

Figure 9A:
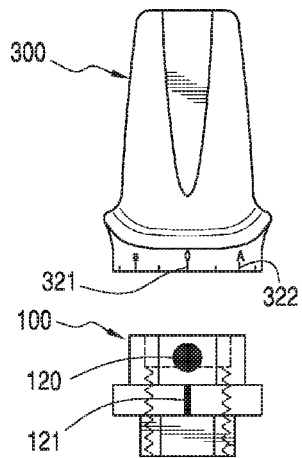
FIGS. 9A-C and 10A-C are frontal views showing two methods of connecting an adaptor and abutment assembly to an implant.

FIGS. 9A, B, and C illustrate the universal aligning adaptor and the abutment post first being combined by using their primary indicia followed by the seating of the assembly on the implant without any rotation. The abutment post (300) has its primary indicium (321) and its secondary indicium (322) on its collar. As depicted, the primary indicium (321) is shown as "0". Clockwise around the collar of the post are indices "A," "B," "C," etc. (although only position "A" is visible). Counter clockwise around the collar of the post are indices "a," "b," "c," etc. (although only position "a" is visible). Although depicted as a combination of capital and lowercase letters to allow the surgeon or restorative dentist to easily visualize the position of the index, in this example, it is understood that the indices can be represented by any combination of letters, numbers, or symbols. Also shown in FIGS. 9A, B, and C, the adaptor has one primary indicia on one flat (120) and the collar (121). The primary indicia on the flat and/or the collar could also be a doublet line. There is no specific number of indicia on any adaptor or abutment.

Figure 9B:
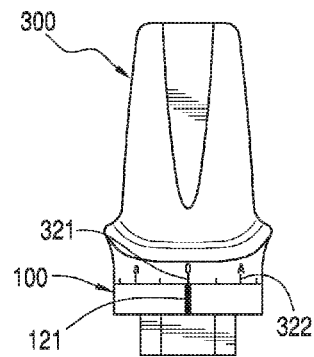
Figure 9C:
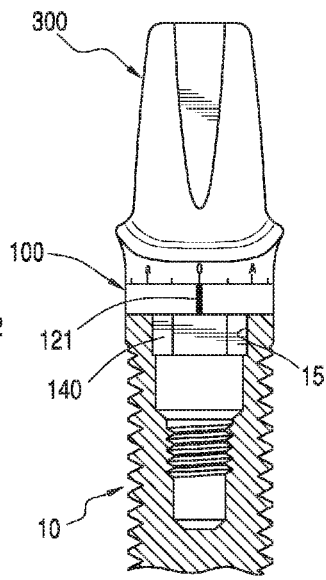
Figure 10A:
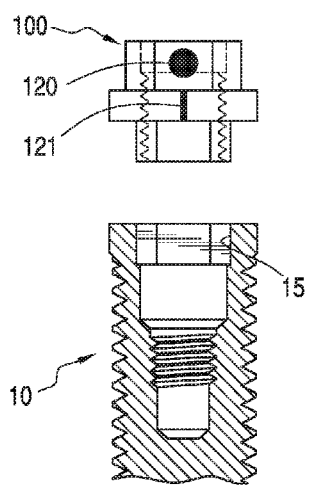
Figure 10B:
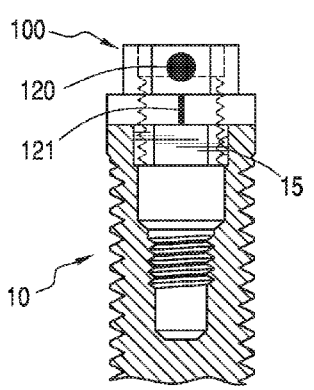
Figure 10C:
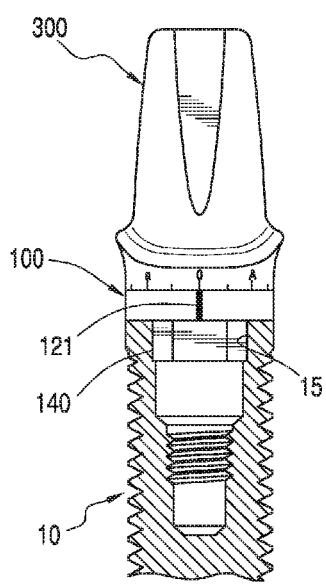
Figures 11A, 11B, 11C:
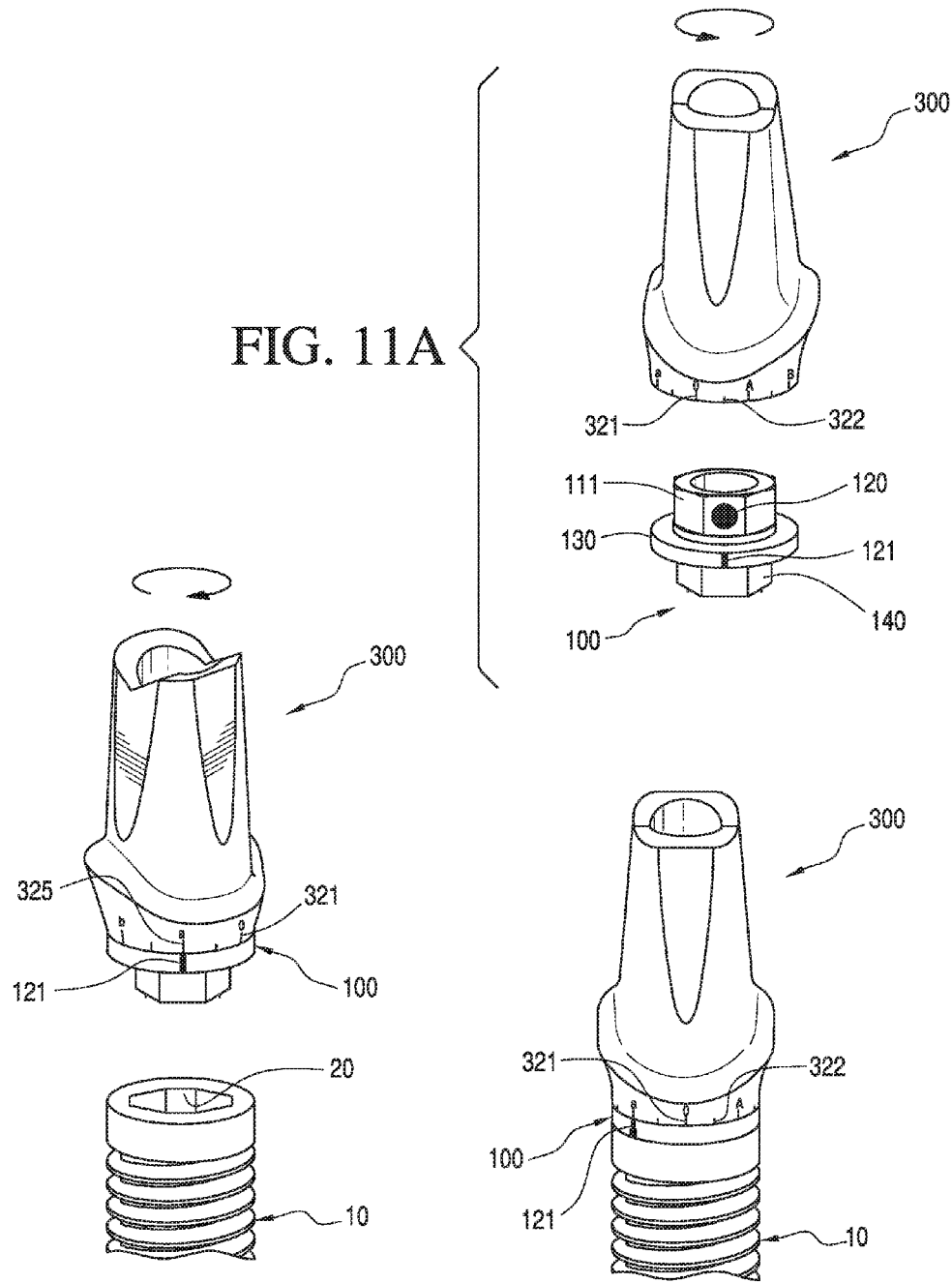
FIGS. 11A-C show the predetermined counter clockwise rotation around the vertical axis of the implant such that the adaptor's primary indicia is one stop under the abutment's first secondary indicia followed by the adaptor/abutment assembly to realign the abutment so that it is within a maximal 7.5° deviation from the ideal direction.
Figure 16A:
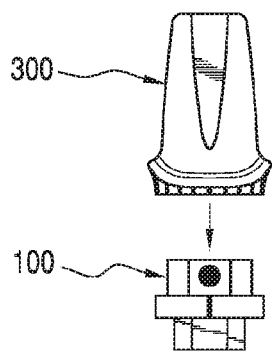
Figure 16B:
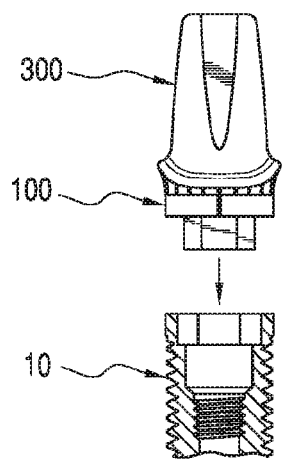
Figure 17:
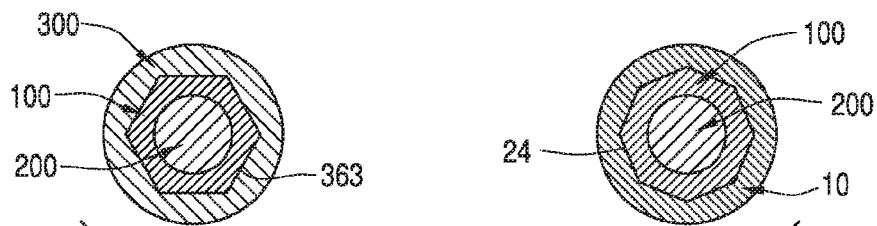

As shown in FIGS. 9A and 9B, the primary indicia of the abutment and the adaptor are aligned and the abutment and adaptor are combined together. In this combined configuration, the abutment/adaptor assembly is seated on the implant and the position can be evaluated. If the abutment is seated in its preferred, aesthetically correct position, the fixation screw (200) is inserted and the assembly is affixed to the implant. The fixation screw can also be threaded into the internal threads of the adaptor (152) prior to seating the assembly to make it easier to carry it to the implant to prevent screw droppage. The internal threads are merely one embodiment and do not dictate the design of the adaptor. If the abutment is in an incorrect orientation, the abutment/adaptor assembly is removed from the implant and the surgeon or restorative dentist can rotate the abutment about the adaptor such that the abutment and adaptor are aligned about a secondary indicia, i.e., indicia "a". The process can then be repeated as needed until either the surgeon or restorative dentist has confirmed that the abutment is in the most aesthetically correct orientation.

Figure 48:
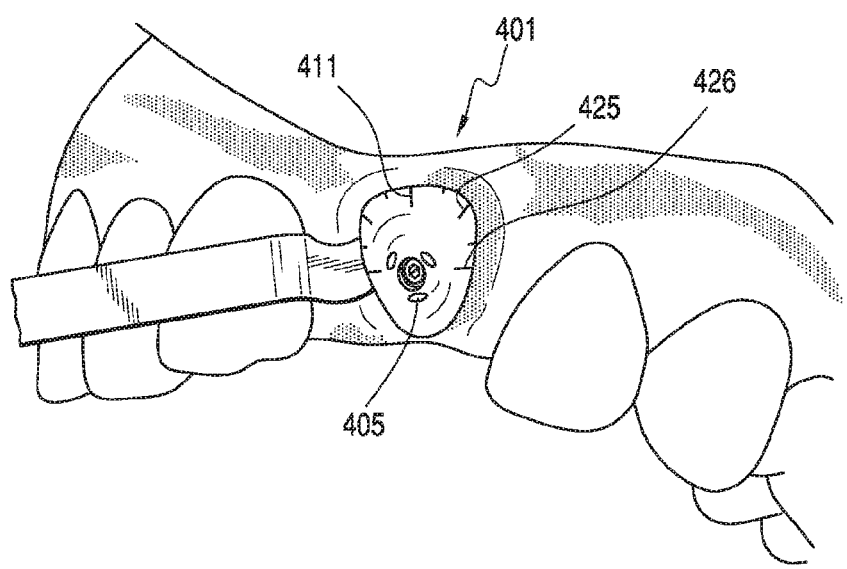

FIG. 48 shows the adaptor (100) first being seated on the implant, followed by the abutment (300) being seated on the adaptor (shown in FIG. 10C) such that their primary indicia (121 and 321) line up. To the extent that the abutment is positioned in the aesthetically correct orientation, the abutment is secured to the implant with the fixation screw. However, if the orientation is suboptimal, the abutment can be removed from the adaptor, which is left in contact with the implant, and the abutment can be rotated about the adaptor to the next indicia. If a different orientation is desired, the adaptor can also be removed and rotated about the abutment with the assembly then being rotated about the implant. Once the abutment is in the aesthetically correct orientation, the abutment is secured to the implant with the fixation screw.

In another method, the adaptor can be first rotated over the implant to a predetermined position with the abutment then inserted over the adaptor in its preferred position.

Figures 49, 50:
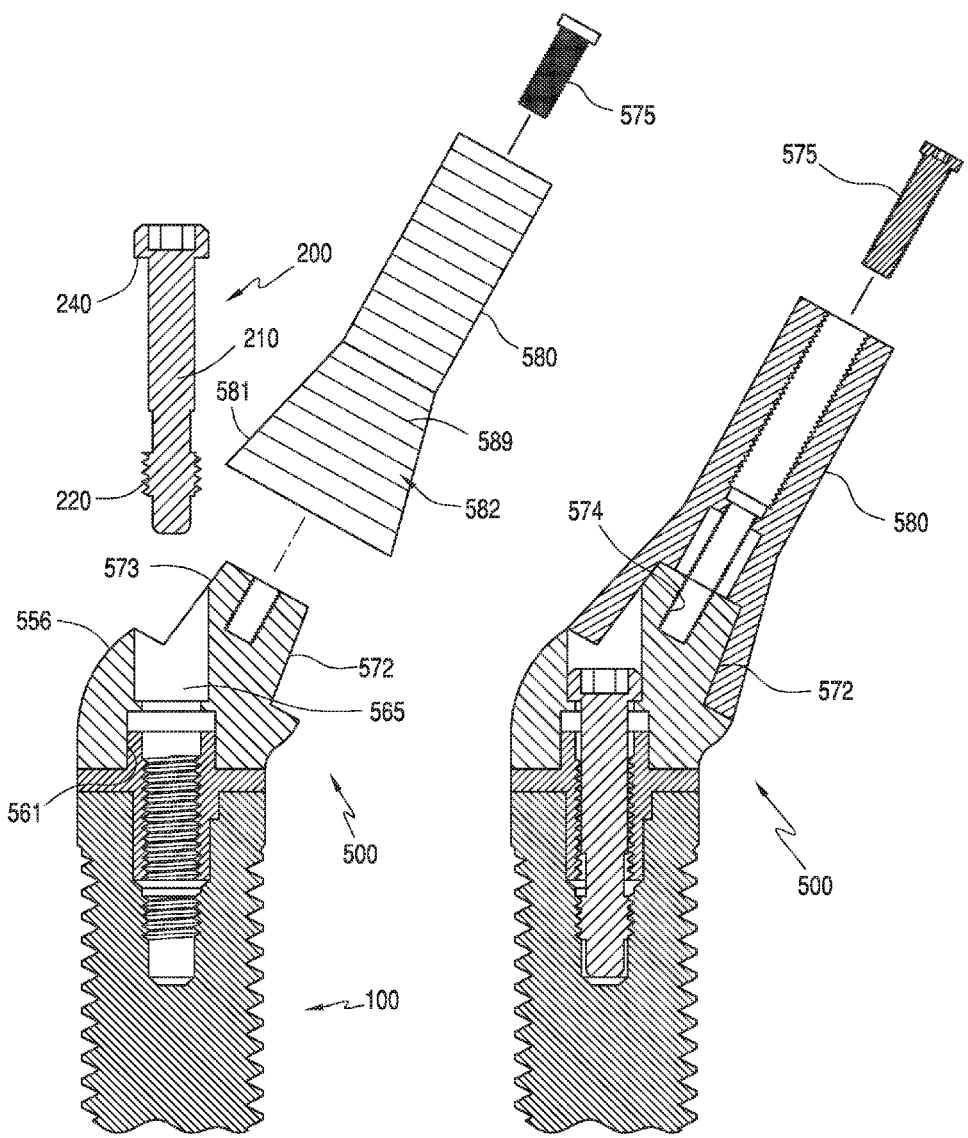
FIGS. 49-53 disclose the universal multifunction abutment for the fabrication of any screw down prosthesis.

FIG. 49 shows the abutment (300) being rotated 1 stop as a first step to ideally situate it, such that the primary abutment indicium (321) no longer lines up with the primary indicium of the adaptor (121), but, rather, has been rotated counter clockwise to position "a" (325). The single stop rotation in this particular example represents a 15° rotation once the assembly is subsequently rotated to center the abutment over the implant, but these rotations are not limited by these 15° increments (or 7.5° increments), but rather can be in any chosen preset increments that are used in combination with an automated and/or an interactive clinical and/or digital protocol. If one rotation of 15° does not center the abutment, the assembly can be removed, the adaptor can then be rotated to another secondary indicium of the abutment (in this example, position "B"), and the assembly is reseated on the implant. These steps can be repeated until the abutment is situated in an optimal position over the implant after the rotation of the assembly. Alternatively, the abutment can be rotated about the adaptor to the extent that the adaptor is in the correct orientation but it is the abutment that is misaligned.

Figures 51, 52:
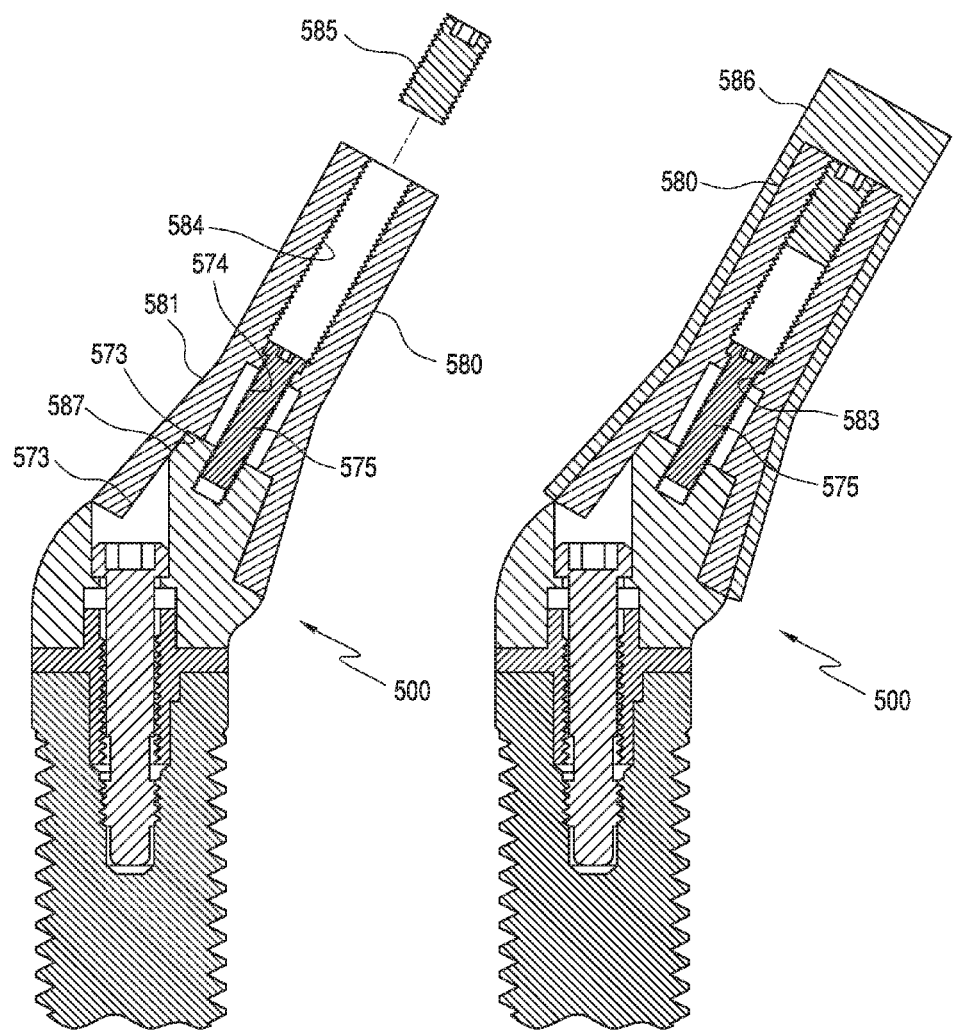

FIG. 50 shows the adaptor/abutment assembly ready to be seated on the implant with its flange engaging the top of the implant after being optimally situated to within 7.5° of the ideal position. These methods are exactly the same for any trichannel, hexagon, dodecagon, octagon, quadragon, nonagon implant or any other implant having other type of index configuration, although the increments of rotation may vary, depending upon that configuration in relationship to the adaptor's abutment engaging stud. All other components are seated in relation to the primary indicia of the universal aligning adaptor after its rotation with its external stem engaging the receptacle inside of the component, which establishes all of them in a set relationship to the implant's indexing, and, thereby, reduces operator error. For example, FIGS. 70 and 75, and 85A and 85B show the impression post (600) and the scanning post (700) being seated on the implant with their primary indicia (621 and 721) overlying the primary indicia of the adaptor (120), which, in combination, serve as an aligning/synchronizing mechanism wherein the repositioned abutment is precisely reproduced. FIG. 51 is a frontal view showing the rotation of the abutment on the adaptor with the primary indicium of the abutment (321) and its secondary indicium (322) facilitating this rotation in relation to the primary indicia of the adaptor (120, 121), which, in this case, is a 15° rotation. The method of rotating the abutment and its adaptor are also demonstrated in FIGS. 1, 24-25F, 32-39B, 54A-55, 58A, 69A-C, and 88-96.

Even though the examples shown in FIGS. 1-23 are the crown and bridge abutments of the universal contour abutment system, the principles presented here are exactly the same for the screw retaining abutments of the universal multifunction abutment system as well, which is shown in FIGS. 49-76.

At least one embodiment provides an assembly for use in the process of dental restoration relevant to dental implant prosthetics comprising a preexisting abutment that is converted to an aligning, contour abutment comprised of an adaptor and the abutment, wherein co-operable indicia are added to the preexisting abutment which is rotated at about and combined the adaptor that also has co-operable indicia means (FIGS. 1-11C). The co-operable indicia can include graduations for indicating the degree of rotation of the abutment and the adaptor relative to each other. The co-operable indicia can include primary and secondary indicia such that the primary indicium of the adaptor is rotatable in relation to the primary or secondary indicium of the abutment as it is rotated to its desired predetermined position.

Certain embodiments provide a method of converting any preformed abutment of any type, size, or configuration to an aligning, rotatable abutment composed of an adaptor in association with the abutment that are rotatable around each other via co-operable indicia that are incorporated into the abutment, which, when combined with an automated and interactive clinical and/or digital protocol reposition the abutment to a predetermined, preferred vertical and horizontal predetermined position. Rotating the adaptor and the abutment can be performed such that the abutment is ideally situated. Then one can either create a milled, cast, or pressed abutment with the parameters of the rotated abutment such that it either engages the index of the adaptor with the assembly then being seated on the implant or directly engages the index of the implant and is seated on the implant without the adaptor or using a preformed abutment as the final abutment seated on an adaptor.

FIGS. 13-23 illustrate the insertion of the abutment on the adaptor with its flange contacting the collar of the adaptor as it is seated over its external stem and the assembly on to the implant, and illustrates many of the possible combinations of implant to adaptor indexing (right hand drawing) and abutment to adaptor indexing (left hand drawing) that are available when rotating the adaptor around the abutment according to the automated and/or interactive clinical and/or digital protocol. When an abutment with an octagon internal mating configuration (361) is seated on an octagon stud of the adaptor, it can be rotated on a trichannel (21, FIG. 13), hexagon (22, FIG. 14), or dodecagon (23, FIG. 15) index in 15° increments, which can also be achieved with an abutment having an internal hexagon configuration (363) that is seated on a hexagon stud of the adaptor over an implant with an octagon index (24, FIG. 17). If an abutment with a hexadecagon (16 sided) internal configuration (362) is seated on the octagon stud of the adaptor it can be rotated on any implant index, for example a trichannel (21, FIG. 18), hexagon (22, FIG. 19), or dodecagon (23, FIG. 21) to achieve a 7.5° horizontal rotation. The same result can also be achieved with an abutment having an internal dodecagon configuration (364) that is seated on a hexagon stud of the adaptor over an implant with an octagon index (24, FIG. 22) to also achieve a 7.5° horizontal rotation. FIG. 23 illustrates an adaptor/implant index combination, wherein the implant has an internal nonagon (9 sided index) (25) and an adaptor with a nonagon projection that interfaces with it, while maintaining the projection of the octagon stud (361) that has been described in the implant/adaptor combinations, above. The unique nonagon implant index has a singular reference polyhedron or vertex that is the only one, which, when a line is drawn across the cylinder, bisects the opposing flat at a 90° angle. This vertex can be the primary indicium of the nonagon implant (920, FIGS. 98-102), which guides the surgeon to center the implant's index when inserting the fixture. In addition, the vertex can serve as a reference point for placement of all overlying components. When the implant index is misaligned, an adaptor with an octagon abutment engaging stud is rotated in combination with an abutment over a nonagon implant makes a consistent 5° horizontal rotation while maintaining an absolute reference relationship to the implant's primary vertex. The Nonagon Implant index is intended for use with any implant having any appropriate, effective external bone engaging configuration of any type. In all of these cases, the index relationships are not limited to specific polyhedrons of the abutment mating index and/or the implant mating index in order to have appropriate rotations to center components. This is shown in FIGS. 98 and 99A-B and is covered, in detail, in the Nonagon Implant section of this application. While FIGS. 13-23 show the possible combinations that establish the finite increments of predetermined rotation, the final position of the primary indicium of the adaptor becomes the reference point for synchronizing all prosthetic componentry and referencing them to the adaptor according to an automated and/or an interactive clinical and/or digital protocol.

FIG. 24 shows two methods of connecting an abutment to an implant with the abutment's primary indicium being positioned in relation to a sagittal plane that bisects the ridge of the jaw at its individual center point. The rotation is not limited to this specific position, since the preferred position can also be in another location to accommodate esthetic and functional needs for the prosthesis. FIGS. 24A-D show the rotation of the abutment on the adaptor, combining them such that the flange of the abutment (300) is seated on the collar of the adaptor (100) while its internal index engages the matching external projection of the adaptor, after rotating the assembly and inserting it onto the implant such that the abutment's primary indicium (321) is optimally situated to within 7.5° of the ideal position, which has the center line of the tooth preparation bisecting the ridge. FIGS. 24E-I show the rotation of the adaptor over an implant into a predetermined position, followed by the abutment being rotated such that one of its primary or secondary indicia (325) are aligned with the primary indicium of the adaptor (120, 121) until its primary indicium (321) is ideally situated. The abutment (300) is seated over the adaptor (100) and the assembly is secured to the implant. FIG. 24I shows the rotation of a 0° abutment such that the tooth preparation and gingival contour are optimally situated over the implant as dictated by the protocol and the indicia, and FIG. 24J shows the rotation of a 30° vertical angle correcting abutment to achieve the same result.

The following descriptions provide the details of each drawing. In the embodiment in FIG. 24A, the abutment (300) is being counter rotated (counter clockwise) one stop to position "a" (325) such that it is positioned over the primary indicium (120, 121) of the adaptor, and in FIG. 24B the adaptor/abutment assembly is then being rotated in a clockwise direction for ideal placement of its tooth preparation and gingival contour. FIG. 24C depicts the rotated assembly having been inserted onto the implant with its engaging stud engaging the implant index (not shown), such that the abutment's primary indicium (321) is optimally situated over the implant, while the adaptor's primary indicium (121) has been relocated clockwise to the abutment's first secondary indicium (325). FIG. 24D shows the tooth preparation optimally situated after the rotations are completed.

Figure 24E:
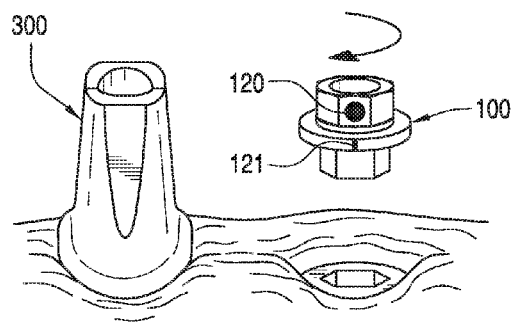
Figure 24F:
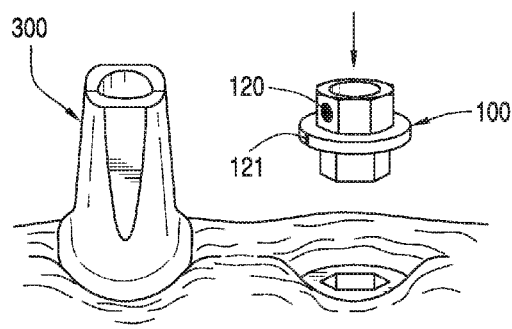
Figure 24H:
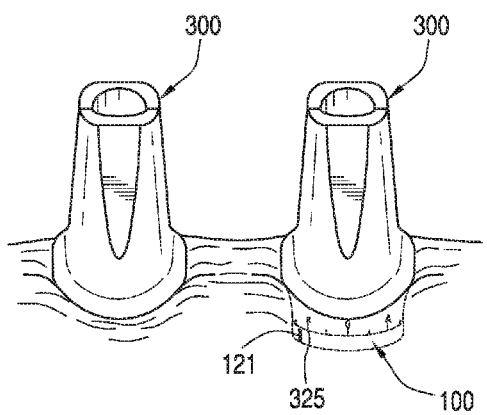
Figure 24G:
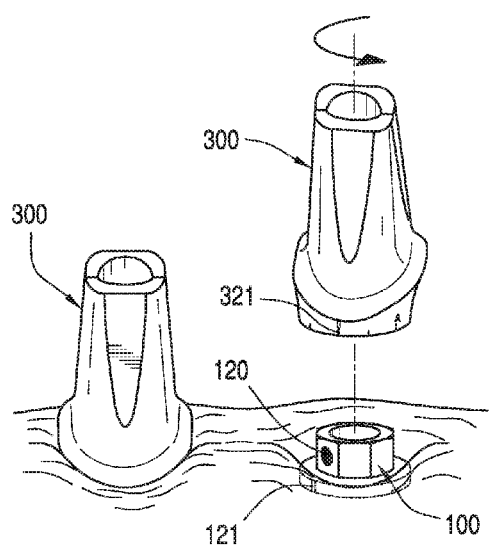
Figure 24I:
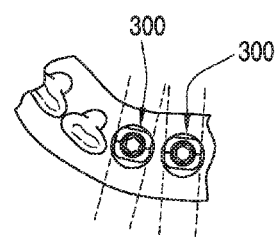
Figure 24J:
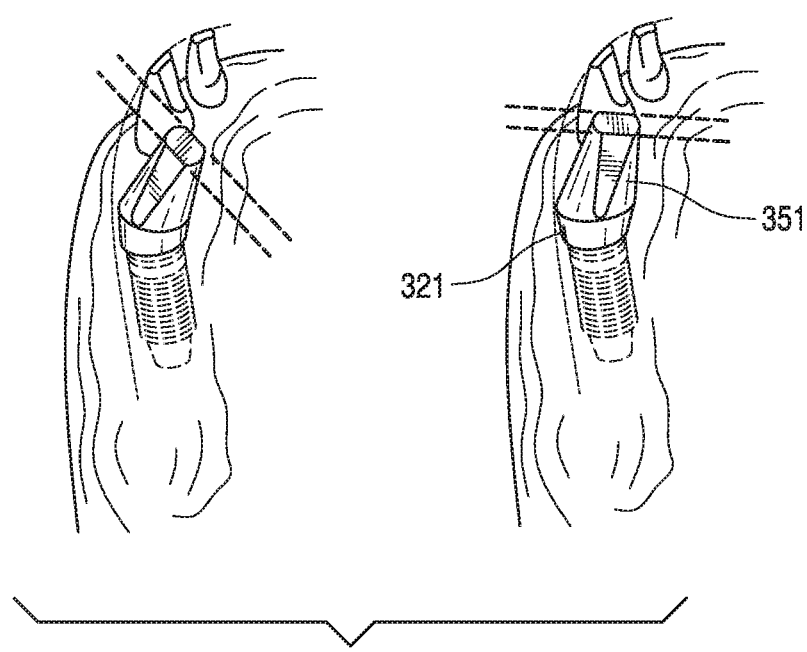

FIGS. 24E-6I show the rotation and situation of the abutment by first rotating the adaptor. In FIG. 24E, the adaptor is first being rotated clockwise to a predetermined position and is then inserted in the implant as shown in FIG. 24F. In FIG. 24G, the abutment (300) is then rotated in a counterclockwise direction such that its primary indicium (321) is ideally situated, with it then being seated on the implant as shown in FIG. 24H. Once again, FIG. 24I shows the tooth preparations having been rotated into ideal, situated positions.

FIGS. 25A-F show the repositioning of a tooth preparation (373, 372) and asymmetric gingival contour (331) in a proper position over the implant via the technique shown in FIGS. 24A-D. FIGS. 25A and B show the abutment's tooth preparation (373) with its chamfer (372) and its gingival contour (331) from a frontal view and a slightly rotated view, after the abutment is rotated counter clockwise one stop to its first secondary indicium position (325), (a), which, in this embodiment, is a 45° counter clockwise rotation. FIG. 25C shows the abutment being connected to the adaptor at that rotation point such that the secondary indicium (325) is lined up over the adaptor's primary indicia (120, 121). 25D shows the adaptor/abutment assembly then being rotated over the implant such that the abutment's primary indicium, 321, is optimally situated over the implant which, in this example, positions it to the right of the adaptor's primary indicium (121). FIG. 25E shows the rotated assembly of abutment (300) and adaptor (100) being inserted in the implant (10) with the abutment's primary indicium (321) optimally situated over it. And FIG. 25F shows the assembly (300/200) having been inserted into the implant (10) in the optimally situated position. This "optimally situated" position may not have its final position exactly at the 0° line of the center axis, but will be located 7.5° or less from that position, which is clinically imperceptible in relation to a 360° rotation, and is determined by the degree of the misalignment of the implant's index during its insertion. The principles shown above for FIG. 6 can be used in exactly the same way for any type of abutment, including the universal multifunction abutment, which is shown in FIGS. 49-69C.

In certain embodiments, the polygonal structure at top end of the adaptor is an octagon stud and the bottom end of the adaptor is a hexagon, tripod, dodecagon or other configuration wherein the number of polygonal sides of the implant engaging polyhedron is a multiple of 3 and the contour or multifunction abutment have an octagon or hexadecagon receptacle that engages the octagon stud of the adaptor such that the relative angular position of the adaptor to the contour or multifunction abutment followed by their assembly to the implant results in net 15° increments of horizontal rotation when the engaging receptacle of the abutment is an octagon or results in net 7.5° increments of horizontal rotation when the engaging receptacle of the abutment is a hexadecagon.

In other embodiments, the polygonal structure at the top end of the adaptor is a hexagon stud and the bottom end of the adaptor is an octagon or other configuration wherein the number of polygonal sides is a multiple of 8 and the contour or multifunction abutment have a hexagon or dodecagon receptacle that engages the hexagon stud of the adaptor such that the relative angular position of the adaptor to the contour or multifunction abutment followed by their assembly to the implant results in net 15° or 7.5° increments of horizontal rotation when the engaging receptacle of the abutment is an octagon or results in net 7.5° or 3.75° increments of horizontal rotation when the engaging receptacle of the abutment is a hexadecagon.

The polygonal structure at the top end of the adaptor can also be a nonagon stud and the bottom end of the adaptor a quadragon. In such embodiments, the prosthetic component has an nonagon receptacle that engages the nonagon stud of the adaptor such that the relative angular position of the adaptor to the prosthetic component followed by their assembly to the implant results in net 10° increments of horizontal rotation when engaging the receptacle of the prosthetic component.

When these rotations are performed to align the adaptor's primary indicium in relation to a specific primary or secondary indicium of the abutment such that the abutment's primary indicium is ideally situated, and when the registration devices are synchronized to the adaptor's or indexed healing cap's primary indicia, then the impression or intraoral, bench, or cone beam (CBCT) scan techniques are simplified and consistent. In addition, when this technique is performed prior to the impression or scan, then the milled, pressed, and/or cast abutment will have a more natural emergence profile and ideal positioning, regardless of the coarseness of the implant's rotation increments (trichannel at 120° vs. a hexagon at 60°), etc., and the degree of misalignment. Once the abutment has been ideally positioned, the pertinent data such as location of the adaptor's primary indicium in the vertical axis of rotation, the type of abutment at that "tooth" position, the desired vertical angle correction of the abutment, the identification of the primary or secondary indicium that was chosen to ideally situate the abutment, the desired gingival architecture, and other pertinent data are conveyed to the milling program's milling device codes to create an improved abutment. Of course, with the Universal System's scan code being conveyed to milling device codes of the program, the milling process becomes automated, but it can also be interactive in that the technician can manually manipulate the virtual components. Of course, a cast or pressed abutment is fabricated in the same manner by realigning and preparing an abutment pattern.

Figure 26A:
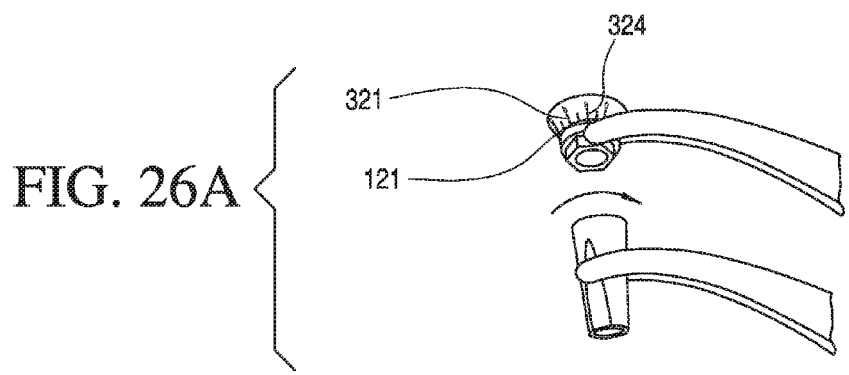
FIGS. 26A-C illustrate how a surgeon or restorative dentist can rotate an abutment about the universal adaptor to achieve the proper aesthetic alignment of the abutment.

In FIG. 26A, it is shown how a surgeon or restorative dentist could rotate an abutment about an adaptor to achieve aesthetic alignment of the abutment. For example, using the automated and/or interactive clinical protocol, the surgeon or restorative dentist can determine the extent that the implant index is out of proper aesthetic alignment. Using the universal adaptor, the surgeon or restorative dentist can rotate an abutment about the adaptor to the correct indicia to achieve proper realignment of the abutment relative to the proper aesthetic angle. The rotation can be in the clockwise or counterclockwise direction depending on the orientation of the underlying implant.

Figure 26B:
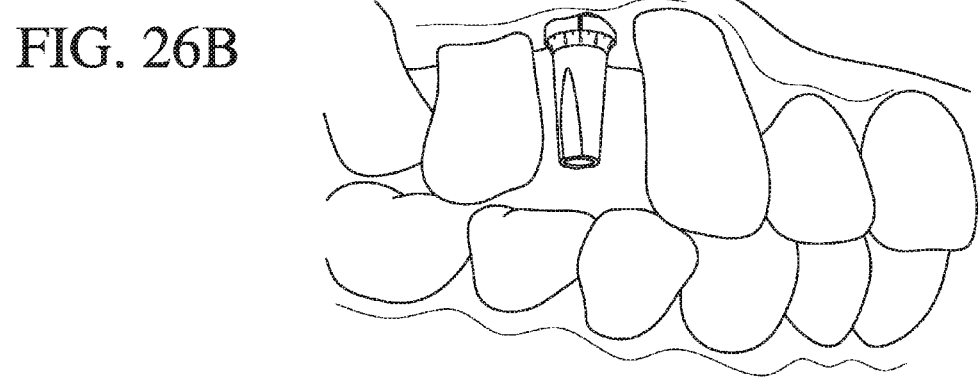
Figure 26C:
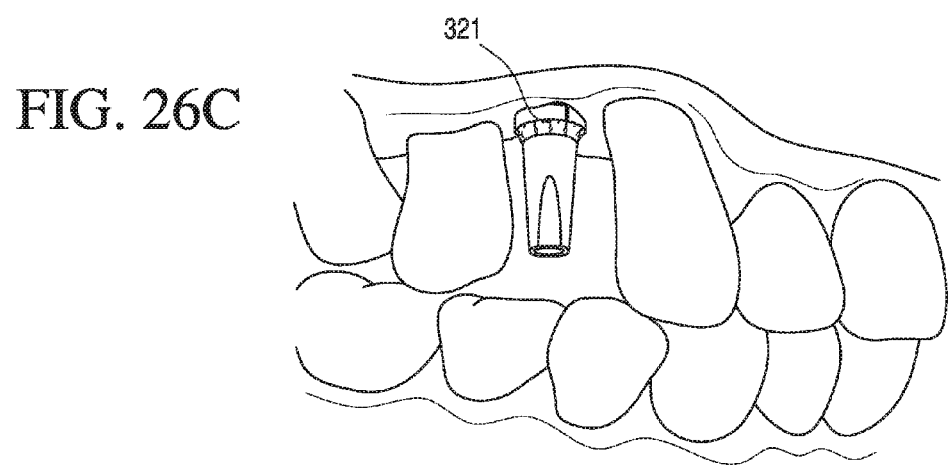

FIG. 26B shows how the abutment would be out of proper orientation if it were implanted in convention manner and FIG. 26C shows how the universal adaptor and clinical protocol allow for the simple reorientation of an abutment.

Figure 96:
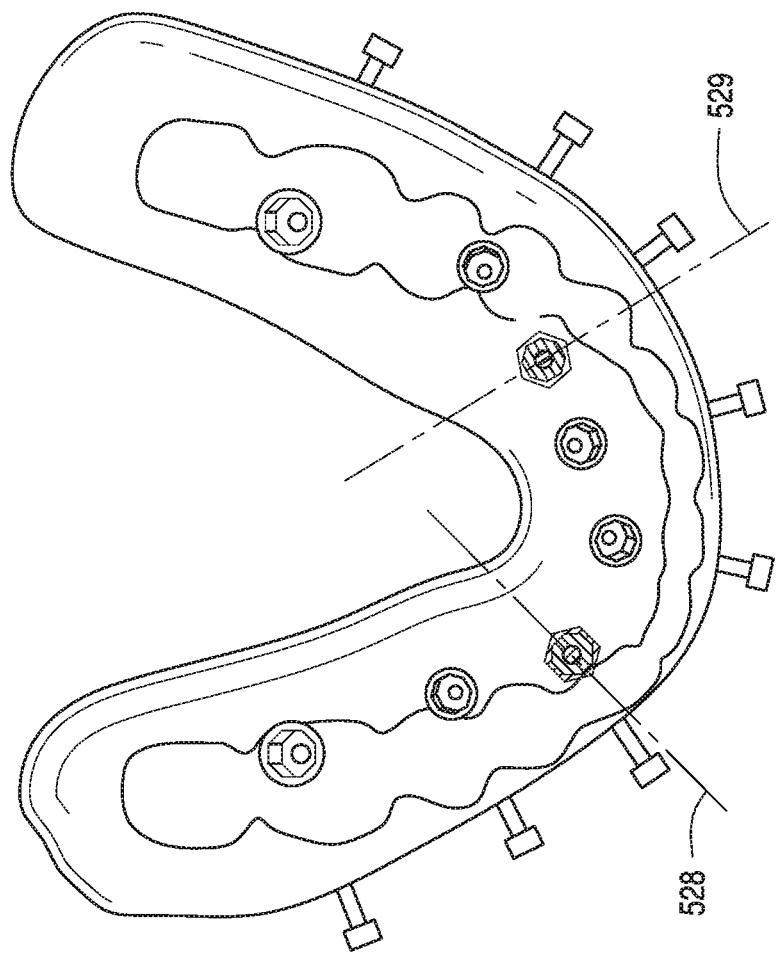

II. The Universal Abutment Systems' Common Features (FIGS. 1-96)

The Universal Contour Abutment System illustrated in FIGS. 1-39B and the Universal Multifunction Abutment System shown in FIGS. 49-69, 93-96 are two abutment systems that, in combination with the Universal Aligning Adaptor System are used to restore dental implants. The Universal Contour Abutment System is used for the restoration of dental implants with traditional "crown and bridge" abutments and their overlaying cement-on or screw retained crowns, sets of splinted crowns, or bridges, whereas the Universal Multifunction Abutment System is used when restoring implants with any screw borne prosthesis in an area of the jaw which could be receiving a removable appliance. It either replaces the removable appliance with a screw retained (fixed) hybrid denture or upgrades the removable denture or partial denture with a screw borne overdenture prosthesis. In addition, due to the versatility of the Universal Multifunction System in those areas that emanates from decoupling the abutments' dependence upon the coarse increments of rotation of their implants and replacing them with the finite increments of rotation (15° or less) provided by the Universal System, the abutments of the Universal Multifunction Abutment System can also be used for creating screw retained crowns, a set of crowns, or bridge without any flange. In other words, where appropriate, a full denture can even be replaced with a full set of screw retained crowns (no denture flanges) on the same day that the implants are inserted.

As used herein, an "ideally situated" contour abutment refers to the specific alignment which yields a tooth preparation as straight up and parallel to other abutments as possible, for proper aesthetics and function. An "ideally situated" multifunction abutment, however, is one in which the fixation mechanisms are positioned as close as possible to the center of the occlusal table of the replacement tooth overlaying the implant, which, in certain embodiments, focuses on the alignment and positioning of screw access holes for proper aesthetics and function. Although the present application uses the same "ideal alignment", "ideal situation" and/or "ideally situated" terms when discussing both contour and multifunction abutments, it is understood that, based on the distinct underlying purposes of the abutment types, these terms have different meanings with respect to the definition of "ideal" as it relates to criteria for preferred positioning. A surgeon or restorative dentist would necessarily understand the difference in usage of this terminology, as it applies to the classes of abutment componentry.

All types of abutments can be rotated into position over a universal aligning adaptor such that the abutment is situated in an ideal position in relation to the implant's index as needed. From this ideal position, an impression or scan can be performed with a crown or other prosthetic device then being fabricated to fit on it.

All abutments can be fabricated out of a variety of restorative materials and techniques. In at least certain embodiments, a castable abutment is rotated into position over a universal aligning adaptor such that the abutment is situated in an ideal position in relation to the implant's index and is prepared as needed such that a final cast abutment for engaging the adaptor's index is fabricated. The assembly can then be inserted on the implant with its primary indicium in the same preferred position, which can then receive a crown or other prosthetic device.

In certain embodiments, a titanium, zirconia, or other preformed, prepable abutment can be rotated over an adaptor and prepped with the combined adaptor/abutment assembly then being affixed to the implant.

In certain embodiments, a castable abutment composed of a castable material suitable for casting abutments is rotated into position over a cast-to adaptor which is also composed of a suitable castable material such that the abutment is rotated to an ideal position in relation to the implant's index. In this position, the abutment can be affixed to the cast-to adaptor. The abutment and adaptor can then be cast as a single piece, final abutment for engaging the implant's index without an interfacing adaptor, and is then inserted on the implant. A crown or other prosthetic device is seated on this abutment.

In certain embodiments, a zirconia abutment is rotated into position over a universal aligning zirconia adaptor, affixed to the adaptor, prepared as needed as a final abutment with the analog being directly inserted on the implant which then receives a crown or other prosthetic device. The zirconia abutment and the zirconia can be fused together to become a single abutment.

In certain embodiments, a pressable abutment composed of a ceramic or other pressable material suitable for pressing abutments is rotated into position over an adaptor which is also composed of a ceramic, Zirconia or other suitable pressable material such that the abutment is rotated to an ideal position in relation to the implant's index. In this position, the abutment can be affixed to the pressable adaptor. The abutment can then be pressed as a single piece, final abutment for engaging the implant's index without an interfacing adaptor, and is then inserted on the implant. A crown or other prosthetic device is seated on this abutment. The abutment could also be pressed to an adaptor composed of a dissimilar material that would accept the pressable porcelain or other suitable material without distorting.

A milled abutment comprised of any suitable restorative material can be virtually rotated into an ideal position over an adaptor using the universal aligning system's automated and interactive clinical protocol in a milling software program to eliminate mesial-distal misalignment prior to milling the abutment and then milled either as a single piece, final abutment for insertion on the implant as it engages its index without an interfacing adaptor or is milled to be receivable on the adaptor with the assembly then being inserted on the implant with a crown or other prosthetic device being seated upon it. In an alternate aspect of the invention, the abutment can be manufactured from an additive manufacturing process, such as stereolithography or 3D printing.

All abutments are decoupled from their implant indexes and are recoupled to adaptors, and, therefore, have the ability to be rotated as needed in 15° or less increments. In certain embodiments, the adaptor and the abutment can have dissimilar polygonal structures and co-operable indicia such that the rotation of the adaptor and abutment results in increments of horizontal rotational adjustment over the implant to a predetermined position. The polygonal structure at the top end of the adaptor can be an octagon stud and the end of the adaptor can be a hexagon, tripod, dodecagon or other configuration wherein the number of polygonal sides is a multiple of 3 and the abutment has an octagon or hexadecagon receptacle that engages the octagon stud of the adaptor such that adjusting the relative angular position of the adaptor to the abutment followed by their assembly to the implant results in net 15° increments of horizontal rotation when the engaging receptacle of the abutment is an octagon or results in net 7.5° increments of horizontal rotation when the engaging receptacle of the abutment is a hexadecagon.

In other embodiments, the polygonal structure at the top end of the adaptor is a hexagon stud and the end of the adaptor is an octagon or other configuration wherein the number of polygonal sides is a multiple of 8 and the abutment has a hexagon or dodecagon receptacle that engages the hexagon stud of the adaptor such that adjusting the relative angular position of the adaptor to the abutment followed by their assembly to the implant results in net 15° increments of horizontal rotation when the engaging receptacle of the abutment is an octagon or results in net 7.5° increments of horizontal rotation when the engaging receptacle of the abutment is a hexadecagon In other embodiments, the polygonal structure at the top end of the adaptor is a nonagon stud and the bottom end of the adaptor is a quadragon and the prosthetic component has an nonagon receptacle that engages the nonagon stud of the adaptor such that adjusting the relative angular position of the adaptor to the prosthetic component followed by their assembly to the implant results in net 10° increments of horizontal rotation when engaging the receptacle of the prosthetic component.

In certain embodiments, the co-operable indicia include graduated reference points and/or a mechanism of primary and secondary indicia that establish the rotation and synchronization points.

In certain embodiments, the co-operable indicia include graduations for indicating the degree of rotation of the abutment and the adaptor relative to each other. The co-operable indicia can also include primary and secondary indicia such that the primary indicium of the adaptor is rotatable in relation to the primary or secondary indicium of the contour or multifunction abutment as it is rotated to its desired predetermined position such that its primary indicium is ideally situated. In this way, the primary indicium of the abutment can determine the position of the contour or multifunction abutment post/adaptor assembly as it is rotated into its preferred position.

The primary indicium of the adaptor can be an engaging polyhedral fixture. In such embodiments, the engaging polyhedral fixture provides a positive seat when engaging the primary or secondary indicia of the abutment possessing a mating reciprocal polyhedral fixture.

The Multifunction Abutment can also have a polyhedron on its top surface that is shaped to receive another polyhedron with a matching engaging configuration that is inserted over it, engages it, and is, in turn, connected to the prosthetic device via a chemically cured, light cured, or other combination method to create the screw retained prosthesis.

In certain embodiments, that polyhedron on the abutment can be a cone whose primary indicium is approximately 180° from the midpoint of the vertical angle correction point on the abutment and the engaging polyhedron is a cylinder. The cone can also have a flat at its primary indicium which provides a positive seat at its primary indicium of the connecting cylinder during the assembly phase, which also prevents natural rotational forces associated with a cylinder on a cone from dislodging it.

III. The Universal Contour Abutment System (FIGS. 1-26C)

The Universal Contour Abutment can be one of a plurality of devices including but not limited to temporary abutment posts, final preformed abutment posts, cast abutment posts, pressed abutment posts, or milled abutment posts, or other posts fabricated by another suitable means that receive implant crowns, set of crowns, bridges, and other prostheses for restoring dental implants that can either be cemented or screw retained.

Specifically, in certain embodiments, the base of the abutment has a preformed symmetrical configuration such as a cylinder, conical shaped cylinder, or other appropriate configuration to support the gingiva. Once the abutment has been rotated to ideally situate it, its base can also have a preformed asymmetrical configuration to support the gingiva with an emergence profile that is similar to a natural tooth that would be in that implant fixture's position. Additionally, interim abutments or healing caps, and impression, scanning, or imaging posts or other tissue engineering prosthetic devices can share the same preformed symmetrical or asymmetrical configuration as the base of the abutment to develop a custom emergence profile.

In certain embodiments, the abutment has standardized preformed anterior and posterior tooth abutment preparations over custom contour gingival bases. Ideally, the abutment can also have preformed tooth abutment preparations of maxillary or mandibular incisors, canines, premolars, or molars over custom contour gingival bases.

The Preformed Standard Abutment (Unprepped) Features:

Further provided is an assembly for initiating tissue training comprising, in combination, a polyhedron device to be received in a dental implant and a guided tissue punch having an internal configuration to match to the configuration of the polyhedron device with a preferred diameter for the tissue opening over an implant, wherein the tissue punch is rotated over the polyhedron which centers the tissue punch such that it creates the exact opening over the implant as it is rotated over the polyhedron until it excises the tissue along the central axis of the implant, regardless of its vertical angulation (FIGS. 7 and 8). The polyhedron can be a surgical guiding screw with a long cylindrical shank, which is first threaded in the dental implant and is followed by the rotation of the guided tissue punch having an internal configuration to match to the shank of the screw until it excises the tissue over the implant.

In an alternate aspect of the invention, a hand piece drill including a drill bit can also be used to excise the tissue along the central axis of the implant. The drill bit can be rotated over the guiding screw or other polyhedron which centers the drill bit such that it creates the exact opening over the implant as it is rotated over the polyhedron.

Use of the Preformed, Unprepared Abutment:

Also provided is an automated, simplified crown and bridge implant restoration, wherein an adaptor to be received and seated on a dental implant in a predetermined position relative to the implant, which, in turn, receives a preformed, unprepared abutment having an asymmetric configuration upon which an interim coping and a referencing coping are individually seated, all of which have cooperable indicia for aligning, synchronizing, and referencing the interim abutment to create the final abutment, comprising the steps of rotating the adaptor and abutment relative to each other such that the abutment is in a predetermined, preferred position that is then noted, aligning and seating an interim preformed coping composed of acrylic or another suitable temporary restorative material for molding a temporary crown to it such that it is automatically in the preferred position, removing the interim coping/temporary crown assembly, seating a referencing coping with the same alignment as the interim coping to identify and register the position of the adaptor and the abutment, and fabricating a final crown to seat on the abutment or another final abutment having the same preferred horizontal and vertical position as the interim abutment.

The co-operable indicia can include graduations for indicating the degree of rotation of the abutment and adaptor relative to each other. The co-operable indicia can include primary and secondary indicia such that the primary indicium of the adaptor is rotatable in relation to the primary or secondary indicium of the abutment as it is rotated to its desired predetermined position.

The acrylic coping can be seated on the abutment such that its primary indicium is aligned with the primary indicium of the abutment prior to relining a previously fabricated or molded temporary crown. The referencing coping can be seated on the abutment to identify and reference its primary indicium that is aligned with the primary indicium of the abutment along with registering the primary and secondary rotation points of the abutment in relation to the primary indicium of the adaptor that were previously noted.

The referencing coping can be an impression coping that is removed within the impression and serves as a referencing and seating device for an abutment replica with the same geometry as the interim abutment with the model being poured and the final abutment being cast, pressed, or milled or fabricated by some other type of method such that it has the same relationship to the implant's index as the interim abutment or healing cap, which is followed by the fabrication of the overlying prosthesis.

In certain embodiments, the prosthesis is fabricated, and then seated on the interim abutment after the removal of the temporary crown or prosthesis, which, as a result, becomes the final abutment.

In certain embodiments, the referencing coping is a scanning coping with a geometric configuration that is ideal for an intraoral or bench scan to register the position and configuration of the interim abutment to create a milled abutment. The referencing coping can also be an imaging coping with a geometric configuration that is ideal for a CBCT scan to register the position and configuration of the interim abutment which is the matrix for creating the milled crown and/or abutment. In a preferred embodiment, the abutment's primary indicium itself is easily identifiable by a scanner.

The preformed abutment can have either a symmetric or asymmetric base with a preferred geometry of appropriate configuration and depth to vertically position the base in relation to the gingival architecture, because it is always in a preferred position.

The Universal Healing Cap and Interim Abutment with Preformed Gingival Architecture The Universal System provides preformed custom gingival contours, regardless of the degree of asymmetry of its healing caps or misalignment of implant index. An adaptor to be received and seated on a dental implant is rotated about in a predetermined position relative to the implant. The adaptor and the healing cap have co-operable indicia to direct the rotation of the healing cap to a generally desired horizontal predetermined position, when the adaptor is seated on the implant with the healing cap's primary indicium situated such that an abutment in that position would have its primary indicium in that ideal position.

In one aspect of the invention, the healing cap having a symmetric configuration is a cylindrical healing cap. In a further aspect of the invention, the healing cap having an asymmetric configuration is a non-cylindrical polyhedron. The asymmetric healing cap more naturally simulates a natural tooth, and can, therefore, facilitate soft tissue healing better than the symmetric healing cap.

The adaptor can also be first rotated over the implant to a predetermined position with the healing cap then being inserted over the adaptor in its preferred position. With either rotation, the co-operable indicia can include graduations for indicating the degree of rotation of the healing cap and the adaptor relative to each other. The co-operable indicia can include primary and secondary indicia such that the primary indicium of the adaptor is rotatable in relation to the primary or secondary indicium of the healing cap as it is rotated to its desired predetermined position.

The Indexed Healing Cap

Certain embodiments provide a method of restoring dental implants by using indexed healing caps or similar tissue supporting interim devices that are also referencing devices which have co-operable indicia for identifying and referencing adaptor and abutment positions without having to be removed from the implant. This thereby simplifies the fabrication of abutments and/or prosthetic devices for restoring dental implants. In certain embodiments, rotating the healing caps over their adaptors and the adaptor/healing cap assemblies over their implants according to an automated and interactive clinical and/or digital protocol are performed such that they are situated in preferred vertical and horizontal predetermined positions over their implants. The referencing posts such as impression posts, or the scanning posts can be inserted over an index on each healing cap such that the primary indicium of the referencing post is aligned in relation to the primary indicium on the healing cap's index with an impression, intraoral or bench scan, or a CBCT scan being taken of the healing cap/referencing post assembly such that it registers the adaptor's position in relation to the implant index, the indexed healing cap position in relation to the adaptor, the referencing post in relation to the indexed healing cap along with the other anatomic structures in the jaw. A cast, milled, or other abutments to those preferred positions, can be fabricated by following the implant prostheses.

The co-operable indicia can include graduated reference points and/or a mechanism of primary and secondary indicia such that the primary indicium of the adaptor is rotatable in relation to the primary and secondary indicia of the indexed healing cap as defined by the desired predetermined position of the healing cap.

The automated and interactive clinical and/or digital protocol includes choosing the appropriate indexed healing cap or similar prosthetic component having the desired geometric shape for the tissue over the implant, rotating it as necessary in either a predetermined clockwise or counterclockwise direction such that the primary indicium of the adaptor is positioned at a particular primary or secondary indicium point of the healing cap and is set in relation to the index of the implant such that its gingival contours are ideally situated in a preferred, predetermined position over the implant.

In certain embodiments, the primary indicium of the healing cap is located at the center point of the healing cap as it bisects the ridge at a 90° angle in the sagittal plane or another preferred position, which, therein, identifies the location for seating the impression or scanning post.

In certain embodiments, the primary indicium of the impression post, or scanning post overlay the primary indicium of the healing cap. The index of the healing cap can have a polyhedron adjacent to the primary indicium of the healing cap such that the polygon of the polyhedron is bisected at that point. The primary indicium on the polygon of the healing cap receives the impression or scanning post such that the primary indicia overlay each other and, thereby, capture the primary indicium at its center point.

In certain embodiments, the polygon is an index that is an exact replica of the abutment engaging index on the open end of the adaptor. The adaptors and healing caps can be appropriately positioned on a model fabricated from a fixture level impression with implant analogs in order to seat scanning posts for a bench scan.

The multiple indexed healing caps can be used in an impression, an intraoral scan, a bench scan, or a cone beam CT scan to create a set of abutments, along with either a screw borne prosthesis or a crown's bridge prosthesis over tooth abutment preparations. In certain embodiments, multiple indexed healing caps can be used to create a full arch splint over crown and bridge abutments or over screw receiving abutments to receive a screw-retained prosthesis.

The primary indicia of the adaptor determines the seating of the impression, scanning, or imaging post in relation to the healing cap's position via the primary indicia of the healing cap, therein, determining the preferred position of the final abutment whose primary indicia is similarly situated.

The primary indicium of the adaptor can be an engaging polyhedral fixture to provide a positive seat when engaging the primary or secondary indicia of the healing cap possessing a mating reciprocal polyhedral fixture.

The assembly can include a single screw for securing the healing cap onto the adaptor and the adaptor onto the implant in their predetermined positions.

The healing cap can be one of a plurality of symmetrical and asymmetrical devices of varying configurations that are seated on adaptors. The plurality of devices include gingivo-adaptors which are healing caps and adaptors that are combined into one-piece assemblies for connection to the implant (FIG. 8G), wherein the open end of the devices have the preferred configuration and/or index of the chosen adaptors and the free end has the configuration and/or index of the particular implants.

The healing cap can be composed from a plurality of materials including titanium, titanium alloy, zirconia, porcelain, or other suitable materials and can be coated by anodizing or some other method. The primary indicia of the healing cap can determine the position of the abutment post when it is to be rotated such that its primary indicium and that of the abutment are in the same preferred position.

The impression posts, scanning or imaging posts or other prosthetic devices can have preformed symmetrical configuration that match the configuration of the healing cap's base.

The healing cap can have an index on its open or top end with a primary indicium for situating a registering device such as an impression post or a scanning or imaging post for impression taking or intraoral or bench scanning or CBCT scan imaging after the healing cap has been rotated into a preferred position. The index is not limited to any one polyhedron and can be protruding or recessed. The index can have the same configuration as the underlying adaptor stud, and has the same geometry and position of its polyhedrons.

FIGS. 27-31 show representative configurations of the universal contour healing caps and abutment posts, which, in this embodiment, mimic the shape at the gingival margin of natural teeth from the gingival attachment to the free gingival margin. These polyhedrons are examples of a large array of possible gingival contour healing caps or abutments, and are, therefore, not limited to the configurations shown here. For instance, even though these healing caps show recessed prosthetic component engaging polyhedrons (405), the universal contour healing caps can come with an array of internal or external engaging polyhedrons or can come without any prosthetic component engaging points. Although the prosthetic component engaging polyhedrons (405) (e.g., FIG. 28) are depicted as being oval cylindrical recesses of equal dimensions, it is understood that the prosthetic component engaging polyhedron can be any polyhedron shaped recess or protrusion, i.e., circular, rectangular, square, pentagonal, in any combination, etc. In at least certain embodiments, the prosthetic component engaging polyhedrons (405) are non-uniformly positioned about the surface of the healing cap such that they can only be paired with their counterpart protrusion or recess in a predetermined configuration. Alternatively, the prosthetic component engaging polyhedrons (405) are uniformly positioned about the surface of the healing cap, but at least one of the set of prosthetic component engaging polyhedrons (405) has a different shape or size than the other prosthetic component engaging polyhedrons (405) such that they can only be paired with their counterpart protrusion or recess in a predetermined configuration.

FIG. 27 shows examples of maxillary teeth in the axial plane at their cervix: a representative central incisor (441), lateral incisor (442), canine (443), premolar (444), and molar (445), and FIG. 28 shows examples of mandibular teeth in the axial plane at their cervix: a representative central incisor (446), canine (447), first premolar (448), second premolar (449), and molar (450). The examples shown have primary reference indicia (421) and secondary reference indicia (422, 423, 424) that are located counter clockwise to the primary indicium and secondary reference indicia (425, 426, 427) that are located clockwise to the primary indicium, which in this embodiment are located at 45°, 90°, and 135° away from the primary indicium (421). This invention is not limited to these rotation points, which can be established in any manner which would provide a preferred rotation.

In one aspect of the invention, a kit can contain a library of healing caps including at least one of each of the maxillary central incisor (441), maxillary lateral incisor (442), maxillary canine (443), maxillary premolar (444), maxillary molar (445), mandibular central incisor (446), mandibular canine (447), mandibular first premolar (448), mandibular second premolar (449), and mandibular molar (450).

Recessed engaging polyhedrons (405) for receiving impression posts or scanning posts (shown here) are located on the top surface of these and other healing caps and are described in detail in FIG. 28, which also shows an external index in another embodiment. There are many permutations and combinations of these healing caps, including those that have different reference indicia and engaging polyhedrons, and those that may not have any recessed or external engaging polyhedrons or indexes, at all. Versions of these healing caps that are symmetrical (cylindrical, etc.) are shown in (FIGS. 30, 37, 38 and 47) with some or all of the reference markings and polyhedrons described above can also be used. Even though depicted as being symmetrical, their primary indicia are set in relation to the primary indicium of the universal aligning adaptor for the purpose of situating, aligning, synchronizing and referencing all other components. For example they help set all impression and scanning posts and abutments in relation to the implant's index. The universal contour healing caps and/or their facsimile can be used for surgical excision and gingival shaping (see FIGS. 47-48 below), for tissue training after implant exposure or during immediate load or immediate tissue load procedures, as the base for temporary and permanent abutments, and as a platform for receiving impression and scanning posts and other restorative devices.

FIGS. 29A-B illustrates a frontal and side view of an abutment with an asymmetric maxillary premolar tooth preparation (344) and preformed, scalloped gingival contours (340) with an extended depth (338). The extended depth (338) of the abutment allows for the preformed, scalloped gingival contours (340) to be positioned above the gum line. The length of the extended depth (338) can be increased or decreased depending on the health of a patient's gum tissue or other considerations by the surgeon. While FIG. 30 illustrates an array of generic anterior and posterior abutments with symmetrical cylindrical collars: an anterior tooth preparation (332) making a 30° vertical angle correction (356), a medium sized posterior tooth abutments (333) making 0° (353), 15° (354) and 30° (356) vertical angle correction, and a larger posterior abutment (334) making a 0° (353) angle correction. There are a variety of abutment shapes and gingival contours of changeable depths that can be used for the healing caps and abutments.

It is also possible to make horizontal angle corrections with the devices and methods of the present invention. Therefore, for example, with 351 it is possible to achieve a 15° horizontal angle correction. It is further contemplated that the devices and methods of the present invention can achieve 7.5° horizontal angle correction (by doubling the number of internal engaging flats of the abutment).

All of the abutments and healing caps in FIGS. 27-31 have the same horizontal rotation capability as delineated above. Specific interoperable devices and methods that the surgeon or restorative dentist uses when working with asymmetric and symmetric healing caps and abutments are shown in many figures throughout these drawings.

FIGS. 32-38, 39A, and 39B illustrate several configurations of universal healing caps that can be used to establish tissue training. Many of the universal healing cap configurations can serve as platforms for impression and scanning posts and abutments. Some of the universal healing cap configurations can be asymmetrical, as shown in FIGS. 32-36 and other ones can be symmetrical as shown in FIGS. 37 and 38. Anatomically correct healing caps expand the capabilities of immediate tissue loading (no occlusal forces) and can train the tissue to a preformed, custom contour without any occlusal loading forces. Final preformed, cast and milled abutments can be made having matching gingival contours, which provides greater precision with less work by the technician or the restorative dentist. All of them are fabricated, rotated and seated on the implant in the same manner as shown for the abutments, in FIGS. 9A-25F with the adaptor or base unit and the healing cap either being rotated or counter rotated to reposition it to an ideal situation over the implant. Since the healing cap's primary indicium is set in relation to that of the adaptor such that it bisects the ridge in the sagittal plane, it establishes the reference plane for seating final abutments and all other cooperable components. This aligns impression posts, scanning posts, and other such componentry in a set way in relation to the universal aligning adaptor's primary indicia, and, therefore, to the implants' indexes, whether the impression is taken on the healing cap or directly on the adaptor.

FIGS. 32-39B illustrate a variety of healing cap/adaptor combinations that are set in relation to the primary indicium of the adaptor. They come either with a smooth top surface such as the non-indexed asymmetric healing cap that is shown in FIG. 32, or the non-indexed cylindrical version (not shown in these drawings), or have external or internal indexes or polyhedrons on their surface that allow the surgeon or restorative dentist to insert impression posts or scanning posts directly on them, after they have been rotated, thereby capturing the exact position, vertical angulation, tissue contour and depth, and other pertinent information without having to remove them. This dramatically simplifies implant restoration technique. The registration techniques (impression or scan) are shown in detail in FIGS. 70-92.

FIG. 32 shows an asymmetric healing cap (400) having primary indicia (421 and 411) that have been placed in a predetermined position on the healing cap, which, in this embodiment, is configured to be seated on the adaptor (100) such that the primary indicia of the healing cap (411, 421) and those of the adaptor (120, 121) overly each other, which signifies that no rotation is to be performed (0° rotation) in relation to its primary indicia (120 and 121). Once the assembly is inserted on the implant, a single fixation screw (200) secures the healing cap to the adaptor and their assembly to the implant.

FIGS. 33-39B also demonstrate the relationship of their individual healing caps to their adaptors without any horizontal angle correction. FIGS. 33 and 34 show the asymmetric indexed healing cap (401), with an external index (406) configured to receive a universal impression post or scanning post in order to take a direct impression or take a scan without having to remove the healing cap. FIG. 33 shows an embodiment of the indexed asymmetrical healing cap (401) having an external index (406) or an internal index (not shown) such that one of its flats is bisected by a line drawn from the primary indicia of the healing cap (411, 421) and has a primary indicium (418) that is aligned with them at that point. This determines the seating of all components on the healing cap that has been positioned in a set way in relation to the adaptor and to the underlying implant. In this example, the index is an octagon that mimics and overlays the octagon stud of the adaptor upon which it is seated with its primary indicia (120, 121) directly below. But, once again, the index can be any external or internal polyhedron that serves as a reference guiding plane for a paired polyhedron index on the impression post, scanning post or any other component seated on it in relation to the adaptor stud. This index can be a match to the underlying adaptor's or implant's index (e.g., octagon healing cap index (406) to an adaptor's octagon index) such that their flats are aligned in relationship to each other, or can also have some other index that is set in relation to the underlying index of an adaptor or implant. Certain embodiments have an external or internal index surrounding the screw access hole with the same number of flats as the adaptor upon which the impression posts or scanning posts are seated such that their primary indicia overlay those of the healing cap, which therein registers the exact position of the adaptor's index and primary indicium in relation to the healing cap's primary indicia.

FIG. 34 shows the indexed healing cap (401) being seated on a generic adaptor (100), which does not have any primary and secondary indicia, but utilizes the same situating techniques outlined above. In this illustration, the primary indicia of the healing cap (411, 421), along with the first rotation stop (415 on the collar, 425 on the top), which here represents a 15° horizontal rotation and the second rotation stop (426) for a 30° horizontal rotation are shown. These rotation points (425, 426) are some of the secondary indicia located in the clockwise rotation sequence.

These primary and secondary indicia of the healing cap and their relationship to the primary indicium of the adaptor help define the predetermined increments of rotation for repositioning, aligning, synchronizing, and referencing all other co-operable abutments and other prosthetic components according to an automated and/or integrated clinical and/or digital protocol. Once again, the prosthetic components, therein, are decoupled from dependence upon the coarse rotations around the implant's index, which is substituted by the much more refined increments of rotation of the adaptor system, such that the surgeon or restorative dentist can precisely position the healing caps or abutments and, therein, establish the most natural gingival contours of the gingiva over each implant. It is important to note that the techniques for ideally situating the gingival contours of the healing caps are applicable to the universal contour abutments, as well. Furthermore, it is understood that the surgeon or restorative dentist may elect to use an interim abutment having the same gingival architecture instead of the matching healing cap.

FIG. 35 illustrates the use of the universal asymmetric indexed healing cap (401) that directly connects to the implant having a base unit with an external index (406), in this case an octagon, on the top that receives the impression post or scanning post, and has a hexagon protrusion at the base for insertion into a hexagon implant, in this example. This embodiment will fit into any implant having any index, but the adaptor and the abutment or healing cap must first be rotated or counter rotated to position it such that the overlaying abutment will be ideally situated over the implant. It is understood that, as used herein, the concept of rotation and counter-rotation involves the separation of the adaptor from the abutment or healing cap, as the case may be, and then rotating or counter-rotating it to reposition the indicia relative to each other. The technique is detailed in the description of FIG. 38, below. In this case, the direct connect indexed healing cap (or referencing abutment) can also be used, at the time of implant insertion, to serve as a guide for situating the fixture when it is being secured to the bone by centering the primary indicium of the healing cap in the sagittal plane as it bisects the jaw at that point. The examples shown above are for demonstration purposes only, and are not limited to the use of any specific polyhedrons being used to center the healing caps and receive the impression posts and scanning posts. The universal indexed healing cap can have several versions of external or internal polyhedrons, including ones that have been separately positioned in relation to the healing cap's indicia or those that are indexes over the screw access hole and are set in relation either to the healing cap's primary indicium or to the underlying adaptor's primary indicium where applicable.

As an example, FIG. 36 shows another asymmetric healing cap (408) which can receive the impression post or scanning post in recessed polyhedrons (405) of any type. Of course external polyhedrons of a similar position and shape can also accomplish the indexing of the impression or scanning post. Shown in this example are the primary indicia (411, 421) and the secondary indicia (425, 426). Also shown are standard gingival contours (430). It is understood however that gingival contours can be provided as preformed custom bases depending on the intended location of the healing cap. Therefore, it is contemplated that healing caps could be made with gingival contours configured for the mandibular, maxillary, posterior or anterior positions or orientations.

FIG. 37 provides a universal cylindrical (symmetric) indexed healing cap (403) that is optimally situated with the techniques outlined above in the description of FIG. 33 in order to establish the ideal situation of the primary indicium of the healing cap (421) and its index (411). These primary indicia serve as the reference points for seating the impression posts, scanning posts, and abutments seated, even though the rotation of the healing cap does affect any change in gingival contours. This healing cap has a cylindrical collar (437). The impression or scan is achieved without the restorative dentist having to remove the healing cap. FIG. 38 discloses a direct connect, one piece, cylindrical healing cap (404) that, when rotated with an interfacing abutment, will find the ideal position for restoring the implant with any angle correcting abutment such that the misalignment of the implant's index has been eliminated.

FIG. 38 illustrates, as another embodiment, an example of the direct connect, universal aligning symmetrical healing cap (404) that can be connected to any implant, rotated in set, horizontal increments until its external index is situated such that an abutment can be placed in a preferred position over the implant, regardless of the misalignment of the implant's index. In this example, a hexagon implant is receiving the healing cap (404) which has an external octagon stud. This embodiment is demonstrating that, even though the octagon stud on top of the cylindrical healing cap and the hexagon projection that is inserted in the implant are one piece, it can be finely rotated about the vertical axis, achieving an optimal positioning within a maximal 7.5° deviation from the ideal direction until the healing cap is positioned until an overlaying abutment is ideally situated. When the primary indicia of the healing cap (421, 411) are in a sagittal plane that bisects one of the hexagon flats of the projection that is inserted into the implant, the abutment can be seated on the index and simultaneously rotated over the healing cap to assist in locating the center point. Unlike the previous examples, the primary indicia of the healing cap (421, 411) are not optimally situated, but rather are rotated until the overlying abutment is ideally placed within 7.5° of the ideal configuration. In these examples, the impression and scan posts are seated such that their primary indicia are aligned with the primary indicium of the healing cap (411), which registers the primary indicium of the adaptor, as well. This embodiment is not limited to this healing cap with an octagon index stud and a hexagon implant projection, but, rather, can be used in any number of combinations of dissimilar indexes.

FIG. 39A and FIG. 39B illustrate the low profile, scalloped healing cap with sides that are higher than the recessed center, which keeps the margins of the gingiva from growing over the healing cap, while providing enough room to receive an overlaying interim replacement tooth. FIG. 39A shows a scalloped healing cap (407) that maintains the opening over the implant having been seated on an adaptor (120). FIG. 39B shows the indexed version of the scalloped healing cap (409), which is seated on an adaptor and has an external index (406) having a primary indicium (428) that, without any rotation, overlays the primary indicium of the adaptor (120) and receives an impression or scan post for registration. An internal index on top of the healing cap can also be used to receive the impression or scan post.

Tissue Engineering

The Contour Abutment System applies a systematized tissue engineering protocol wherein abutments are created to match to gingival contours that are established when the implants are ready for tissue loading or occlusal loading. Rather than adjusting the gingival contours of the final abutments to match to the gingiva, the gingiva is sculpted to blend with the preformed gingival contours of the healing caps or interim abutments. Due to the unique rotations of the contour abutment system components in 15° or less increments along with their synchronization to the Universal Aligning Adaptor, even asymmetrical gingival contours can be created, registered, and translated in exact form to the gingival architecture of the final abutments.

Tissue engineering can begin with the use of a guided tissue punch having an internal configuration to match to the configuration of a polyhedron device that is first inserted in an implant, followed by the tissue punch being rotated over the polyhedron. This centers the tissue punch, regardless of its vertical angulation, such that it creates an exact opening over the implant as it is rotated over the polyhedron until it excises the tissue along its central axis of the implant. The polyhedron can be a surgical guiding screw with a long cylindrical shank, which is first threaded in the dental implant and is followed by the rotation of the guided tissue punch having an internal configuration to match to the shank of the screw until it excises the tissue over the implant. The Guided Tissue Punch excision is an optional procedure prior to creating the custom gingival contour, below.

Custom tissue engineering at the time of implant loading is provided by an adaptor and a set of tissue engineering components having co-operable indicia, including a healing cap, interim abutment or other prosthetic component whose preferred, preformed gingival contours serve as a template to develop the gingival architecture over an implant, a referencing device such as an impression, scan, or imaging post, whose base is a replica of the interim component such that it has the same gingival contours, and a final abutment whose base is also a replica of the interim component. In this embodiment, the tissue over the implant is initially opened. Then an adaptor and a chosen interim component is rotated relative to each other and their assembly relative to the implant via their co-operable indicia such that the desired gingival contours of the interim abutment are ideally situated over the implant to most naturally support the tissue with the proper emergence profile. The gingival tissue is sculpted as the adaptor/interim prosthetic component assembly is seated on the adaptor so that the tissue conforms to the architecture of the interim component. The interim component is removed from the adaptor and the appropriate referencing device is seated with the same relationship to the primary indicium of the adaptor. In this manner, it is possible to identify and register the component's gingival contours when they are ideally positioned.

The preformed abutment can have a symmetric or asymmetric base with a preferred geometry of appropriate configuration and depth to vertically position the base in relation to the gingival architecture.

Figure 42:
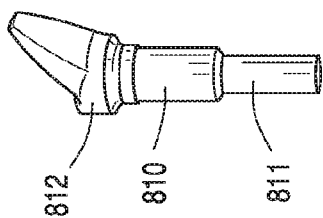
Figure 41:
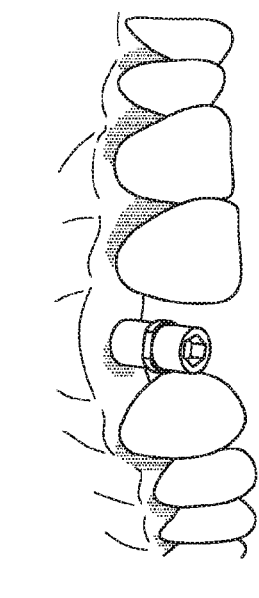
Figure 44:
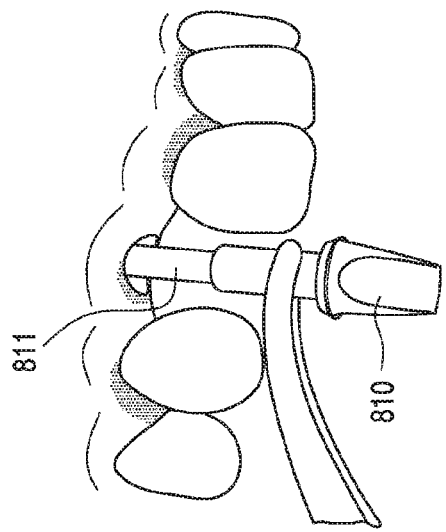
Figure 40:
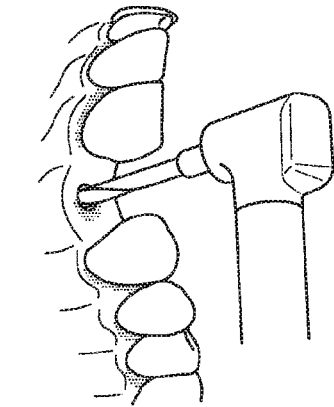
Figure 43:
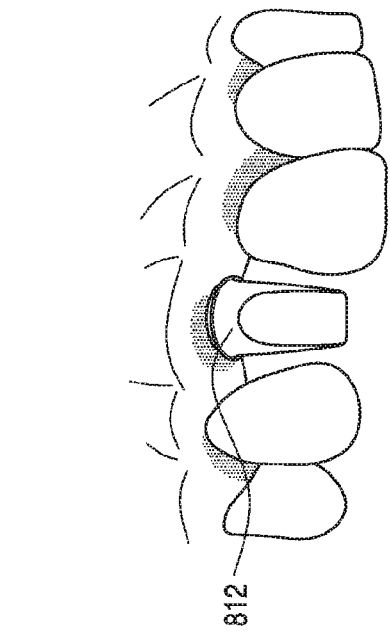

Once ideally positioned, the final abutment can be fabricated such that its base mimics the subgingival contours of the interim abutment, and removing the adaptor and the interim abutment and replacing it with a final abutment which also has co-operable indicia for precisely positioning its gingival contours with its gingival architecture having the identical gingival architecture over the implant FIGS. 40-46B disclose, in detail, devices and methods to control the insertion of the implant and the manipulation of the tissue above the site as described above. To begin with, FIGS. 40-46B show the use of anatomic universal paralleling posts during implant site preparation for the surgeon to visualize the adaptor/abutment assembly as the surgeon or restorative dentist will see it. FIG. 42 shows a universal anatomic paralleling tool, which provides the surgeon with the ability to see what the restorative dentist will have as a fully contoured abutment on an adaptor, as dictated by the osteotomy being drilled. In FIG. 40 the surgeon is drilling the first pilot hole, and in FIG. 41 the angulation of the projected implant as dictated by the underlying bone is illustrated, and in FIG. 42 it is shown that a 30° angle correcting paralleling post (810) with an anterior tooth abutment design (812) has been chosen to fit via a stem (811) with the same diameter as the sizing drill such that it fits into the osteotomy site. FIG. 44 shows the paralleling post (810) being seated in the osteotomy site. FIG. 43 shows that the paralleling post (810) with the abutment (812) near the crest of the bone can be used to assess angulation, position and parallelism using a replica of the future abutment.

Figure 45C:
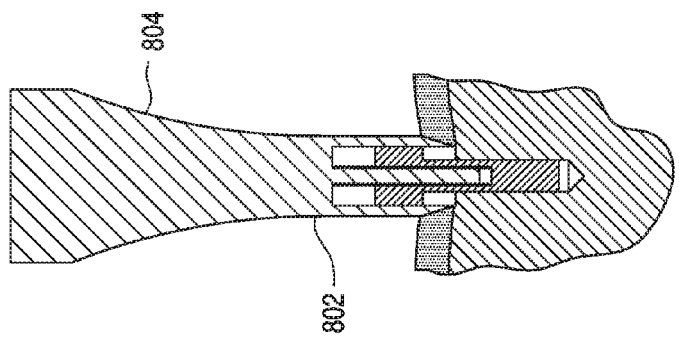
Figure 45B:
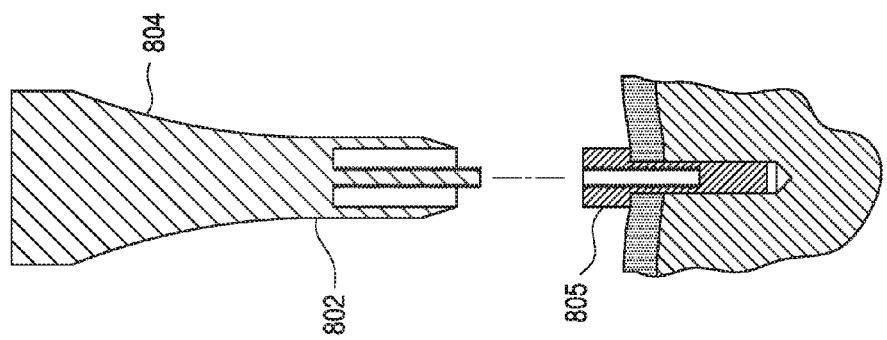
Figure 45A:
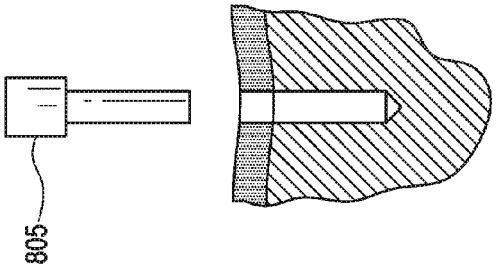
Figures 46A, 46B:
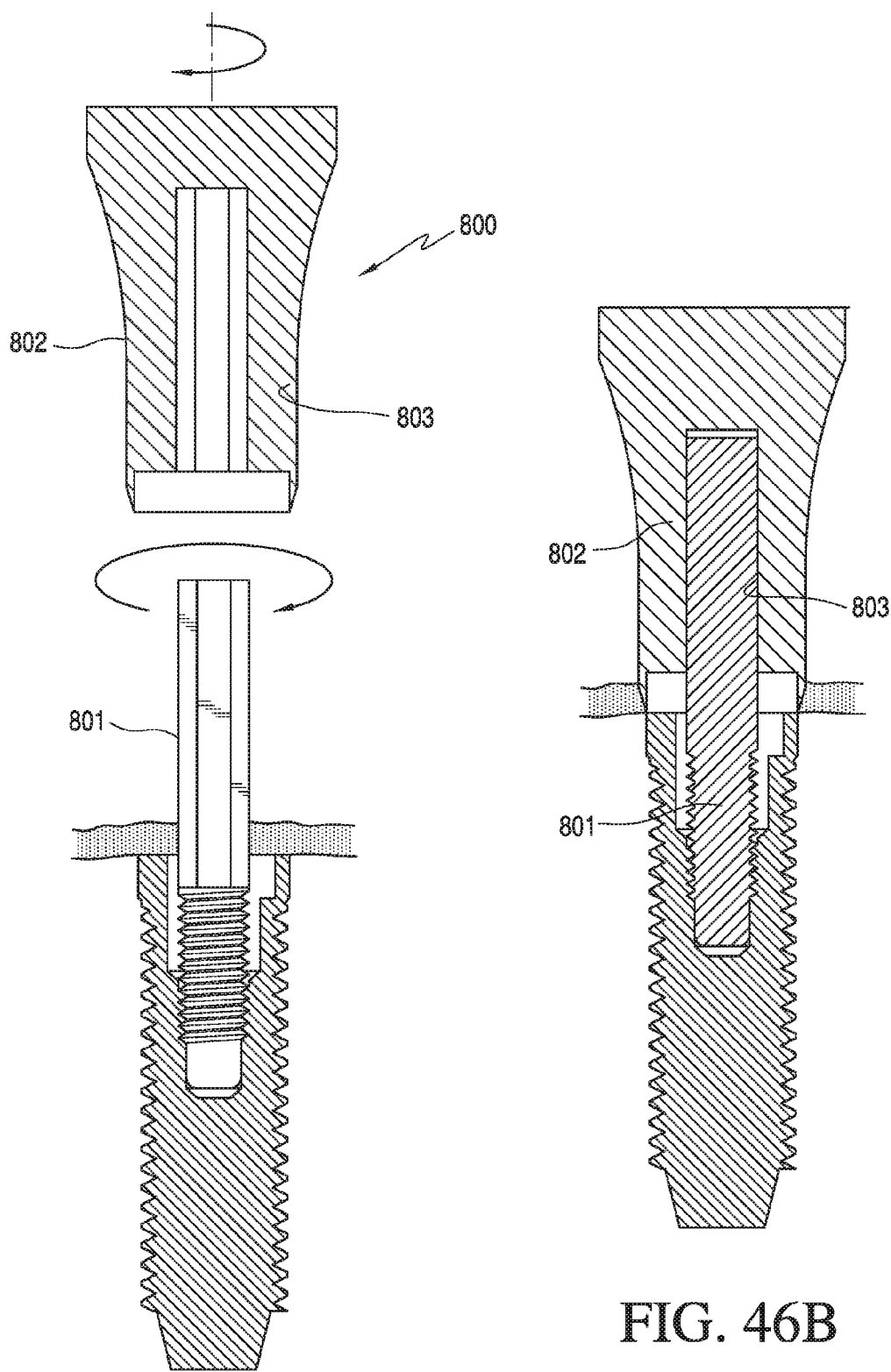

FIGS. 45A-46B show the use of universal guided tissue punches for creating a precisely positioned, minimally invasive tissue opening when creating the osteotomy for implant insertion, or exposing the implant for restoration. FIG. 45A shows the use of the universal guided tissue punch to create a precise excision of the gingival tissue overlying the osteotome site using a guiding tool, and is particularly useful during the "flapless" surgical technique or when immediately loading a healing cap or abutment. After an initial tissue opening is created at the projected implant site, initial drills of appropriate diameter are used to drill the initial osteotomy and the guiding cylinder is inserted. In FIG. 45B an initial preparation of the osteotomy has been done and a guiding cylinder (805) has been inserted in the site. A guided tissue punch (804) is rotated over the guiding cylinder (805) in FIG. 45B until it is seated as shown in FIG. 45C. The universal guided tissue punch (800) shown in FIGS. 46A-B provides an exact tissue opening over a previously inserted implant with a significant savings in implant exposure time, as well as providing tissue preservation as a precise cut is created over the implant head. The cutting edge (802) of the tissue punch has an outer diameter of about the same outer diameter as the top of the implant. A surgical guiding screw (801) with an extra-long shank is threaded into the implant's internal thread, once its cover screw has been located and removed. The guided tissue punch (800) is then inserted over the guiding screw such that its internal polyhedron (803) engages the shank of the punch, which is then rotated until the tissue is removed over the implant. This preferred embodiment is not limited to the use of a guiding screw, when, in fact, any polyhedron that is inserted in the implant, such as an adaptor, can also provide the reference plane for rotating the universal guided tissue punch as it cuts the tissue.

In another embodiment, one can expose the cover screw to locate its index. A guided tissue punch (804) with a polyhedron configured to mate with the polyhedron of the cover screw can be inserted such that it is seated. The cutting edge (802) of the tissue punch has an outer diameter of about the same outer diameter as the top of the implant. The guided tissue punch can then be rotated until the tissue is removed over the implant.

Figure 47:
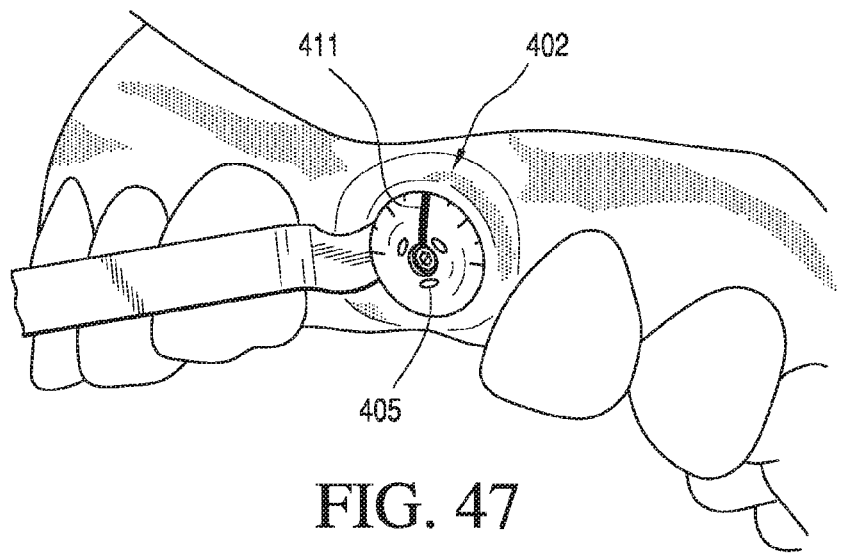
FIGS. 47-48 illustrate the use of a previously rotated healing cap as a surgical template to initiate tissue training.

To summarize, the Universal System provides automated tissue engineering from implant exposure to creation of the final abutment and its insertion. First, a precise cut over the implant establishes the initial opening, as described above. Then a preformed universal contour healing cap or interim abutment (FIGS. 47, 48) is used as a surgical template to scallop the gingival tissue over the implant to a predetermined contour, which is followed by using an impression or a scan registration device having the identical gingival architecture (FIGS. 76, 77, 81 and 86, 88-92). The final abutment or other prosthetic component is either fabricated utilizing this preformed gingival architecture or another one that can be modified, but effectively blends with the newly sculpted "sulcus". To start the process, either a symmetrical, cylindrical healing cap ((402), FIG. 47) or an asymmetrical custom contour healing cap (401, FIG. 48) is first repositioned by rotating the primary indicium of the adaptor to one of the primary (411) or secondary (425 or 426) indicium positions of the healing cap such that the primary indicium of the healing cap (411) is ultimately situated within 7.5° of the ideal position over the implant, when rotating in 15° increments (as previously shown in FIGS. 1-39B). As the adaptor/healing cap assembly is seated, the tissue is sculpted to blend with its subgingival contours (in this case, to the shape in the cross section plane at the gingival margin of a maxillary central incisor). A matching universal contour abutment can also be used as a surgical template via the steps outlined above for the healing cap. When the tissue is ready, the appropriate universal impression post (600) or scanning post (700) having the matching base is selected to register that gingival contour as well as other pertinent configurations for physical abutments and devices or translates the configuration data for virtual abutments and devices to a software program (see FIGS. 70-92). Final abutments are chosen with the identical gingival architecture, which completes the fully automated process of establishing ideal subgingival anatomy around an abutment that is ideally situated on an implant. It at least certain embodiments, as illustrated in FIGS. 47 and 48, the healing cap has recessed engaging polyhedrons (405) to facilitate the attachment of the abutment, post, or other devices to be attached to the healing cap.

IV. The Universal Multifunction Abutment System (See FIGS. 49-69C)

FIGS. 49-69C illustrate the use of the universal multifunction abutment to retain a screw borne prosthesis such as a hybrid screw down denture, an over denture, a screw down crown, set of crowns or bridge, or any other type of screw borne prosthesis. The post head (300) shown in FIGS. 1-3 and the multifunction (500) shown in FIG. 49 are two different abutment versions of the universal system that fit on the same universal aligning adaptor (100). Therefore, the configurations and descriptions of the adaptor (100) and fixation screw (200) used to secure the post head (300) to the implant shown in FIGS. 1-3 are exactly the same for the multifunction abutment (500) shown in FIGS. 49 and 50. The primary and secondary indicia (321 and 325) for the post head in FIG. 1 are the same for the multifunction abutment, but have different part numbers to show that they are primary and secondary indicia on the multifunction abutment, instead (521, 522, FIGS. 54A and 526 FIG. 54B,C). The bottom end at the abutment's base (369, FIG. 1) of the post head is the same for the multifunction abutment (not shown), since they both fit on the same adaptor collar (130, FIGS. 1 and 54C). FIG. 49 illustrates an angle correcting universal multifunction abutment (500) seated on a universal aligning adaptor (100) that is seated on an implant (10) with a trichannel index (21). The fixation screw (200) is inserted into the screw access channel (565) and secures the universal aligning adaptor (100)/universal multifunction abutment (500) assembly to the implant. This particular multifunction abutment is making a 30° vertical angle correction (556). In this embodiment, the universal multifunction abutment has a cone projection (572), which receives a prosthesis connecting polyhedron, in this example a cylinder (580) in a specific manner over its primary indicium (see FIG. 54A, 520), which is, in turn, affixed to the abutment with a fixation screw (575) as it is inserted into the guiding/retaining threads inside the cone (574). The cylinder has scribe lines in mm increments (581) for sizing it and for retention inside of a prosthesis restorative material, and is described, in detail, below. FIG. 50 shows the cylinder (580) seated on the cone projection of the abutment (572), which is then secured to the abutment with the fixation screw (575), which engages threads within the cone (574).

It is also possible to design a particular multifunction abutment making a 0° vertical angle correction (553).

Figure 54C:
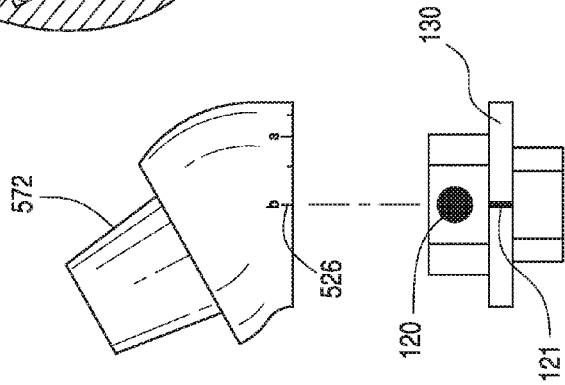

FIG. 51 shows the cylinder seated and affixed to the multifunction abutment. In this embodiment, the cylinder (580) has a flat surface (581) that is set in relation to the flat of the cone (573), which is, in turn, in a set relationship to the primary indicium of the universal aligning adaptor (not shown). FIG. 54A shows a multifunction abutment that has not been rotated, as indicated by its primary indicium (521) being in line with the primary indicium of the cone's flat (FIG. 54A, 520) and the primary indicium of the adaptor (121). This flat or other polyhedron can be in any number of positions and provides a positive seat for consistent seating of the cylinder. This flat (573) to flat mating surface (587) provides an antirotation of the cylinder, which, in turn, resists breakage of the bond between the cylinder and the prosthesis, when the prosthesis is under occlusal load from function, especially when a cantilever tooth or set of teeth are a part of the overlying prosthesis. In at least certain embodiments, the flat of the cone (573) along with the primary indicium are located at a center line that is 180° from the midpoint of the angle correcting polygon. In another embodiment, the cone of the universal multifunction abutment does not have a flat, but rather has a primary indicium at its center line. A cylinder that does not engage any flat on the cone can also be used with the multifunction abutment. The cylinder (580), in this embodiment, has an internal thread (574) at its base to receive the fixation screw (575) prior to seating the cylinder which prevents screw droppage, and also has an internal thread (584) at its top to receive a sealing screw (585) after the cylinder has been sized. This sealing screw allows quick access to the fixation screw of the cylinder when the appliance is to be removed, thereby eliminating the need for the restorative dentist to drill out a composite or acrylic plug during hygiene or other appliance removal appointments. The external surface of the cylinder has external configurations for retention (589) which, in this embodiment, are actually measurement score lines (582) that serve as cut lines for the surgeon or restorative dentist or dental technician to size the cylinder such that it does not protrude beyond the prosthesis. In addition, in another embodiment, the bonding sleeve has an external configuration to receive a connecting ring and bar (not shown).

Although FIGS. 49-55 show one embodiment of the abutment and connecting devices, there is a wide array of possible configurations of the universal multifunction abutment's shape, projections, polyhedrons and their relationship to the universal aligning adaptor which, in general, is configured such that the abutment's cone and the mating cylinder are aligned according to the primary reference indicium of the multifunction abutment, which, therein aligns them with other prosthetic components in the system, including those registration devices that are seated on the cones. Although the preferred internal configuration of the cylinder shown here is a cone or similar polyhedron to guide and secure the fixation screw, it can have any other matching configuration to mate with a cone or other polyhedron projection on the abutment, or have no internal configuration at all.

FIG. 52 illustrates another method of bonding the implant supported prosthesis to the cylinder using an interfacing bonding sleeve (586), which is made of a suitable material according to the composition of the appliance and provides a stronger connection to the appliance, since it is first fused directly to the cylinder with an appropriate adhesive or cement. The bonding sleeve can also serve as a vertical stop during procedures for converting the denture to a transitional hybrid, which can save significant "chair time". The cylinder (580) can also have internal threads (583) to secure the cylinder fixation screw. The cylinder (580) can also have internal threads (584) to secure the sealing screw (585). Although exemplified as a threaded sealing screw and matching internal threads, in at least certain embodiments, the sealing screw could be a pressable cap that does not require a threading action to secure the sealing screw to the cylinder. In such an embodiment, friction or an outwardly expanding radial force seals the cylinder with the sealing screw.

Figure 53:
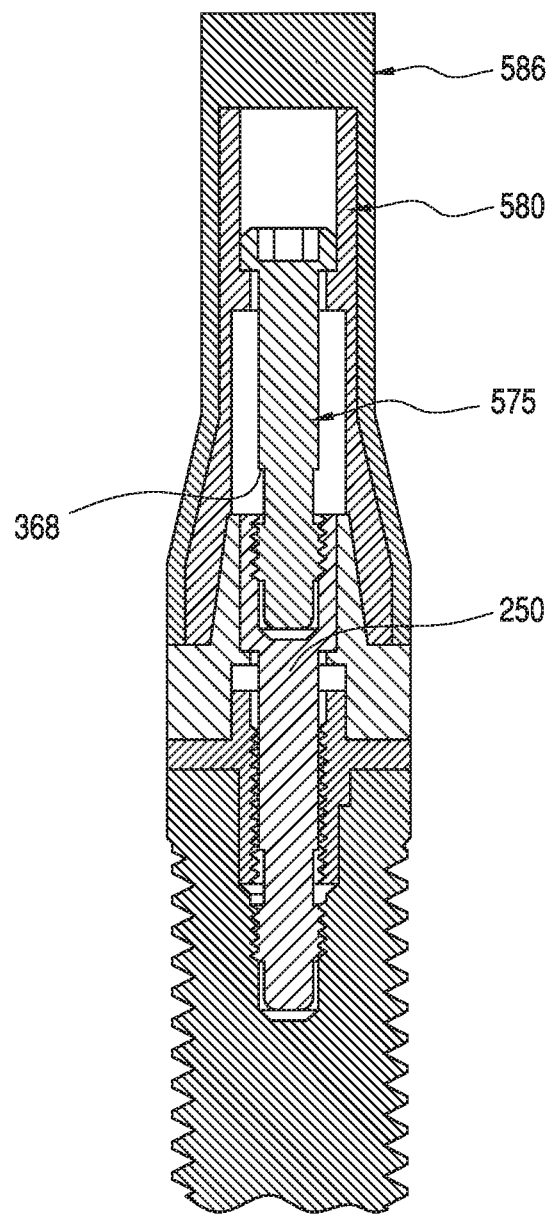

FIG. 53 shows that the 0° abutment has been seated such that the primary indicia of the adaptor and the abutment are aligned without any rotation having been performed. The 0° abutment can still be rotated to any one of the secondary indicia to ideally situate the tooth preparation and/or the gingival architecture. Once aligned, the assembly is secured with a fixation screw (575) that secures the cylinder to the abutment as it engages internal threads of the abutment fixation screw (250).

Figure 54B:
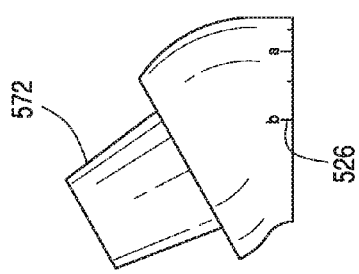
Figure 54A:
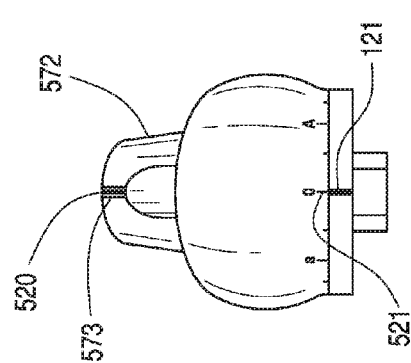

FIG. 54B illustrates a 30°, angle correcting universal multifunction abutment that is being rotated to an ideal position and then being seated on an implant which has been inserted into the jaw with a 30° horizontal misalignment. Once appropriately seated, the cylinder is connected to the abutment such that the prosthetic device (in this case a single crown) is secured to the abutment with the fixation screw (575). While this technique is the same for all screw bearing abutments and screw borne prostheses (according the techniques outlined in FIGS. 1-39B), it is particularly useful for creating a screw retained crown (shown here), set of crowns, bridge, or splinted "teeth" in an arch without any flange or wide occlusal tables to compensate for the implant misalignment. The components are decoupled from the coarse increments of rotation provided by the implant's index, realigned by rotation of the primary indicium of the adaptor to a predetermined primary or secondary indicium of the abutment in finite increments of rotation. The multifunction abutment (500) and the connecting cylinder (580) can be preformed, cast, pressed, or milled, whichever is the preference of the restorative team. The Universal System provides the ability to fabricate a screw retained crown with either the multifunction abutment, presented here, or with the contour abutment described in FIGS. 1-39B.

Figure 55:
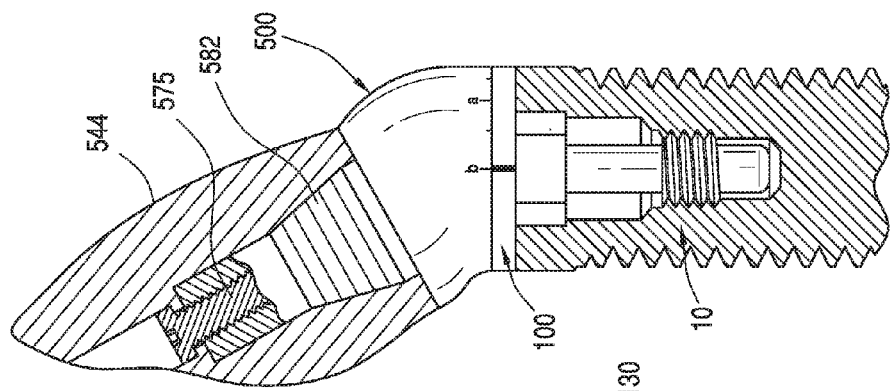
FIGS. 54A-55 is a frontal and side view demonstrating the rotation of the universal multifunction abutment and its adaptor via their primary and secondary indicia to predetermined positions to optimally position the abutment.
Figure 56A:
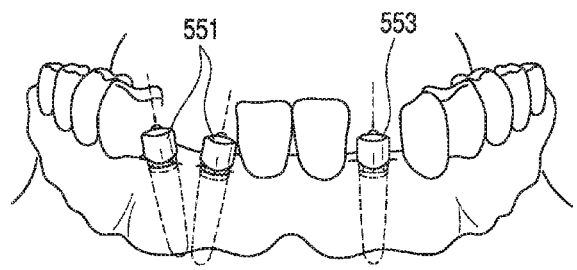
FIGS. 56A-57B reveal the rotation of the universal multifunction abutment to axially reposition the screw access holes.
Figure 56B:
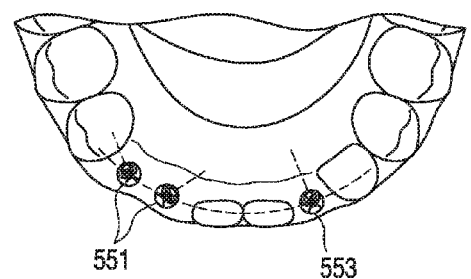
Figure 57A:
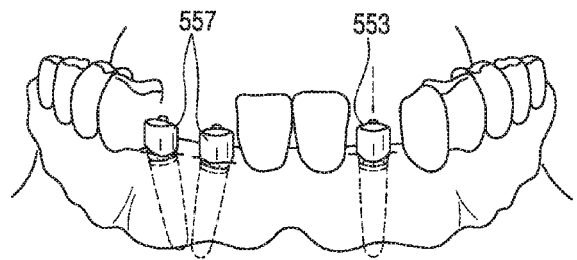
Figure 57B:
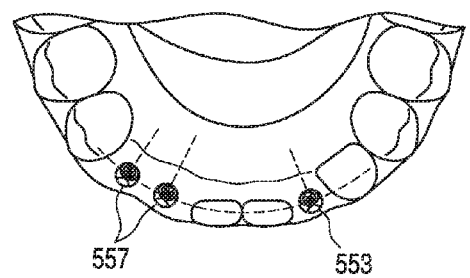

FIG. 54A shows the primary indicia of the universal multifunction abutment, one of which (520) is on a flat (573) of the cone (572), which serves as a seating index of the overlying cylinder, and the other one is directly below it on the collar of the abutment (521). In the embodiment shown in FIG. 54B, this abutment is being rotated counter clockwise to secondary indicium (b) (526), which results in a 30° rotation in this case, since the adaptor's index is an octagon and the implant's index is a hexagon (see Table 4). In FIG. 54C, the rotated abutment (500) is being connected with its secondary indicium (526) at position (b) which is being lined up with the adaptor's primary indicia (120, 121) prior to rotating the assembly over the implant (10). A prosthesis, which, in this case, is an anterior crown (544), is shown in FIG. 55, as having the cylinder being cast, pressed or milled as a part of the coping, which, in turn, converts the coping to a screw down crown. This method is particularly effective when restoring an anterior implant, wherein a screw down crown is preferred, but the screw access hole would be unsightly. FIGS. 56A and B and 57A and B show two misaligned multifunction abutments (551) being realigned (557) to an ideal position, which situates and aligns their screw access holes for better esthetics and function.

Figure 60A:
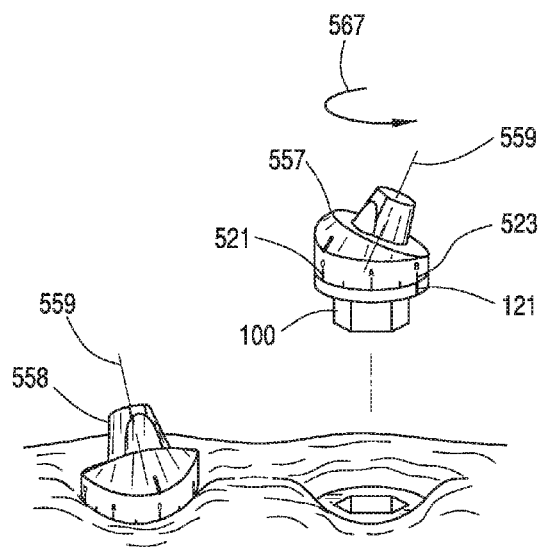
Figure 60B:
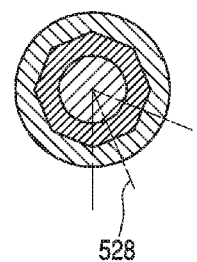
Figure 60C:
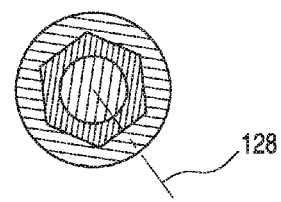
Figure 61:
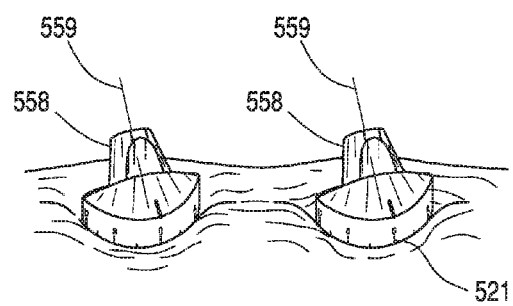

Illustrated in FIGS. 58A-6I are the methods for realigning a misaligned universal multifunction abutment to reposition its screw access hole to approximate the center of the occlusal table for a particular replacement tooth seated over the implant. FIG. 58A shows an implant that has been inserted such that its internal index, which in this case is a hexagon, is not located in an ideal position for restoration, such that the adaptor's octagon center line (528, FIG. 58B) and the implant's hexagon center line (128, FIG. 58C) are aligned with each other and the center line of the abutment's 30° angle correcting axis (559), but the assembly is misaligned in relation to the implant's central axis in the sagittal plane as it bisects the ridge. This skews the abutment (557) in relation to another one that has been aligned and optimally situated (558, FIG. 58A). In FIG. 58A the adaptor is being rotated counter clockwise to position (B) to achieve a 30° horizontal rotation and, in FIG. 59, the adaptor and the abutment are being connected after the rotation such that the adaptor's primary indicia (120, 121) are in the abutment's ("B") position (523). FIG. 60B, (c) illustrate the assembly being rotated such that the center lines (559) of each abutment are in line with each other, but that the center lines of the adaptor's octagon (528) and the implant's hexagon (128) are no longer aligned. The end result is that the misaligned abutment (557) is now in line and parallel with the one next to it (558) by the rotation of the adaptor around the abutment and the assembly around the implant as shown in FIG. 61. Note the location of the primary indicium (128) in relation to the nearest vertex (line over the center of the vertex) in FIG. 58B vs. its location after the rotation as shown in FIG. 60C.

FIGS. 62-67, illustrate problems associated with restoring misaligned implants with crown and bridge abutments and FIGS. 68-69 show the challenges of restoring an arch with screw retained abutments (in this example hexagon indexed), since angle correcting abutments that directly engage the implant index are encumbered by its coarse increments of rotation (60°). The effect of restoring misaligned, anterior angled implants is also demonstrated in FIGS. 62-67, and the compounding effects of restoring misaligned, angled implants around the curve of the arch is shown in FIGS. 68-69C.

FIG. 62 illustrates the use of a stent having ideal crown contours and positions, which gives the technician a perspective on the required abutment corrections needed to achieve the preferred profiles and positions. As an example, in FIG. 63, implants 8 and 9 having been inserted with misaligned indexes such that both of the angle correcting abutments, in this case, are angled distally as shown by the off-angle abutment center lines (557). FIG. 64 shows the rotation of the abutment in implant #8 one hex stop or 60°, which results in the abutment center line (557) still being misaligned, except that it is now angled mesially. In this example, when restoring a screw borne prosthesis, the screw access hole ends up angled towards the mesial or distal line angle of the projected crown, which effects esthetics and/or function. When using crown and bridge milled abutments, the milling program will have to overcompensate for the mesial-distal misalignment by an extra milling of the mesial or distal side of the abutment in order for it to be parallel, which will give it a reduced emergence profile. However, as shown in FIG. 65, this problem has been resolved by the dual rotation of the universal multifunction abutment or the universal contour abutment in combination with the universal aligning adaptor with a more refined 30° horizontal rotation, which results in the center lines of 8 and 9 (558, 559) now being situated in ideal positions. FIGS. 66-67 show a side view of the anterior angle correcting abutment at #8 or 9. In the left hand drawing, it can be seen that the compounding problem that results when angle correcting abutments are also misaligned, which results in these 30° angle correcting abutments being unable to provide the full vertical angle corrections, since they are not optimally positioned. In the right hand drawing, the improved angle correction in the vertical plane as demonstrated by the axis line (559) can be seen, once the abutment has been realigned. Overall, realigning and reestablishing the restorative index to an ideal plane as the initial procedure prior to fabricating a screw borne prosthesis or, in this case, a set of anterior milled abutments can make a dramatic difference in maintaining ideal screw access holes for the screw borne prosthesis or improved emergence profiles for the milled abutments. The techniques of rotating the components according to the primary and secondary indicia have been covered, in detail, in the previous drawings.

FIGS. 68-69C illustrate how the problem is further compounded coming around the curve of the arch, which, once again, further complicates the geometrical discrepancies, and, therein, decreases the likelihood that a full arch set of screw down crowns without denture flanges can be fabricated, because the screw access holes will be off-angle and result in bulky crowns. In addition, a full arch set of milled abutments will lose a significant portion of their emergence profile as the milling machine parallels all of them. For the first time, a screw retained full arch bridge or a full arch of anatomically correct milled abutments can be consistently fabricated for any set of implants that are in almost any position. For example, in FIG. 68, with implant #10 being misaligned distally and implant #12 being misaligned mesially, the crowns will either be misshaped and bulky and have screw access holes (568) that are not in ideal positions (i.e., off angle), or the milled abutments may not be able to have adequate contours, once they are milled for parallelism, because the abutment is seated on the hexagon index, and, thereby, rotates in 60° increments, which means that a misaligned index causes its abutment to be off-angle to a maximal 30° deviation from the ideal direction to achieve optimal positioning. This drawing show the results when the abutments are off angle at that maximal misalignment. FIGS. 69A-C show the rotation of the adaptor such that its primary indicium is repositioned prior to the combined assembly being horizontally rotated so that it rotates in 15° increments. FIG. 69C illustrates how the resulting repositioning of the abutment and/or screw access holes in 15° increments such that its abutment to be off-angle to a maximal 7.5°, which precisely compensates for the misalignment and solves the problem. Therefore, as shown in FIG. 69C the present invention centers the screw access hole (569).

Certain embodiments provide an assembly for use in the process of dental restoration relevant to dental implant prosthetics comprising, in combination, an adaptor to be received and seated on a dental implant in a predetermined position relative to the implant and a multifunction abutment seated on the adaptor's end. The adaptor's end is configured to receive the multifunction abutment which is first rotatable about the adaptor followed by the adaptor/abutment assembly around the implant until the abutment's screw access hole is realigned to a generally desired vertical and horizontal predetermined position to approximate the center of the occlusal table of the tooth replica for that particular implant that has been fabricated on the screw borne prosthesis. The adaptor and the abutment have co-operable indicia for identifying and registering the predetermined position of the abutment, wherein the co-operable indicia permits the adaptor and the abutment to be rotated relative to each other into a predetermined position of the abutment while the adaptor is detached from the implant. The primary indicia of the cone on the multifunction abutment can determine the seating of an impression post, a scanning post, or CBCT scan imaging post, each of which can also have co-operable indicia such that they reference the realignment of the abutment to its predetermined, preferred position that ideally situates the screw access hole when fabricating the final abutment and/or the prosthesis that is seated on it.

The abutment can be one of a plurality of devices including but not limited to preformed temporary abutment posts, preformed final abutment posts, cast abutment posts, pressed abutment posts, or milled abutment posts, or other fabricated posts wherein they receive the prosthesis that is screw retained to them when restoring the implants.

The prosthesis can be one of a plurality of devices including but not limited to an overdenture bar for receiving a snap on denture, a snap on denture that is connected to retaining devices seated directly on the adaptors or implant abutments seated on adaptors without a connecting bar, a transitional hybrid prosthesis that has been converted from a denture to a fixed, screw retained prosthesis during the insertion of a set of implants in an immediate load procedure, a screw retained denture or similar prosthesis with flanges, a screw retained crown, set of crowns or bridge with or without flanges.

The prosthesis can have a preformed, cast or milled framework or other suitable framework incorporated within it, or can be seated on copings or other interfacing prosthetic devices, that are, in turn, seated on implant abutments.

The multifunction abutment and an adaptor can both be composed of the same suitable restorative material.

In certain embodiments, the multifunction abutment and adaptor are rotated around each other followed by the rotation of their assembly around the implant such that the abutment is ideally situated. The abutment is prepared, if desired, and the abutment and the adaptor are combined by an appropriate method to create a single piece abutment/adaptor assembly that is directly connected to the implant without a separate adaptor interface, which then receives the screw borne prosthesis.

In certain embodiments, a milled multifunction abutment comprised of any suitable restorative material is fabricated by first rotating a virtual multifunction abutment into a preferred position over a virtual adaptor using the universal aligning system's automated and interactive clinical protocol in a milling software program to define the synchronized axis of rotation and, thereby, eliminate the mesial-distal misalignment prior to milling the abutment, followed by milling the abutment according to the parameters established by the rotation such that either a single piece, final abutment for insertion on the implant which engages its index without an interfacing adaptor or a final abutment to be receivable on the adaptor with the assembly then being inserted on the implant is milled with the prosthetic device then being milled and affixed to it.

In certain embodiments, the multifunction abutments are virtually rotated to the same positions as the ones that were registered during an impression or 3D imaging procedure, but the framework or overlying coping or set of copings is milled to fit on the previously seated intraoral abutments. In certain embodiments, the framework is fabricated after the autorotation with the abutments being milled first followed by the framework, or with the framework only being milled such that it will be inserted over clinically placed abutments.

In certain embodiments, the abutments can be virtually auto rotated in a software program into their appropriate positions according to the automated and/or interactive digital protocol scan code, which uses the location of each abutment's primary or secondary indicia in relation to the adaptor's primary indicium along with a library of abutment digital data to mill the abutments to either be seated on the adaptors or to be seated directly on the implants.

In certain embodiments, the abutments can be virtually autorotated in a software program, after an intraoral, impression or scan, bench scan, or a CBCT scan that registers the alignment of the implant's index in either the sagittal, coronal, or axial plane, wherein the automated and/or interactive digital protocol is translated to the program.

In certain embodiments, the adaptor and the multifunction abutment have dissimilar polygonal structures and co-operable indicia such that the rotation of the adaptor and the abutment results in increments of horizontal rotational adjustment over the implant to a predetermined position.

In certain embodiments, a healing cap can be removed from the cone on multifunction abutment and an impression post or an intraoral or bench scanning post or a CBCT scan imaging post is seated over the cone such that its primary indicium is situated over the primary indicium of the abutment to register the abutment position, rotation, angle correction, gingival contours in relationship to the abutment, and the relationship to adjacent anatomic structures.

In certain embodiments, the abutment can have a 0° score line opposite the midpoint of the vertical angle correction to show the orientation of the multifunction abutment. The abutment can also have additional score lines, for additional rotational stops to show the number of rotation stops to achieve the desired horizontal correction of abutment angulation to quickly reproduce the rotation.

In certain embodiments, a bonding sleeve can be seated over a cylinder or other polyhedron for securing a hybrid screw down denture, a screw down crown or fixed bridge, or other prosthetic device that is seated on a receiving polyhedron on the abutment, which has, in turn, been seated either directly on to an implant or indirectly on the implant via first being seated on an interfacing adaptor chosen to be compatible to and receivable on an associated implant and having a first portion dimensioned to extend above an associated implant, and the bonding sleeve can be connected to the overlying implant prosthesis. The bonding sleeve can be inserted over the cylinder or other polyhedron and bonded to it with an adhesive prior to or after seating the cylinder on to the abutment. The adhesive can be a biocompatible adhesive. The adhesive can be a composite, dual cure composite, acrylic, or other suitable bonding material.

The cylinder or other polyhedron can be seated on the abutment and appropriately torqued and the bonding sleeve can then be inserted over the cylinder with an adhesive.

The bonding sleeve can be used as a vertical stop for taking the bite prior to or after connecting the bonding sleeve to the prosthesis.

In certain embodiments, a customizable reinforcing bar of a suitable material can be connected to multiple bonding sleeves to provide resistance to fracture of the screw borne prosthesis. A reinforcing ring with a receptacle to receive the reinforcing bar which has been sized to fit between implants can also be seated on the bonding sleeve.

The Immediate Load Transitional Hybrid Prosthesis

Certain embodiments provide a method of immediately restoring dental implants at the time of their insertion with an immediate load transitional screw retained prosthesis by first using a set of aligning multifunction abutments and universal adaptors having co-operable indicia wherein they are rotated and situated in finite increments such that the screw access holes of the abutments receiving the prosthesis are ideally located regardless of the type of implant indexes or their misalignment. In certain embodiments, the rotation of the adaptor and the abutment having the co-operable indicia around each other are performed. Following rotation of the adaptor and abutment, the assembly can be rotated around the implant according to an automatic and interactive clinical protocol with the abutment now being in a preferred vertical and horizontal predetermined position when it is seated on the previously inserted implant such that the screw access hole is as close to the center of the occlusal table of the replacement tooth as possible. The denture can be placed over the abutments and the holes where they seat over the abutments. A connecting cylinder can then be placed over each abutment until it engages its receiving polyhedron. The prosthesis can be affixed by connecting the cylinders to the denture therein creating the transitional screw retained prosthesis.

The automated and interactive clinical and/or digital protocol can include choosing the appropriate multifunction vertical angle correcting abutment or equivalent prosthetic component having the desired geometric shape for that type of restoration over the implant, rotating it as necessary in either a predetermined clockwise or counterclockwise direction such that the primary indicium of the adaptor is positioned at a particular primary or secondary indicium point of the abutment and is set in relation to the index of the implant when the multifunction abutment is being positioned in a preferred, predetermined horizontal and vertical location over the implant such that the screw access hole approximates the center of the occlusal table of the replacement teeth.

The primary indicium of the multifunction abutment is ideally situated in relation to the sagittal plane as it bisects the ridge when it is at a 90° angle to ridge and the abutment is in its ideal position.

In certain embodiments, a preop CT scan can be used to preplan the placement of the implants and abutments prior to the surgery such that the primary indicia of the abutments are ideally situated. The implant can be inserted in the bone according to its position in the CT scan.

The adaptor can be rotated around the abutment and the assembly can be rotated over the implant such that the primary indicium of the adaptor is aligned with a specific primary or secondary indicium of the abutment when it reestablishes the preplanned, preferred position of the multifunction abutment to compensate for implant index misalignment.

In certain embodiments, the restorative dentist seats the abutments and adaptors on the implants according to their position in the CT scan generated model, reassesses their positions, and rotates them with rotatable, universal aligning analogs until they are ideally situated in the CT scan generated model. Once ideally situated, the prosthetic device can be seated over the abutments on the model and be prepared to receive them. The restorative dentist then seats them on their implants using those rotation points as a guide.

In certain embodiments, cylinders that are antirotational having an internal flat that matches to the configuration of the cone or other projection on the multifunction abutment are placed over the projections that have a flat at their primary indicium to provide resistance to dislodgement such that the primary indicium of the cylinder overlays the primary indicium of the cone. This technique is not limited to cylinders with an asymmetric internal configuration.

In certain embodiments, a bonding sleeve that adheres to acrylic or other restorative material can be used in the conversion of the denture is seated over the cylinder with an adhesive and is connected to the denture with an appropriate acrylic or composite to create a one-piece screw retained transitional prosthesis.

In certain embodiments, a transitional appliance is replaced with a final appliance by first removing the transitional appliance from the multifunction abutment and seating an impression post or scanning post over the abutment post such that their primary indicia are aligned, and, either an impression or an intraoral or a bench scan is taken to identify and register the location of the abutment's primary indicium in relation to the primary indicium of the abutment and the implant's index, wherein either an analog is placed in the impression such that its primary indicium is positioned at the same reference points as established by the adaptor's primary indicium, or the data is conveyed to the scan code of a milling software program with the virtual abutments being rotated to the same positions or to new, preferred positions with the final prosthesis being fabricated and seated on the abutments.

In certain embodiments, the transitional, preformed multifunction abutments are replaced with milled ones that provide preferred contours, refined changes in position, gingival architecture, and other improvements when inserting the final screw retained prosthesis. In other situations, milled, Universal Multifunction Abutments can be replaced with milled Universal Contour Abutments at the restorative dentist's option, since they are interchangeable by virtue of the Universal Automated and/or Interactive Clinical and/or Digital Protocol. It does not matter whether they are seated on an adaptor or an implant or whether the crowns are cemented or screw retained.

A steriolithograph or other CT scan software generated model can be used with a removable, rotatable aligning analog that is used in combination with the overlaying abutment or other prosthetic component to reposition the abutment such that its primary indicium is repositioned in the mouth as it is on the universal aligning analog, using the adaptor's primary indicium to direct that repositioning.

VI. The Universal Impression System

There are at least six possible methods for taking impressions or intraoral scans with the universal impression system or scanning system, and FIGS. 70-83 illustrates four of them. These methods are placing the impression or scan post on the universal aligning adaptor (FIGS. 70-75) with its primary indicium overlaying that of the adaptor; placing the impression or scan post directly on the indexed healing cap with their primary indicia overlaying each other, but without having to remove the healing cap (FIGS. 66-67 and 32-37); removing a previously placed temporary abutment, inserting an indexed healing cap with matching gingival contours and placing an impression or scan post on it with its primary indicium overlaying that of the adaptor (FIG. 76); inserting an impression or scan post on the cone of the universal multifunction abutment (FIG. 82) such that its primary indicium overlays the primary indicium of the abutment at the flat side. A fifth method of taking an impression with or without a transfer coping on an unprepared, preformed abutment that has been previously rotated, aligned and synchronized such that aligning the primary indicium of the impression or scan post with that of the abutment registers that ideally established position (not shown in these drawings). Finally, a sixth method, allows for the fabrication of a universal generated prosthesis off any model that was fabricated by taking an implant impression at the fixture level; pouring up the model with implant fixtures analogs or replicas; inserting adaptors on the implant analogs or replicas, and rotating the adaptors and appropriate abutments over the analogs as described for the intraoral insertion of adaptors, above. Additional details that are specific for taking an intraoral scan are shown in FIGS. 84-92, and FIG. 83.

FIGS. 70-71 provide an exploded view of the impression post (604) with an internal channel (665) to receive a fixation screw (200) that is seated on the collar of the universal aligning adaptor (100) having primary indicia (120, 121) that has a registration coping (672) for optional use during a direct impression. A registration coping with a different configuration can be used for the indirect (through the tray) technique, as well. The impression post has an internal index (in this case an octagon configuration) (661)

that interfaces with the indexed projection (in this case an octagon stud) of the adaptor and has a cylindrical external shape (637) and a reference polyhedron, in this case a flat surface (611) with a primary indicium (621) overlying the primary indicium of the adaptor (120, 121). FIG. 71 shows that the impression post (604) is engaging the octagon (661) of the aligning adaptor (100) with their assembly seated on the implant (10) with the adaptor's primary indicia (120, 121) facing outward, and affixed to it by the fixation screw (200) that has been inserted in the channel (665). The collar (637) of the impression post (664) can be cylindrical or it can have a gingival shape to fit the intended position of the impression post. Thus, as previously discussed with regard to the gingival collars of other components of the described system, the gingival collars of the impression post can be shaped for the mandibular contour, maxillary contour, anterior contour, or medium or large posterior contour.

The registration coping (672) is seated on the impression post, and is included in each drawing for demonstration purposes only of a preferred embodiment, since the impression can be taken without using it (see FIGS. 72-74). In addition, this embodiment of the impression post can come in many different shapes and polyhedron styles and can have the primary indicia of the adaptor set in relation to the impression post and scanning post in other locations, as well.

FIGS. 72-74 show an impression post (604) configured to receive a registration coping (672) for taking a direct impression, and an impression post for either a direct impression or a "through the tray" impression (673) without the use of a registration coping. Impressions can be taken with or without the registration coping. The impression post (604) can have a 0° reference indicia on its collar (621). Although shown on the collar, it is understood that the 0° reference indicia could also be positioned on the flat (611) or even the mated registration coping (672). Similarly, although shown with only the 0° reference indicia, it is understood that the impression post can have additional reference indicia.

FIG. 75 shows the insertion of the impression post (604)/registration coping (672) assembly being inserted on an adaptor that has been rotated to a preferred position. If it was rotated to align and/or optimally position an abutment or healing cap, then the primary indicium or specified polyhedron of the impression post will be situated such that it is positioned over the primary indicium of the adaptor. The techniques shown in FIGS. 70-75 can even be performed if the surgeon or restorative dentist inserts the universal aligning adaptor with its primary indicia randomly positioned without first being optimally situated, since the universal aligning analog (FIG. 94, 171) can be removed and rotated in 15° increments such that the abutment is repositioned to an ideal situation on the model. FIGS. 76 and 77 show the impression post being seated directly on two variations of an indexed healing cap without its removal from the implant and are now ready for the impression. In FIG. 76, the impression post (602) with an internal octagon (661) and a direct impression registration coping (672) is being inserted and engaging an external octagon (406) on the top of the healing cap, which, in this embodiment, replicates a medium sized premolar contour (433). Collectively, this is shown as a universal impression post over a healing cap (605). In FIG. 77, another embodiment of the healing cap shows an exploded view of the engagement of the impression post (602) with a registration coping having engaging protrusions (612) that are received in the recessed polyhedron receptacles (408) of the contour healing cap (433).

Figure 78:
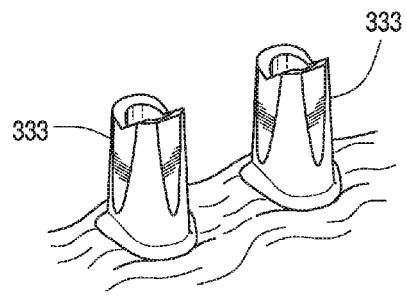
Figure 79:
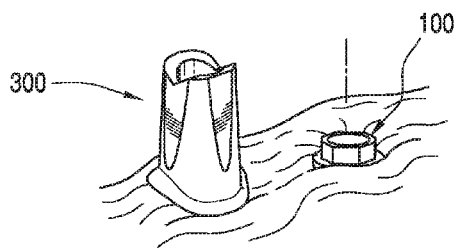
Figure 80:
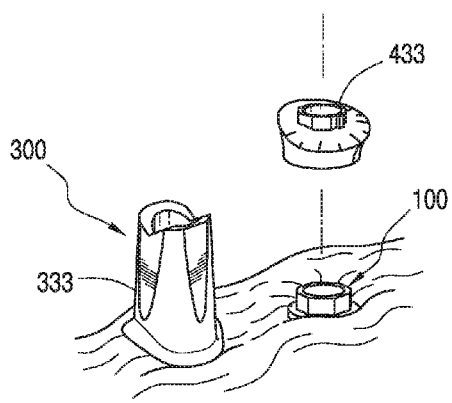
Figure 81:
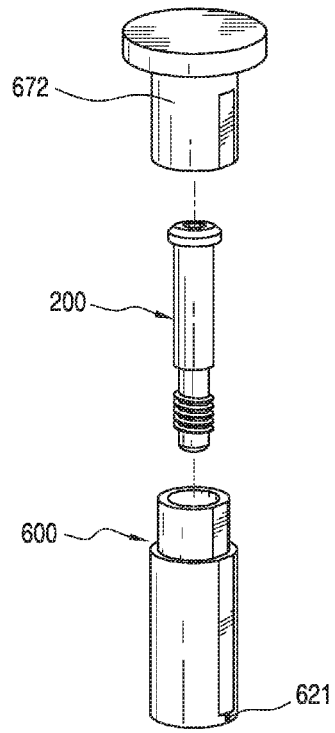
Figures 82, 83:
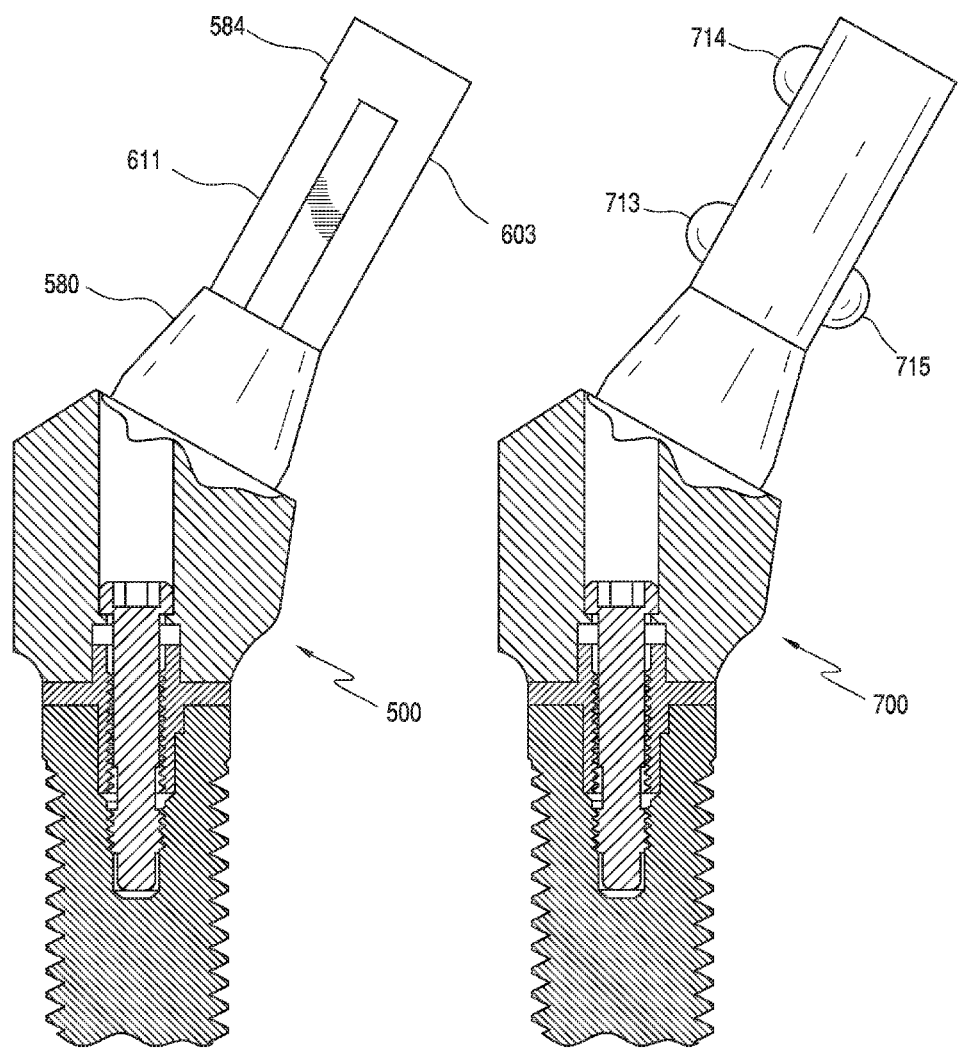

FIGS. 78-81 show the impression post on an indexed healing cap whose gingival contours match the temporary abutment that has been removed from the adaptor and replaced with the indexed healing cap for impression taking. FIG. 78 shows the removal of a medium sized premolar temporary abutment (333), which exposes the adaptor (100) as seen in FIG. 79, and, in FIG. 80, an indexed contour healing cap (433) is chosen that matches the gingival contours of the abutment and is seated on the previously rotated adaptor. Since the adaptor is rotated around the abutment into a preset position so that the abutment/adaptor assembly is optimally situated to within 7.5° of the ideal position of an abutment in that configuration (e.g. molar vs. an incisor), and since the abutment and the indexed contour healing cap have their primary indicia set in relation to the primary indicia of the adaptor, then the indexed contour healing cap will seat with the same relationship such that its primary indicium is also to within 7.5° of the ideal configuration (see FIGS. 24A-D for the contour abutment rotation FIGS. 58A-C, 59-61). In FIG. 81 the impression post (600) is then seated on the indexed healing cap (433) with its primary indicium overlaying that of the index, which is then secured with a fixation screw (200). FIG. 82 shows an impression post (603) seated on a multifunction abutment (500) with the flat (611) and primary indicium overlying the primary indicium of the abutment, which, in turn, has been rotated to be optimally situated. This is the same technique used for taking an impression on the previously rotated indexed healing cap. The impression posts and registration copings are shown here for demonstration purposes and are not limited as to size, polyhedron shape, or asymmetries or positioning relative to their primary indicia. FIG. 83 shows the scanning post seated on the multifunction abutment with exactly the same relationship as the impression post, after it has been rotated as in FIGS. 58A-61 with its primary indicium and reference polyhedron directly over the primary indicium of the abutment post, which is now in an optimally situated position. The universal system has one set of impression posts for all implants.

The techniques described in FIGS. 70-83, above, are also used for taking an intraoral or bench scan, since the universal scanning post and the universal impression post are interchangeable on all of the universal platforms: on the aligning adaptor and analog, on an abutment, and on the indexed healing cap. They are interoperable, since all components, via their primary and secondary indicia, are set in relation to the primary indicia of the universal aligning adaptor, no matter how it is positioned.

In certain embodiments in the process of dental restoration, an impression post assembly can be used. For example, a Universal Aligning Adaptor can be seated on an implant that, at its bottom end, engages the implant index, and on its top end has a polyhedron to engage an impression post. The adaptor and the impression post can have co-operable indicia for identifying and registering the predetermined position of the adaptor the steps comprising a rotation of the adaptor and a prosthetic component also having co-operable indicia such that the prosthetic component establishes a preferred vertical and horizontal predetermined position over the implant. The prosthetic component can then be removed from the adaptor and an impression post seated on the adaptor such that the cooperable indicia of the adaptor and the impression post register the newly established position of the adaptor. An impression can be taken to form a model for fabrication of a final prosthetic component.

The primary indicium of the adaptor can be an engaging polyhedron which provides a positive seat when engaging the primary indicium of the impression post possessing a mating polyhedron. The polyhedron at the primary indicium of the adaptor can be a protruding sphere and the polyhedron at the primary and secondary indicia of the impression post can be a reciprocal, concave sphere.

The impression post can have an external polygonal configuration that is set in relation to its primary indicium and defines its insertion in the impression after its removal from the mouth, such that the adaptor analog is connected to the impression post as defined by the relationship of their primary indicia and the assembly is inserted inside the impression, which references the position of the primary indicium of the adaptor.

An impression coping having a primary indicium and an internal configuration that matches to the external configuration of the impression post can be seated on the impression post such that their primary indicia are synchronized prior to taking the impression, which references the primary indicium of the adaptor when it is incorporated into the impression after the impression is taken. The impression coping inside the impression can receive the impression post after it has been connected to an adaptor analog with their primary indicia overlying each other with the assembly then being poured as part of a working model. In certain embodiments, the impression coping can protrude through the tray for use in an indirect impression technique.

In certain embodiments, connecting rods can be affixed to impression copings prior to taking an impression of the universal aligning adaptors seated on multiple implants in order to better stabilize them during model fabrication. The impression post/base assembly being connected to the universal aligning analog translates the gingival contours and configurations established during tissue training by the inserted healing cap or temporary abutment to the pattern used for the final cast abutment or to the software program whose milling device codes and controls create the milled abutment or other prosthetic device.

The final abutments can be fabricated from preferred castable or pressable patterns when they are cast or pressed using a suitable casting metal or pressable material, identical preformed abutments that are inserted on the working model when simplicity is desired, or fabricated from the data conveyed to a milling program from a bench scan of the working model when milled abutments are preferred.

In certain embodiments, an interim prosthetic device can be used to determine the ideal, predetermined position of a future final prosthetic device that is seated on an adaptor's top end. An impression post having co-operable indicia for identifying and registering that predetermined position of the interim prosthetic device can be used. The impression post can be situated in relation to the position of the interim abutment over the implant.

In certain embodiments, rotation of the adaptor and the interim prosthetic device via their co-operable indicia can be performed such that the interim prosthetic device is positioned in a preferred vertical and horizontal predetermined position over the implant. Afterward, an impression post can be seated on a polyhedron on the top end of the prosthetic device which has been configured to synchronize with the primary indicia of the adaptor and, thereby, register the adaptor's newly established position.

The primary indicium of the prosthetic device can be located on the polyhedron of the indexed prosthetic device which is in line with the primary indicium of the healing cap. In this configuration, the aligned indicium identify the preferred vertical and horizontal predetermined position.

The primary indicium on the polygonal structure can be an engaging polygonal structure which provides a positive seat for engaging the impression post with a reciprocal polygonal structure that aligns their respective primary indicia. In certain embodiments, the polyhedron on the bottom end of the prosthetic device is an index with the same polygonal configuration as the index of the underlying adaptor such that their polygonal sides are aligned. For example, the polyhedron on the bottom end of the prosthetic device is an octagon when the adaptor's top end is also an octagon, or is a hexagon when the open end of the adaptor is also a hexagon.

The prosthetic device can be a gingivo-adaptor which is a prosthetic device comprising a one-piece assembly of an adaptor stud on its open end and the configuration of an implant engaging stud on its free end such that the open end index receives the impression post.

In one aspect of taking an impression of a multifunction abutment, an assembly for use in the process of dental restoration relevant to dental implant prosthetics can include an adaptor, a multifunction abutment seated on the adaptor's open end which will, in turn, receive a screw borne prosthesis on its own open end and an impression post having co-operable indicia for identifying and registering the predetermined position of the multifunction abutment, which has been situated in relation to the cooperable indicia of the adaptor. The operable steps include rotation of the adaptor and the multifunction abutment, also having co-operable indicia, such that the multifunction abutment is situated in a preferred vertical and horizontal predetermined position over the implant. Next, an impression post can be seated on a screw bearing polyhedron on the open end of the abutment that receives the screw borne prosthesis such that the cooperable indicia on the screw bearing polyhedron and those on the impression post together register the newly established position of the multifunction abutment, which, in turn, has been set in relation to the adaptor's cooperable indicia. Next, an impression can be taken to form a model for the fabrication of a final prosthetic device.

In certain embodiments, co-operable indicia includes primary and secondary indicia such that the primary indicia of the multifunction abutment, which is set in relation to the primary indicium of the adaptor and the primary indicium of the impression post, determine the proper seating of the impression post. The primary indicium of the multifunction abutment and impression post can overlie each other.

In certain embodiments, a screw bearing polyhedron can be used with the multifunction abutment. In such an embodiment, an engaging polygonal structure provides a positive seat for engaging the impression post with a mating polygonal structure that aligns their respective primary indicia.

The impression post can have an external polygonal configuration that is set in relation to its primary indicium and to that of the multifunction abutment. The external polygonal configuration can define the insertion of the impression post in the impression such that the multifunction abutment analog is inserted inside of it in the same manner as the abutment, which references the position of the primary indicium of the multifunction abutment, and, thereby, the adaptor, as well.

An impression coping having an internal configuration that matches to the external configuration of the impression post can be seated on the impression post on the previously inserted multifunction abutment prior to taking the impression such that the coping's primary indicium overlies the primary indicium of the impression post, which, in turn, is superimposed over the primary indicium of the abutment such that it is then incorporated in the impression when the impression tray is removed from the mouth.

The impression coping seated in the impression can receive the impression post after it has been connected to a multifunction abutment analog such that its primary indicium is in its preferred position and the primary indicium of the analog is located at the same secondary indicium position as the corresponding adaptor when seated on the implant, and the assembly is incorporated in the working model when it is poured.

In another aspect of taking an impression of a preformed, unprepared contour abutment with a predetermined tooth preparation and a desired gingival configuration at its bottom end, an impression coping having co-operable indicia for identifying and registering the predetermined position of the contour abutment is used to register the abutment after it has been set in relation to the cooperable indicia of an adaptor can be used. The adaptor and the contour abutment can be rotated via their co-operable indicia such that the contour abutment is situated in a preferred vertical and horizontal predetermined position over the implant. An impression coping can then be seated on the abutment such that the cooperable indicia on the impression coping and the abutment post register the newly established position of the contour abutment, which has been set in relation to the adaptor's cooperable indicia. An impression can then be taken to form a model for fabrication of a final prosthetic device to fit on the preformed abutment.

In certain embodiments, another preformed abutment post can be directly inserted in the impression or inside the impression coping and the final prosthesis fabricated, when the abutment is satisfactory as is and has not been prepared.

The impression coping can be fabricated of a suitable restorative material and can be used after the model is poured to serve as a crown or other prosthetic device coping and, thereby receive the appropriate veneering material.

The Universal 3D Imaging, and Milling System

The Universal System is capable of digitally registering an implant via an intraoral or bench scan or a CBCT scan. The terms, "imaging" or "3D Imaging", are used when referring to all three scans. Each of the three scans has a scan post that is either seated on an adaptor or on an indexed healing cap prior to taking the scan.

Figures 86, 87:
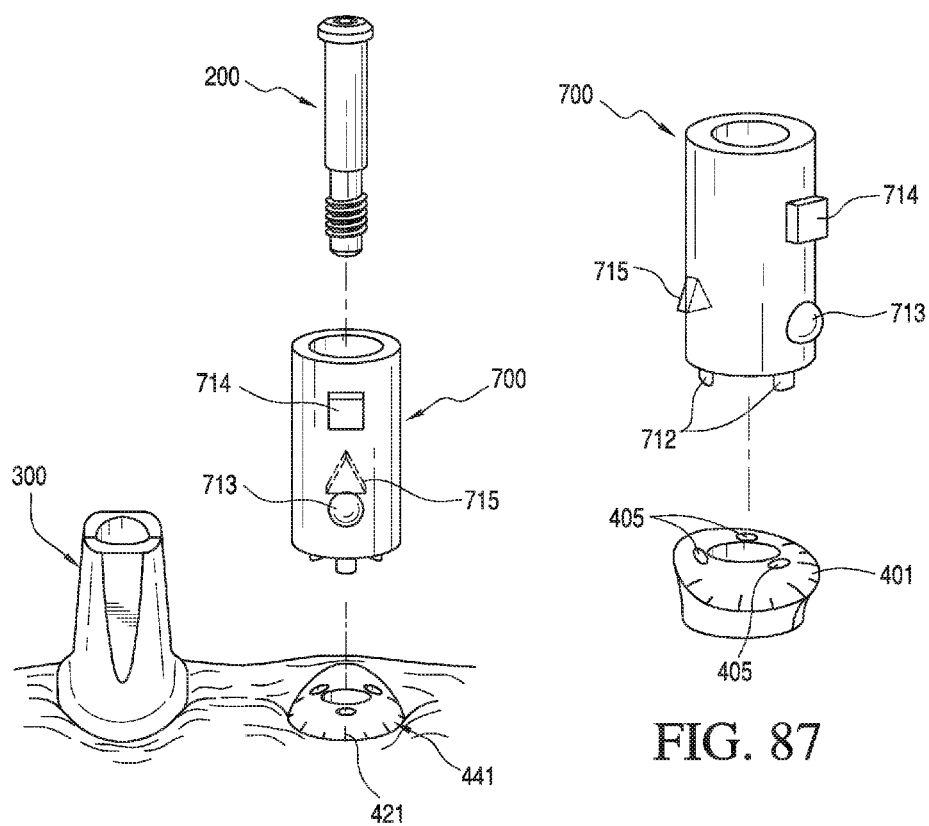

FIG. 84 is a frontal view of the universal scanning post seated on a universal adaptor for taking an intraoral scan or a CBCT scan. It can also be seated on an adaptor analog or on an adaptor, which, in turn, is seated on an implant analog, either of which is seated in a model for taking a bench scan. In the embodiment shown in FIG. 84, the universal scanning post (700) with a polyhedron (715) is seated on the adaptor (100), both of which are connected to the implant (10) with a fixation screw (200). In FIGS. 85A and 85B show the scanning post (700) and its primary indicia, (713) and (714), and its secondary indicium (715). In FIG. 85A, the scan post is being rotated so that its primary indicia, (713) and (714) will be directly over the primary indicia of the aligning adaptor (120, 121) as shown in FIG. 85B. This figure shows a recessed octagon index (661) that engages the octagon protrusion of the adaptor in the mouth, or on an adaptor analog seated in a model. In FIG. 17B(2), the first primary indicium is an "X" sphere (713) located over the primary indicia of the adaptor (120, 121), the second primary indicium is a "Y" rectangle (714) located vertically a set distance from the "X" sphere (713), and the secondary indicium is a "Z" triangle (715) located in a different plane, in this case, opposite the "X" sphere having been seated on an adaptor. In certain embodiments, the "Z" triangle (715) is located directly or 180° behind the "X" sphere and the "Y" rectangle (714) is an equal distance from the "X" sphere. However, the scanning post can have any number of markings or polyhedrons of varying configurations and relationships to each other and to the primary indicium of the adaptor, itself, for the scan to be taken, since the scan code has the necessary information to register the location, angulation, rotation points, anatomic contours, and other pertinent information in relation to the configuration of the scanning posts. In short, the potential embodiments of the universal scan post configuration are not limited by the descriptions shown here. FIG. 17B shows the universal scan post being seated on a previously rotated adaptor prior to taking an intraoral scan or on analogs in a model before completing a bench scan. In certain embodiments, the same post can be used for both the intraoral and bench scan, but the intraoral scan post can have a different design than the bench scan post, because they are synchronized via their relationship to the reference points of the adaptor (primary indicia). In this example, the universal scan post's "X" and "Y" polyhedrons are being seated over the adaptor's primary indicia (120, 121), while in FIGS. 86 and 87, the universal scan post's "X" and "Y" polyhedrons are being positioned over the primary indicium of the healing cap (421) and the projections (712) are seated in the recesses (412) in the healing cap that serve as the connecting index. These polyhedrons are not limited by this embodiment, which can, for example, be reversed with projections on the healing cap and recesses in the scan (or impression) post. As in the impression technique shown in FIG. 71, the healing cap does not have to be removed for the intraoral scan to be performed, since the post is directly connected to it. FIG. 87 shows an exploded view of the connection of the scanning post with the indexed healing cap with the polyhedron projections inserted in the matching recesses.

FIGS. 88-92 show additional embodiments of the indexed contour healing cap (401) that share a matching gingival contour (444, FIGS. 89-90) with the temporary abutment (344, FIG. 89) that has been seated on the aligning adaptor. It has an aligning external index (406) which is a geometric and positional facsimile of the index of the underlying adaptor, in this case, an octagon. Once again, any type of indexable polyhedron can be used in this technique, including an internal octagon (not shown).

In certain embodiments, the indexed contour healing cap (401) has a primary indicium on its collar (411) and on its top surface (421), and has one on the index (428) which is in line with them. FIG. 88, illustrates a maxillary premolar temporary abutment with a scalloped gingival contour (344) that is seated on an aligning adaptor, while FIGS. 89-90 shows that temporary abutment and an indexed healing cap having the same gingival contour (344, 444). FIG. 91 shows an indexed contour healing cap being rotated until position "b" is overlaying the adaptor's primary indicium (120), which centers its primary indicium (421) in relation to the jaw. The scanning post (700) is now seated on the indexed contour healing cap (401) such that its primary indicia (713) and (714) overlay the primary indicia of the healing cap (428) and (421), which is then secured with a fixation screw. The intraoral or bench scan will now capture the angle and index alignment of the implant, the type of preformed gingival architecture being used for this implant, and the soft tissue relationship to the preformed gingival architecture. The CBCT scan will capture the absolute position of the primary indicia of the scan post (713) and (714) and the indexed contour healing cap in relation to hard jaw structures (such as bone, teeth, and implant fixtures), and create a set positional relationship of those structures to the scan post (700). The intraoral or bench scan images can now be merged to the CBCT image using the scan posts' polyhedron primary indicia (713) and (714), as well as the geometry of the chosen healing cap (401). The technician can now fabricate a milled final abutment and crown (or other restorations) with the geometry of the gingival base already preset to that of the chosen contour healing cap, or can have models fabricated to create lab processed restorations. Of course, if the indexed contour healing was placed instead of the temporary abutment, then an intraoral scan is performed and the final restorations can be fabricated without even having to remove it.

In certain embodiments, all scanning posts for taking an intraoral, CBCT, or bench scan have the same configuration, although they will have varying compositions, depending upon the type of scan being taken. Given the fact that the scan post polyhedrons shown in the examples above are either primary (713) and (714) or secondary indicia (715) and given the fact that they are positioned either directly over the primary indicia of the aligning adaptor (120, 121), or the primary indicia of the indexed healing cap (428), which has been set in relation to the primary indicia of the aligning adaptor (120, 121), the merging of the intraoral or bench scan images with the CBCT scan image is automatable as the polyhedrons can automatically stitched together by combining the multiple reference points, once the location of the adaptor primary indicium, implant angulation, position in the jaw, and other appropriate data are input into via the Universal System scan code into the program.

Milling Abutments and Prosthetic Devices

For the purposes of discussion in this application, the terms "milled abutments" or "milling" connote any computer generated method for fabricating prosthetic components and devices to fit over implants, including, but not limited to, CNC milled components, stereolithography generated components, and other components.

In certain embodiments, an imaging post assembly can be used for fabricating milled abutments and prosthetic devices. The imaging post assembly can comprise an adaptor seated on an implant such that the adaptor index at its bottom end engages the implant's index. The imaging post can be seated on a polyhedron on the top end of the adaptor such that the adaptor and the imaging post have co-operable indicia for digitally identifying and registering the predetermined position of the adaptor. For example, a prior rotation of the adaptor and a prosthetic component also having co-operable indicia can be performed such that the prosthetic component establishes the preferred vertical and horizontal predetermined position over the implant. The prosthetic component can then be removed from the adaptor and the imaging post can be seated on the adaptor such that the cooperable indicia of the adaptor and the imaging post register the newly established position of the adaptor when taking an intraoral scan or similar scan. From this digital data, an abutment configuration can be rendered and conveyed to the milling program for abutment fabrication. Co-operable primary and secondary indicia can be used such that the primary indicia of the adaptor and imaging post determine the proper seating of the imaging post. The primary indicium of the adaptor and the imaging post can overlie each other.

The primary indicium of the adaptor can be an engaging polyhedron which provides a positive seat when engaging the primary indicium of the imaging post having a mating polyhedron.

The primary indicium position of the adaptor can be translated to a chosen milling program for creating a milled abutment, other prosthetic device, and/or prosthesis framework. The milling program uses the primary indicium position as part of the milling code for the manufacturing of the milled abutment, other prosthetic device, and/or prosthesis framework. For example, the primary indicium position informs the milling code how to control the milling process to thereby properly orient the manufactured item when seated on the adaptor or directly to the implant such that the manufactured item is properly, aesthetically, aligned.

In addition to the adaptor's primary indicium, the primary and secondary indicia of the abutment can be translated to the milling code of a milling software program. In such a manner, an ideally positioned virtual abutment or prosthetic device can be rendered first in the software and then integrated with the milling device codes and controls of a software program for the manufacture of a physical abutment or prosthetic device.

In certain embodiments, the abutment or prosthetic device can be manually rotated with the adaptor within the program by a user to a preferred position on the adaptor. In other embodiments, the software is programmed to automatically rotate the abutment or prosthetic device when the data input indicate the location of the primary indicium of the adaptor in relation to the primary or secondary indicia of the abutment or prosthetic device. In other instances, the universal automated and/or interactive digital protocol is translated to a milling software program, after taking an intraoral, bench, or CBCT scan that identifies the index align In certain embodiments, the imaging post has one or more markings or polyhedrons that are identifiable by the scan code of the program fabricating the milled abutment. For example, the markings or polyhedrons are enhanced by a substance that is readily visualized by the intraoral or bench scanner such as titanium dioxide or other suitable material, and may be enhanced by using barium or other suitable material for the CBCT X-ray scanner. In other embodiments, the imaging post has similar or dissimilar scanner identifiable polyhedrons which are located in an X-Y-Z plane to facilitate the virtual positioning of the implant abutment and the adaptor via the program's scan code. For example, the imaging post can have dissimilar scanner identifiable polyhedrons in the X-Y-Z plane such that the polyhedron in the "Z" location is 180° and a set distance from the "X" polyhedron as partially determined by the thickness of the imaging post and the "Y" polyhedron is a set 90° vertical distance from the "X" polyhedron that facilitates the scan process and accuracy. In at least certain embodiments, the imaging post's "Z" and "Y" scanner identifiable polyhedrons are the same distance from the "X" polyhedron which defines a precise isosceles triangle.

The Indexed Healing Cap and 3D Imaging

The indexed healing cap can be used to register the adaptor's reference indicium as well as the preferred gingival architecture that was developed by the geometry of the previously inserted healing cap.

In certain embodiments, an indexed healing cap or other referencing prosthetic component can be used to determine the ideal, predetermined position of a future final abutment or other prosthetic component that is seated on an adaptor's top end, and an imaging post having co-operable indicia for digitally identifying and registering that predetermined position of the healing cap or other prosthetic component, after rotation to the preferred vertical and horizontal predetermined position over the implant. This can involve the rotation of an adaptor and the healing cap or other prosthetic component via their co-operable indicia such that the healing cap or other prosthetic component is positioned in a preferred vertical and horizontal predetermined position over the implant. Then an imaging post is seated on a polyhedron on the top end of the healing cap which has been configured to synchronize with the primary indicia of the adaptor, which registers the adaptor's newly established position.

The co-operable indicia can include primary and secondary indicia such that the primary indicia of the healing cap, which is set in relation to the primary indicium of the adaptor, and the primary indicium of the imaging post, determine the proper seating of the imaging post. The primary indicium of the indexed healing cap can be identified by its preferred vertical and horizontal predetermined position and designates the insertion point of the imaging post.

The primary indicium of the indexed healing cap can be located on the polyhedron of the indexed base unit of the referencing device which is in line with the primary indicium that is identifying its preferred vertical and horizontal predetermined position. The primary indicium on the polygonal structure can engage a polygonal structure which provides a positive seat for engaging the imaging post with a reciprocal polygonal structure that aligns their respective primary indicia. The polyhedron on the end of the prosthetic device can be an index with the same polygonal configuration as the index of the underlying adaptor such that their polygonal sides are aligned. The polyhedron on the end of the prosthetic device can, for example, be an octagon when the adaptor's open end is also an octagon, or is a hexagon when the open of the adaptor is also a hexagon.

The indexed healing cap can have either symmetrical or asymmetrical contours such as cylinders, conical cylinders, or custom contours that extend from its free end to its open end as it emerges from the implant through the gingiva to the free gingival margin over the implant. The indexed healing cap has been previously situated in combination with an adaptor over an implant such that the restorative dentist can register the position of the adaptor via an intraoral, bench, or CBCT scan without removing the healing cap from the implant. The prosthetic device can also be a gingivo-adaptor which is a prosthetic device comprising a one-piece assembly of an adaptor stud on its end and the configuration of an implant engaging stud on its end such that the end index receives the impression post.

The primary indicium of the indexed healing cap can therein be conveyed to the milling device codes and controls to the chosen milling program for creating a milled abutment or other prosthetic device and prosthesis framework. The abutment or prosthetic device can be milled such that the scan code incorporates the location of the primary and secondary indicia of the ideally positioned virtual abutment and integrates it with the milling device codes and controls of a software program.

As previously explained, the abutment or prosthetic device is either manually rotated with the adaptor within the program to ideally position it or automatically rotated when the data input indicate the location of the primary indicium of the adaptor in relation to the primary or secondary indicia of the abutment or prosthetic device. The imaging post can have one or more markings or polyhedrons that are identifiable by the scan code of the program fabricating the milled abutment.

The indexed healing cap can have the same gingival contours as the interim healing cap or temporary abutment, which are also identifiable by the universal scan code from a library, and translates that information towards either choosing the correct base for the castable or pressable abutment or inserting the data in the scan code's milling device codes and controls of a software program used when creating the milled abutment.

Scanning the Preformed Unprepared Abutment:

Further embodiments provide an assembly for use in the process of dental restoration relevant to dental implant prosthetics comprising an adaptor, a preformed, unprepared contour abutment with a predetermined tooth preparation and a desired gingival configuration at its end, and a coping having co-operable indicia for digitally identifying and registering the predetermined position of the contour abutment, which has been set in relation to the cooperable indicia of the adaptor. This procedure can involve the rotation of the adaptor and the contour abutment also having co-operable indicia such that the contour abutment is situated in a preferred vertical and horizontal predetermined position over the implant. An imaging coping can be seated on the abutment such that the cooperable indicia on the imaging coping and the scan post register the newly established position of the contour abutment, which has been set in relation to the adaptor's cooperable indicia. In this position, a scan can be taken for fabrication of a final prosthetic device to fit on the preformed abutment.

In certain embodiments, the scan coping has the appropriate data for milling the abutment which has a matching configuration to its internal configuration. The scan data can include the configurations of the temporary abutment that holds the scan coping.

The abutment or prosthetic device can then be milled from the scan code incorporating the location of the primary and secondary indicia of the ideally positioned scanned abutment.

Scanning the Multifunction Abutment:

Further embodiments provide an assembly for use in the process of dental restoration relevant to dental implant prosthetics that can include an adaptor, a multifunction abutment seated on the adaptor's end and a imaging post having co-operable indicia for digitally identifying and registering the predetermined position of the multifunction abutment, which has been set in relation to the cooperable indicia of the adaptor. The multifunction abutment can receive a screw borne prosthesis on one end. In certain embodiments, the adaptor and the multifunction abutment, also having co-operable indicia, can be rotated such that the multifunction abutment is situated in a preferred vertical and horizontal predetermined position over the implant. Once properly situated, an imaging post can be seated on the end of the abutment that receives the screw borne prosthesis such that the cooperable indicia on the screw bearing polyhedron and those on the imaging post together register the newly established position of the multifunction abutment, which has been set in relation to the adaptor's cooperable indicia. In this position, it is possible to take a scan for the fabrication of a final prosthetic device.

In one aspect, the co-operable indicia can include primary and secondary indicia such that the primary indicia of the multifunction abutment, which is set in relation to the primary indicium of the adaptor and the primary indicium of the imaging post, determine the proper seating of the imaging post. The primary indicium of the multifunction abutment and imaging post can overlie each other.

In a further aspect of the invention, the primary indicium on the screw bearing polyhedron of the multifunction abutment can have an engaging polygonal structure which provides a positive seat for engaging the imaging post with a mating polygonal structure that aligns their respective primary indicia.

The primary indicium of the adaptor can be conveyed by its scan code's milling device codes and controls to the chosen milling program for creating a milled abutment or other prosthetic device and prosthesis framework. The abutment or prosthetic device can be milled from the scan code incorporating the location of the primary and secondary indicia of the ideally positioned virtual abutment are integrated with milling device codes and controls of a software program. The abutment or prosthetic device can be either manually rotated with the adaptor within the program to ideally position it or it can be automatically rotated when the data input indicate the location of the primary indicium of the adaptor in relation to the primary or secondary indicia of the abutment or prosthetic device.

The scan post can have one or more markings or polyhedrons that are identifiable by the scan code of the program used to fabricate the milled abutment. The markings or polyhedrons can be enhanced by a substance that is readily visualized by the scanner such as titanium dioxide or other suitable material. The scan post can have similar or dissimilar scanner identifiable polyhedrons which are located in an X-Y-Z plane to facilitate the virtual positioning of the implant abutment and adaptor via the program's scan code. In certain embodiments, the scan post has dissimilar scanner identifiable polyhedrons in the X-Y-Z plane such that the polyhedron in the "Z" location is 180° and a set distance from the "X" polyhedron as partially determined by the thickness of the scan post and the "Y" polyhedron is a set 90° vertical distance from the "X" polyhedron that facilitates the scan process and accuracy. The scan post's "Z" and "Y" scanner identifiable polyhedrons can be the same distance from the "X" polyhedron, which defines a precise isosceles triangle.

In addition to an intraoral scan, a CBCT scan can be performed in the same manner, although the CBCT scan post is composed of a nonmetallic material to prevent X-ray scatter. In a preferred technique, the CBCT and the intraoral scans can be merged by overlaying their referencing polyhedrons, etc.

In certain embodiments, an impression is first taken of the implant using the impression post of the company supplying the implant and a model is poured using an implant replica. A bench scan is then taken, by seating a universal scan post on an implant replica such that it captures the implant's index relationship, which is translated to a software program having the universal automated and/or interactive digital protocol within the universal scan code which virtually rotates an abutment into a preferred position. In another embodiment, an adaptor is first seated on the implant replica with a referencing post then being used to determine the ideal position of an abutment on the model prior to removing the referencing post and placing the scan post such that its primary indicium is set in relation to the primary indicium of the adaptor. A bench scan is then performed with the data translated to the milling software program for the fabrication of the milled prosthetic components. In another embodiment, a CBCT scan can be taken and the bench scan polyhedrons can be merged with those of the CBCT scan, thereby eliminating any error resulting from any inaccurate impression. The CBCT scan registers the absolute position of the universal aligning adaptor's primary indicium (and, therefore, the implant's index alignment).

The Universal Automated and/or Interactive Clinical and/or Digital Protocol:

The Universal Automated and/or Interactive clinical and/or digital protocol is a translational, integrating treatment protocol and makes use of cooperable componentry to synchronize them to a primary reference point.

One embodiment provides a method of restoring an implant having any index configuration and alignment by realigning, synchronizing, and referencing all restorative prosthetic components to set reference points wherein an automated and interactive clinical and/or digital protocol is used to realign and synchronize an implant prosthetic insert and a prosthetic component via their co-operable indicia such that the prosthetic component is situated in a preferred, predetermined position, which ideally situates its subgingival and supergingival configurations. The surgeon can select the desired vertical angle correcting prosthetic component having the appropriate geometric shape for restoring the implant. The prosthetic component can be rotated over the prosthetic insert via their co-operable indicia in relation to each other such that the prosthetic component is ideally situated. Once ideally situated, the co-operable indicia at that position can be identified and referenced. The identified, reference positions serve as reference points for fabricating the final prosthetic components and devices.

In certain embodiments, the co-operable indicia include graduated reference points and/or a mechanism of primary and secondary indicia that establish the rotation and synchronization points.

The implant prosthetic insert can be an adaptor whose primary indicium is one of the reference points that define the synchronization of all other prosthetic components as well as their relationship to the implant's index.

In certain embodiments, all other componentry are synchronized to the primary indicium of the adaptor, to the specific primary or secondary indicium of the prosthetic device that overlays the primary indicium of the adaptor, and to the primary indicium of the prosthetic component which defines its preferred horizontal and vertical position.

The adaptor and the prosthetic component can be rotated about each other such that the primary indicium of the prosthetic component is aligned with a particular primary or secondary indicium of the prosthetic component when it is situated in a predetermined, preferred horizontal and vertical position. The adaptor and the prosthetic component can be positioned such that the primary indicia of the adaptor and the abutment overlay each other when no rotation was performed, and a specific secondary indicium of the abutment overlays the primary indicium of the adaptor as determined by the degree of horizontal rotation that was necessary.

The rotation of an abutment or other prosthetic component to its preferred position synchronizes its primary and secondary indicia in relation to the primary indicia of the adaptors, thereby, the indexes of the implants, including the referencing devices such as an impression post or a scanning or imaging post or CT scan post, which automates impression taking or 3D imaging.

In certain embodiments, identifying the rotation and synchronization points prior to taking an impression for a bench scan, automatically identifies and references them during the bench scan, and, thereby, lessens the effects of any distortion that can occur from expansion and contraction of materials, when taking an impression for fabricating a model.

One embodiment provides a method of restoring any implant with any index configuration and/or misalignment which is positioned at any vertical angulation, wherein an aligning, synchronizing, referencing device defines the preferred, predetermined position of an interim or final prosthetic component or device such that it is ideally situated. In such an embodiment, an aligning, synchronizing, referencing device can be used in combination with an automated and interactive clinical and/or digital protocol to realign the referencing device to an ideal position, wherein the device is composed of an adaptor and an abutment having co-operable indicia that permits them to be rotated relative to each other to identify the abutment's preferred position. All other co-operable componentry can be synchronized to the newly repositioned cooperable indicia. The synchronized indicia can be used to register that position. Using the registered position information, the final prosthetic components and devices can be fabricated according to those reference points.

The co-operable indicia can include graduated reference points and/or a mechanism of primary and secondary indicia such that the primary indicium of the adaptor is rotatable in relation to the primary and secondary indicia of the abutment as defined by the desired predetermined position. The automated and interactive clinical and/or digital protocol can include a plurality of realigning and synchronizing prosthetic components and/or establishing or refining the gingival contours of interim or final prosthetic components, such that they are ideally situated, for replicating the tissue contours established by interim prosthetic components during the tissue engineering phase.

The chosen prosthetic component is rotated in either a predetermined clockwise or counterclockwise direction over an adaptor such that the primary indicium of the adaptor is positioned at a particular primary or secondary indicium of the prosthetic component, with the primary indicia of both components now being situated in relation to the index of the implant.

The realignment of the abutment or other prosthetic component or prosthesis can be preformed clinically in the treatment room or on the laboratory bench or is done virtually within a software program.

The aligning, synchronizing, referencing device can also serve as an interim abutment, healing cap or other interim prosthetic component. The abutment can be preformed, cast, milled or fabricated by another prosthetic means and is used for restoring a crown, bridge, or set of crowns with a preferred emergence profile, angulation, tooth preparation form, gingival architecture or other aspects for creating a preferred crown, set of crowns, bridge or similar prosthesis.

The abutment can also be preformed, cast, pressed, milled or fabricated by another prosthetic method and is used to restore an implant with a screw down prosthesis, wherein the repositioning of the abutment ideally positions the screw access channel for receiving the prosthesis anchoring screw.

The final aligning, synchronizing, referencing device can also be used to ideally position an implant during insertion. It is seated in the implant prior to its final torqueing during its insertion to assess the alignment of the index so that it can be ideally situated as the implant is tightened.

Universal Aligning Analog

Figure 18:
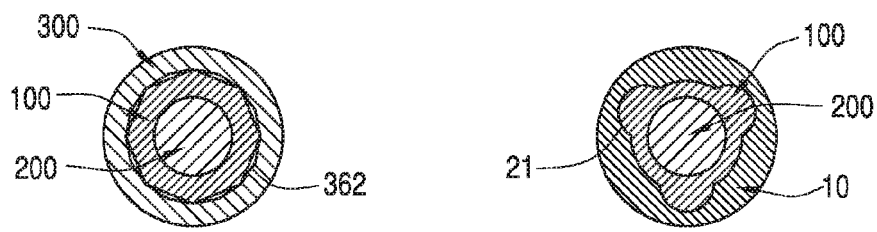
Figure 19:
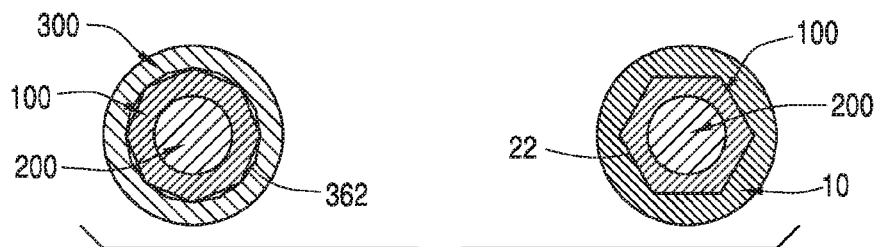
Figure 94:
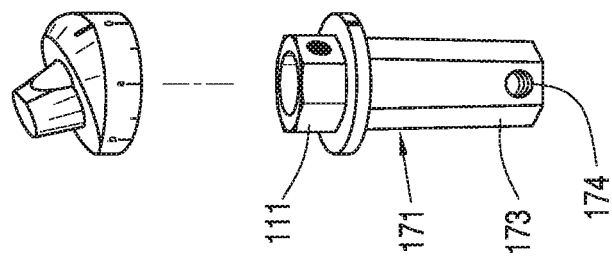
FIGS. 93-96 display a universal aligning analog for use in any lab fabricated model or with any CT scan generated model which is used for the fabrication of any screw borne or cement on prosthesis.

FIG. 18 shows a universal aligning analog (171), which is the ideal analog for the laboratory fabricated model or the CT scan generated model because, in certain embodiments, it repositions an abutment by rotating it in 15° increments; is antirotational in the model; can be removed, rotated and reinserted accurately to create that 15° horizontal rotation; can internally receive a set screw, and can be used for restoring any implant. In combination with the universal impression post, it provides mistake free models that are particularly effective when creating one piece castings and milled frameworks. In certain embodiments, the aligning analog has a shank with an external configuration (173) which has the same type of polygonal configuration as the index of the implant, which, in the exemplified case of FIG. 94, is an external hexagon which is an external version of the internal hexagon index of the implant. The top of the analog is a dissimilar index that receives an abutment or healing cap, which allows the analog with the abutment or healing cap to create a rotation that replicates the rotation that is accomplished with an universal aligning adaptor and abutment. When the top of the analog is an octagon (111), it is intended for use with trichannel, hexagon, and dodecagon implants, which can now be finely rotated about the vertical axis, achieving an optimal positioning of the abutment within a maximal 7.5° deviation from the ideal direction. This embodiment is not limited to an octagon/hexagon combination shown here, but, rather, the top configuration and the shank configuration can be any combination of dissimilar polyhedrons that will create a rotation as noted above in some other set increment of degrees of horizontal rotation. For example, a dodecagon (12 sided) shank could be used with the octagon index on top in order to achieve a 7.5° horizontal rotation, or, if the implant has an internal octagon, the shank of the analog is an octagon or hexadecagon, but the stud that receives the abutment is a hexagon, which is the same relationship described above for the adaptor seated on an octagon indexed implant. Once again, this external polyhedron also serves as an antirotational device when the analog is seated in the model. In the embodiment shown here, the "implant" hex hole is either created when the model is poured around the analog or is created in the model when milled, fabricated by stereolithograph, or other method, which, in this case, is a hexagon, but can be any type of polyhedron. In an additional embodiment, the analog has one or more internal screw holes (174) that are at an angle (as much as 90°) to the shank, which allows them to receive a set screw which provides additional retention and prevents vertical movement.

Figure 93:
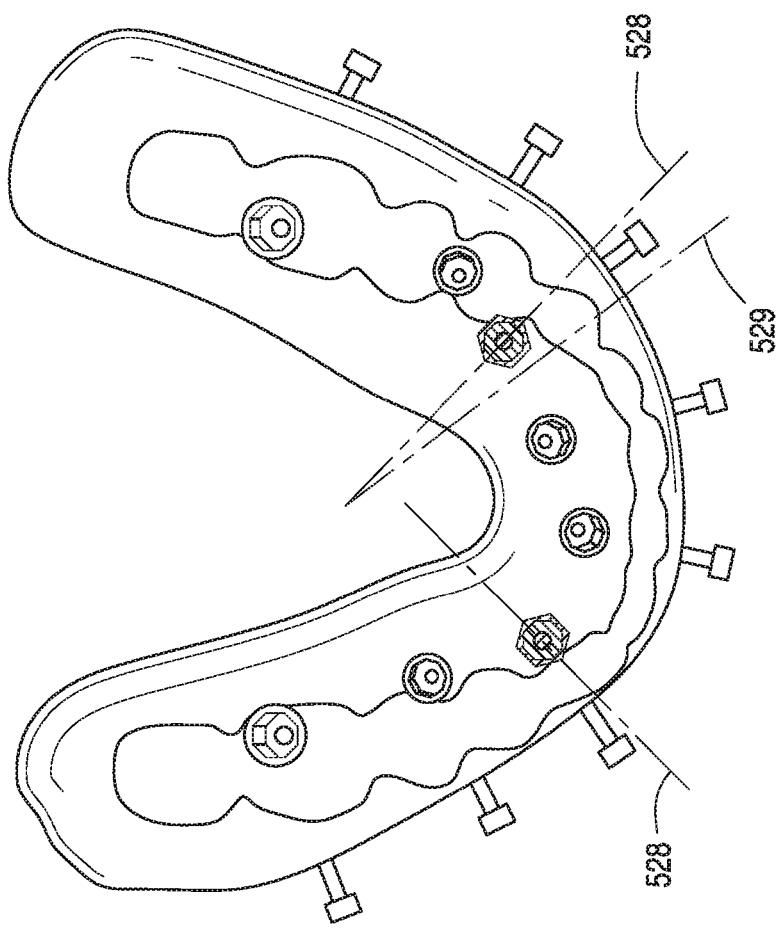
Figure 95:
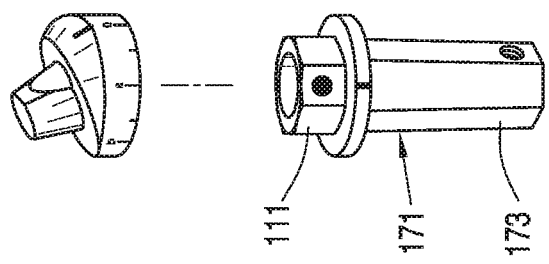

FIG. 93 shows a 30° angle correcting multifunction abutment seated on a universal aligning analog (171) having an external configuration (173) that, in this case, is a hexagon. FIGS. 94 and 95 provide a representation of either a poured model with universal aligning analogs in them or a CT scan generated image showing the "placement" of the analogs according to the surgeon's preferences. In this case, the implant in tooth position #22 has its center line (528) angled towards the distal solder joint, rather than in the ideal position (529). FIG. 96 shows that the rotation of the analog one stop of the its hexagon shank has turned the necessary 15° to situate the abutment (529) within the anatomic crown of tooth #22. This ability to achieve a finite horizontal rotation fosters the fabrication of a full arch bridge with screw access holes ideally positioned towards the central axes of the replacement teeth on the prosthesis, or allows a full arch set of milled abutments to be created with an improved emergence profile, since the milling machine has to cut less of the abutment from the mesial or distal sides as it parallels them. Thus, the above figures show that the implant in the tooth #27 position does not require any rotation to center it (528).

The universal aligning analog can be used interchangeably with the universal contour abutment system and the universal multifunction abutment system, and can be cross transferred from a model of implant replicas so that universal system components can be used to fabricate the restorations.

The co-operable indicia can include primary and secondary indicia such that the primary indicium of the adaptor is rotatable in relation to the secondary indicium of the abutment as defined by the desired predetermined position and the location of the abutment's primary indicium determines the location of the fixation screw threads.

The adaptor can be rotated around the abutment and the assembly is rotated over the implant such that the primary indicium of the adaptor is aligned with a specific primary or secondary indicium of the abutment when it reestablishes the preplanned, preferred position of the multifunction abutment to compensate for implant index misalignment, and the screw thread is positioned approximately 180° from the primary indicium.

In another method, the adaptor can be first rotated over the implant to a predetermined position with the abutment then inserted over the adaptor in its preferred position.

The Universal Aligning Tool

FIGS. 97A-D reveal a carrier/aligning tool that is used to position and/or rotate an adaptor into an abutment. In this embodiment an adaptor carrier (815) with a releasing screw tool (818). Another embodiment can have the carrier without the releasing screw or vice versa. In FIG. 97A, the carrier has a primary indicium (816) that is positioned in line with the primary indicia (120, 121) of the adaptor to allow it to reposition it in line with a secondary indicium of the abutment to position (a) (525) as shown in FIG. 97B. In certain embodiments, there is a way on the adaptor for a positive seat of the holder, which, in this case, is the primary indicium of the adaptor that is engaged by the holding tool's primary indicium. FIG. 97C shows the aligning adaptor having been rotated with the carrier's primary indicium (816), which overlays the primary indicium of the adaptor, to position "a" (secondary indicium, 525) to achieve a predetermined horizontal rotation. FIG. 97D shows the turning of a releasing screw (818) into threads inside of the abutment such that it releases the abutment from the adaptor (100) as it bottoms out in the carrier.

The Universal Aligning, Synchronizing Implant

FIGS. 98 and 99A-B show the nonagon implant which has a nine sided index with a vertex or situating primary reference indicium, and, which, in combination with a universal aligning adaptor, provides an absolute 5° horizontal rotation of all healing caps, abutments, impression posts, scanning posts, and other restorative components that are misaligned by the implant's index. This makes the nonagon the ideal implant for positioning and situating of healing caps, abutments, impression posts, scanning posts, and other restorative components. FIGS. 98 and 99A-B show an abutment post being inserted over the primary indicium (111) of its octagon stud, which, in turn, overlies the vertex (145) of the nonagon stud at its base, which is inserted into the nonagon index of the implant at its vertex (920). As such, the vertex (145) serves as the implant's primary indicium, and, in this example, the abutment (300) is being inserted without any rotation, presumably because the implant's index is situated in relation to a sagittal plane that bisects the ridge of the jaw at its individual center point. FIG. 100A shows an implant fixture mount, (930) having a primary reference vertex (932) overlying the primary reference vertex (933) of the nonagon male index (931) that is connected to the internal nonagon index (901) of the implant, at its own primary reference vertex (920). FIG. 100B shows the implant seated. FIG. 100C shows the implant's vertex (920) in line with a primary indicium scribe line (921) on the collar of the implant. The vertex of the fixture mount (933) serves as a positional device that allows the surgeon to precisely see when he is situating the implant so that a line drawn through the implant in the sagittal plane bisects the ridge at that point at approximately 90°. The vertex of the extender is its primary indicium or relational device. This invention of using the fixture mount as a relational device when seating an implant is not limited to the nonagon implant, but, in fact, can be used with any fixture mount having any polyhedrons on its shank which can be used to center the implant.

Figure 101:
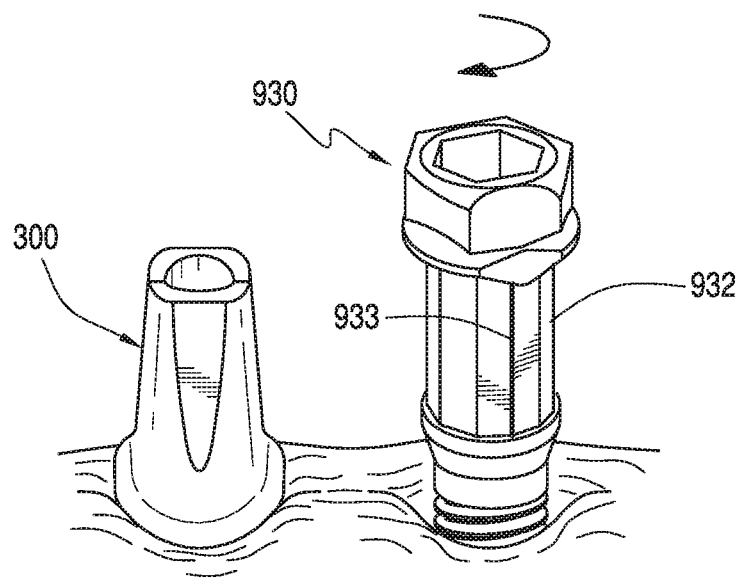
Figure 102:
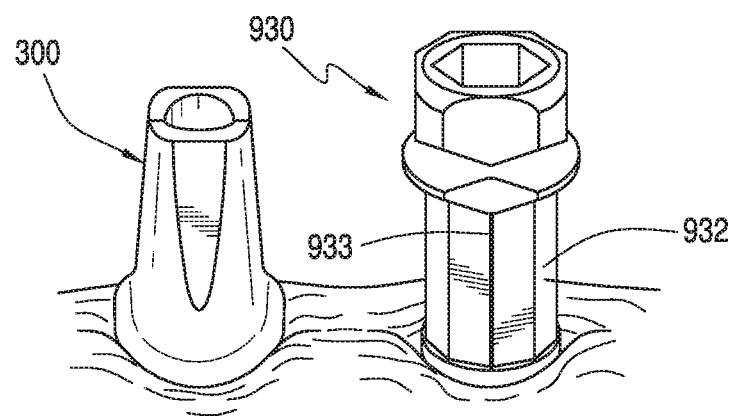

FIGS. 101 and 102 show a nonagon implant being seated such that the vertex of the fixture mount (933) and, therefore, that of the implant (920). Once inserted, if the nonagon index is not optimally situated in relation to a sagittal plane that bisects the ridge of the jaw at its individual center point, then a universal aligning adaptor and abutment are rotated on each other and the abutment/adaptor assembly is then rotated in 5° increments until the abutment is ideally positioned within a maximal 2.5° deviation from the ideal direction.

One embodiment provides an assembly for restoring an edentulous site with a nonagon aligning, synchronizing implant fixture composed of a regular 9 sided polygon having 9 equal sides and 9 vertexes with 9 lines of symmetry each of which extend from a particular vertex 180° to an opposing side, wherein only one of the 9 vertexes had a symmetry line that bisects its opposing side, and, therefore, serves as the index's primary indicium reference point for the ideal insertion of the implant such that a sagittal plane drawn at that reference point bisects the ridge at a 90° angle when the implant is ideally situated with its axis of rotation and synchronization being in a preferred horizontal and vertical predetermined location in the bone and a set of prosthetic componentry for restoring the implant that are synchronized to the implant's primary indicium and to each other via their co-operable indicia are, therefore, also situated in a preferred horizontal and vertical predetermined location for creating the ideal restoration when their primary indicia overlay each other.

The nonagon implant can either have an internal or an external index. The co-operable indicia can include graduations for indicating the degree of rotation of the prosthetic componentry relative to the implant's primary indicium reference point. The co-operable indicia can include primary and secondary indicia such that the primary and secondary indicia of the prosthetic componentry are rotatable in relation to the primary indicium of the implant as they are rotated to a desired predetermined position. The primary indicium of the nonagon implant determines the positioning of the prosthetic componentry into their preferred positions as they are rotated with their primary and secondary indicia in a set position relative to the implant's primary indicium.

The bisecting vertex can serve as a primary indicium. In one such embodiment, the bisecting vertex has a different shape to distinguish it from the other vertexes.

In one embodiment, the nonagon implant and prosthetic components can be ideally situated. An abutment, impression post, scanning post, healing cap, similar prosthetic component or prosthetic device for restoring the implant to be received can be seated on the nonagon implant with its primary indicium overlaying the implant's primary indicium with the final prosthetic component, device or restoration being fabricated from that reference point, when the implant has been positioned in its preferred, preplanned position.

When the nonagon implant has not been ideally situated and the prosthetic components correct for index misalignment, an aligning adaptor to be received and seated on the nonagon can be used to align and synchronize an abutment in a predetermined position relative to the implant's primary indicium. An abutment post or healing cap, prosthetic device or similar prosthetic component for restoring the implant can be received on and rotated about the adaptor to reposition the prosthetic component in a generally desired vertical and horizontal predetermined position when the adaptor/prosthetic component assembly is seated on the implant, wherein the adaptor and the prosthetic component have co-operable indicia for identifying and registering the predetermined position of the prosthetic component.

The co-operable indicia include primary and secondary indicia such that the primary and secondary indicia of the prosthetic componentry are rotatable in relation to the primary indicium of the implant as they are turned into a desired predetermined position.

The polygonal structure at the top end of the adaptor can be an octagon stud and the bottom end of the adaptor that interfaces with the implant is a nonagon with the prosthetic component having an octagon or hexadecagon receptacle that engages the octagon stud of the adaptor. The means for adjusting the relative angular position of the adaptor to the prosthetic component followed by their assembly to the implant results in net 5° increments of horizontal rotation when the engaging receptacle of the prosthetic component is an octagon or results in net 2.5° increments of horizontal rotation when the engaging receptacle of the prosthetic component is a hexadecagon.

Methods of Aligning, Synchronizing, Referencing and Forming a Set of Universal Abutments and Prosthetic Devices In the methods described, below, it is understood that the Universal System rotates all abutments and other prosthetic components in 15° increments, or less, for the trichannel, quadragon, hexagon, octagon, and dodecagon implants. In these discussions, when a scan post is seated for an intraoral scan, it is assumed that an impression post can first be inserted followed by a bench scan.

Automated Technique Via Integrated Componentry in Combination with a Specific Clinical and Digital Protocol:

The Universal System is a comprehensive system for restoring any type of implant restoration using either clinical prosthetic components or virtual components in a software program, or both. It provides a method of restoring an implant having any index configuration and/or alignment by realigning, synchronizing, and referencing all restorative prosthetic components to set reference points. In certain embodiments, an automated and interactive clinical and/or digital protocol can be used to realign and synchronize a physical or virtual implant prosthetic insert and a prosthetic component via their co-operable indicia. In this manner, the prosthetic component can be situated in a preferred, predetermined position, which ideally situates its subgingival and supergingival configurations and provides the ideal position for the restoration.

One embodiment involves choosing the desired vertical angle correcting prosthetic component having the appropriate geometric shape for restoring the implant. The prosthetic insert can be rotated about the abutment via their co-operable indices in relation to each other such that the prosthetic component is ideally situated over the implant. The co-operable indices can then be identified and referenced at that position, which are the reference points for fabricating the final prosthetic components and devices.

In a preferred, but by no means the only, embodiment, the cooperable componentry have graduated reference points and/or a mechanism of primary and secondary indicia that establish the rotation and synchronization points, and the prosthetic insert is a universal aligning adaptor that has a specific primary reference indicium to which all other cooperable componentry are synchronized. It is the synchronization of all of the componentry that contributes to automating the restorative procedures with a dramatic reduction in operator error.

In addition, the system transforms the rotation of abutments from being around the central axis of the implant to a redefined central axis of rotation that has been developed using a series of predefined points of rotation with the result being that all interim and final abutments and healing caps are ideally situated after being rotated in 15° increments or less. As such, this is accomplished by rotating the universal aligning adaptor in a clockwise or counter clockwise direction about an abutment or healing cap, wherein its primary indicium is positioned under a predetermined primary or secondary indicium of the prosthetic component to achieve the desired rotation.

The rotation by primary and secondary indicia of the co-operable adaptor and its overlying prosthetic component is facilitated by dissimilar polygonal structures at the free end and open end of the adaptor such that the rotation of the adaptor and prosthetic component results in increments of horizontal rotational adjustment over the implant.

In certain embodiments, the polygonal structure at the open end of the adaptor is an octagon stud and the free end of said adaptor is a hexagon, tripod, dodecagon or other configuration wherein the number of polygonal sides is a multiple of 3 and said prosthetic component has an octagon or hexadecagon receptacle that engages the octagon stud of the adaptor. This configuration allows for adjustment of the relative angular position of the adaptor to the prosthetic component followed by their assembly to the implant results in net 15° increments of horizontal rotation when the engaging receptacle of said prosthetic component is an octagon. One can achieve net 7.5° increments of horizontal rotation when the engaging receptacle of said prosthetic component is a hexadecagon. When the polygonal structure at the open end of said adaptor is a hexagon stud and the free end of said adaptor is an octagon or other configuration wherein the number of polygonal sides is a multiple of 8 and the prosthetic component has an hexagon or dodecagon receptacle that engages the hexagon stud of the adaptor such that the means for adjusting the relative angular position of the adaptor to said prosthetic component followed by their assembly to the implant also results in net 15° increments of horizontal rotation when the engaging receptacle of said prosthetic component is an octagon. One can achieve net 7.5° increments of horizontal rotation when the engaging receptacle of said prosthetic component is a dodecagon.

When the polygonal structure at the open end of said adaptor is a nonagon stud and the free end of the adaptor is a quadragon and the prosthetic component has an nonagon receptacle that engages the nonagon stud of the adaptor such that the adjustment of the relative angular position of the adaptor to the prosthetic component followed by the rotation of their assembly to the implant results in net 10° increments of horizontal rotation. Finally, the ideal adaptor/implant rotation occurs in 5° increments of rotation, when the open end of the adaptor is an octagon and the free end is a nonagon that engages the unique nonagon implant index.

These finite increments of rotation in stark contrast to the coarse increments of rotation provided by the indexes of the implants such that the contour abutments, healing caps and prosthetic devices are ideally situated, or even "centered" in the sagittal plane, allows the operator to restore implants with asymmetric healing caps and abutments which fosters a more natural emergence profile. As a result of those finite increments of rotation, the securing device of the multifunction abutment aligns the screw access hole as close as possible to the center of the occlusal table of the replacement tooth overlaying the implant.

The Universal System, as such, allows the restoration of any implant type, regardless of its index misalignment with any implant restoration, whether they are well customized with milled, pressed, or cast abutments or are more simplistic with preformed, unprepared abutments that allow a "plug and play" operative routine.

In short, the prosthetic components are of a plurality of devices including but not limited to healing caps, referencing abutment posts and healing caps, indexed healing caps, abutment posts, temporary abutment posts, milled abutment posts, cast abutment posts, pressed abutment posts, zirconia abutment posts, impression posts, scanning posts, implant crowns, bridges, dentures, over dentures, screw down crowns, hybrid dentures, and other prostheses for restoring dental implants. They can have asymmetrical or symmetrical contours at their bases.

As stated, the prosthetic components and devices can be fabricated clinically using physical devices and methods or can be constructed in a software program to create milled, stereolithograph generated, or other computer generated components.

Method of Fabricating a Set of Anatomic Abutments for Crown and Bridge Restorations for Implant Restoration:

A method of fabricating anatomic abutments by inserting an adaptor on a dental implant in a predetermined position relative to the implant is also disclosed. A preformed abutment having an asymmetric configuration can be seated on the adaptor's open end. The open end is configured to, in turn, receive a crown, bridge, set of crowns or other similar prosthesis. The crown, bridge, set of crowns or similar prosthesis can be first rotated about the adaptor followed by the adaptor/abutment assembly around the implant until the abutment is in a generally desired vertical and horizontal predetermined position when the adaptor is seated on the implant. This realigns the abutment such that its asymmetric configuration is properly situated to reestablish ideal form, function and esthetics even when the implant index is misaligned and sets them off angle, wherein the adaptor and abutment have co-operable indices for identifying and registering the predetermined position of the abutment. The co-operable indicia also permits the adaptor and abutment to be rotated relative to each other into the predetermined position of the abutment while the adaptor is detached from the implant. The abutment has now been set to a specific position in relation to the primary reference indicium of the adaptor. From this point on, the primary reference indicium of the adaptor dictates the restoration of the final abutment and overlying prosthetic device.

With this in mind, primary indicium of the adaptor then determines the seating of an impression post, an intraoral or bench scanning post, or a CBCT scan post also having co-operable indices such that they reference the abutment's predetermined, preferred position for fabricating the final abutment and/or the prosthesis that is seated on it.

The abutment is of a plurality of devices including but not limited to temporary abutment posts, final preformed abutment posts, castable abutment posts, pressable posts, or milled abutment posts, or other posts fabricated by another suitable means that receive implant crowns, set of crowns, bridges, and other prostheses for restoring dental implants that are either cemented or screw retained.

There are many ways to fabricate crown and bridge restorations that are seated over implants, some of which are specifically described herein for exemplification purposes, but are not intended to be inclusive of all abutments: the preformed, unprepared crown and bridge abutment that is intended to be used for the simplest technique; the preformed, customizable abutment pattern that is intended to be rotated and aligned and then customized prior to being converted to a cast or pressed ceramic abutment via a burnout of the pattern in the "lost wax" technique. The castable or pressable abutments can be fabricated to be received on an adaptor or can be "cast-to" or "pressed-to" an adaptor of a complimentary material, and can, therefore, be created such that it engages the index of the implant without any interfacing adaptor. The Universal System's versatility allows the creation of either type of implant connection-with or without a titanium connector, depending upon the preference of the operator.

When choosing the abutment, the operator can also elect to have a standard symmetrical base for the abutment or can choose a more custom, preformed asymmetrical configuration to support the gingiva with an emergence profile that is similar to a natural tooth in that implant fixture's position, after it has been rotated to ideally situate that gingival contour. When contours are already incorporated in the interim abutments or healing caps, and impression, scanning, or imaging posts or other prosthetic devices that share the same preformed symmetrical or asymmetrical configuration as the base of the abutment, the process becomes automated while being customized, as well. Even if the impression or scan is taken of the adaptor (without an indexed base or healing cap), the preferred gingival contour base or healing cap can be "dialed-in" to the virtual abutment to establish the preferred emergence profile. When the abutment is inserted, the tissue can be scalloped to accommodate it.

Because of the unique centering of the abutment's primary indicium such that the component is ideally situated, the Universal Contour Abutment can consistently have all of its abutments with internal lingual threads to receive screw retained crowns. The internal thread for the crown fixation screw is placed in the esthetic zone, which is predictably 180° from the buccal aspect of the abutment. Practitioners have been seeking a retrievable crown as an alternative to permanently cemented crowns over implants.

The Preformed, Unprepared Contour Abutment for Simplified, Standard Implant Restoration A method for restoring a dental implant wherein the operator is seeking a simplified, basic technique using standardized componentry and a single process. An adaptor is seated on a dental implant in a predetermined position relative to the implant, which, in turn, receives a preformed, unprepared abutment having an asymmetric configuration upon which an interim coping and a referencing coping are seated. All of them have cooperable indices for aligning, synchronizing, and referencing the interim abutment to create the final abutment. This method can comprise the steps of rotating the adaptor and abutment relative to each other such that the abutment is in a predetermined, preferred position that is noted. An interim preformed coping composed of acrylic or another suitable temporary restorative material for molding a temporary crown to it can be aligned and seated such that it is automatically in the preferred position. One can then remove the interim coping/temporary crown assembly and seat a reference coping with the same alignment as the interim coping to identify and register the position of the adaptor and the abutment. One can then fabricate a final abutment having the same preferred horizontal and vertical position as the interim abutment.

The process begins with the seating of the acrylic coping on the ideally positioned abutment such that its primary indicium is aligned with the primary indicium of the abutment prior to relining a previously fabricated or molded temporary crown. In most instances, the temporary crown has been prefabricated by the laboratory.

When ready to fabricate the final abutment and crown, the referencing impression coping is seated on the abutment to identify and reference its primary indicium that is aligned with the primary indicium of the abutment, along with registering the primary and secondary rotation points of the abutment in relation to the primary reference indicium of the adaptor that were previously noted. The impression coping is lifted in the impression and serves as a referencing and seating device for an abutment replica with the same geometry as the interim abutment with the model being poured and the final abutment being cast, pressed, or milled or fabricated by some other type of method such that it has the same relationship to the implant's index as the interim abutment or healing cap. Following the step, one can fabricate the overlying prosthesis.

In certain embodiments, the referencing coping is a scanning coping with a geometric configuration that is ideal for an intraoral or bench scan and/or CBCT scan to register the position and configuration of the interim abutment to create a milled abutment.

The final abutment is either a replica of the interim abutment, or, if the operator so choses, can be fabricated by one of the methods outlined above. The preformed abutment can have a symmetric or asymmetric base with a preferred geometry of appropriate configuration and depth to vertically position the base in relation to the gingival architecture. In certain embodiments, the crown is fabricated to fit the interim abutment, which, therein, becomes the final abutment.

The Universal Contour Screw Retained Crown

This method describes the predictable fabrication of screw retained crowns via a contour abutment seated an adaptor having co-operable indices wherein the abutment has the geometry of a natural tooth preparation and has internal screw threads that are positioned in the esthetic zone approximately 180° from the primary indicium of the abutment after it has first been ideally situated such that a crown, set of crowns, or bridge are receivable on the abutment and are retained by the fixation screws that engage the abutment fixation screw threads. In certain embodiments, the method involves rotating an abutment to a preferred horizontal and vertical position. From this position, one can create the screw threads by milling them, setting internally threaded tubes, die tapping, or by another appropriate method at that location such that the threads are ideally positioned in the esthetic zone and at the most ideal pitch for receiving a driver that is carrying the screw. The proper esthetic zone and ideal pitch would be known for the dental surgeon. One can then create the overlying prosthetic component with a stop for securing the prosthetic component on the abutment and affix it with a fixation screw that engages the internal threads.

In certain embodiments, the method makes use of co-operable indicia that includes primary and secondary indicia such that the primary indicium of said adaptor is rotatable in relation to the secondary indicium of the abutment as defined by the desired predetermined position and the location of the abutment's primary indicium determines the location of the fixation screw threads.

In certain embodiments, the adaptor is rotated around the abutment and the assembly is rotated over the implant such that the primary indicium of the adaptor is aligned with a specific primary or secondary indicium of the abutment when it reestablishes the preplanned, preferred position of the multifunction abutment to compensate for implant index misalignment, and the screw thread is positioned approximately 180° from the primary indicium.

The Universal Contour Healing Cap

This method discloses the creation of preferred gingival architecture over an implant using a contoured healing cap that is seated on an adaptor, with the adaptor/healing cap assembly being seated on a dental implant in a predetermined position. The preformed, contoured healing cap has a specific symmetric or asymmetric configuration that is suitable for protecting the adaptor and maintaining a desired gingival opening over an implant. It is receivable on and rotatable about said adaptor, wherein the adaptor and the healing cap have co-operable indices to position said healing cap in a generally desired horizontal predetermined position when said adaptor is seated on the implant with the healing cap's primary indicium situated such that a replacement abutment also has its primary indicium in an ideal position with said adaptor and healing cap whose co-operable indices permit said adaptor and healing cap to be rotated relative to each other into the predetermined position of said healing cap while said adaptor is detached from the implant.

The healing cap is of a plurality of devices including gingivo-adaptors which are healing caps and adaptors that are combined into one-piece assemblies for connection to the implant, wherein the open end of the devices have the preferred configuration and/or index of the chosen adaptors and the free end has the configuration and/or index of the particular implants. The healing cap is composed from a plurality of materials including titanium, titanium alloy, zirconia, or other suitable materials and can be coated by anodizing or some other method.

The primary indicia of the healing cap determines the positioning of the abutment post when it is to be rotated such that its primary indicium and that of the healing cap are in the same preferred position.

The contour healing cap can have a gingival geometry that is appropriate for that implant at that site for that type of tooth abutment that would be located there, because of the realignment that occurs independently of the implant's index.

Tissue Engineering from A to Z

Also provided is a method of tissue engineering over a dental implant wherein a particular gingival architecture is developed using an adaptor in combination with an interim healing cap, abutment, or other interim component having co-operable indices for repositioning the adaptor/interim prosthetic component assembly to a predetermined, preferred position wherein its gingival contours are used as a template by the surgeon to shape the tissue over the implant. In certain embodiments, it is possible to open the tissue over the implant and rotate an adaptor and a chosen interim component relative to each other and the assembly relative to the implant via their co-operable indices such that the desired gingival contours are ideally situated over the implant to most naturally support the tissue with the proper emergence profile. Gingival tissue can then be sculpted as the adaptor/interim prosthetic component assembly is seated. In this manner it is possible to mold the tissue to the architecture of the interim component, rather than molding the abutment to match the tissue with inconsistent results. The interim component can be removed from the adaptor and an impression or scanning post or other registering device can be seated in relation to the primary indicium of the adaptor. Once seated, it is possible to register and identify the ideal position and type of final abutment or prosthesis to be inserted over the implant. A final abutment can then be fabricated such that it mimics the subgingival contours of the interim abutment and integrated with the image of the surface topography. In certain embodiments, the adaptor and the interim abutment can be removed and replaced with a final abutment which has co-operable indices for precisely positioning its gingival contours with the same relationship as the interim component.

The co-operable indices can include a mechanism of primary and secondary indicia such that the primary indicium of said adaptor is rotatable in relation to the secondary indicium of the abutment as defined by the desired predetermined position. The rotation of the adaptor to the prosthetic component followed by their assembly to the implant results in net 15° increments of horizontal rotation when the open end of the adaptor is an octagon and the free end that engages the implant is a tripod, hexagon, or dodecagon or the open end of the adaptor is a hexagon and the free end that engages the implant is an octagon. In addition, the rotation of the adaptor to the prosthetic component followed by their assembly to the implant results in net 10° increments of horizontal rotation when the open end of the adaptor is a nonagon and the free end that engages the implant is a quadragon.

The interim healing caps and abutments have a plurality of preferred gingival contours and serve as surgical and design templates for the tissue training around the interim abutment and the fabrication of the final abutments when they are in their preferred positions. The final abutments can be cast, pressed, milled, or preformed, and can be fabricated such that they either interface with an adaptor to the implant or interface directly with the implant without an adaptor.

In certain embodiments, the tissue architecture is first analyzed in a CT scan wherein the prosthesis is also scanned to capture the tissue architecture, prior to the surgery as a part of choosing the preferred interim healing cap, abutment or other prosthetic component. In certain embodiments, a virtual adaptor can be chosen and the preferred virtual prosthetic component, having co-operable indices, can be rotated over the virtual adaptor in a CT scan program to a predefined position as delineated by the primary indicia of the adaptor in relation to the primary and secondary indicia of the prosthetic component. In the rotated position, one can measure the depth from the bone to the location where the virtual prosthetic component exits the gingiva at predetermined points on the healing cap. The preferred clinical prosthetic component to be used during the surgery according to the desired gingival architecture and its depth can then be selected and, when applicable, the vertical angle correction also made.

The initial tissue opening can be precisely created by a universal guided tissue punch comprising the steps of locating the open end of the implant and removing the cover screw, inserting a surgical guiding screw with an extra-long shank and threading it into the implant's internal thread, followed by the rotation of a universal guided tissue punch having an internal polyhedron to receive the guiding screw and having the exact outside diameter as the implant such that the guiding screw precisely guides the tissue punch as it excises the tissue over the implant. In certain embodiments, a guiding polyhedron is inserted into the index of the cover screw of the implant with the guided tissue punch, having a matching internal configuration, being rotated over the implant until the tissue is excised, as described above. The universal guided tissue punch can also demarcate when the tissue should not be excised because of implant angle in relation to the attached gingival tissue, but, rather, should be repositioned to prevent its loss over the implant.

The universal guided tissue punch can be used with any implant at any angle and can be used to excise the tissue removal as directed by any polyhedron seated on the implant or its cover screw that is in line with its long axis.

Finally, the repositioned prosthetic component can be registered via impression or scan of the adaptor or overlying indexed healing cap such that its gingival architecture in its preferred position is translated to the final abutment and/or prosthesis, which is then inserted over the implant with the same gingival contour in the same position.

The Indexed Healing Cap for a Simplified Impression or Scan

One embodiment provides a method of restoring dental implants by using indexed healing caps or similar tissue supporting interim devices that are also referencing devices which have co-operable indices for identifying and referencing adaptor and abutment positions without having to be removed from the implant. This can, thereby, simplify the fabrication of abutments and/or prosthetic devices for restoring dental implants. In certain embodiments, the healing caps can be rotated over their adaptors and the adaptor/healing cap assemblies over their implants according to an automated and interactive clinical and/or digital protocol such that they are situated in preferred vertical and horizontal predetermined positions over their implants. Once rotated, the referencing posts such as impression posts, the scanning posts, or imaging posts can be inserted on each healing cap such that the primary indicium of the referencing post is aligned in relation to the primary indicium on the healing cap's index with an impression, intraoral or bench scan, or a CBCT scan being taken of the healing cap/referencing post assembly such that it registers the adaptor's position in relation to the implant index, the indexed healing cap's position in relation to the adaptor, the referencing post in relation to the indexed healing cap along with the other anatomic structures in the jaw. It is then possible to fabricate cast, pressed, milled, or other abutments to those preferred positions, followed by the fabrication of the implant prostheses.

The co-operable indices include graduated reference points and/or a mechanism of primary and secondary indicia such that the primary indicium of the adaptor is rotatable in relation to the primary and secondary indicia of the indexed healing cap as defined by the desired predetermined position of the healing cap.

The automated and interactive clinical and/or digital protocol can include choosing the appropriate indexed healing cap or similar prosthetic component having the desired geometric shape for the tissue over the implant, rotating it as necessary in either a predetermined clockwise or counter-clockwise direction such that the primary indicium of the adaptor is positioned at a particular primary or secondary indicium point of the healing cap, and is, in turn, set in relation to the index of the implant such that its gingival contours are ideally situated in a preferred, predetermined position over the implant. The indexed healing cap can also be used as a template for sculpting the gingiva.

The primary indicium of the healing cap is located at the center point of the healing cap as it bisects the ridge at a 90° angle in the sagittal plane or another preferred position, which, therein, identifies the location for seating the impression or scanning post. In certain embodiments, the primary indicium of the impression post, scanning post, or imaging post overlay the primary indicium of the healing cap. The index of the healing cap can have a polyhedron adjacent to the primary indicium of the healing cap such that the polygon of the polyhedron is bisected at that point. The primary indicium on the polygon of the healing cap receives the impression or scanning post such that the primary indicia overlay each other and, thereby, capture the primary indicium at its center point. The polygon can be an index that is an exact replica of abutment engaging index on the open end of the adaptor.

The Method of Using the Universal Multifunction Abutment to Realign Screw Access Holes:

The multifunction abutments can be used for restoring any screw borne prosthesis such that its screw access holes are realigned into preferred positions is disclosed. The multifunction abutments are seated on and rotatable about universal aligning adaptors followed by the adaptor/abutment assemblies around the implants until said abutments' screw access holes are realigned to generally desired vertical and horizontal predetermined positions, which approximate the center of the occlusal tables of the tooth replicas for those implants being restored with the screw borne prosthesis. Said adaptors and said abutments have co-operable indices for identifying and registering the predetermined position of said abutments, after permitting the adaptors and the abutments to be rotated relative to each other such that the abutments are in ideal positions.

Said co-operable indices include graduations for indicating the degree of rotation of said abutment and said adaptor relative to each other, which can include primary and secondary indicia, wherein the primary indicium of said adaptor is rotatable in relation to the primary or secondary indicium of the multifunction abutment as it is rotated to its desired predetermined position such that its primary indicium is ideally situated.

The multifunction abutment has a polyhedron that is shaped to receive another polyhedron over it, which has a matching engaging configuration that engages it, and is, in turn, connected to the prosthetic device via a chemically cured, light cured, or other combination method to create the screw retained prosthesis. In a preferred embodiment the abutment polyhedron is a cone with an asymmetrical flat at its primary indicium which is located approximately 180° from the midpoint of the vertical angle correction of the abutment and the engaging polyhedron is inside a connecting cylinder. The flat provides a positive seat at its primary indicium and prevents rotation of the connecting cylinder during the assembly phase along with preventing natural rotational forces associated with a cylinder on a cone from dislodging it.

The primary indicia of the cone on the multifunction abutment determines the seating of an impression post, an intraoral or bench scanning post, or CBCT scan post also having co-operable indices such that they reference the realignment of the abutment at its predetermined, preferred position that ideally situates the screw access hole when fabricating the final abutment and/or the prosthesis that is seated on it.

The multifunction abutment is of a plurality of devices including but not limited to preformed temporary abutment posts, preformed final abutment posts, castable posts, pressable abutment posts, or milled abutment posts, or other posts fabricated by another suitable means wherein they receive the prosthesis that is screw retained to them when restoring the implants.

The prosthesis that is seated on the multifunction abutment is of a plurality of devices including but not limited to an overdenture bar for receiving a snap on denture, a snap on denture that is connected to retaining devices seated directly on the adaptors or implant abutments seated on adaptors without a connecting bar, a transitional hybrid prosthesis that has been converted from a denture to a fixed, screw retained prosthesis during the insertion of a set of implants during an immediate load procedure, a screw retained denture or similar prosthesis with flanges, a screw retained crown, set of crowns or bridge with or without flanges.

The multifunction abutment can be milled out of any suitable restorative material and is fabricated by first rotating a virtual multifunction abutment into a preferred position over a virtual adaptor using the universal aligning system's automated and interactive clinical protocol in a milling software program to define the synchronized axis of rotation and, thereby, eliminate the mesial-distal abutment misalignment prior to milling it, followed by milling the abutment according to the parameters established by the rotation such that either a single piece, final abutment for insertion on the implant which engages its index without an interfacing adaptor or a final abutment to be receivable on the adaptor with the assembly then being inserted on the implant is milled with the prosthetic device then being milled and affixed to it.

The Universal Multifunction Abutment System's Use in Simplifying Procedures for the Immediate Load Transitional Hybrid Prosthesis:

A method of immediately restoring dental implants at the time of their insertion with an immediate load transitional screw retained prosthesis by first using a set of aligning multifunction abutments and universal adaptors having co-operable indices wherein they are rotated and situated in finite increments such that the screw access holes of the abutments receiving the prosthesis are ideally located regardless of the type of implant indexes or their misalignment, the steps comprising the rotation of the adaptor and the abutment having the co-operable indices around each other, followed by the assembly around the implant according to an automatic and interactive clinical protocol with the abutment now being in a preferred vertical and horizontal predetermined position when it is seated on the previously inserted implant such that the screw access hole is as close to the center of the occlusal table of the replacement tooth as possible, trying in the denture or other prosthesis over the abutments and adjusting the holes where they seat over the abutments, placing a connecting cylinder over each abutment until it engages its receiving polyhedron, affixing it to the abutment, connecting the cylinders to the denture therein creating the transitional screw retained prosthesis, and removing, finishing, and reinserting the transitional screw retained prosthesis.

In certain embodiments, in order to provide additional strength to the appliance, a bonding sleeve that adheres to acrylic or other restorative material used in the conversion of the denture is seated over the cylinder with an adhesive and is connected to the denture with an appropriate acrylic or composite to create a one-piece screw retained transitional prosthesis.

The co-operable indices includes a mechanism of primary and secondary indicia such that the primary indicium of said adaptor is rotatable in relation to the primary and secondary indicia of the prosthetic component as defined by its desired predetermined position.

The automated and interactive clinical and/or digital protocol includes choosing the appropriate multifunction vertical angle correcting abutment or equivalent prosthetic component having the desired geometric shape for that type of restoration over the implant, rotating it as necessary in either a predetermined clockwise or counterclockwise direction such that the primary indicium of the adaptor is positioned at a particular primary or secondary indicium point of the abutment and is set in relation to the index of the implant when the multifunction abutment is being positioned in a preferred, predetermined horizontal and vertical location over the implant such that the screw access holes approximate the center of the occlusal tables of the replacement teeth. In certain embodiments, the primary indicium of the multifunction abutment is centered in the sagittal plane as it bisects the ridge when it is at a 90° angle to the ridge and the abutment is in its ideal position.

This preferred location is created when the adaptor is rotated around the abutment and the assembly is rotated over the implant such that the primary indicium of the adaptor is aligned with a specific primary or secondary indicium of the abutment when it reestablishes the preplanned, preferred position of the multifunction abutment to compensate for implant index misalignment.

In certain embodiments, the restorative dentist can seat the abutments and adaptors on the implants according to their position in CT scan generated or other model, can then reassess their positions, and then rotates them with rotatable, universal aligning analogs until they are ideally situated in the CT scan generated or other model. He then seats the denture over the abutments on the model and prepares it to receive them, and then removes them from their analogs and seats them on their implants in the same positions, using those rotation points as a guide.

In certain embodiments, antirotational cylinders having an internal flat that matches to the configuration of the cone or other projection on the multifunction abutment are placed over these projections which have a matching flat at their primary indicium such that the primary indicium of the cylinder overlays the primary indicium of the cone. This connection provides a positive seat during manipulation and affords resistance to dislodgement.

In certain embodiments, a bonding sleeve that adheres to acrylic or other restorative material used in the conversion of the denture is seated over the cylinder with an adhesive and is connected to the denture with an appropriate acrylic or composite to create a one-piece screw retained transitional prosthesis.

To register the multifunction abutments, the transitional appliance is removed from the abutments and impression posts or scanning posts are inserted over the multifunction abutment posts such that their primary indicia are aligned, and, either an impression or an intraoral, bench, or CBCT scan is taken to identify and register the location of the abutments' primary indicia in relation to the adaptors' primary indicia. Either an analog is placed in the impression such that its primary indicium is positioned at the same reference points as established by the adaptor's primary indicium with the bench scan then being taken, or the data is directly conveyed to the scan code of a milling software program which directs the rotation of chosen virtual abutments prior to milling the final prosthesis, which is seated on the abutments or on replacement milled ones that are also being fabricated.

In certain embodiments, a Steriolithograph or other CT scan software generated model receives a removable, rotatable universal aligning analog that is used to rotate an overlaying abutment or other prosthetic component to a preferred position to ideally situate the abutment's screw access hole.

A Method of Taking an Intraoral or Bench Scan and/or a CBCT Scan Using Universal Scan Posts and the Universal Automated Protocol for Fabricating Milled Abutments An intraoral or bench scan and/or a CT scan can be taken after implants have been inserted and are ready for restoration with final abutments and prosthetic devices created by milling or another computer generated process, as directed by an automated and/or interactive clinical and/or digital protocol. The scan posts for the intraoral or bench scan and/or the CT scan have readily identifiable primary reference points that are set in relation to the adaptor's primary reference indicium, and, therefore, to the implant index's alignment in the jaw. First, any one of a number of universal aligning, synchronizing, and referencing devices is repositioned over each implant into a preferred, predetermined position. The referencing device can be composed of a healing cap, interim abutment, or other prosthetic component seated on an adaptor, both of which have co-operable indices for directing their rotation and, thereafter, serve as reference points for identifying and registering the new prosthetic component position, wherein the automated and/or interactive clinical and/or digital protocol is used to ideally position the prosthetic component of each device over its implant and to then synchronize all other components to those repositioned reference points. The adaptor is rotated about the prosthetic component, followed by the adaptor/prosthetic component assembly around the implant such that the prosthetic component is now in a preferred, predetermined vertical and horizontal predetermined position when it is seated on the previously inserted implant. The prosthetic component is removed from the adaptor, the location of the reference points in relation to each other as well as to the implant's index is identified, along with the desired vertical angle correction for each implant. A scanning post is seated on the adaptor such that its co-operable indices and those of the adaptor are aligned in some manner, and an intraoral or CT scan is taken to identify and reference the relative positions of the adaptors and the imaging posts to their implants' indexes along with their anatomical gingival architecture around each implant and the geometry of the jaw or jaw segment. In certain embodiments, an impression post is seated at the same location on the implants and an impression is taken, a model is poured, and a bench scan is taken to achieve the results.

The data is then translated, including the relational positions of the co-operable indices and other aspects of the universal aligning scan code to the milling device codes and controls of a software program for milling prosthetic components after importing the CT scan images. A virtual automated rotation or a virtual manual rotation of each preferred abutment is then performed over its virtual universal aligning adaptor for each implant site such that its co-operable indices are located in the clinically desired positions for the prosthetic component and the adaptor of the referencing device, such that the prosthetic component is ideally situated on the monitor, milling the abutment for each site according to the parameters of the virtually rotated abutment, milling the copings or framework that will be receiving any veneering material, inserting the milled abutments on their respective implants and inserting the milled copings or framework over the abutments, taking a bite relationship as needed, and fabricating the final prosthesis. In certain embodiments, the prosthetic device can be designed over the rotated virtual abutment and then milled to fit on the previously seated abutment without also milling the abutment.

In a preferred, but by no means only, embodiment, the co-operable referencing devices and other componentry have graduated reference points and/or a mechanism of primary and secondary indicia that establish the rotation and synchronization points, and the virtual abutment is composed of a virtual universal aligning adaptor that has a specific primary indicium to which all other cooperable componentry are synchronized. It is the synchronization of all of the componentry that contributes to automating the restorative procedures with a dramatic reduction in operator error.

The prosthetic component of the referencing device can be rotated in either a predetermined clockwise or counter-clockwise direction over an adaptor such that its primary indicium is ideally situated, while the primary indicium of said adaptor is positioned at a particular primary or secondary indicium of said prosthetic component, with the primary indicia of both components now being situated in relation to the index of the implant for that rotation. The scanning posts are synchronized to the primary reference indicium of the adaptor, and, thereby register the central axis of rotation that establishes the preferred, predetermined position of an abutment on the implant.

In another embodiment associated with the above techniques, an indexed healing cap of any configuration having primary and secondary indicia can first be rotated such that its primary indicium is centered in the sagittal plane as it bisects the ridge when it is at a 90° angle to ridge, wherein any abutment that would be exchanged for the healing cap in that position would also be ideally situated. The impression post (for the bench scan) or the scan post (for the intraoral or CBCT scan) is merely seated on the index with their primary indicia overlaying.

The automated and/or interactive digital protocol includes choosing the appropriate physical or virtual vertical angle correcting abutment, healing cap, or other prosthetic component having the desired geometric shape for that type of restoration over the implant from a library, rotating it as necessary in either a predetermined clockwise or counter-clockwise direction such that the primary indicium of the adaptor is positioned at a particular primary or secondary indicium point of the abutment whose primary indicium has been ideally situated, and is, therein, set in relation to the index of the implant.

Once the scan process is completed with the data having been translated to the software program by inputting the primary or secondary rotation point that is overlaying the primary indicium of the adaptor, the virtual abutment is auto-rotated when the abutment is in its preferred position such that its primary indicium is in the established position of the clinically rotated and inserted abutment. The practitioner can also interactively manipulate the virtual abutment into a more preferred position.

In certain embodiments, the practitioner can elect to by-pass the insertion of the multifunction abutment prior to fabricating the milled prosthesis. He first rotates the interim abutments or healing caps into their preferred positions and makes note of the locations of the adaptors' primary reference indicia. The interim abutments or healing caps are removed with the appropriate impression and/or scanning posts being seated in relation to the adaptors' primary reference indicia. The steps outlined above are then followed in preparation for the milling of the prosthesis and/or abutments. The design of the scan posts, along with the universal automated and/or interactive clinical and/or digital protocol provides a high degree of accuracy. To the extent that an impression can be avoided with the intraoral or CBCT scan. Combining the intraoral or bench scan with the CBCT scan further assures accurate results, since the CBCT scan data is absolute.

The contour or multifunction abutments are then milled according to the milling device codes of the particular milling program. The overlaying prosthetic devices are then milled to fit the abutments. In certain embodiments, the prosthetic devices are milled such that they directly engage either the adaptor index or the implant index without any interfacing abutment.

In those situations when automated tissue engineering has been instituted and established, wherein the gingival architecture of the healing cap is to be replicated, data for that particular base member and the topography of the overlying tissue are combined to create the characteristics of the developed gingival architecture, which are then incorporated into the data set.

The abutments are milled according to the program's milling device codes and controls either to fit on an implant with an interfacing adaptor or to be milled directly to the implant index, such that they are ideally positioned, regardless of the configuration of the implant index or its alignment. The final abutment are being milled with the appropriate form for that abutment type, implant site, implant angulation, gingival architecture and any other pertinent characteristics being applied to the milling.

Subsequently, the copings or the framework of the prosthesis that is to be seated on the milled abutments is milled to fit on the previously milled abutments, or on already seated preformed abutments.

In certain embodiments, a stereolithograph or other CT scan software generated model is fabricated which reproduces the adaptors' primary reference indicia in their exact positions to receive the milled abutments, and, if applicable, the framework. In another embodiment, a stereolithograph or other CT scan software generated model with reproductions of the milled abutments in their exact positions as established in the software program. In, yet, another embodiment, a stereolithograph or other CT scan software program generates a model that has a receptacle that is created at each implant site in the model to receive a universal aligning analog whose shank configuration has the same polygonal configuration as the free end of the adaptor that engages the index of the implant being restored and whose open end has the appropriate index to engage the abutment that is seated on it with the analog being removable and rotatable such that, when rotated with the abutment, the analog allows for a horizontal angle correction of the abutment in 15° increments, or less. This allows the technician the flexibility of further customizing the abutment and prosthesis.

Merging the Intraoral or Bench Scan with the CBCT Scan Using the Universal Scan Posts and the Universal Automated and/or Interactive Clinical and/or Digital Protocol for Implant Restoration:

An Intraoral and/or bench scan and a CBCT scan are taken using scan posts having co-operable indices as well as a common geometric configurations such that they can be synchronized to each other via a common reference indicium, which has either been set in relation to the alignment of the implant's index in the jaw, or, more specifically, has been oriented in relation to a well-defined primary reference points or set of points of the Universal Aligning Adaptors. The intraoral/bench scan image is merged with the CBCT scan image as they are aligned according to the shared common reference indicia that are on the prosthetic component and the co-operable adaptor. Additional common reference points may be used, as well, such as one or more polyhedrons on the scan posts. In a preferred embodiment, a universal aligning, synchronizing and referencing device having a primary reference indicium is first positioned over an implant in relation to the primary reference indicium of the adaptor that has been rotated such that its prosthetic component is in a preferred position. The prosthetic component of the referencing device can be an actual abutment. The prosthetic component is removed and the appropriate scanning post for the intraoral or bench scan or the CT scan post for the CT scan having co-operable indices are seated with their primary indicia such that they are aligned in relation to the adaptor's primary reference indicium with the scan then being taken to identify and register the location of the adaptor's primary reference indicium, which has been positioned in relation to the index of the implant.

In certain embodiments, the scan posts have one or more polyhedrons on their external surfaces that serve as their primary referencing indicia. The polyhedrons provide an additional means for merging the intraoral or bench scan images with the CT scan image. The former images provide a relationship of the implant index via the scan post to the surrounding gingiva and adjacent teeth, whereas the CBCT image provides an absolute relationship of the scan post, and, therefore, the implant index to the hard structures of the jaw (the implant, the bone and the teeth). This relationship of the implant index (via the primary referencing indicium of the adaptor) is absolute and provides a set of reference points for merging the soft tissues around and over the implant to the absolute position in the sagittal, axial, and coronal planes of the implant, as well. The Universal System allows the fabrication of final abutments and/or prosthetic devices from intraoral, bench, or CBCT scan to register the implant position, because it transforms the central axis of the implant to a preferred central axis of rotation via predetermined reference points so that the virtual abutment rotated into a preferred position. However, the process becomes even more precise when the intraoral or bench scan is merged with the CBCT scan, which, once again, establishes the absolute position. Furthermore, if the images are taken with the data of the configuration of the bases having preferred gingival architecture, the fabrication of the abutment with custom gingival contours becomes automated. To the extent that the therapists (surgeon, restorative dentist, and technician) pool their efforts by matching the final contour base to the original healing cap or interim abutment base, the process becomes further automated with greater precision and a dramatically reduced margin of error. If the scan posts are seated on indexed healing caps, the registration is even more streamlined.

In certain embodiments, the polyhedrons can be arranged in an X-Y-Z plane to facilitate their imaging and subsequent merging, since the merging of the images is accomplished by aligning three different images. In a preferred embodiment, these polyhedrons on the scan posts (and, therefore, in the images) are dissimilar and, therefore, most easily picked up by the scanner. In fact, with the appropriate programming, the intraoral or bench scanner does not even have to image the complete post, but, rather, once it has located the polyhedrons, it will fill in the images, since it has the configurations of the scan posts input into the library within the universal scan code.

The base member's geometry can also be used as a reference plane to merge the intraoral/bench scan and CBCT scan images. The base members can be an indexed healing scan caps that have previously been repositioned in preferred, predetermined vertical and horizontal positions, wherein the scanning posts are individually inserted over the indexes of the healing caps such that the primary indicia of the scanning posts are aligned in relation to the primary indicia on the healing caps' indexes with an intraoral or bench scan and a CBCT scan then being taken of the healing cap/scanning post assemblies such that it registers the adaptors' positions in relation to the implant indexes, the indexed healing caps' positions in relation to their adaptors, the scanning posts in relation to the indexed healing caps, along with the other anatomic structures in the jaw, in relation to the preformed gingival architecture of the healing caps.

To summarize, a preferred technique employing tissue engineering, the surgeon rotates the adaptor around the chosen healing cap and the assembly around the implant and notes the location of the adaptor's reference indicium. He sculpts the tissue as he seats the assembly so that the tissue matures and forms to its geometry, The restorative dentist either takes an impression and the laboratory performs a bench scan, or he takes an intraoral scan an adaptor, indexed healing cap, or abutment, either procedure of which captures the developed soft tissue in relation to the underlying implant in its existing alignment (via the adaptor referencing indicium location). In a preferred embodiment, an indexed healing cap is used to receive the impression or scan post. If more than one scan has been taken, the images can be merged using the universal scan posts reference points to merge the images. The technician then performs an autorotation in a milling software program as dictated by the location of the adaptor reference indicium for that implant with its specific index, and, then, "inserts" the healing cap that is a replica of the one that is seated on the implant. The contour abutment or the multifunction abutment is then milled. The contour abutment is milled with the ideal tooth preparation form, angle correction, and gingival architecture, or the multifunction abutment is milled with the screw access hole relocated to its ideal position and the coping, set of copings, or framework are milled to fit either the existing multifunction abutments that are seated on the implants or on the newly milled abutments.

The Use of a Virtual Referencing Device in a Milling Software Program for Fabricating Milled Abutments and Prosthetic Devices:

The Universal System is a comprehensive system for fabricating milled abutments, other prosthetic components or devices, or dental prostheses by means of a virtualized aligning, synchronizing and referencing device operable in any milling software program, consisting of a virtual adaptor and an associated virtual abutment or other component, each rotatable about the other via their co-operable indices as directed by an automated and/or interactive clinical and/or digital protocol such that the virtual abutment is situated in a preferred, predetermined vertical and horizontal position over the virtual implant prior to the milling of the physical abutment, the steps comprising rotation of the virtual adaptor and virtual abutment such that said abutment becomes ideally situated, selection of the appropriate virtual abutments for each implant site from a library of said abutments and situating them, and milling the physical abutments as determined by the virtual reference points and the resulting preferred abutment geometry for an ideally situated virtual abutment at each implant site.

In a preferred, but by no means only, embodiment, the co-operable abutments and other componentry have graduated reference points and/or a mechanism of primary and secondary indicia that establish the rotation and synchronization points, and the referencing device is composed of a virtual universal aligning adaptor that has a specific primary indicium to which all other cooperable componentry are synchronized. It is the synchronization of all of the componentry that contributes to automating the restorative procedures with a dramatic reduction in operator error.

The virtual prosthetic component is rotated in either a predetermined clockwise or counterclockwise direction over a virtual adaptor such that the primary reference indicium of said adaptor is positioned at a particular primary or secondary indicium of said prosthetic component, resulting in the primary indicia of both components being situated in relation to the index of the implant. This rotation can be performed in any software program for milling or fabricating prosthetic components and devices such that the scan code for the universal automated and/or interactive clinical and/or digital protocol is capable of being integrated with the device controls of the program.

In certain embodiments, the rotation of the virtual aligning, synchronizing and referencing device in combination with the automated and/or interactive clinical and/or digital protocol can be used in any CT scan program to plan and visualize abutment type and rotation prior to surgery. As a result of this planning, the abutment can be prepackaged along with a designation of its insertion protocol including the appropriate primary or secondary rotation on the abutment for rotating the adaptor.

With this technique, the milled contour abutments or other prosthetic components can be used for restoring a crown, bridge, or set of crowns with an ideal emergence profile, angulation, tooth preparation form, gingival architecture or other aspects of an "ideal" crown and bridge abutment. In addition, the milled multifunction abutments or other prosthetic components are used to restore implants with a screw-down prosthesis, wherein the repositioning of the abutment ideally positions the screw access channels for receiving the prosthesis fixation screws, which improves contour, esthetics, and function. The system provides a versatile connection of the abutment to the implant. The milled abutment, other prosthetic component, or prosthetic device can be milled or fabricated by any other computer generated means such that it either engages the index of the adaptor with the assembly then being seated on the implant, or can directly engage the index of the implant and be seated on the implant without the adaptor.

Due to the precise positioning of all components when fabricating and inserting them via the universal automated and/or interactive clinical and/or digital protocol, the overlying coping, set of copings, or a framework for fabricating a set of splinted crowns can also be fabricated to fit on the milled abutments, when clinical conditions are appropriate. This can be performed to a high degree of certainty, when the intraoral or bench scan are merged with the CT scan via the universal protocol. The prosthetic device can also be a screw borne fixed or removable prosthesis. Both the crown and bridge prosthesis and the screw borne prosthesis can be seated on either milled or preformed abutments.

A Universal Set of Milled Contour Abutments for the Crown and Bridge Restoration Over Implants:

The Universal System can translate and integrate clinical contour healing caps or abutments and other componentry prior to taking an intraoral or bench scan and/or CBCT scan using universal scanning posts seated on previously rotated universal aligning adaptors. The system can also be used to translate and integrate data from an implant scan at the fixture level via its universal automated and/or interactive clinical and/or digital protocol in a milling software program to create milled abutments and frameworks. The former technique is presented in this section with the latter one having been presented in the previous section (The Virtual Referencing Device for Intraoral or Bench Scanning and/or CBCT Scanning). In both methods, an overlaying milled framework or coping for a crown, set of crowns, or bridge is seated on preformed or milled anatomic abutments. Adaptors are rotated about chosen angle correcting abutments, having tooth preparations and gingival contours with a variety of geometries, to predetermined positions as established by their co-operable indices and an automated and/or interactive clinical and/or digital protocol such that the abutments are ideally situated in preferred, predetermined vertical and horizontal positions over their implants. Once positioned, universal scanning posts are seated on the indexes of said adaptors such that the co-operable indices of the adaptor and the scanning posts register the newly established positions of the abutments and the adaptors. The universal automated and/or interactive clinical protocol is translated as a digital protocol by integrating the universal aligning scan code with the milling device codes and controls of a software program for milling prosthetic components, whereupon, a virtual rotation of each preferred abutment over its universal aligning adaptor for each implant site as determined by either the previous clinical rotation of the abutment or its by known predetermined points of rotation per implant index to ideally situate an abutment over a misaligned implant. The abutment is then milled for each site according to the parameters of the virtually rotated abutment, and, when appropriate, the copings or framework that will be receiving a porcelain, composite, or other veneering material are milled to fit over the abutments. Once the copings and/or framework are completed, the milled abutments are positioned on their respective implants with the milled coping(s) or framework then being inserted over the abutments. It the final veneering material has not been applied, the coping(s) or framework are lifted in an impression, models are poured and mounted, and the final restoration is fabricated. These steps can also be applied. Once again, the framework and/or copings can be milled to fit preformed abutments that have already been seated or to be seated on their implants.

In a preferred, but by no means only, embodiment, the co-operable abutments and other componentry have graduated reference points and/or a mechanism of primary and secondary indicia that establish the rotation and synchronization points, and the virtual abutment is composed of a virtual universal aligning adaptor that has a specific primary indicium to which all other cooperable componentry are synchronized. It is the synchronization of all of the componentry that contributes to automating the restorative procedures with a dramatic reduction in operator error.

The automated and/or interactive clinical and/or digital protocol includes selecting the appropriate vertical angle correcting abutment or other prosthetic component having the desired geometric shape for that type of restoration over the implant from a library, rotating it as necessary in either a predetermined clockwise or counterclockwise direction such that the primary indicium of the adaptor is positioned at a particular primary or secondary indicium point of the abutment and is set in relation to the index of the implant when the prosthetic component is being situated in a preferred, predetermined horizontal and vertical position over the implant.

In certain embodiments, a universal aligning, synchronizing and referencing device that is used to clinically to establish the preferred position of a seated abutment along with the location of the primary and secondary indicia or other indicia means for referencing the desired position, which is followed by a virtual rotation of the appropriate abutment for a particular restoration at that implant site in a software program, prior to milling the abutment or framework.

The rotation of the abutment or the virtual aligning, synchronizing and referencing device in combination with the automated and/or interactive clinical and/or digital protocol can be performed in any milling software program having the universal aligning scan code which includes the universal automated and/or interactive clinical and/or digital protocol. With this technique, the virtual abutment is auto-rotated by inputting the primary or secondary rotation point that is overlaying the primary indicium of the adaptor when the abutment is preferentially situated, automatically positioning the virtual abutment such that its primary indicium is in the established position of the clinically rotated and inserted healing cap or abutment.

Fully anatomic abutments with specific "tooth" abutment preparations and gingival contours are then planned for each implant site, therein requiring very precise positioning of the abutments for paralleling the tooth preparations and for establishing the appropriate abutment/gingival relationships, which is accomplished either prior to impression taking or scanning and/or is performed digitally in a software program after the initial referencing. A virtual bite registration is taken as a part of the process of taking an intraoral or bench scan and/or CBCT scan, and may be repeated after the framework is fabricated.

In certain embodiments, the adaptors and healing caps have been rotated and inserted over the implants in preferred positions without the abutments, themselves, being in place, wherein the healing caps are removed, scanning posts are inserted over the repositioned adaptors such that their primary indicia overlay, and an intraoral scan and/or CBCT scan is taken and the abutments and framework are then fabricated. The abutments are either milled to the adaptor's index or directly to engage the implant index. In another embodiment, the framework, alone, is milled and seated on preformed, ideally positioned abutments having the preferred configuration and position.

In certain embodiments, the abutment has been rotated such that its primary indicium is ideally located on the buccal, and a lingual crown fixation screw thread is milled to receive a crown fixation screw which is in a range of locations on the lingual surface which is approximately 180° from the primary indicium of the abutment such that a crown fixation screw is inserted to aesthetically and retrievably secure the crown, set of crowns, or bridge. After the completion of the above steps for the cement-on or screw retained crowns, the crown veneer is fabricated by stacking porcelain or other veneering material or is milled from an appropriate restorative material In certain embodiments, the scanning program fabricates a working model with replicas of the preformed or milled contour abutments that area seated on analogs for each implant site such that they are situated as developed in the program. As an alternative model formation, the scanning program fabricates a model with milled receptacles at each implant site to receive universal aligning analogs that are inserted by the technician to fabricate the screw borne prosthesis. The universal aligning analog has an index at the open end with the same configuration as the adaptor's abutment engaging index, configuration, and position, and its shank has the same polygonal configuration as the free end of the adaptor that engages the index of the implant being restored. The universal aligning analog and abutment can be removed, rotated about each other and then rotated as an assembly, and seated in the model to allow the abutment to be placed in a preferred position.

Forming a Set of Universal Milled Multifunction Abutments for the Screw Borne Prosthesis Over Implants:

The Universal Multifunction Abutment realigns the screw access holes for any fixed or removable screw borne prosthesis. Universal System's unique automated and/or interactive clinical and/or digital protocol translates and integrates clinical multifunction abutments and other componentry prior to taking an intraoral or bench scan and/or CBCT scan using universal scanning posts seated on previously rotated universal aligning adaptors or provides said translation and integration of virtual componentry in a software program after the scan data is received prior to the fabrication of a set of milled multifunction abutments and/or prosthetic devices. A method of fabricating a set of milled abutments and/or an overlaying milled framework for a screw borne prosthesis seated on screw retaining multifunction abutments by using either a full or a segmented arch intraoral or bench scan or a CT scan, the steps comprising the rotation of adaptors and chosen angle correcting, multifunction abutments about each other to predetermined positions as established by their co-operable indices and an automated and/or interactive clinical and/or digital protocol such that the abutments are ideally situated in preferred, predetermined vertical and horizontal positions over their implants, inserting universal scanning or imaging posts on the indexing polyhedrons of the multifunction abutments such that their co-operable indices and those of the scanning or imaging posts register the newly established positions of the abutments and the adaptors when the intraoral or bench scan or CT scan is taken, translating the automated and/or interactive clinical protocol to a digital protocol by integrating the universal aligning scan code with the milling device codes and controls of a software program for milling prosthetic components within the software program, performing a virtual rotation of each preferred abutment over its universal aligning adaptor for each implant site until each one is ideally situated, milling the screw retaining abutment for each site based on the parameters of the virtually rotated abutment, milling the framework to fit over the abutments that will be integrated into the prosthesis, if possible, inserting the milled abutments on their respective implants and inserting the milled framework over the abutments, and affixing the framework with impressions screws which are long enough to fit through an impression tray, taking an impression and unscrewing it such that the framework is lifted with the impression when it is removed from the mouth, fabricating the models, taking bite registrations, mounting the models, and fabricating the final restoration.

In a preferred, but by no means only, embodiment, the co-operable multifunction abutments and other componentry have graduated reference points and/or a mechanism of primary and secondary indicia that establish the rotation and synchronization points, and the virtual abutment is composed of a virtual universal aligning adaptor that has a specific primary indicium to which all other cooperable componentry are synchronized. It is the synchronization of all of the componentry that contributes to automating the restorative procedures with a dramatic reduction in operator error.

The automated and/or interactive clinical and/or digital protocol includes selecting the appropriate vertical angle correcting multifunction abutment or other prosthetic component having the desired geometric shape from a library, rotating it as necessary in either a predetermined clockwise or counterclockwise direction such that the primary indicium of the adaptor is positioned at a particular primary or secondary indicium point of the abutment and is set in relation to the index of the implant when the prosthetic component is being situated in a preferred, predetermined horizontal and vertical position over the implant.

The rotation of the virtual multifunction abutment, in combination with the automated and/or interactive clinical and/or digital protocol, can be performed in any milling software program having the scan code for said device. In certain embodiments, the abutment can be automatically rotated in the software program by indicating which primary or secondary rotation point is overlaying the primary indicium of the adaptor, such that it automatically positions the abutment with its primary indicium in the established position of the clinically rotated and inserted multifunction abutment.

In certain embodiments, the adaptors and healing caps or interim abutments are seated on the implants after having been repositioned such that their primary indicia bisect the ridge at a 90° angle in the sagittal plane, and when said healing caps are removed, the primary or secondary indicia overlaying the primary indicia of their adaptor are identified, scanning or imaging posts are inserted over the adaptors such that their primary indicia overlay each other, and an intraoral scan is taken to reference the primary indicia of the adaptors, which, when combined with the location of the adaptor in relation to the primary or secondary indicia of the healing caps, uniquely identifies the preferred position of the healing caps. The virtual multifunction abutments are rotated such that their primary or secondary indicia overlay the primary indicia of the virtual adaptors and are milled. The multifunction abutments can be milled to fit on adaptors or to directly engage the implants' index. The framework is then milled to fit the abutments.

In certain embodiments, an impression post is seated at the same location on the implants and an impression is taken, a model is poured, and a bench scan is taken.

The framework, alone, can be milled and seated on preformed multifunction abutments that are situated with their reference points in the same locations as the virtual abutments.

In certain embodiments, a bite block is milled to fit over the framework and is returned with the milled abutments and framework such that the abutments, framework, and milled bite block are seated with a bite and aesthetic registration being taken to establish the vertical bite, smile line and other denture parameters, prior to taking a transfer impression.

In certain embodiments, the precise repositioning of the screw access holes such that they more closely approximate the occlusal tables of the replacement teeth, a full arch of screw retained crowns can be fabricated without flanges. The patient can now receive a full arch of screw retained crowns in preference to a screw retained denture having acrylic flanges, which is applicable to either the standard fabrication process after implants have integrated or to the immediate load screw retained transitional hybrid denture conversion process that is performed at the time of implant insertion. The net benefit is a significant improvement in patient hygiene, when the flanges are eliminated. Esthetics in many cases is also vastly improved.

Using the Universal Aligning Analog

A universal aligning analog model can be either fabricated by a dental technician in the laboratory or is fabricated by a computer software program. Both models have receptacles for receiving the universal aligning analog, which has an index at the open end with the same configuration as the adaptor's abutment engaging index, configuration, and position, and has a shank with the same polygonal configuration as the free end of the adaptor that engages the index of the implant being restored. For example, if a 15° angle correction is wanted for the hexagon implant, then the top index of the analog is an octagon and the shank is a tapered hexagon. The universal aligning analog and abutment can be rotated and reseated into the receptacle in the model to allow the abutment to be placed in a more preferred position. The universal aligning analog also has a referencing indicium that is rotated in the same manner as the adaptor such that the indicium is positioned under one of the primary or secondary indicia of the abutment being rotated.

If an abutment an abutment has been rotated to one of its alternative primary or secondary indicia on the analog, the restorative dentist merely rotates it over the adaptor seated on that particular implant.

The universal aligning adaptor is particularly useful with the immediate load transitional hybrid conversion technique for ideally positioning screw access holes.

Methods of Inserting and Restoring the Nonagon Implant

In certain embodiments, the automated and interactive clinical and/or digital protocol when restoring the Universal Nonagon Implant with a primary indicium includes choosing the appropriate vertical angle correcting abutment or other prosthetic component having the desired geometric shape for that type of restoration over the implant, rotating it as necessary in either a predetermined clockwise or counterclockwise direction such that the primary indicium of the adaptor is positioned at a particular primary or secondary indicium point of the abutment and is automatically set in relation to the index of the implant when the prosthetic component is being positioned in a preferred, predetermined horizontal and vertical situation over the implant as determined by the primary indicium (FIG. 99B). The Nonagon Implant, in association with the Universal Aligning Adaptor having an octagon abutment engaging projection, has a distinct advantage over all other implant indexes with its 5° increments of rotation guided by its primary indicium.

In certain embodiments, the implant has a nonagon index which, being symmetrical, allows for abutment rotation, while one of the vertices serves as a primary indicium or vertex and reference point for all of the co-operable indicia of its componentry, since it is the only vertex that bisects the opposing flat at a 90° angle that is located 180° away from it in the sagittal plane.

In certain embodiments, the fixture mount that carries the implant to the osteotomy site and is used with an engaging tool to secure the implant in the bone has a primary indicium or vertex that indicates the location of the implant's primary indicium or vertex that assists the surgeon with placing the implant with its index ideally situated. After the fixture mount is removed, the insertion tool that engages the implant index can also have a primary indicium that guides the surgeon as he completes the insertion of the implant in order to ideally position the implant index.

In one embodiment, a method of restoring a Universal Aligning Implant having any index configuration and alignment with a referencing indicium by realigning, synchronizing, and referencing restorative prosthetic components to set reference points to realign and synchronize an implant prosthetic insert. The restorative dentist can choose the desired vertical angle correcting prosthetic component having the appropriate geometric shape for restoring the implant. The prosthetic component can be rotated over a prosthetic insert with the assembly over the implant in 5° increments via co-operable indicia on the component and prosthetic insert such that the prosthetic component is ideally situated in a position. When in the ideal position, the co-operable indicia can be identified at that position, and the reference points can be used for fabricating the final prosthetic components.

The co-operable indicia can include graduated reference points and/or primary and secondary indicia that establish the rotation and synchronization points.

All componentry can be synchronized to the primary indicium of the adaptor, to the specific primary or secondary indicium of the prosthetic device that overlays the primary indicium of the adaptor, and to the primary indicium of the prosthetic component which defines its preferred horizontal and vertical position.

In certain embodiments, identifying the rotation and synchronization points prior to taking an impression for a bench scan, automatically identifies and references them during the bench scan, and, thereby, lessens the effects of any distortion that can occur from expansion and contraction of materials, when taking an impression for fabricating a model.

At least one embodiment provides a method of restoring a dental implant having an index of "n" sides, one of which has the primary indicium, that has been inserted in the jaw with an arbitrary alignment of the index by combining a prosthetic insert whose mutual geometry at its end that extends into the implant index and at its end that receives prosthetic components having co-operable indices allows for a directed rotation of the components, such that they are first decoupled from dependence upon the coarse rotations around the implant's index, and are then aligned and synchronized according to an automated and/or interactive clinical and/or digital protocol, wherein the prosthetic components are rotated about a reestablished vertical axis of rotation which results in more refined increments of the rotation using either a predetermined counter or straight rotation to ideally situate the prosthetic components and to synchronize them to a defined reference point or set of reference points on the prosthetic insert, which is then identified and referenced for fabricating the restoration that is seated on the implant. Therefore, in at least certain embodiments, it is possible for one or more scanners and associated computers to recognize or identify this primary indicium automatically. This computer identified primary indicium enables autorotation of the virtual abutment such that it is ideally situated prior to milling the physical abutment and the overlying prosthetic device.

Certain embodiments provide a method of using a universal aligning implant for restoring an edentulous site wherein it has a primary indicium as a reference point in its index to better position it in an ideal alignment in the ridge along with a set of prosthetic componentry that are synchronized to the implant's primary reference points and to each other via their co-operable indicia when the implant is restored such that the abutment and/or overlaying prosthesis is in an ideal position or, in combination with an aligning, synchronizing, referencing device and an automated and interactive clinical and/or digital protocol, reestablishes the preferred abutment position. The implant can be inserted such that its primary indicium is situated in a sagittal plane that bisects the ridge at a 90° angle, inserting an impression post, scanning post, or other referencing device into the implant such that the primary indicium of the referencing device is aligned with the primary indicium of the implant. When aligned a final abutment or prosthesis can be fabricated that is seated on the implant such that its primary indicium is overlaying the implant's primary indicium, and is, therein, ideally positioned over the implant.

In certain embodiments, the fixture mount that carries the implant to the osteotomy site and is used with an engaging tool to secure the implant in the bone has a primary indicium that indicates the location of the implant's primary indicium wherein the surgeon is able to ideally align the implant index.

In certain embodiments, the insertion tool that engages the implant index has a primary indicium that guides the surgeon as he completes the insertion in order to ideally position the implant index. The set of prosthetic componentry can have co-operable primary and secondary indicia or other co-operable indicia are used in combination with the automated and interactive clinical and/or digital protocol when the primary indicium of the implant does not bisect the ridge at a 90° angle in the sagittal plane, wherein the adaptor and the prosthetic component are rotated individually and as an assembly as determined by the protocol such that their primary and secondary indicia reposition the device to an ideal position in order to compensate for the implant's misalignment.

Figure 103:
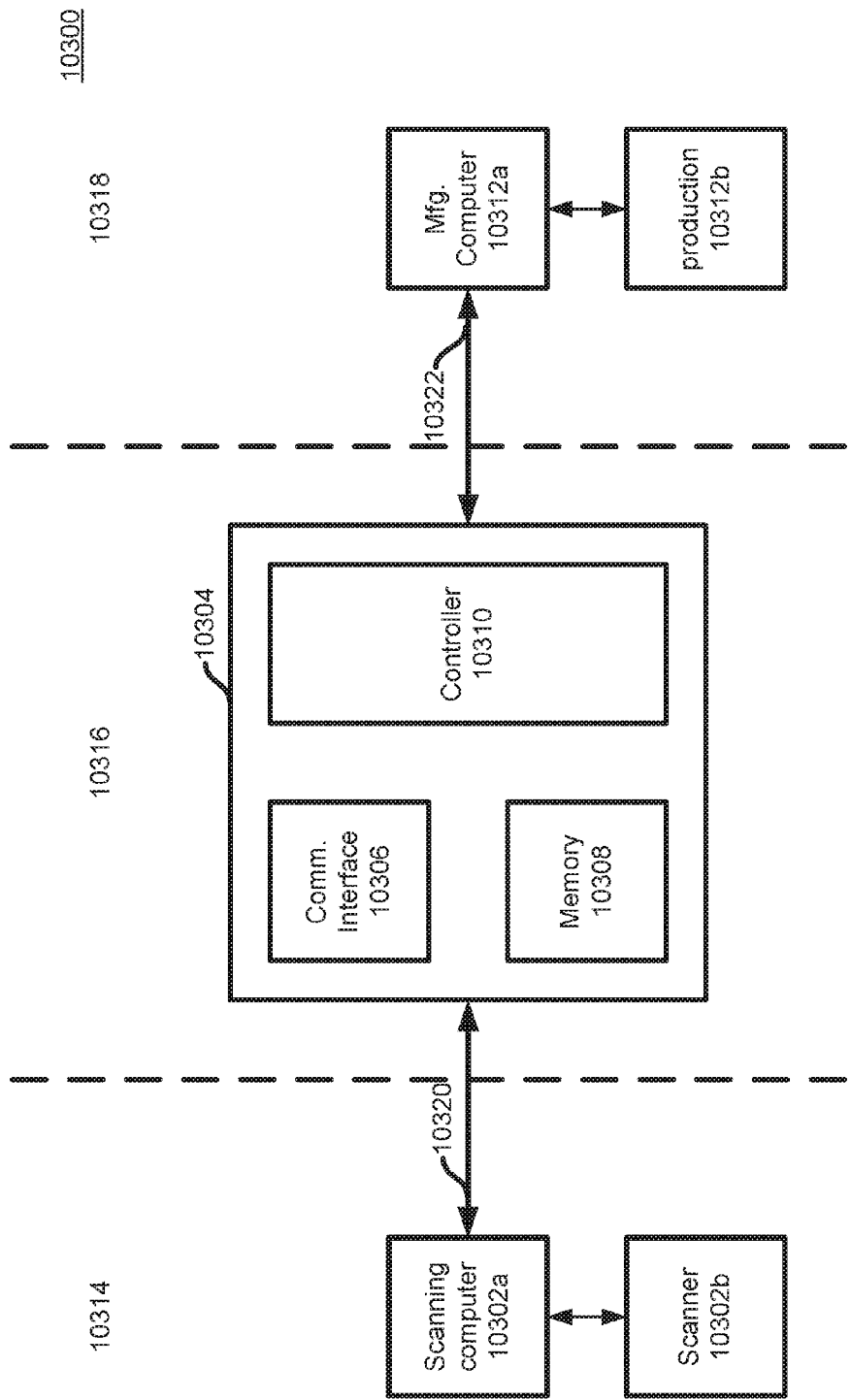
FIG. 103 is a functional block diagram depicting a system for producing dental fixtures according to various embodiments of the disclosure.

FIG. 103 depicts a system 10300 for use in producing properly fitting and aesthetic dental fixtures according to various embodiments. The system 10300 may, in general, include a scanning component 10314, a correction component 10316, and a manufacturing system 10318. The scanning component 10314 may include a scanning computer 10302a and a scanner 10302b. The scanner may be any appropriate scanner for taking scans of aspects of a patent's mouth. For instance, according to some embodiments, the scanner may comprise an intraoral scanner or a cone beam computed tomography (CBCT) scanner. As discussed above, the scanner 10302b may be operable to scan the scanning post 700 and record the relative position of its various indicia (e.g., primary indicia 713 and 714 and secondary indicium 715) in space. Additionally, the scanner may be operable to perform an oral scan without the use of scanning post 700 such that virtual indicia may later be extracted from the scan data.

The scanning computer 10302a may receive data from the scanner 10302b and compile and/or process the data to achieve a usable scan data. The scan data may include information about the oral geometry of a patient. If using scanning post 700, the scan data may include information indicative of the relative position of the various indicia and/or virtual indicia. The scan data may also contain information relating to a patient's oral features (e.g., the relative position of teeth, gums, and other tissue). Additionally, the scanning computer 10302a may be configured to transmit the scan data to the correction component 10316 via communication channel 10320.

The correction component 10316 may comprise a system 10304 that is configured to receive the scan data from the scanning component 10314 via communication channel 10320. System 10304 may include a communications interface 10306 suitable for communicating with various communications channels 10320 10322, a memory 10308, and a controller 10310. Additionally, correction component 10316 may be operable to communicate with manufacturing component 10318 via communication channel 10322. According to various embodiments, the correction component 10316 is operable to generate appropriate manufacturing instructions for the production of a dental fixture based on the received scan data and, in particular, the scanned indicia and/or virtual indicia. For instance, if the correction component 10316 determines that one or more of the indicia (actual or virtual) indicate a misalignment, the correction component 10316 can generate appropriate manufacturing instructions that offset and account for the misalignment in the dental fixture.

Manufacturing component 10318 may comprise a manufacturing computer 10312*a* coupled to a production facility 10312*b*. The manufacturing computer 10312*a* may be configured to receive manufacturing instructions from the correction component 10316 via communication channel 10312. Additionally, the manufacturing computer 10312*a* may be configured to compile and/or parse the instructions to place them in suitable form for the production facility 10312*b*.

FIG. 103 depicts system 10300 as having a single scanner component 10314, a single correction component 10316, and a single manufacturing component 10318. However, this need not be the case. It is also possible to have a plurality of each of components 10314, 10316, and 10318 in the system 100. Such an embodiment is depicted in FIG. 104.

Figure 104:
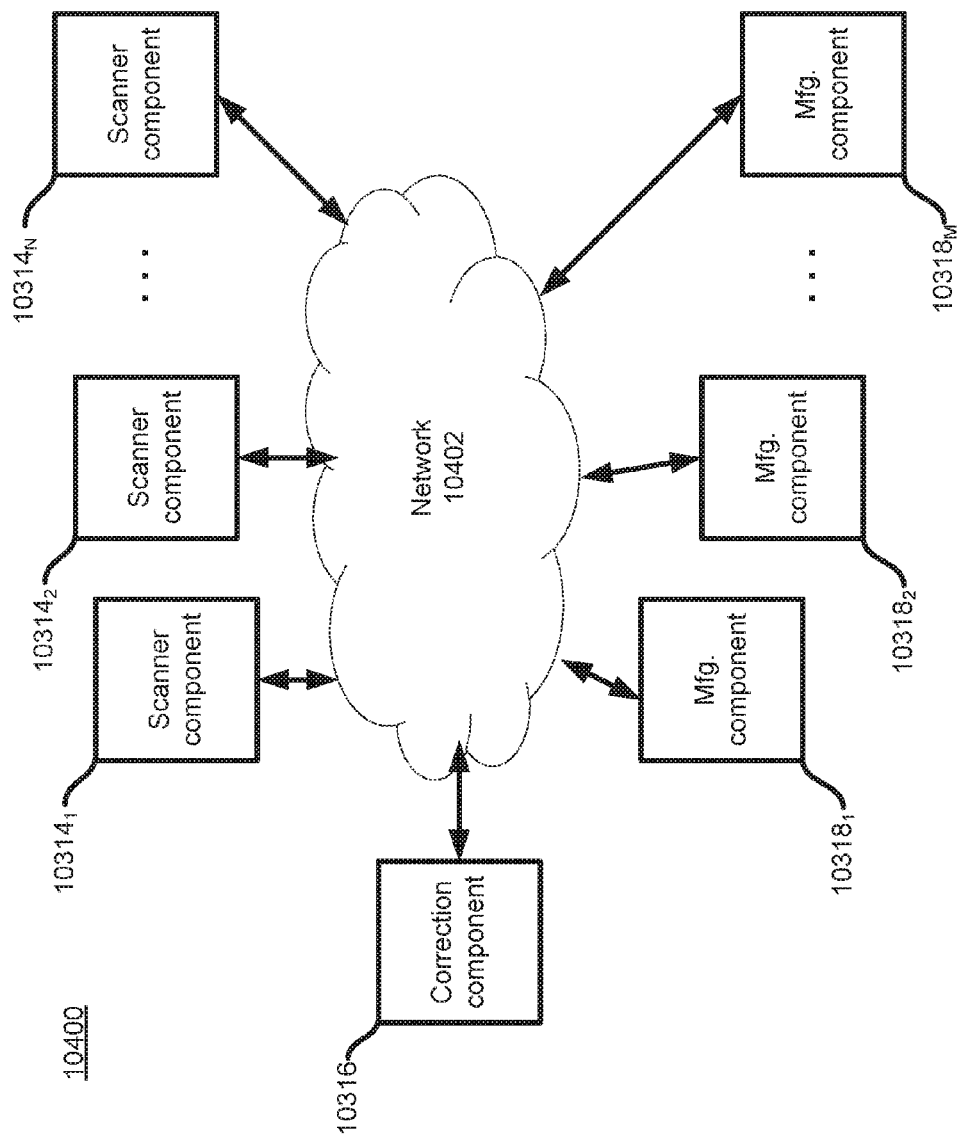
FIG. 104 is a flow chart depicting a process of producing dental fixtures according to various embodiments of the disclosure.

FIG. 104 is a functional block diagram depicting a system 10400 with a plurality of scanner components 103141, 103142, . . . , 10314N (collectively referred to as scanner components 10314), a correction component 10316, and a plurality of manufacturing components 103181, 103182, . . . , 10318M (collectively referred to as manufacturing components 10318). While only a single correction component 10316 is shown in FIG. 104, it should be understood that system 10400 may contain a plurality of correction component 10316. Each of the scanner components 10314, the correction component 10316, and the manufacturing components 10318 is connected to an electronic communication network 10402.

In practice, a system such as system 10400 allows for increased flexibility in receiving scan data and in producing the dental fixture. For instance, correction component 10316 can be configured to receive multiple instances of scan data relating to a single patient from multiple scanner components 10314. By way of example, scanner component 103141 may be able to only provide intraoral scan data to correction component 10316 and scanner component 103142 may only be configured to provide CBCT scan data to correction component 10316. The correction component 10316 can then merge the scan data to generate more accurate manufacturing instructions. These manufacturing instructions can, then, be sent to one of the appropriate manufacturing components 10318 for execution. The appropriate manufacturing component 10318 can be selected based on, for instance, physical proximity, workload, production facilities, etc. Thus, a system that allows a correction component 10316 to interact with a number of different scanner components 10314 and a number of different manufacturing components 10318 allows for greater flexibility.

Figure 105:
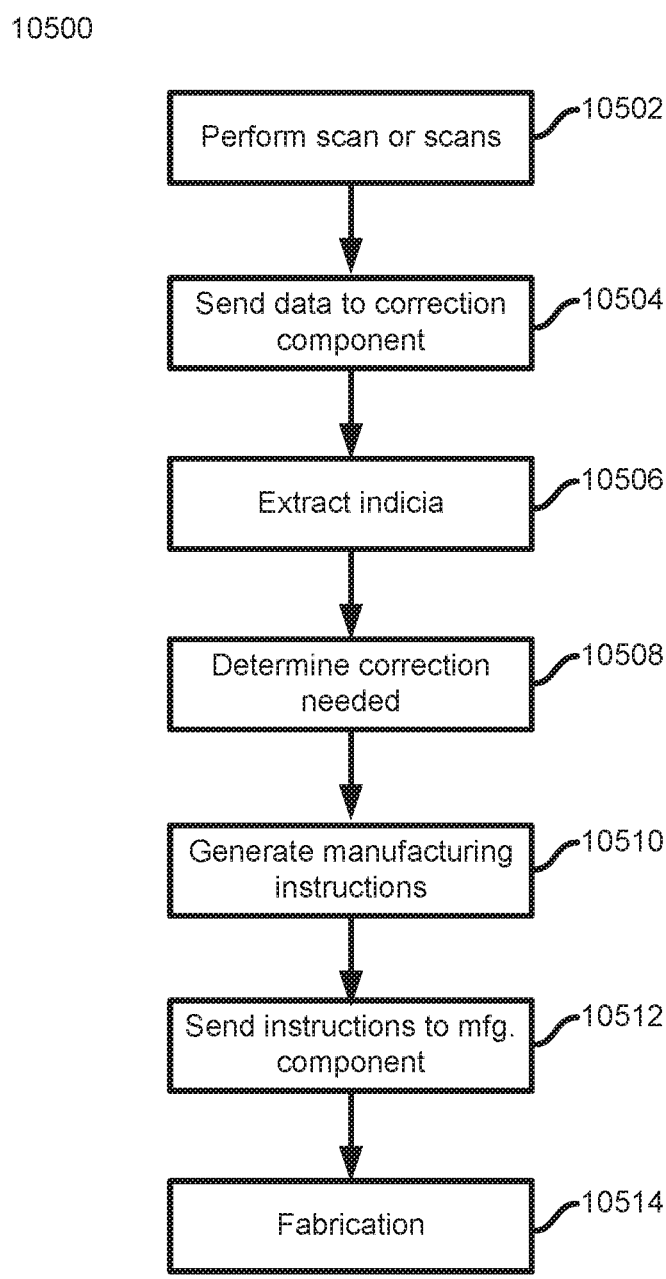
FIG. 105 is a flow chart depicting a process of producing dental fixtures according to various embodiments of the disclosure.

FIG. 105 is a flow chart depicting a method 10500 of fabricating a dental fixture using scan data according to various embodiments. According to method 10500 one or more scans can be performed at step 10502 by, for instance, scanner 10302*b*. The scan or scans may comprise, intraoral scans, CBCT scans, x-ray scans, or any suitable scan capable of taking appropriate oral measurements. After the scan or scans are performed scan data can be generated and sent to the correction component 10316 at step 10504.

At step 10506, the correction component 10316 can extract indicia from the scan data. For instance, if a scanning post 700 was used, the correction component 10316 can extract the primary and secondary indicia 713, 714, and 715. Alternatively, virtual indicia may be generated based on, for instance, a sidewall of the scanning post or various other features of the implant and/or the patients features.

At step 10508, the correction component 10316 can determine whether a correction is needed in the dental fixture based on the scan data. For instance, the correction component 10316 may determine that the indicia (actual or virtual) indicate a misalignment of the implant 10. Once a determination is made about whether correction is needed at step 10508, appropriate manufacturing instructions can be generated at step 10510. For instance, if the correction component 10316 determines that the indicia indicate a misalignment, the manufacturing instructions can account for the misalignment by offsetting, rotating, or otherwise cancelling out the misalignment in the manufacturing instructions. The manufacturing instructions can then be sent to the manufacturing component 10388 at step 10512 and the dental fixture can be produced by the production facility 10312*b*.

Figure 106:
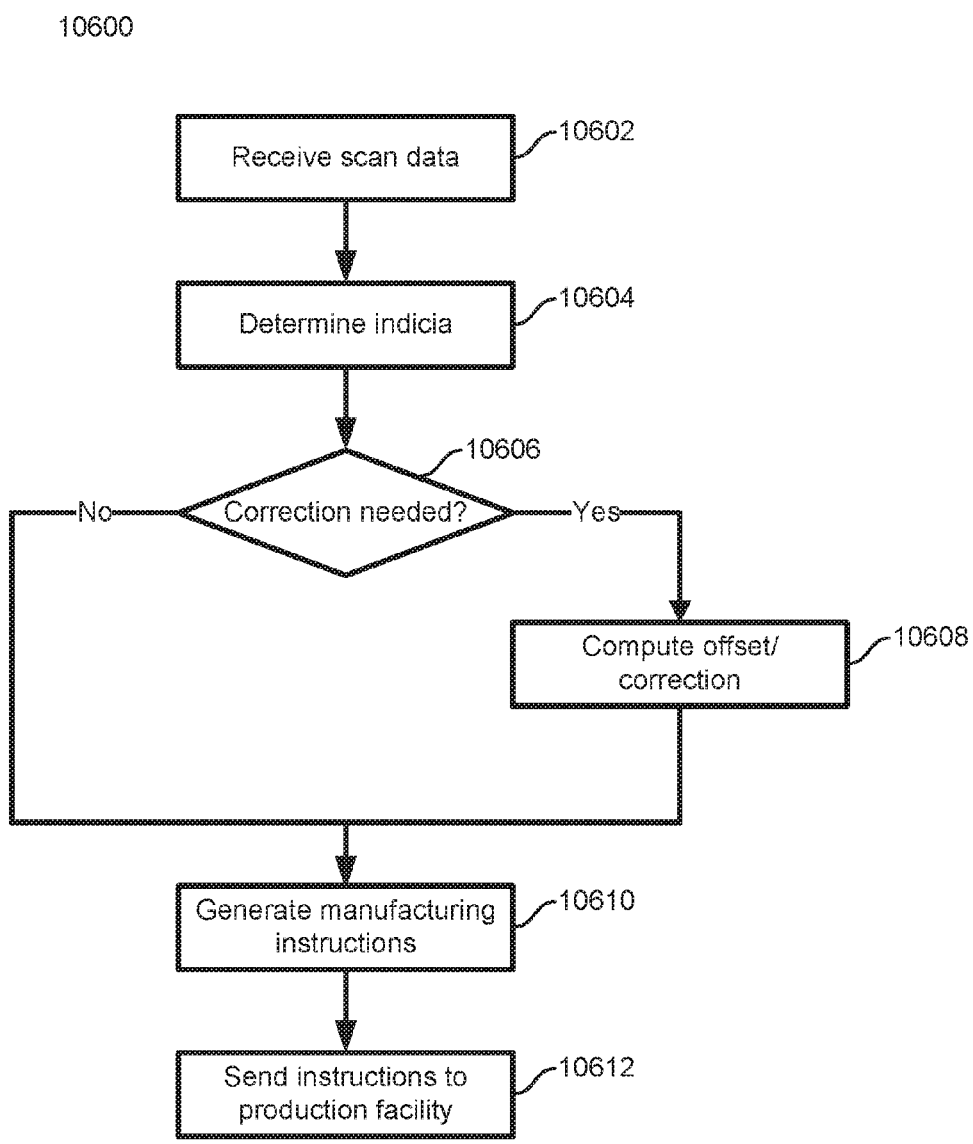
FIG. 106 is a flow chart depicting a process of producing dental fixtures according to various embodiments of the disclosure.

FIG. 106 is a flow chart depicting a method 10600 of generating the appropriate manufacturing instructions based on received scan data according to various embodiments.

The method may be performed by any suitable component such as correction component 10316. According to the method 10600, scan data is received at step 10602 from, for instance, scanning component 10314. At step 10604, one or more indicia are determined from the scan data. If, for instance, a scan post is used (e.g., scan post 700), then actual indicia (e.g., primary and secondary indicia 713, 714, and 715) can be extracted from the scan data and their relative positions determined. However, according to some embodiments, the indicia may be determined by generating virtual indicia based on various features of the scan data.

At step 10606, the indicia are examined to determine whether correction is needed. For instance, the indicia can be analyzed to determine whether there will be a misalignment in the dental fixture if it is inserted into position. This can happen when the indicia are offset spatially from where they are otherwise expected in the x, y, or z directions. If, at step 10606, it is determined that a correction is needed, then an appropriate offset and/or correction is computed to adjust for the misalignment. This offset and/or correction can be used to generate appropriate manufacturing instructions at step 10610. If, on the other hand, it is determined that no correction is needed at step 10606, then the manufacturing instructions for the dental fixture can be generated without computing an offset and/or correction at step 10610. Finally, at step 10612, the instructions can be sent to the production facility so that the dental fixture can be produced.

Figure 107:
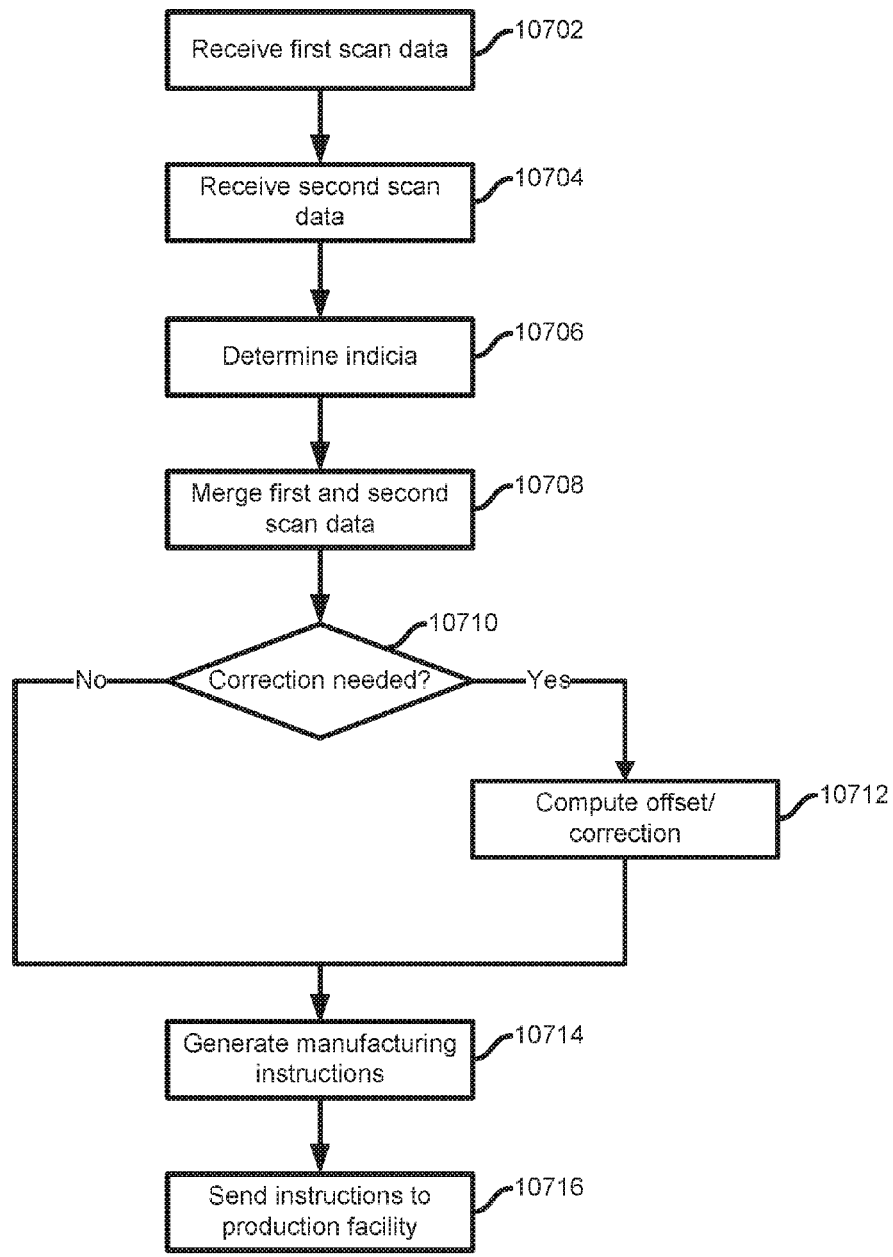
FIG. 107 is a flow chart depicting a process of producing dental fixtures according to various embodiments of the disclosure.

FIG. 107 is a flow chart depicting a method 10700 of generating the appropriate manufacturing instructions based on received scan data according to various embodiments.

The method may be performed by any suitable component such as correction component 10316. According to the method 10700, first scan data is received at step 10702 from, for instance, scanning component 103141 (shown in FIG. 104). At step 10704, second scan data can be received from, for instance, scanning component 103142. While not necessary, it is possible for the first and second scan data to be generated using different scanning methods. By way of example, it would be possible for the first scan data to be generated using an intraoral scanning device and for the second scan data to be generated by a CBCT scan. At any rate, the scans need not be of the same type.

At step 10606, one or more indicia are determined from each of the first and second scan data. If, for instance, a scan post is used (e.g., scan post 700), then actual indicia (e.g., primary and secondary indicia 713, 714, and 715) can be extracted from the scan data and their relative positions determined. However, according to some embodiments, the indicia may be determined by generating virtual indicia based on various features of the scan data.

At step 10706, the data from the first and second scan data can be merged to generate a combined set of scan data. The first and second scan data can be merged by aligning like indicia so that the relative position of the various scanned features is known. This merging of multiple kinds of scan data allows for a more complete picture of a patient's oral features. Continuing with our example where the first scan data comprises intraoral scan data and the second scan data comprises CBCT scan data, the advantage of this process can be seen; intraoral scans register soft tissue (e.g., the gum line, etc.) better and CBCT scans register bone (e.g., teeth) and metallic objects (e.g., implant 10) better. Accordingly, it is possible, by merging the two kinds of scan data to have a better view of the soft tissue in relation to the bone and metallic objects and to, therefore, generate a better correction.

At step 10710, the merged scan data is examined to determine whether correction is needed. For instance, the indicia can be analyzed to determine whether there will be a misalignment in the dental fixture if it is inserted into position. This can happen when the indicia are offset spatially from where they are otherwise expected in the x, y, or z directions. If, at step 10710, it is determined that a correction is needed, then an appropriate offset and/or correction is computed at step 10712 to adjust for the misalignment. This offset and/or correction can be used to generate appropriate manufacturing instructions at step 10714. If, on the other hand, it is determined that no correction is needed at step 10710, then the manufacturing instructions for the dental fixture can be generated without computing an offset and/or correction at step 10712. Finally, at step 10716, the instructions can be sent to the production facility so that the dental fixture can be produced.

Figure 108:
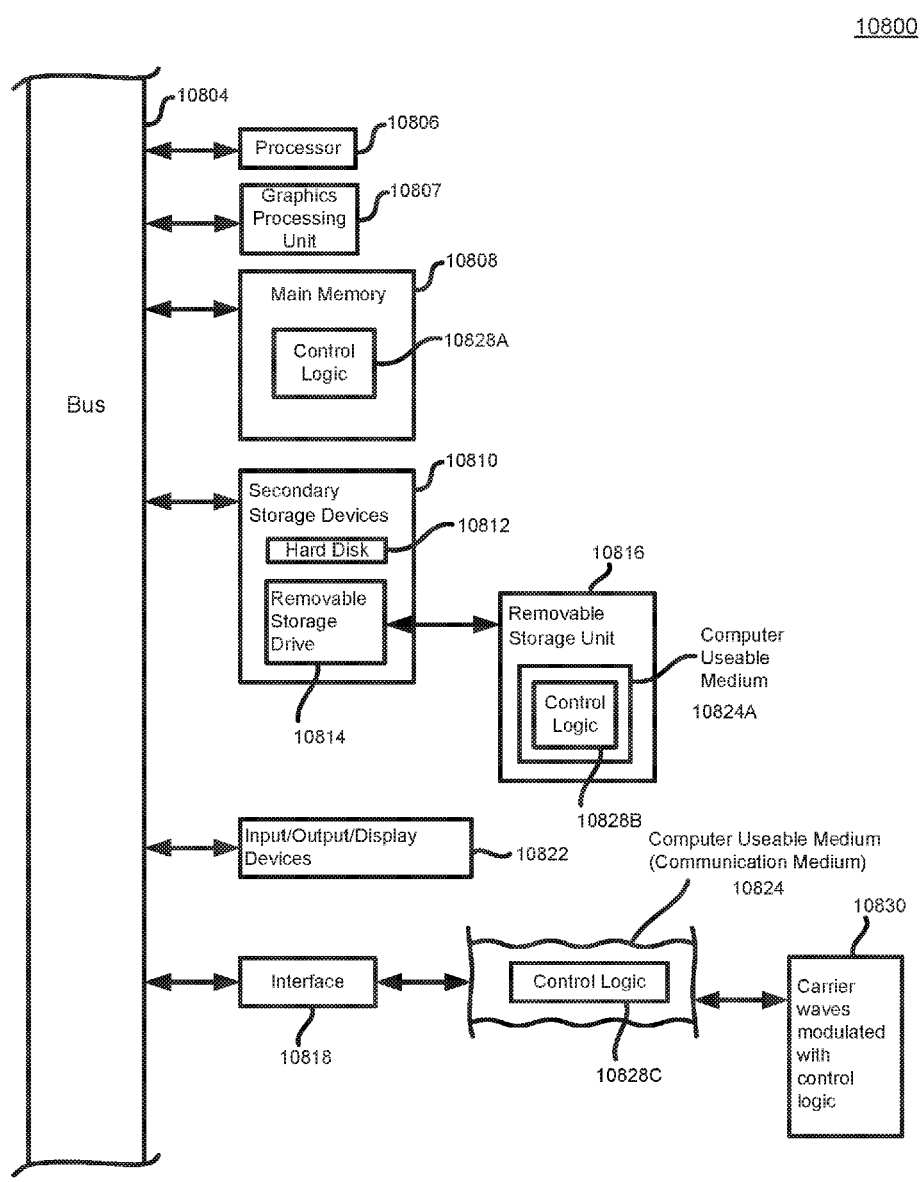
FIG. 108 is an example computer system useful for implementing various embodiments.

In an embodiment, the system and components described herein are implemented using well known computers, such as computer 10800 shown in FIG. 108. For instance, any of the hardware and/or software processes depicted in FIGS. 103-105 could be performed by a computer or computers such as computer 10800.

Computer 10800 may comprise any commercially available computer capable of performing the functions described herein, such as computers available from International Business Machines, Apple, Sun, HP, Dell, Digital, Cray, etc.

Computer 10800 includes one or more processors (also called central processing units, or CPUs), such as a processor 10806. Processor 10806 may comprise one or more processors. The processor 10806 is connected to a communication bus 10804. Processors 10806 may include any conventional or special purpose processor, including, but not limited to, digital signal processor (DSP), field programmable gate array (FPGA), and application specific integrated circuit (ASIC).

Computer 10800 includes one or more graphics processing units (also called GPUs), such as GPU 10807. GPU 10807 is a specialized processor that executes instructions and programs selected for complex graphics and mathematical operations in parallel.

Computer 10800 also includes a main or primary memory 10808, such as random access memory (RAM). The primary memory 10808 has stored therein control logic 10828A (computer software), and data.

Computer 10800 also includes one or more secondary storage devices 10810. The secondary storage devices 10810 include, for example, a hard disk drive 10812 and/or a removable storage device or drive 10814, as well as other types of storage devices, such as memory cards and memory sticks. The removable storage drive 10814 represents a floppy disk drive, a magnetic tape drive, a compact disk drive, an optical storage device, tape backup, USB Flash memory, etc.

The removable storage drive 10814 interacts with a removable storage unit 10816. The removable storage unit 10816 includes a computer useable or readable storage medium 10824 having stored therein computer software 10828B (control logic) and/or data. Removable storage unit 10816 represents a floppy disk, magnetic tape, compact disk, DVD, optical storage disk, USB Flash memory, or any other computer data storage device. The removable storage drive 10814 reads from and/or writes to the removable storage unit 10816 in a well-known manner.

Computer 10800 also includes input/output/display devices 10822, such as monitors, keyboards, pointing devices, touch-screen displays, etc.

Computer 10800 further includes a communication or network interface 10818. The network interface 10818 enables the computer 10800 to communicate with remote devices. For example, the network interface 10818 allows computer 10800 to communicate over communication networks or mediums 10824B (representing a form of a computer useable or readable medium), such as LANs, WANs, the Internet, etc. The network interface 10818 may interface with remote sites or networks via wired or wireless connections.

Control logic 10828C may be transmitted to and from computer 10800 via the communication medium 10824B. More particularly, the computer 10800 may receive and transmit carrier waves (electromagnetic signals) modulated with control logic 10830 via the communication medium 10824B.

Any apparatus or manufacture comprising a computer useable or readable medium having control logic (software) stored therein is referred to herein as a computer program product or program storage device. This includes, but is not limited to, the computer 10800, the main memory 10808, the secondary storage devices 10810, the removable storage unit 10816 and the carrier waves modulated with control logic 10830. Such computer program products, having control logic stored therein that, when executed by one or more data processing devices, cause such data processing devices to operate as described herein, represent embodiments.

Although, several of the preferred embodiments of the present inventions have been shown and described above, other embodiments will be readily apparent to those skilled in the art. Therefore, the scope of the present invention is not limited to the specific embodiments shown and described, but, rather, is defined in the appended claims.

For the Examiner's convenience, given the complexity of the present system and the interrelationship of the various part numbers used in the present application, Applicant has provided the following parts list table. It is understood that the detailed description is controlling and that the description in this parts list is for convenience sake only. In other words, the part list does not limit the claims or the description of the system in the detailed description.

| | |
|---|---|
| 10 | implant |
| 12 | internal threaded portion |
| 15 | index |
| 21 | trichannel |
| 22 | hexagon |
| 23 | dodecagon |
| 24 | octagon |
| 25 | nonagon |
| 100 | Universal Aligning Adaptor |
| 111 | octagon projection |
| 120 | primary reference indicium on octagon |

-continued

| | |
|---|---|
| 121 | primary reference indicium on collar |
| 122 | indicia in increments |
| 128 | centerline for external hexagon |
| 130 | collar on adaptor |
| 140 | index to interface with the implant |
| 141 | trilobe external index |
| 145 | nonagon external index |
| 151 | channel for screw |
| 152 | thread for abutment screw |
| 171 | Universal Aligning Analog with recess for set screw |
| 173 | universal analog external configuration of shank |
| 174 | screw hole to receive set screw |
| 200 | Universal Fixation Screw |
| 210 | shank |
| 220 | thread |
| 230 | internal hex |
| 240 | shoulder of screw head |
| 300 | Universal Contour Abutment |
| 321 | primary indicium on collar of post |
| 322 | (A) first indicium clockwise rotation stop |
| 324 | (C) third indicium clockwise rotation stop |
| 325 | (a) first indicium counter clockwise rotation stop |
| 326 | (b) second indicium counter clockwise rotation stop |
| 330 | standard gingival contours |
| 331 | collar scalloped gingival contour-generic |
| 332 | collar gingival shape-contour Anterior |
| 333 | collar gingival shape-contour medium posterior |
| 334 | collar gingival shape-contour large posterior |
| 337 | collar-cylindrical |
| 338 | gingival depth extension |
| 340 | custom gingival contours |
| 344 | maxillary premolar tooth preoaration |
| 351 | 15° horizontal angle correction |
| 353 | 0° vertical angle correction |
| 354 | 15° vertical angle correction |
| 356 | 30° vertical angle correction |
| 361 | octagon indexing |
| 362 | hexadecagon indexing |
| 363 | hexagon indexing |
| 364 | dodecagon (12 sided) indexing |
| 365 | screw access channel |
| 367 | rotation of abutment/adaptor mating index |
| 369 | open end at the base |
| 372 | tooth preparation chamfer |
| 373 | tooth preparation for an abutment |
| 390 | screw down crown |
| 391 | crown fixation screw |
| 392 | thread to receive crown fixation screw |
| 393 | channel in crown to receive crown fixation screw |
| 400 | universal asymmetric contour healing cap |
| 401 | universal asymmetric indexed contour healing cap |
| 402 | universal cylindrical (symmetric) healing cap |
| 403 | universal cylindrical (symmetric) indexed healing cap |
| 404 | symmetrical, cylindrical indexed healing cap to implant |
| 405 | asymmetric contour indexed healing cap to implant |
| 406 | aligning external index |
| 407 | universal scalloped top contour healing cap |
| 408 | recessed polyhedron for impression/scan/abutment |
| 409 | universal scalloped top indexed contour healing cap |
| 411 | primary indicia on collar |
| 415 | (a) first indicium counter clockwise rotation stop |
| 418 | Primary indicium |
| 421 | primary indicia on top of healing cap |
| 422 | (A) first indicium clockwise rotation stop |
| 423 | (B) second indicium clockwise rotation stop |
| 424 | (C) third indicium clockwise rotation stop |
| 425 | (a) first indicium counter clockwise rotation stop |
| 426 | (b) second indicium counter clockwise rotation stop |
| 427 | (c) third indicium counter clockwise rotation stop |
| 428 | primary indicium on the external index on top of the healing cap |
| 430 | standard gingival contours |
| 433 | collar gingival contour-medium posterior |
| 437 | collar-cylindrical |
| 441 | maxillary central incisor |
| 442 | maxillary lateral incisor |
| 443 | maxillary canine |
| 444 | maxillary premolar |
| 445 | maxillary molar |
| 446 | mandibular incisor |
| 447 | mandibular canine |
| 448 | mandibular 1st premolar |
| 449 | mandibular 2nd premolar |
| 500 | Universal Multifunction Abutment |
| 520 | primary indicium |
| 521 | primary indicium on collar |
| 523 | (B) second indicium clockwise rotation stop |
| 525 | (a) first indicium counter clockwise rotation stop |
| 526 | (b) second indicium counter clockwise rotation stop |
| 528 | center line of an internal octagon flat |
| 529 | off center line |
| 544 | maxillary premolar |
| 551 | abutment rotating in 15° increments |
| 553 | 0° vertical angle correcting abutment |
| 556 | 30° vertical angle correcting abutment |
| 557 | misaligned abutment from central axis |
| 558 | aligned abutment to central axis |
| 559 | center line of the angle correcting abutment |
| 561 | octagon |
| 565 | screw access channel |
| 572 | cone on abutment |
| 573 | flat surface on the cone |
| 574 | internal thread in the cone |
| 575 | cylinder fixation screw |
| 580 | cylinder |
| 581 | flat surface positioned over flat of cone |
| 582 | mm score lines |
| 583 | internal threads to secure fixation screw |
| 584 | internal threads to receive sealing screw |
| 585 | sealing screw |
| 586 | bonding sleeve |
| 589 | external configuration for retention |
| 600 | Universal Impression Post |
| 601 | universal impression post over adaptor |
| 602 | universal impression post over healing cap |
| 603 | universal impression post over multifunction abut |
| 604 | Universal Impression Post plus transf |
| 611 | flat on impression post overlying reference adaptor flat |
| 612 | mating projections for top of healing cap |
| 621 | primary indicium on collar |
| 637 | collar-cylindrical |
| 661 | collar-cylindrical |
| 665 | screw access channel |
| 672 | transfer cap-direct impression |
| 673 | transfer cap-through the tray |
| 700 | Universal Scanning Post |
| 712 | mating projections for top of healing cap |
| 713 | X sphere protrusion |
| 714 | y rectangle protrusion |
| 715 | z triangle protrusion |
| 800 | Universal Guided Tissue Punch |
| 801 | surgical guiding screw |
| 802 | cutting edge of tissue punch |
| 803 | internal guiding polyhedron |
| 804 | universal guided tissue punch-implant insertion |
| 805 | surgical guiding cylinder |
| 810 | universal paralleling posts |
| 811 | stem of the paralleling post |
| 812 | abutment head of the paralleling post |
| 815 | adaptor carrier/releasing screw tool |
| 816 | primary indicium on the shank |
| 818 | releasing screw |
| 900 | Nonagon Implant |
| 901 | Internal nonagon implant index |
| 920 | Primary vertex of nonagon index |
| 921 | "0" reference indicium on top of implant collar |
| 930 | fixture mount |
| 931 | external nonagon index of fixture mount to implant |
| 932 | external nonagon index of fixture mount shank |
| 933 | vertex configuration overlying vertex of nonagon |

What is claimed is:

1. A method for manufacturing a dental component comprising:

receiving electronic vertical and horizontal position data of an adaptor seated on an implant in a patient's jaw, said adaptor having an adaptor reference indicium that is co-operable with a prosthetic reference indicium of a prosthetic component to position the adaptor into a repeatable vertical and horizontal predetermined position in relation to the implant, the electronic vertical and horizontal position data including electronic adaptor reference indicium data representative of the adaptor reference indicium position and electronic prosthetic reference indicium data representative of the prosthetic reference indicium position;

translating the electronic position data into electronic manufacturing device codes for a milling or printing program;

transmitting the electronic manufacturing device codes to a device configured to manufacture the prosthetic component, such that the manufactured prosthetic component is configured to be inserted on the implant such that the prosthetic component is in the preferred position; and manufacturing the prosthetic component.

2. The method of claim 1, wherein the electronic vertical or horizontal position data is generated by an intraoral scan, CBCT scan, or other scan device of the adaptor or prosthetic component.

3. The method of claim 1, wherein the prosthetic reference indicium and the adaptor reference indicium include graduations for indicating the degree of rotation of the prosthetic component and adaptor relative to each other.

4. The method of claim 1, wherein the prosthetic component is a base of the final abutment with a configuration to match a configuration of the healing cap.

5. The method of claim 1, wherein a rotational relationship of an octagon stud on an open end to receive an abutment and a tripod, hexagon, or dodecagon stud on a free end which interfaces with a corresponding implant index results in a virtual horizontal rotation of the abutment in 15° increments of horizontal rotation when an engaging receptacle of the prosthetic component is an octagon.

6. The method of claim 1, wherein a rotational relationship of an octagon stud on an open end to receive an abutment and a tripod, hexagon, or dodecagon stud on a free end which interfaces with a corresponding implant index results in a virtual horizontal rotation of the abutment in 7.5° increments of horizontal rotation when an engaging receptacle of the prosthetic component is a hexadecagon.

7. The method of claim 1, wherein a relationship of a hexagon stud on an open end to receive an abutment and an octagon stud on a free end that interfaces with a corresponding octagon implant index results in a virtual horizontal rotation of the abutment in 15° increments of horizontal rotation when an engaging receptacle of the prosthetic component is a hexagon.

8. The method of claim 1, wherein a relationship of a hexagon stud on an open end to receive an abutment and an octagon stud on a free end that interfaces with a corresponding octagon implant index results in a virtual horizontal rotation of the abutment in 7.5° increments of horizontal rotation when an engaging receptacle of the prosthetic component is a dodecagon.

9. The method of claim 1, wherein a polygonal structure at an open end of the adaptor is a nonagon stud and a free end of the adaptor is a quadragon or octagon and the prosthetic component has an nonagon receptacle that engages the nonagon stud of the adaptor such that the interface results in net 10° increments of horizontal rotation when engaging the receptacle of the prosthetic component.

10. The method of claim 1, wherein a polygonal structure at an open end of the adaptor is a quadragon or octagon stud and a free end of the adaptor is a nonagon and the prosthetic component has a quadragon or octagon receptacle that engages the quadragon or octagon stud of the adaptor such that the interface results in a net 10° or 5° increments of horizontal rotation when engaging the receptacle of the prosthetic component.

11. The method of claim 1, further comprising:
taking an impression of the implant;
scanning the implant analog and creating data based on the positioning of the implant analog; and
conveying the data to the milling program.

* * * * *